US012384794B2

(12) United States Patent
Yoshinari et al.

(10) Patent No.: US 12,384,794 B2
(45) Date of Patent: Aug. 12, 2025

(54) QUINAZOLINE COMPOUND FOR INDUCING DEGRADATION OF G12D MUTANT KRAS PROTEIN

(71) Applicant: Astellas Pharma Inc., Tokyo (JP)

(72) Inventors: Tomohiro Yoshinari, Tokyo (JP); Hiroki Ishioka, Tokyo (JP); Eiji Kawaminami, Tokyo (JP); Hideyuki Watanabe, Tokyo (JP); Kenichi Kawaguchi, Tokyo (JP); Kazuyuki Kuramoto, Tokyo (JP); Tomoyoshi Imaizumi, Tokyo (JP); Takahiro Morikawa, Tokyo (JP); Hisao Hamaguchi, Tokyo (JP); Sunao Imada, Tokyo (JP); Mitsuaki Okumura, Tokyo (JP); Takeyuki Nagashima, Tokyo (JP); Kohei Inamura, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 248 days.

(21) Appl. No.: 18/268,001

(22) PCT Filed: Feb. 14, 2022

(86) PCT No.: PCT/JP2022/005582
§ 371 (c)(1),
(2) Date: Jun. 16, 2023

(87) PCT Pub. No.: WO2022/173032
PCT Pub. Date: Aug. 18, 2022

(65) Prior Publication Data
US 2024/0182483 A1    Jun. 6, 2024

(30) Foreign Application Priority Data
Feb. 15, 2021   (JP) .................. 2021-021656

(51) Int. Cl.
*C07D 487/08*    (2006.01)
(52) U.S. Cl.
CPC .................. *C07D 487/08* (2013.01)
(58) Field of Classification Search
CPC .................................................. C07D 487/08
See application file for complete search history.

(56) References Cited

U.S. PATENT DOCUMENTS

| 2018/0015087 A1 | 1/2018 | Liu et al. |
| 2019/0292182 A1 | 9/2019 | Kuramoto et al. |

FOREIGN PATENT DOCUMENTS

| JP | 2015-508414 A | 3/2015 |
| WO | WO 2013/106643 A2 | 7/2013 |
| WO | WO 2015/160845 A2 | 10/2015 |
| WO | WO 2016/049565 A1 | 3/2016 |
| WO | WO 2016/049568 A1 | 3/2016 |
| WO | WO 2017/172979 A1 | 10/2017 |
| WO | WO 2018/143315 A1 | 8/2018 |
| WO | WO 2019/195609 A2 | 10/2019 |
| WO | WO 2020/018788 A1 | 1/2020 |
| WO | WO 2021/041671 A1 | 3/2021 |
| WO | WO 2021/051034 A1 | 3/2021 |
| WO | WO 2021/106231 A1 | 6/2021 |
| WO | WO 2021/107160 A1 | 6/2021 |
| WO | WO 2021/207172 A1 | 10/2021 |
| WO | WO 2022/061348 A1 | 3/2022 |
| WO | WO 2022/148421 A1 | 7/2022 |
| WO | WO 2022/148422 A1 | 7/2022 |

OTHER PUBLICATIONS

Bond et al., (2020) "Targeted Degradation of Oncogenic KRAS$^{G12C}$ by VHL-Recruiting PROTACs," *ACS Cent. Sci.*, 6:1367-1375.
International Patent Application No. PCT/JP2022/005582, by Astellas Pharma Inc., filed Feb. 14, 2022, International Search Report and Written Opinion, mailed Apr. 26, 2022 (translation—4 pages).
Zeng et al., (2020) "Exploring Targeted Degradation Strategy for Oncogenic KRAS$^{G12C}$," *Cell. Chem. Biol.*, 27:19-31.

*Primary Examiner* — Renee Claytor
*Assistant Examiner* — Christopher Lindsay Johnson
(74) *Attorney, Agent, or Firm* — Finnegan, Henderson, Farabow, Garrett & Dunner, LLP

(57) ABSTRACT

[Problem] To provide a compound useful as an active ingredient of a pharmaceutical composition for treating pancreatic cancer.
[Means for resolution] The present inventors have studied about a compound that is useful as an active ingredient of a pharmaceutical composition for treating pancreatic cancer and have found that a quinazoline compound has an excellent degradation-inducing action on a G12D mutant KRAS protein and a G12D mutant KRAS inhibition activity and can be used as a therapeutic agent for pancreatic cancer, thus completing the present invention. The quinazoline compound or a salt thereof of the present invention can be used as a therapeutic agent for pancreatic cancer.

37 Claims, No Drawings

QUINAZOLINE COMPOUND FOR INDUCING DEGRADATION OF G12D MUTANT KRAS PROTEIN

CROSS-REFERENCE TO RELATED APPLICATIONS

This application is a United States national stage application under 35 U.S.C. § 371 of International Application No. PCT/JP2022/005582, filed Feb. 14, 2022, which claims priority to Japanese Patent Application No. 2021-021656, filed Feb. 15, 2021. The contents of the aforementioned applications are incorporated by reference herein in their entirety.

TECHNICAL FIELD

The present invention relates to pharmaceutical compositions and, in particular, to a quinazoline compound that is excellent in a degradation-inducing action on a G12D mutant KRAS protein and that is expected to be useful as a G12D mutant KRAS inhibitor and to be useful as an active ingredient of, for example, a pharmaceutical composition for treating pancreatic cancer.

BACKGROUND ART

Pancreatic cancer mainly including pancreatic ductal adenocarcinoma is a cancer with a very poor prognosis having a five-years survival rate of 10% or less (CA Cancer J. Clin., 2016, 66, p. 7-30), and about 460,000 new cases are reported per year in the world (CA Cancer J. Clin., 2018, 68, p. 394-424). The most effective therapy for treating pancreatic cancer is a surgery. However, the cancer has often metastasized since early detection is difficult, and the therapeutic effect of a surgery cannot be expected in many cases. When the cancer is not treated by operation, chemotherapy or radiotherapy is adopted, but the survival rate is not so good. Today, the FOLFRINOX therapy (multidrug treatment of three chemotherapy agents of 5-FU, irinotecan and oxaliplatin, plus levofolinate) is used as a standard therapy of pancreatic cancer. However, due to the strong toxicity, the subject patient has to be cautiously selected, for example, the therapy is to be applied only to patients of an ECOG performance status of 1 or less (J. Clin. Oncol., 2018, 36, p. 2545-2556). As a molecular target drug, an epidermal growth factor receptor (EGFR) inhibitor, Erlotinib, has been approved in a combination therapy with Gemcitabine. However, the extension of the overall survival is only about two weeks as compared with Gemcitabine alone, and no satisfying therapeutic effect has been achieved. A highly effective therapeutic agent remains needed (J. Clin. Oncol., 2007, 25, p. 1960-1966).

RAS proteins are low molecular weight guanosine triphosphate (GTP)-binding proteins of about 21 kDa constituted of 188-189 amino acids and include four main types of proteins (KRAS (KRAS 4A and KRAS 4B), NRAS and HRAS) produced by three genes of a KRAS gene, an NRAS gene and an HRAS gene. RAS proteins are divided into an active GTP-binding type and an inactive GDP-binding type. A RAS protein is activated by replacement of guanosine diphosphate (GDP) with GTP due to, for example, ligand stimulation to a membrane receptor, such as EGFR. The active RAS binds to effector proteins as much as twenty, such as RAF, PI3K and RALGDS, to activate the downstream signal cascade. On the other hand, the active RAS is converted to the inactive type by replacement of GTP with GDP due to the intrinsic GTP hydrolysis (GTPase) activity. The GTPase activity is enhanced by a GTPase-activating protein (GAP). As can be seen from the above statement, RAS bears an important function of "molecular switch" in an intracellular signal transduction pathway for EGFR or the like and plays a critical role in the processes of cell growth, proliferation, angiogenesis and the like (Nature Rev. Cancer, 2011, 11, p. 761-774, Nature Rev. Drug Discov., 2014, 13, p. 828-851, Nature Rev. Drug Discov., 2016, 15, p. 771-785).

Substitution of an amino acid by spontaneous mutation of the RAS gene results in a constant activated state due to hypofunction of RAS as GTPase or hyporeactivity to GAP, and then, signals are continuously sent downstream. The excessive signaling causes carcinogenesis or cancer growth acceleration. It is said that pancreatic ductal adenocarcinoma occurs through a weakly heteromorphic stage and a subsequent highly heteromorphic stage in the pancreatic intraepithelial neoplasia (PanIN), and mutation of the KRAS gene has already been recognized in an initial stage of PanIN. Subsequently, abnormality occurs in INK4A, p53 and SMAD4, which are tumor suppression genes, leading to malignancy (Nature Rev. Cancer, 2010, 10, p. 683-695). Furthermore, in 90% or more of the cases of pancreatic ductal adenocarcinoma, mutation is seen in the KRAS gene, and a majority of them are a spontaneous point mutation in the codon 12 located in the KRAS exon 2 (Cancer Cell 2017, 32, p. 185-203). As can be seen from the above statement, KRAS plays a critical role in the processes of carcinogenesis and development of pancreatic cancer.

As a mutation of a KRAS gene, KRAS G12C mutation, KRAS G12D mutation and the like are known. G12C mutant KRAS frequently occurs in non-small-cell lung cancer but occurs few percent in pancreatic cancer (Cancer Cell 2014, 25, p. 272-281), and a therapeutic agent against another KRAS mutation is desired. G12D mutant KRAS is seen in about 34% of the cases of pancreatic cancer, and this rate is reported to be the highest in KRAS mutations (Nat. Rev. Cancer, 2018, 18, p. 767-777).

Patent Documents 1, 2 and 3 disclose RAS inhibitors, and Patent Documents 2 and 3 disclose compounds represented by the following formula (A) and formula (B), respectively. Patent Documents 1, 2 and 3 state that the agents are useful for a cancer with a mutation in the codon 12 of KRAS. The G12D mutation is one of such mutations, but any effect on the G12D mutant KRAS cancer is not described.

[Chem. 1]

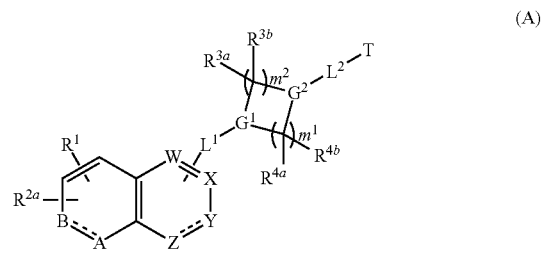

(A)

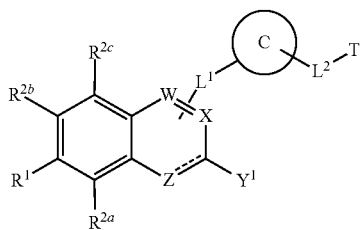

(The meanings of the signs in the formulae can be found in the patent documents.)

Moreover, Patent Documents 9, 10 and 11 disclose a KRAS G12D inhibitor.

In recent years, as a technique for inducing degradation of a target protein, bifunctional compounds collectively called as PROTAC (PROteolysis-TArgeting Chimera) or SNIPER (Specific and Nongenetic IAP-dependent Protein Eraser) are found and are expected as one novel technique of drug development modality (Drug. Discov. Today Technol., 2019, 31, p 15-27). Such a bifunctional compound promotes formation of a composite of the target protein and an E3 ligase in a cell, and degradation of the target protein is induced using the ubiquitin-proteasome system. The ubiquitin-proteasome system is one of intracellular protein degradation mechanisms. A protein called E3 ligase recognizes a protein to be degraded to convert the protein into ubiquitin, whereby degradation by proteasome is promoted.

600 or more E3 ligases are present in an organism and are roughly divided into four types of HECT-domain E3s, U-box E3s, monomeric RING E3s and multi-subunit E3s. E3 ligases used as a bifunctional degradation inducer which are called PROTAC, SNIPER or the like are currently limited, and typical examples thereof include Von Hippel-Lindau (VHL), celebron (CRBN), inhibitor of apoptosis protein (IAP) and mouse double minute 2 homolog (MDM2). In particular, VHL is reported in Patent Document 4, and CRBN is reported in Patent Document 5.

The bifunctional compounds are compounds in which a ligand of a target protein and a ligand of an E3 ligase are bound via a linker, and some bifunctional compounds for degrading a KRAS protein have ever been reported (Non-patent Document 1, Non-patent Document 2, Patent Document 6, Patent Document 7, Patent Document 8 and Patent Document 12). However, no bifunctional compound targeting the G12D mutant KRAS is reported now.

CITATION LIST

Patent Document

[Patent Document 1] WO 2016/049565
[Patent Document 2] WO 2016/049568
[Patent Document 3] WO 2017/172979
[Patent Document 4] WO 2013/106643
[Patent Document 5] WO 2015/160845
[Patent Document 6] US Patent Application Publication No. 2018/0015087
[Patent Document 7] WO 2019/195609
[Patent Document 8] WO 2020/018788
[Patent Document 9] WO 2021/041671
[Patent Document 10] WO 2021/106231
[Patent Document 11] WO 2021/107160
[Patent Document 12] WO 2021/051034

Non-Patent Document

[Non-patent Document 1] Cell. Chem. Biol., 2020, 27, p. 19-31
[Non-patent Document 2] ACS Cent. Sci., 2020, 6, p. 1367-1375

SUMMARY OF INVENTION

Technical Problem

A pharmaceutical composition, for example, a quinazoline compound that is excellent in a degradation-inducing action on a G12D mutant KRAS protein and that is expected to be useful as a G12D mutant KRAS inhibitor and to be useful as an active ingredient of a pharmaceutical composition for treating pancreatic cancer, in particular, G12D mutant KRAS-positive pancreatic cancer, is provided.

Solution to Problem

The present inventors have intensively and extensively studied about a compound that is useful as an active ingredient of a pharmaceutical composition for treating pancreatic cancer. As a result, the present inventors have found that a quinazoline compound of a formula (I), in particular, a bifunctional compound of the formula (I) characterized in that a substituent on the position 8 of quinazoline is bound to a ligand of an E3 ligase or that a substituent on the position 8 of quinazoline is bound to a ligand of an E3 ligase via a linker, has an excellent degradation-inducing action on a G12D mutant KRAS protein and a G12D mutant KRAS inhibition activity, thus completing the present invention.

Specifically, the present invention relates to a compound of the formula (I) or a salt thereof and a pharmaceutical composition that contains a compound of the formula (I) or a salt thereof and one or more pharmaceutically acceptable excipients.

[Chem. 2]

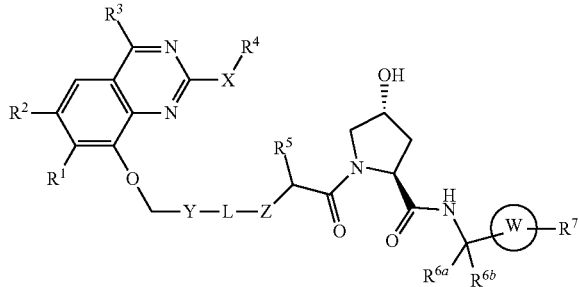

(In the formula,
$R^1$ is naphthyl optionally substituted with OH or a group selected from the group consisting of the formula (II) and the formula (III) below,

[Chem. 3]

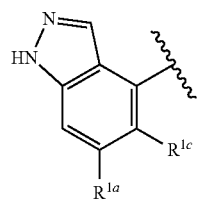

-continued (III)

$R^{1a}$ and $R^{1b}$, which are the same as or different from each other, are H, methyl, F or Cl,
$R^{1c}$ is F, Cl, methyl or ethyl,
$R^2$ is H, halogen, optionally substituted $C_{1-3}$ alkyl, cyclopropyl or vinyl,
$R^3$ is a 7-membered or 8-membered saturated or unsaturated bridged heterocyclic group containing one or two nitrogen atoms,
$R^4$ is optionally substituted $C_{1-6}$ alkyl, a 4-membered to 6-membered optionally substituted saturated heterocyclic group containing one or two hetero atoms selected from oxygen, sulfur and nitrogen, 5-membered optionally substituted heteroaryl containing one to four hetero atoms selected from oxygen, sulfur and nitrogen or 6-membered optionally substituted heteroaryl containing one to three nitrogen atoms,
$R^5$ is optionally substituted $C_{1-6}$ alkyl, optionally substituted $C_{3-6}$ cycloalkyl or a 4-membered to 6-membered optionally substituted saturated heterocyclic group containing one hetero atom selected from oxygen, sulfur and nitrogen,
$R^{6a}$ and $R^{6b}$, which are the same as or different from each other, are H or optionally substituted $C_{1-6}$ alkyl, or $R^{6a}$ and $R^{6b}$ form optionally substituted $C_{3-6}$ cycloalkyl or an 4-membered to 6-membered optionally substituted saturated heterocyclic ring containing one hetero atom selected from oxygen, sulfur and nitrogen together with the carbon to which they are attached,
$R^7$ is H, halogen, $C_{1-3}$ alkyl, —$SO_2CH_3$, $C_{3-6}$ cycloalkyl, a 4-membered to 6-membered optionally substituted saturated heterocyclic group containing one or two hetero atoms selected from oxygen, sulfur and nitrogen, 5-membered optionally substituted heteroaryl containing one to four hetero atoms selected from oxygen, sulfur and nitrogen or 6-membered heteroaryl containing one to three nitrogen atoms,
W is optionally substituted phenyl or 6-membered optionally substituted heteroaryl containing one to three nitrogen atoms,
X is a bond, $CH_2$, O, S or $NR^{4x}$,
$R^4$ is H or $C_{1-3}$ alkyl,
Y is phenylene or pyridinediyl, wherein the phenylene may be substituted with F,
L is -($L^1$-$L^2$-$L^3$-$L^4$)-,
$L^1$, $L^2$, $L^3$ and $L^4$, which are the same as or different from each other, are a group selected from the group consisting of a bond, O, $NR^{L1}$, optionally substituted pyrrolidinediyl, optionally substituted piperidinediyl, optionally substituted piperazinediyl, optionally substituted $C_{1-3}$ alkylene and C=O,
$R^{L1}$ is H or $C_{1-3}$ alkyl, and
Z is NH or 5-membered heteroarenediyl containing one to four hetero atoms selected from oxygen, sulfur and nitrogen,
or Y-L-Z is the formula (XIII) below.)

[Chem. 4]

(XIII)

Furthermore, the present invention relates to a compound of the formula (Ib) or a salt thereof and a pharmaceutical composition that contains a compound of the formula (Ib) or a salt thereof and one or more pharmaceutically acceptable excipients. The compound of the formula (Ib) is included in the compound of the formula (I).

[Chem. 5]

(Ib)

(In the formula,
$R^1$ is the formula (IIa) or the formula (IIIa) below,

[Chem. 6]

(IIa)

(IIIa)

$R^{1a}$ and $R^{1b}$, which are the same as or different from each other, are H or F, $R^2$ is halogen, $C_{1-3}$ alkyl, cyclopropyl or vinyl, $R^3$ is the formula (IV) below,

[Chem. 7]

(IV)

$R^4$ is $C_{1-3}$ alkyl, oxetanyl, tetrahydrofuranyl, tetrahydropyranyl, optionally substituted pyrazolyl, optionally substituted pyridyl, optionally substituted pyrimidinyl, optionally substituted pyrrolidinyl or optionally substituted piperidinyl, $R^5$ is ethyl, isopropyl, tert-butyl or $C_{3-6}$ cycloalkyl, $R^{6a}$ and $R^{6b}$, which are the same as or different from each other, are H or $C_{1-3}$ alkyl optionally substituted with a group selected from the group consisting of F, OH and $N(CH_3)_2$, or $R^{6a}$ and $R^{6b}$ form cyclopropyl together with the carbon to which they are attached, $R^7$ is H, halogen or a group selected from the group consisting of the formula (VI), the formula (VII), the formula (VIII) and the formula (IX) below,

[Chem. 8]

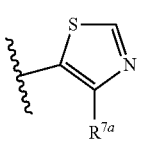

(VI)

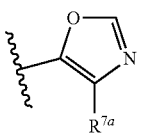

(VII)

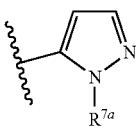

(VIII)

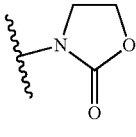

(IX)

$R^{7a}$ is H or $C_{1-3}$ alkyl optionally substituted with OH,

X is O,

Y is phenylene or pyridinediyl,

L is a bond, $C_{1-3}$ alkylene or C=O, and

Z is NH or a group selected from the group consisting of the formula (X), the formula (XI) and the formula (XII) below,

[Chem. 9]

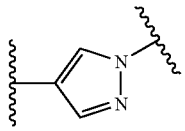

(X)

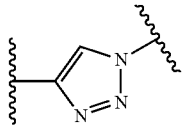

(XI)

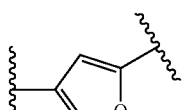

(XII)

or Y-L-Z is the formula (XIII) below.)

[Chem. 10]

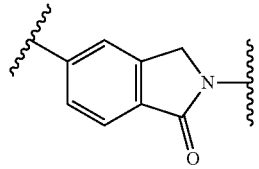

(XIII)

Note that, when a sign in a chemical formula herein is used in another chemical formula, the same sign represents the same meaning unless otherwise specified.

The present invention also relates to a pharmaceutical composition, in particular, a pharmaceutical composition for treating pancreatic cancer, in particular, a pharmaceutical composition for treating G12D mutant KRAS-positive pancreatic cancer, in particular, a pharmaceutical composition for treating metastatic pancreatic cancer, in particular, a pharmaceutical composition for treating locally advanced pancreatic cancer, in particular, a pharmaceutical composition for treating recurrent or refractory pancreatic cancer, in particular, a pharmaceutical composition for treating pancreatic cancer of a patient who is untreated and/or has a medical record, in particular, a pharmaceutical composition for treating metastatic G12D mutant KRAS-positive pancreatic cancer, in particular, a pharmaceutical composition for treating locally advanced G12D mutant KRAS-positive pancreatic cancer, in particular, a pharmaceutical composition for treating recurrent or refractory G12D mutant KRAS-positive pancreatic cancer, in particular, a pharmaceutical composition for treating G12D mutant KRAS-positive pancreatic cancer of a patient who is untreated and/or has a medical record, the composition containing the compound of the formula (I) or a salt thereof and one or more pharmaceutically acceptable excipients. Note that the pharmaceutical composition includes a therapeutic agent for pancreatic cancer, in particular, G12D mutant KRAS-positive pancreatic cancer, the agent containing the compound of the formula (I) or a salt thereof.

The present invention also relates to use of the compound of the formula (I) or a salt thereof for the manufacture of a pharmaceutical composition for treating pancreatic cancer, in particular, G12D mutant KRAS-positive pancreatic cancer, in particular, metastatic pancreatic cancer, in particular, locally advanced pancreatic cancer, in particular, recurrent or refractory pancreatic cancer, in particular, pancreatic cancer of a patient who is untreated and/or has a medical record, in particular, metastatic G12D mutant KRAS-positive pancreatic cancer, in particular, locally advanced G12D mutant KRAS-positive pancreatic cancer, in particular, recurrent or refractory G12D mutant KRAS-positive pancreatic cancer, in particular, G12D mutant KRAS-positive pancreatic cancer of a patient who is untreated and/or has a medical record, to use of the compound of the formula (I) or a salt thereof for treating pancreatic cancer, in particular, G12D mutant KRAS-positive pancreatic cancer, to the compound of the formula (I) or a salt thereof for use in treatment of pancreatic cancer, in particular, G12D mutant KRAS-positive pancreatic cancer and to a method for treating pancreatic cancer, in particular, G12D mutant KRAS-positive pancreatic cancer, the method comprising administering an effective amount of the compound of the formula (I) or a salt thereof to a subject.

The present invention also relates to the compound of the formula (I) or a salt thereof that is a G12D mutant KRAS protein degradation inducer and/or a G12D mutant KRAS inhibitor, to the compound of the formula (I) or a salt thereof for use as a G12D mutant KRAS protein degradation inducer and/or a G12D mutant KRAS inhibitor and to a G12D mutant KRAS protein degradation inducer and/or a G12D mutant KRAS inhibitor comprising the compound of the formula (I) or a salt thereof.

Note that the "subject" is a human or another animal that needs the treatment, and in one embodiment, the "subject" is a human who needs the prevention or treatment.

Advantageous Effects of Invention

The compound of the formula (I) or a salt thereof has a degradation-inducing action on a G12D mutant KRAS protein and a G12D mutant KRAS inhibition activity and can be used as a therapeutic agent for pancreatic cancer, in particular, G12D mutant KRAS-positive pancreatic cancer.

DESCRIPTION OF EMBODIMENTS

The present invention will be described in detail below.

As used herein, "optionally substituted" means being unsubstituted or having one to five substituents. In one embodiment, the "optionally substituted" means being unsubstituted or having one to three substituents. Note that when there are multiple substituents, the substituents may be the same as or different from each other.

"$C_{1-12}$ Alkyl" is linear or branched alkyl having 1 to 12 carbon atoms, and examples thereof include methyl, ethyl, n-propyl, isopropyl, n-butyl, isobutyl, sec-butyl, tert-butyl, n-pentyl, n-hexyl, dodecyl and the like (the carbon atom numbers are described similarly hereinafter). The "$C_{1-12}$ alkyl" is ethyl or dodecyl in one embodiment, $C_{1-6}$ alkyl in one embodiment, methyl, ethyl, n-propyl, isopropyl, n-butyl, isobutyl, sec-butyl, tert-butyl, n-pentyl or n-hexyl in one embodiment, methyl, ethyl, n-propyl, isopropyl or sec-butyl in one embodiment, methyl, ethyl, isopropyl or tert-butyl in one embodiment, methyl, ethyl, n-propyl, isopropyl or n-butyl in one embodiment, $C_{1-3}$ alkyl in one embodiment, methyl, ethyl or isopropyl in one embodiment, methyl or ethyl in one embodiment, methyl or isopropyl in one embodiment, ethyl or isopropyl in one embodiment, methyl in one embodiment, ethyl in one embodiment or isopropyl in one embodiment.

"$C_{3-6}$ Cycloalkyl" is cycloalkyl having 3 to 6 carbon atoms, and examples thereof include cyclopropyl, cyclobutyl, cyclopentyl and cyclohexyl. The "$C_{3-6}$ cycloalkyl" is cyclobutyl, cyclopentyl or cyclohexyl in one embodiment, cyclobutyl or cyclopentyl in one embodiment, cyclopentyl or cyclohexyl in one embodiment, cyclopropyl or cyclobutyl in one embodiment, cyclopropyl in one embodiment, cyclobutyl in one embodiment, cyclopentyl in one embodiment or cyclohexyl in one embodiment.

"$C_{1-3}$ Alkylene" is linear or branched $C_{1-3}$ alkylene, and examples thereof include methylene, ethylene, trimethylene, methylmethylene, 1,1-dimethylmethylene and the like. The "$C_{1-3}$ alkylene" is linear or branched $C_{1-3}$ alkylene in one embodiment, methylene, ethylene or trimethylene in one embodiment, methylene or ethylene in one embodiment, methylene in one embodiment or ethylene in one embodiment.

"7-Membered or 8-membered saturated or unsaturated bridged heterocyclic group" is a saturated 7-membered or 8-membered monocyclic bridged heterocyclic group containing one or two nitrogen atoms as ring-forming atoms or a 7-membered or 8-membered monocyclic bridged heterocyclic group containing one or two nitrogen atoms and having an unsaturated bond. The "7-membered or 8-membered saturated or unsaturated bridged heterocyclic group" is a saturated 7-membered or 8-membered monocyclic bridged heterocyclic group containing two nitrogen atoms in one embodiment or a saturated 7-membered or 8-membered monocyclic bridged heterocyclic group containing two nitrogen atoms in which one of the two nitrogen atoms bonds to one hydrogen atom. Examples thereof include diazabicyclo[2.2.2]octanyl, diazabicyclo[3.2.1]octanyl, diazabicyclo[3.2.1]octenyl, diazabicyclo[3.1.1]heptanyl, diazabicyclo[2.2.1]heptanyl and diazabicyclo[2.2.1]heptenyl. The "7-membered or 8-membered saturated or unsaturated bridged heterocyclic group" is diazabicyclo[2.2.2]octanyl, diazabicyclo[3.2.1]octanyl, diazabicyclo[3.2.1]oct-6-enyl, diazabicyclo[3.2.1]oct-2-enyl, diazabicyclo[3.1.1]heptanyl, diazabicyclo[2.2.1]heptanyl or diazabicyclo[2.2.1]hept-5-enyl in one embodiment, diazabicyclo[2.2.2]octanyl, diazabicyclo[3.2.1]octanyl, diazabicyclo[3.1.1]heptanyl or diazabicyclo[2.2.1]heptanyl in one embodiment, 2,5-diazabicyclo[2.2.2]octanyl, 3,8-diazabicyclo[3.2.1]octanyl, 3,6-diazabicyclo[3.1.1]heptanyl or 2,5-diazabicyclo[2.2.1]heptanyl in one embodiment, diazabicyclo[2.2.1]heptanyl in one embodiment, 2,5-diazabicyclo[2.2.1]heptanyl in one embodiment or 2,5-diazabicyclo[2.2.1]heptan-2-yl in one embodiment.

"4-Membered to 6-membered saturated heterocyclic group" is, for example, a 4-membered to 6-membered saturated heterocyclic group containing one or two hetero atoms selected from the group consisting of oxygen, sulfur and nitrogen as ring-forming atoms, and the sulfur atom contained in the heterocyclic ring is optionally oxidized. The "4-membered to 6-membered saturated heterocyclic group" in one embodiment is a 4-membered to 6-membered saturated heterocyclic group containing one hetero atom selected from the group consisting of oxygen, sulfur and nitrogen, and the sulfur atom contained in the heterocyclic ring is optionally oxidized. The "4-membered to 6-membered saturated heterocyclic group" is a 5-membered or 6-membered saturated heterocyclic group containing one or two hetero atoms selected from the group consisting of oxygen, sulfur and nitrogen in which the sulfur atom contained in the heterocyclic ring is optionally oxidized in one embodiment, a 5-membered saturated heterocyclic group containing one or two hetero atoms selected from the group consisting of oxygen, sulfur and nitrogen in which the sulfur atom contained in the heterocyclic ring is optionally oxidized in one embodiment, oxetanyl, tetrahydrofuranyl, tetrahydropyranyl, azetidinyl, pyrrolidinyl, piperidinyl, oxazolidinyl, imidazolidinyl, piperazinyl, morpholinyl, thiomorpholinyl or dioxothiomorpholinyl in one embodiment, oxetanyl, tetrahydrofuranyl, tetrahydropyranyl, azetidinyl, pyrrolidinyl, piperidinyl, piperazinyl, morpholinyl, thiomorpholinyl or dioxothiomorpholinyl in one embodiment, oxetanyl, tetrahydrofuranyl, tetrahydropyranyl, pyrrolidinyl, piperidinyl or morpholinyl in one embodiment, oxetanyl, tetrahydrofuranyl, tetrahydropyranyl, pyrrolidinyl or piperidinyl in one embodiment, oxetanyl, tetrahydrofuranyl or tetrahydropyranyl in one embodiment, pyrrolidinyl or piperidinyl in one embodiment, oxetanyl in one embodiment, tetrahydrofuranyl in one embodiment, tetrahydropyranyl in one embodiment, pyrrolidinyl in one embodiment, piperidinyl in one embodiment, morpholinyl in one embodiment or oxazolidinyl in one embodiment.

"5-Membered heteroaryl" is, for example, 5-membered cyclic heteroaryl containing one to four hetero atoms selected from the group consisting of oxygen, sulfur and nitrogen as ring-forming atoms. The "5-membered heteroaryl" is pyrazolyl, imidazolyl, triazolyl, tetrazolyl, oxazolyl, isoxazolyl, thiazolyl, isothiazolyl, oxadiazolyl or thiadiazolyl in one embodiment, pyrazolyl, imidazolyl, triazolyl, oxazolyl or thiazolyl in one embodiment, pyrazolyl, imidazolyl, oxazolyl or thiazolyl in one embodiment, pyrazolyl, imidazolyl, triazolyl or isoxazolyl in one embodiment, pyrazolyl, oxazolyl or thiazolyl in one embodiment, pyrazolyl, triazolyl or isoxazolyl in one embodiment, pyrazolyl or thiazolyl in one embodiment, pyrazolyl or triazolyl in one embodiment, pyrazolyl in one embodiment, imidazolyl in one embodiment, oxazolyl in one embodiment, thiazolyl in one embodiment or triazolyl in one embodiment. "5-Membered heteroarenediyl" is a divalent group formed by removal of any one hydrogen atom from the "5-membered heteroaryl".

"6-Membered heteroaryl" is, for example, 6-membered cyclic heteroaryl containing one to three nitrogen atoms as ring-forming atoms. The "6-membered heteroaryl" is pyridyl, pyrimidinyl, pyrazinyl, pyridazinyl or triazinyl in one embodiment, pyridyl or pyridazinyl in one embodiment, pyridyl or pyrimidinyl in one embodiment, pyridyl in one embodiment or pyrimidinyl in one embodiment.

"Halogen" means F, Cl, Br and I. The "halogen" is F, Cl or Br in one embodiment, F or Cl in one embodiment, F or Br in one embodiment, F in one embodiment, Cl in one embodiment or Br in one embodiment.

Substituents acceptable in "optionally substituted $C_{1-6}$ alkyl" and "optionally substituted $C_{1-3}$ alkyl" in one embodiment are F, OH, $OCH_3$, $N(CH_3)_2$, $C_{1-3}$ alkyl, hydroxymethyl, methoxymethyl, difluoroethyl, optionally substituted $C_{3-6}$ cycloalkyl, azabicyclo[3.3.0]octanyl or a 4-membered to 6-membered optionally substituted saturated heterocyclic group containing one or two hetero atoms selected from oxygen, sulfur and nitrogen. The substituents are F, OH, $OCH_3$, $N(CH_3)_2$, methyl, ethyl, hydroxymethyl, methoxymethyl, difluoroethyl, optionally substituted cyclopropyl, tetrahydrofuranyl, optionally substituted tetrahydropyranyl, morpholinyl, optionally substituted pyrrolidinyl, optionally substituted piperidinyl or azabicyclo[3.3.0]octanyl in one embodiment, F, OH, $OCH_3$, $N(CH_3)_2$, methyl, hydroxymethyl, methoxymethyl, optionally substituted cyclopropyl, tetrahydrofuranyl, optionally substituted tetrahydropyranyl, morpholinyl, optionally substituted pyrrolidinyl, piperidinyl or azabicyclo[3.3.0]octanyl in one embodiment, F, OH, $OCH_3$, $N(CH_3)_2$, methyl, hydroxymethyl, methoxymethyl, cyclopropyl, (hydroxymethyl)cyclopropyl, (methoxymethyl)cyclopropyl, tetrahydrofuranyl, tetrahydropyranyl, (hydroxymethyl)tetrahydropyranyl, (methoxymethyl)tetrahydropyranyl, morpholinyl, pyrrolidinyl, methylpyrrolidinyl, piperidinyl or azabicyclo[3.3.0]octanyl in one embodiment, F, OH, $OCH_3$, $N(CH_3)_2$, methyl, cyclopropyl, (hydroxymethyl)cyclopropyl, (methoxymethyl)cyclopropyl, tetrahydrofuranyl, tetrahydropyranyl, (hydroxymethyl)tetrahydropyranyl, (methoxymethyl)tetrahydropyranyl, morpholinyl, pyrrolidinyl, methylpyrrolidinyl or azabicyclo[3.3.0]octanyl in one embodiment, OH, $OCH_3$, $N(CH_3)_2$, (hydroxymethyl)cyclopropyl, tetrahydrofuranyl, (methoxymethyl)cyclopropyl, (hydroxymethyl)tetrahydropyranyl, (methoxymethyl)tetrahydropyranyl, morpholinyl, pyrrolidinyl, methylpyrrolidinyl or azabicyclo[3.3.0]octanyl in one embodiment, F, OH, $OCH_3$, $N(CH_3)_2$, methyl, hydroxymethyl, methoxymethyl, cyclopropyl, tetrahydrofuranyl, tetrahydropyranyl, morpholinyl, pyrrolidinyl, methylpyrrolidinyl or azabicyclo[3.3.0]octanyl in one embodiment, F, OH or $OCH_3$ in one embodiment, F, OH, $OCH_3$ or $N(CH_3)_2$ in one embodiment, F, OH or $N(CH_3)_2$ in one embodiment, OH or $OCH_3$ in one embodiment or OH in one embodiment.

Substituents acceptable in "5-membered optionally substituted heteroaryl", "6-membered optionally substituted heteroaryl", "optionally substituted $C_{3-6}$ cycloalkyl", "optionally substituted pyrazolyl", "optionally substituted pyridyl", "optionally substituted pyrimidinyl", "optionally substituted phenyl" and "optionally substituted cyclopropyl" in one embodiment are $C_{1-3}$ alkyl optionally substituted with a group selected from the group consisting of OH and $OCH_3$, $-SO_2CH_3$, halogen, OH, $OCH_3$ or $C_{3-6}$ cycloalkyl. The substituents are $C_{1-3}$ alkyl optionally substituted with a group selected from the group consisting of OH and $OCH_3$ in one embodiment, $C_{1-3}$ alkyl optionally substituted with OH in one embodiment, $C_{1-3}$ alkyl optionally substituted with $OCH_3$ in one embodiment, $C_{1-3}$ alkyl in one embodiment, $-SO_2CH_3$, F, Cl, OH, methyl or $OCH_3$ in one embodiment, F, Cl, OH, methyl or $OCH_3$ in one embodiment, F, OH or $OCH_3$ in one embodiment, $-SO_2CH_3$, F, Cl or methyl in one embodiment, $-SO_2CH_3$ in one embodiment, F, Cl or methyl in one embodiment, methyl, ethyl, hydroxymethyl or methoxymethyl in one embodiment, methyl, ethyl or hydroxymethyl in one embodiment, $C_{1-3}$ alkyl, $OCH_3$ or cyclopropyl in one embodiment, methyl, ethyl or cyclopropyl in one embodiment, methyl or ethyl in one embodiment, methyl or hydroxymethyl in one embodiment, ethyl or hydroxymethyl in one embodiment, hydroxymethyl or methoxymethyl in one embodiment, methyl in one embodiment, ethyl in one embodiment, hydroxymethyl in one embodiment or methoxymethyl in one embodiment. When the formula (I) is the formula (Ib), substituents acceptable in "optionally substituted pyrazolyl", "optionally substituted pyridyl" and "optionally substituted pyrimidinyl" are $C_{1-3}$ alkyl in one embodiment.

Substituents acceptable in "a 4-membered to 6-membered optionally substituted saturated heterocyclic group", "optionally substituted pyrrolidinyl", "optionally substituted piperidinyl", "optionally substituted oxetanyl", "optionally substituted tetrahydrofuranyl" and "optionally substituted tetrahydropyranyl" in one embodiment are $C_{1-3}$ alkyl optionally substituted with a group selected from the group consisting of F, OH and $OCH_3$, F, OH, $OCH_3$, oxo or oxetanyl. The substituents are F, OH or $OCH_3$ in one embodiment, $C_{1-3}$ alkyl optionally substituted with a group selected from the group consisting of F, OH and $OCH_3$, F, oxo or oxetanyl in one embodiment, $C_{1-3}$ alkyl optionally substituted with a group selected from the group consisting of F, OH and OCH$_3$ or oxo in one embodiment, C$_{1-3}$ alkyl optionally substituted with a group selected from the group consisting of F, OH and OCH$_3$ in one embodiment, C$_{1-3}$ alkyl optionally substituted with F in one embodiment, C$_{1-3}$ alkyl optionally substituted with OH in one embodiment, C$_{1-3}$ alkyl optionally substituted with OCH$_3$ in one embodiment, OCH$_3$, methyl, ethyl, hydroxymethyl, methoxymethyl, difluoroethyl, hydroxyethyl, methoxyethyl or oxetanyl in one embodiment, methyl, hydroxymethyl, methoxymethyl, difluoroethyl, hydroxyethyl, methoxyethyl or oxetanyl in one embodiment, OCH$_3$, methyl, difluoroethyl, hydroxyethyl, methoxyethyl or oxetanyl in one embodiment, methyl, difluoroethyl, hydroxyethyl, methoxyethyl or oxetanyl in one embodiment, difluoroethyl, hydroxyethyl or methoxyethyl in one embodiment, methyl, ethyl, difluoroethyl or oxetanyl in one embodiment, difluoroethyl or oxetanyl in one embodiment, methyl, ethyl, hydroxymethyl, methoxymethyl or oxo in one embodiment, methyl or oxo in one embodiment, hydroxymethyl or methoxymethyl in one embodiment, 2,2-difluoroethyl in one embodiment, oxetanyl in one embodiment, hydroxymethyl in one embodiment, methoxymethyl in one embodiment, methyl in one embodiment, 2-hydroxyethyl in one embodiment, 2-methoxyethyl in one embodiment, OCH$_3$ in one embodiment or oxo in one embodiment. When the formula (I) is the formula (Ib), substituents acceptable in "optionally substituted pyrrolidinyl" and "optionally substituted piperidinyl" in one embodiment are C$_{1-3}$ alkyl optionally substituted with F or oxetanyl.

Substituents acceptable in "optionally substituted pyrrolidinediyl", "optionally substituted piperidinediyl", "optionally substituted piperazinediyl" and "optionally substituted C$_{1-3}$ alkylene" in one embodiment are F, OH, OCH$_3$ or optionally substituted C$_{1-3}$ alkyl. The substituents are F, OH, OCH$_3$, methyl, ethyl, hydroxymethyl or methoxymethyl in one embodiment or F, OH, OCH$_3$ or methyl in one embodiment.

"C$_{1-3}$ Alkyl optionally substituted with F" in one embodiment is methyl optionally substituted with F or ethyl optionally substituted with F. Examples thereof include methyl, ethyl, monofluoromethyl, difluoromethyl, trifluoromethyl, monofluoroethyl, difluoroethyl and trifluoroethyl. The "C$_{1-3}$ alkyl optionally substituted with F" is methyl, ethyl, monofluoromethyl, difluoromethyl or difluoroethyl in one embodiment, monofluoromethyl or difluoromethyl in one embodiment, monofluoromethyl or difluoroethyl in one embodiment, difluoromethyl or difluoroethyl in one embodiment, monofluoromethyl in one embodiment, difluoromethyl in one embodiment, difluoroethyl in one embodiment or 2,2-difluoroethyl in one embodiment.

"C$_{1-3}$ Alkyl optionally substituted with OH" in one embodiment is methyl optionally substituted with one OH group or ethyl optionally substituted with one or two OH groups. Examples thereof include methyl, ethyl, hydroxymethyl, 1-hydroxyethyl, 2-hydroxyethyl and 1,2-dihydroxyethyl. The "C$_{1-3}$ alkyl optionally substituted with OH" is methyl, ethyl or hydroxymethyl in one embodiment, methyl or hydroxymethyl in one embodiment, hydroxymethyl or hydroxyethyl in one embodiment, hydroxymethyl in one embodiment or hydroxyethyl in one embodiment.

"C$_{1-3}$ Alkyl optionally substituted with OCH$_3$" in one embodiment is methyl optionally substituted with one OCH$_3$ group or ethyl optionally substituted with one or two OCH$_3$ groups. Examples thereof include methyl, ethyl, methoxymethyl, 1-methoxyethyl, 2-methoxyethyl and 1,2-dimethoxyethyl. The "C$_{1-3}$ alkyl optionally substituted with OCH$_3$" is methoxymethyl or methoxyethyl in one embodiment, methoxymethyl in one embodiment or methoxyethyl in one embodiment.

"C$_{1-3}$ Alkyl optionally substituted with N(CH$_3$)$_2$" in one embodiment is methyl optionally substituted with one N(CH$_3$)$_2$ group or ethyl optionally substituted with one N(CH$_3$)$_2$ group. The "C$_{1-3}$ alkyl optionally substituted with N(CH$_3$)$_2$" is methyl, ethyl, dimethylaminomethyl or dimethylaminoethyl in one embodiment, methyl or dimethylaminomethyl in one embodiment, dimethylaminomethyl in one embodiment or dimethylaminoethyl in one embodiment.

"Phenylene optionally substituted with F" in one embodiment is phenylene optionally substituted with one or two F atoms. The "phenylene optionally substituted with F" is phenylene optionally substituted with one F atom in one embodiment, phenylene or fluorophenylene in one embodiment, phenylene in one embodiment, 2-fluoro-1,4-phenylene in one embodiment or 3-fluoro-1,4-phenylene in one embodiment.

"G12D Mutation" represents a mutation in which the amino acid residue corresponding to the codon 12 in a wild type protein is converted from glycine to aspartic acid.

"G12D Mutant KRAS" represents KRAS having the "G12D mutation".

"Pancreatic cancer" is a malignant tumor occurring in the pancreas. Examples thereof include pancreatic ductal carcinoma and pancreatic ductal adenocarcinoma, and the "pancreatic cancer" is pancreatic ductal carcinoma in one embodiment or pancreatic ductal adenocarcinoma in one embodiment. Moreover, the "pancreatic cancer" is metastatic pancreatic cancer in one embodiment, locally advanced pancreatic cancer in one embodiment, recurrent or refractory pancreatic cancer in one embodiment or pancreatic cancer of a patient who is untreated and/or has a medical record in one embodiment.

"G12D Mutant KRAS-positive pancreatic cancer" is pancreatic cancer that is positive for G12D mutant KRAS. Examples thereof include a pancreatic cancer in which the KRAS G12D mutation occurs and a pancreatic cancer which has a high positive rate for G12D mutant KRAS. The "G12D mutant KRAS-positive pancreatic cancer" is G12D mutant KRAS-positive pancreatic ductal carcinoma in one embodiment or G12D mutant KRAS-positive pancreatic ductal adenocarcinoma in one embodiment.

Embodiments of the compound of the formula (I) or a salt thereof of the present invention are shown below.

The formula (I) in one embodiment is a compound defined by the following formula (Ia) or a salt thereof.

[Chem. 11]

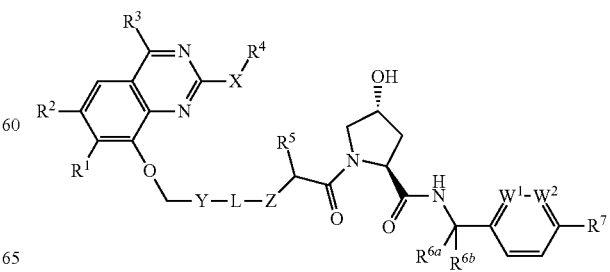

(Ia)

The formula (I) and the formula (Ia) in one embodiment are a compound defined by the following formula (Ib) or a salt thereof.

[Chem. 12]

(Ib)

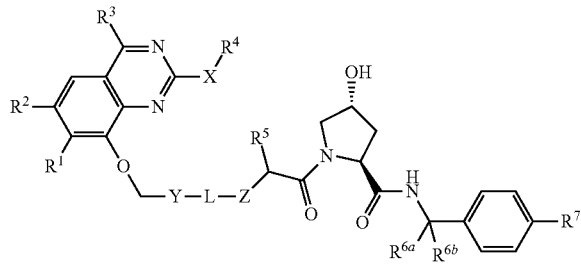

Embodiments of the compounds of the formula (I), the formula (Ia) and the formula (Ib) or a salt thereof of the present invention are shown below.

(1-1) The compound or a salt thereof in which $R^1$ is naphthyl optionally substituted with OH or a group selected from the group consisting of the formula (II) and the formula (III) below,

[Chem. 13]

(II)

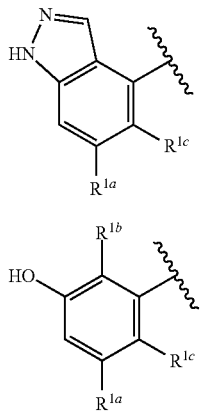

(III)

$R^{1a}$ and $R^{1b}$, which are the same as or different from each other, are H, methyl, F or Cl, and $R^{1c}$ is F, Cl, methyl or ethyl.

(1-2) The compound or a salt thereof in which $R^1$ is the formula (IIa) or the formula (IIIa) below,

[Chem. 14]

(IIa)

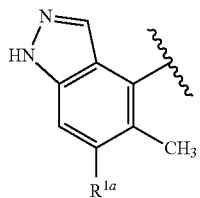

-continued (IIIa)

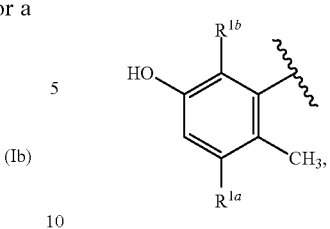

and $R^{1a}$ and $R^{1b}$, which are the same as or different from each other, are H, methyl, F or Cl.

(1-3) The compound or a salt thereof in which $R^1$ is the formula (IIa) or the formula (IIIa), and $R^{1a}$ and $R^{1b}$, which are the same as or different from each other, are H or F.

(1-4) The compound or a salt thereof in which $R^1$ is the formula (IIa) or the formula (IIIa), $R^{1a}$ is F, and Rib is H.

(1-5) The compound or a salt thereof in which $R^1$ is the formula (IIa), and $R^{1a}$ is F.

[Chem. 15]

(IIa)

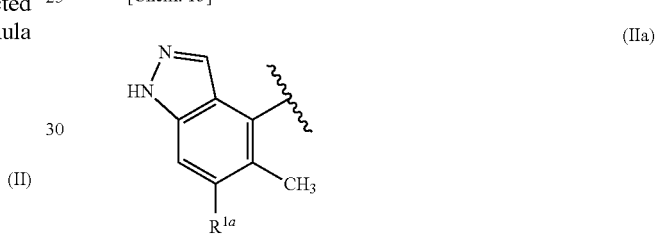

Regarding another embodiment of $R^1$, the compound or a salt thereof in which $R^1$ is the formula (II), $R^{1a}$ is F, and $R^{1c}$ is methyl. In one embodiment, the compound or a salt thereof in which $R^1$ is the formula (IIa), and $R^{1a}$ is H or F. In one embodiment, the compound or a salt thereof in which $R^1$ is the formula (IIa), and $R^{1a}$ is H. In one embodiment, the compound or a salt thereof in which $R^1$ is the formula (IIIa), and $R^{1a}$ and $R^{1b}$, which are the same as or different from each other, are H or F. In one embodiment, the compound or a salt thereof in which $R^1$ is the formula (IIIa), and $R^{1a}$ and $R^{1b}$ are each H. In one embodiment, the compound or a salt thereof in which $R^1$ is the formula (IIIa), $R^{1a}$ is H, and $R^{1b}$ is F. In one embodiment, the compound or a salt thereof in which $R^1$ is the formula (IIIa), and $R^{1a}$ and $R^{1b}$ are each F. In one embodiment, the compound or a salt thereof in which $R^1$ is the formula (IIIa), $R^{1a}$ is F, and $R^{1b}$ is H.

(2-1) The compound or a salt thereof in which $R^2$ is H, halogen, optionally substituted $C_{1-3}$ alkyl, cyclopropyl or vinyl.

(2-2) The compound or a salt thereof in which $R^2$ is halogen, $C_{1-3}$ alkyl, cyclopropyl or vinyl, where the $C_{1-3}$ alkyl may be substituted with a group selected from the group consisting of OH and $OCH_3$.

(2-3) The compound or a salt thereof in which $R^2$ is halogen, $C_{1-3}$ alkyl, cyclopropyl or vinyl.

(2-4) The compound or a salt thereof in which $R^2$ is cyclopropyl.

Regarding another embodiment of $R^2$, the compound or a salt thereof in which $R^2$ is halogen. In one embodiment, the compound or a salt thereof in which $R^2$ is $C_{1-3}$ alkyl. In one embodiment, the compound or a salt thereof in which $R^2$ is vinyl.

(3-1) The compound or a salt thereof in which $R^3$ is a 7-membered or 8-membered saturated or unsaturated bridged heterocyclic group containing one or two nitrogen atoms.

(3-2) The compound or a salt thereof in which $R^3$ is 2,5-diazabicyclo[2.2.2]octanyl, 3,8-diazabicyclo[3.2.1]octanyl, 3,6-diazabicyclo[3.1.1]heptanyl or 2,5-diazabicyclo[2.2.1]heptanyl.

(3-3) The compound or a salt thereof in which $R^3$ is the following formula (IV).

[Chem. 16]

(IV)

(4-1) The compound or a salt thereof in which $R^4$ is optionally substituted $C_{1-6}$ alkyl, a 4-membered to 6-membered optionally substituted saturated heterocyclic group containing one or two hetero atoms selected from oxygen, sulfur and nitrogen, 5-membered optionally substituted heteroaryl containing one to four hetero atoms selected from oxygen, sulfur and nitrogen or 6-membered heteroaryl optionally substituted containing one to three nitrogen atoms.

(4-2) The compound or a salt thereof in which $R^4$ is optionally substituted $C_{1-6}$ alkyl, optionally substituted oxetanyl, optionally substituted tetrahydrofuranyl, optionally substituted tetrahydropyranyl, optionally substituted pyrazolyl, optionally substituted pyridyl, optionally substituted pyrimidinyl, optionally substituted pyrrolidinyl or optionally substituted piperidinyl.

(4-3) The compound or a salt thereof in which $R^4$ is $C_{1-6}$ alkyl optionally substituted with a group selected from the group consisting of OH, $OCH_3$, $N(CH_3)_2$, (hydroxymethyl)cyclopropyl, (methoxymethyl)cyclopropyl, tetrahydrofuranyl, (hydroxymethyl)tetrahydropyranyl, (methoxymethyl)tetrahydropyranyl, morpholinyl, pyrrolidinyl, methylpyrrolidinyl and azabicyclo[3.3.0]octanyl, oxetanyl, tetrahydrofuranyl, tetrahydropyranyl, optionally substituted pyrazolyl, optionally substituted pyridyl, optionally substituted pyrimidinyl, optionally substituted pyrrolidinyl or optionally substituted piperidinyl.

(4-4) The compound or a salt thereof in which $R^4$ is $C_{1-3}$ alkyl, oxetanyl, tetrahydrofuranyl, tetrahydropyranyl, optionally substituted pyrazolyl, optionally substituted pyridyl, optionally substituted pyrimidinyl, optionally substituted pyrrolidinyl or optionally substituted piperidinyl.

(4-5) The compound or a salt thereof in which $R^4$ is $C_{1-6}$ alkyl optionally substituted with a group selected from the group consisting of OH, $OCH_3$, $N(CH_3)_2$, (hydroxymethyl)cyclopropyl, (methoxymethyl)cyclopropyl, tetrahydrofuranyl, (hydroxymethyl)tetrahydropyranyl, (methoxymethyl)tetrahydropyranyl, morpholinyl, pyrrolidinyl, methylpyrrolidinyl and azabicyclo[3.3.0]octanyl, oxetanyl, tetrahydrofuranyl, tetrahydropyranyl, pyridyl optionally substituted with $C_{1-3}$ alkyl, pyrrolidinyl optionally substituted with $C_{1-3}$ alkyl optionally substituted with a group selected from the group consisting of F, OH and $OCH_3$ or piperidinyl optionally substituted with a group selected from the group consisting of $C_{1-3}$ alkyl optionally substituted with F and oxetanyl.

(4-6) The compound or a salt thereof in which $R^4$ is $C_{1-6}$ alkyl optionally substituted with a group selected from the group consisting of OH, $OCH_3$, $N(CH_3)_2$, (hydroxymethyl)cyclopropyl, (methoxymethyl)cyclopropyl, tetrahydrofuranyl, (hydroxymethyl)tetrahydropyranyl, (methoxymethyl)tetrahydropyranyl, morpholinyl, pyrrolidinyl, methylpyrrolidinyl and azabicyclo[3.3.0]octanyl, oxetanyl, tetrahydrofuranyl, tetrahydropyranyl, pyridyl optionally substituted with $C_{1-3}$ alkyl, pyrrolidinyl optionally substituted with a group selected from the group consisting of difluoroethyl, hydroxyethyl and methoxyethyl or piperidinyl optionally substituted with a group selected from the group consisting of difluoroethyl and oxetanyl.

(4-7) The compound or a salt thereof in which $R^4$ is $C_{1-6}$ alkyl optionally substituted with $OCH_3$, tetrahydropyranyl or piperidinyl optionally substituted with difluoroethyl.

Regarding another embodiment of $R^4$, the compound or a salt thereof in which $R^4$ is optionally substituted $C_{1-6}$ alkyl, oxetanyl, tetrahydrofuranyl, tetrahydropyranyl, optionally substituted pyrazolyl, optionally substituted pyridyl, optionally substituted pyrimidinyl, optionally substituted pyrrolidinyl or optionally substituted piperidinyl. In one embodiment, the compound or a salt thereof in which $R^4$ is tetrahydrofuranyl, tetrahydropyranyl, optionally substituted pyrrolidinyl or optionally substituted piperidinyl. In one embodiment, the compound or a salt thereof in which $R^4$ is tetrahydrofuranyl, tetrahydropyranyl or optionally substituted piperidinyl. In one embodiment, the compound or a salt thereof in which $R^4$ is tetrahydropyranyl or optionally substituted piperidinyl. In one embodiment, the compound or a salt thereof in which $R^4$ is optionally substituted $C_{1-6}$ alkyl. In one embodiment, the compound or a salt thereof in which $R^4$ is $C_{1-6}$ alkyl optionally substituted with $OCH_3$. In one embodiment, the compound or a salt thereof in which $R^4$ is $C_{1-3}$ alkyl. In one embodiment, the compound or a salt thereof in which $R^4$ is oxetanyl. In one embodiment, the compound or a salt thereof in which $R^4$ is tetrahydrofuranyl. In one embodiment, the compound or a salt thereof in which $R^4$ is tetrahydropyranyl. In one embodiment, the compound or a salt thereof in which $R^4$ is optionally substituted pyrazolyl. In one embodiment, the compound or a salt thereof in which $R^4$ is optionally substituted pyridyl. In one embodiment, the compound or a salt thereof in which $R^4$ is optionally substituted pyrimidinyl. In one embodiment, the compound or a salt thereof in which $R^4$ is optionally substituted pyrrolidinyl. In one embodiment, the compound or a salt thereof in which $R^4$ is optionally substituted piperidinyl. In one embodiment, the compound or a salt thereof in which $R^4$ is piperidinyl optionally substituted with $C_{1-3}$ alkyl optionally substituted with F. In one embodiment, the compound or a salt thereof in which $R^4$ is piperidinyl optionally substituted with difluoroethyl.

(5-1) The compound or a salt thereof in which $R^5$ is optionally substituted $C_{1-6}$ alkyl, optionally substituted $C_{3-6}$ cycloalkyl or a 4-membered to 6-membered optionally substituted saturated heterocyclic group containing one hetero atom selected from oxygen, sulfur and nitrogen.

(5-2) The compound or a salt thereof in which $R^5$ is methyl, ethyl, isopropyl, tert-butyl or $C_{3-6}$ cycloalkyl.

(5-3) The compound or a salt thereof in which $R^5$ is ethyl, isopropyl, tert-butyl or $C_{3-6}$ cycloalkyl.

(5-4) The compound or a salt thereof in which $R^5$ is isopropyl or $C_{3-6}$ cycloalkyl.

(5-5) The compound or a salt thereof in which $R^5$ is isopropyl.

Regarding another embodiment of $R^5$, the compound or a salt thereof in which $R^5$ is isopropyl, tert-butyl or $C_{3-6}$ cycloalkyl. In one embodiment, the compound or a salt thereof in which $R^5$ is isopropyl or tert-butyl. In one embodiment, the compound or a salt thereof in which $R^5$ is isopropyl or cyclopropyl. In one embodiment, the compound or a salt thereof in which $R^5$ is tert-butyl. In one embodiment, the compound or a salt thereof in which $R^5$ is $C_{3-6}$ cycloalkyl.

(6-1) The compound or a salt thereof in which $R^{6a}$ and R b, which are the same as or different from each other, are H or optionally substituted $C_{1-6}$ alkyl, or $R^{6a}$ and $R^{6b}$ form optionally substituted $C_{3-6}$ cycloalkyl or an 4-membered to 6-membered optionally substituted saturated heterocyclic ring containing one hetero atom selected from oxygen, sulfur and nitrogen together with the carbon to which they are attached.

(6-2) The compound or a salt thereof in which $R^{6a}$ and $R^{6b}$, which are the same as or different from each other, are H or $C_{1-3}$ alkyl, where the $C_{1-3}$ alkyl may be substituted with a group selected from the group consisting of F, OH, $OCH_3$ and $N(CH_3)_2$, or $R^{6a}$ and $R^{6b}$ form $C_{3-6}$ cycloalkyl together with the carbon to which they are attached.

(6-3) The compound or a salt thereof in which $R^{6a}$ and $R^{6b}$, which are the same as or different from each other, are H or $C_{1-3}$ alkyl, where the $C_{1-3}$ alkyl may be substituted with a group selected from the group consisting of F, OH and $N(CH_3)_2$, or $R^{6a}$ and $R^{6b}$ form cyclopropyl together with the carbon to which they are attached.

(6-4) The compound or a salt thereof in which $R^{6a}$ is H, and $R^{6b}$ is $C_{1-3}$ alkyl optionally substituted with OH.

Regarding another embodiment of $R^{6a}$ and $R^{6b}$, the compound or a salt thereof in which $R^{6a}$ and $R^{6b}$, which are the same as or different from each other, are H or $C_{1-3}$ alkyl optionally substituted with a group selected from the group consisting of F, OH and $N(CH_3)_2$. In one embodiment, the compound or a salt thereof in which $R^{6a}$ and $R^{6b}$, which are the same as or different from each other, are $C_{1-3}$ alkyl optionally substituted with a group selected from the group consisting of F, OH and $N(CH_3)_2$. In one embodiment, the compound or a salt thereof in which $R^{6a}$ and $R^{6b}$ are each H. In one embodiment, the compound or a salt thereof in which $R^{6a}$ is H, and $R^{6b}$ is $C_{1-3}$ alkyl optionally substituted with a group selected from the group consisting of F, OH and $N(CH_3)_2$. In one embodiment, the compound or a salt thereof in which $R^{6a}$ is H, and $R^{6b}$ is $C_{1-3}$ alkyl optionally substituted with F. In one embodiment, the compound or a salt thereof in which $R^{6a}$ is H, and $R^{6b}$ is $C_{1-3}$ alkyl optionally substituted with $N(CH_3)_2$. In one embodiment, the compound or a salt thereof in which $R^{6a}$ and $R^{6b}$ form cyclopropyl together with the carbon to which they are attached.

(7-1) The compound or a salt thereof in which $R^7$ is H, halogen, $C_{1-3}$ alkyl, —$SO_2CH_3$, $C_{3-6}$ cycloalkyl, a 4-membered to 6-membered optionally substituted saturated heterocyclic group containing one or two hetero atoms selected from oxygen, sulfur and nitrogen, 5-membered optionally substituted heteroaryl containing one to four hetero atoms selected from oxygen, sulfur and nitrogen or 6-membered heteroaryl containing one to three nitrogen atoms.

(7-2) The compound or a salt thereof in which $R^7$ is H, halogen, $C_{1-3}$ alkyl, —$SO_2CH_3$, $C_{3-6}$ cycloalkyl or a group selected from the group consisting of the formula (VI), the formula (VII), the formula (VIII), the formula (IX), the formula (XX), the formula (XXI), the formula (XXII), the formula (XXIII) and the formula (XXIV) below,

[Chem. 17]

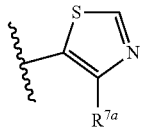
(VI)

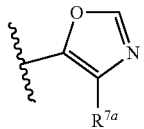
(VII)

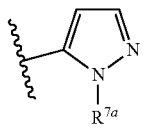
(VIII)

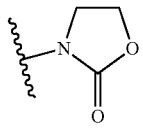
(IX)

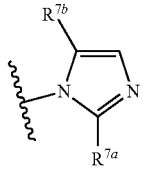
(XX)

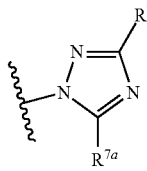
(XXI)

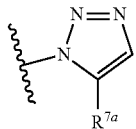
(XXII)

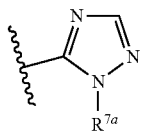
(XXIII)

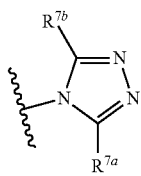
(XXIV)

$R^{7a}$ and $R^{7b}$, which are the same as or different from each other, are H or $C_{1-3}$ alkyl optionally substituted with OH.

(7-3) The compound or a salt thereof in which $R^7$ is H, halogen or a group selected from the group consisting of the formula (VI), the formula (VII), the formula (VIII) and the formula (IX) below,

[Chem. 18]

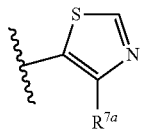 (VI)

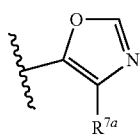 (VII)

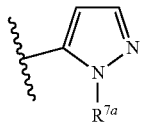 (VIII)

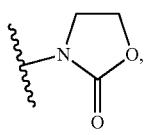 (IX)

and $R^{7a}$ is H or $C_{1-3}$ alkyl optionally substituted with OH.

(7-4) The compound or a salt thereof in which $R^7$ is H, halogen or a group selected from the group consisting of the formula (VI), the formula (VII), the formula (VIII) and the formula (IX), and $R^{7a}$ is $C_{1-3}$ alkyl optionally substituted with OH.

(7-5) The compound or a salt thereof in which $R^7$ is a group selected from the group consisting of the formula (VI), the formula (VII), the formula (VIII) and the formula (IX), and $R^{7a}$ is $C_{1-3}$ alkyl optionally substituted with OH.

(7-6) The compound or a salt thereof in which $R^7$ is H.

Regarding another embodiment of $R^7$, the compound or a salt thereof in which $R^7$ is H, halogen, $C_{1-3}$ alkyl or —$SO_2CH_3$. In one embodiment, the compound or a salt thereof in which $R^7$ is halogen. In one embodiment, the compound or a salt thereof in which $R^7$ is —$SO_2CH_3$. In one embodiment, the compound or a salt thereof in which $R^7$ is a group selected from the group consisting of the formula (VI), the formula (VII), the formula (VIII) and the formula (IX). In one embodiment, the compound or a salt thereof in which $R^7$ is a group selected from the group consisting of the formula (VI), the formula (VIII) and the formula (IX). In one embodiment, the compound or a salt thereof in which $R^7$ is the formula (VI) or (VIII). In one embodiment, the compound or a salt thereof in which $R^7$ is the formula (VI) or (IX). In one embodiment, the compound or a salt thereof in which $R^7$ is the formula (VI). In one embodiment, the compound or a salt thereof in which $R^7$ is the formula (VII). In one embodiment, the compound or a salt thereof in which $R^7$ is the formula (VIII). In one embodiment, the compound or a salt thereof in which $R^7$ is the formula (IX).

(7-8) The compound or a salt thereof in which $R^{7a}$ is H or $C_{1-3}$ alkyl optionally substituted with OH. In one embodiment, the compound or a salt thereof in which $R^{7a}$ is H. In one embodiment, the compound or a salt thereof in which $R^{7a}$ is $C_{1-3}$ alkyl optionally substituted with OH. In one embodiment, the compound or a salt thereof in which $R^{7a}$ is $C_{1-3}$ alkyl.

(8-1) The compound of the formula (I) or a salt thereof in which W is optionally substituted phenyl or 6-membered optionally substituted heteroaryl containing one to three nitrogen atoms.

(8-2) The compound of the formula (Ia) or a salt thereof in which $W^1$ is CH, and $W^2$ is C—$SO_2CH_3$.

(8-3) The compound of the formula (Ia) or a salt thereof in which $W^1$ and $W^2$, which are the same as or different from each other, are CH, CF, CCl, $CCH_3$ or N.

(8-4) The compound of the formula (Ia) or a salt thereof in which $W^1$ and $W^2$, which are the same as or different from each other, are CH, CF or N.

(8-5) The compound of the formula (Ia) or a salt thereof in which $W^1$ is CH, and $W^2$ is CH.

(9) The compound of the formula (Ia) or a salt thereof in which $W^1$, $W^2$ and $R^7$ are as follows, i. $W^1$ is CH, $W^2$ is C—$SO_2CH_3$, and $R^7$ is H, or ii. $W^1$ and $W^2$, which are the same as or different from each other, are CH, CF, CCl, $CCH_3$ or N, and $R^7$ is H, halogen, $C_{1-3}$ alkyl, —$SO_2CH_3$, $C_{3-6}$ cycloalkyl or a group selected from the group consisting of the formula (VI), the formula (VII), the formula (VIII), the formula (IX), the formula (XX), the formula (XXI), the formula (XXII), the formula (XXIII) and the formula (XXIV) below,

[Chem. 19]

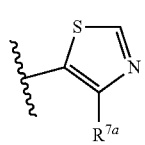 (VI)

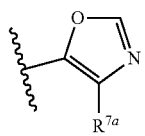 (VII)

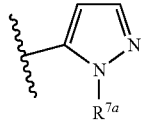 (VIII)

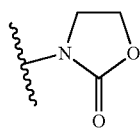 (IX)

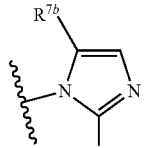 (XX)

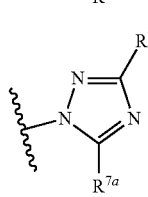 (XXI)

-continued (XXII)

(XXIII)

(XXIV)

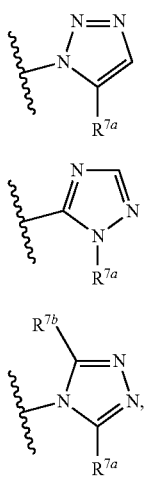

and

R$^{7a}$ and R$^{7b}$, which are the same as or different from each other, are H or C$_{1-3}$ alkyl optionally substituted with OH.

(10-1) The compound or a salt thereof in which X is a bond, CH$_2$, O, S or NR$^{4x}$, and R$^{4x}$ is H or C$_{1-3}$ alkyl.

(10-2) The compound or a salt thereof in which X is O, S or NR$^{4x}$, and R$^{4x}$ is H or C$_{1-3}$ alkyl.

(10-3) The compound or a salt thereof in which X is O or NH.

(10-4) The compound or a salt thereof in which X is O.

(11-1) The compound or a salt thereof in which Y is phenylene or pyridinediyl, where the phenylene may be substituted with F.

(11-2) The compound or a salt thereof in which Y is phenylene or pyridinediyl.

(11-3) The compound or a salt thereof in which Y is phenylene optionally substituted with F.

Regarding another embodiment of Y, the compound or a salt thereof in which Y is 1,4-phenylene or 2,5-pyridinediyl. In one embodiment, the compound or a salt thereof in which Y is phenylene. In one embodiment, the compound or a salt thereof in which Y is 1,4-phenylene. In one embodiment, the compound or a salt thereof in which Y is pyridinediyl. In one embodiment, the compound or a salt thereof in which Y is 2,5-pyridinediyl.

(12-1) The compound or a salt thereof in which L is -(L$^1$-L$^2$-L$^3$-L$^4$)-, L$^1$, L$^2$, L$^3$ and L$^4$, which are the same as or different from each other, are a group selected from the group consisting of a bond, O, NR$^{L1}$, optionally substituted pyrrolidinediyl, optionally substituted piperidinediyl, optionally substituted piperazinediyl, optionally substituted C$_{1-3}$ alkylene and C=O, and R$_{L1}$ is H or C$_{1-3}$ alkyl.

(12-2) The compound or a salt thereof in which L is a bond, C$_{1-3}$ alkylene, C=O or a group selected from the group consisting of the formula (XIV), the formula (XV), the formula (XVI), the formula (XVII), the formula (XVIII) and the formula (XIX) below,

[Chem. 20]

(XIV)

(XV)

(XVI)

(XVII)

(XVIII)

(XIX)

R$^{L1}$ is H or C$_{1-3}$ alkyl,
R$^{L2}$ and R$^{L3}$, which are the same as or different from each other, are H, F, OH, OCH$_3$ or optionally substituted C$_{1-3}$ alkyl,
R$^L$ is CH or N, and
n is an integer of one or two.

(12-3) The compound or a salt thereof in which L is a bond, C$_{1-3}$ alkylene, C=O or a group selected from the group consisting of the formula (XIV)-1, the formula (XV)-1, the formula (XVI)-1, the formula (XVII)-1, the formula (XVIII)-1 and the formula (XIX)-1 below,

[Chem. 21]

(XIV)-1

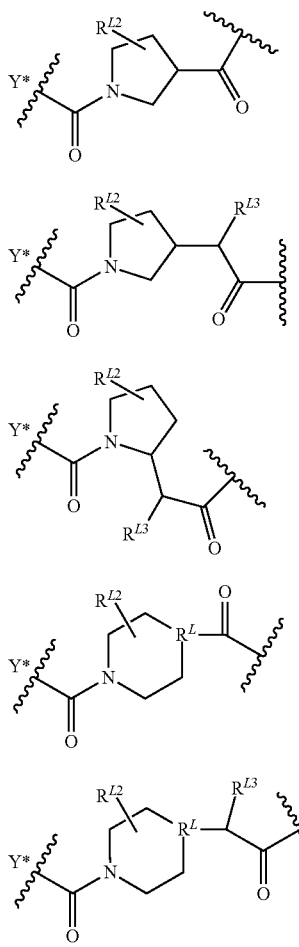

(XV)-1

(XVI)-1

(XVII)-1

(XVIII)-1

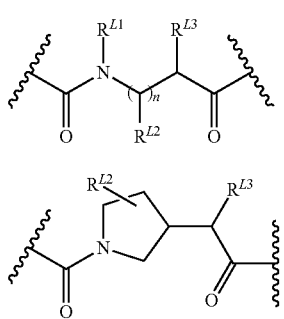

(XIX)-1

(in the formulae, Y* represents linking to Y)
$R^{L1}$ is H or $C_{1-3}$ alkyl,
$R^{L2}$ and $R^{L3}$, which are the same as or different from each other, are H, F, OH, $OCH_3$ or optionally substituted $C_{1-3}$ alkyl,
$R^L$ is CH or N, and
n is an integer of one or two.

(12-4) The compound or a salt thereof in which L is a bond, $C_{1-3}$ alkylene, C=O or a group selected from the group consisting of the formula (XIV) and the formula (XVI) below,

[Chem. 22]

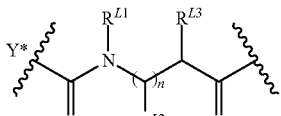
(XIV)

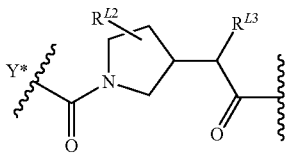
(XVI)

$R^{L1}$ is $C_{1-3}$ alkyl,
$R^{L2}$ and $R^{L3}$ are H, and
n is 1.

(12-5) The compound or a salt thereof in which L is a bond, $C_{1-3}$ alkylene, C=O or a group selected from the group consisting of the formula (XIV)-1 and the formula (XVI)-1 below,

[Chem. 23]

(XIV)-1

(XVI)-1

(in the formulae, Y* represents linking to Y)
$R^{L1}$ is $C_{1-3}$ alkyl,
$R^{L2}$ and $R^{L3}$ are H, and
n is 1.

(12-6) The compound or a salt thereof in which L is a bond, C=O or a group selected from the group consisting of the formula (XIV) and the formula (XVI), $R^{L1}$ is $C_{1-3}$ alkyl, $R^{L2}$ and $R^{L3}$ are H, and n is 1.

(12-7) The compound or a salt thereof in which L is a bond, C=O or a group selected from the group consisting of the formula (XIV)-1 and the formula (XVI)-1, $R^{L1}$ is $C_{1-3}$ alkyl, $R^{L2}$ and $R^{L3}$ are H, and n is 1.

(12-8) The compound or a salt thereof in which L is C=O or a group selected from the group consisting of the formula (XIV) and the formula (XVI), $R^{L1}$ is $C_{1-3}$ alkyl, $R^{L2}$ and $R^{L3}$ are H, and n is 1.

(12-9) The compound or a salt thereof in which L is C=O or a group selected from the group consisting of the formula (XIV)-1 and the formula (XVI)-1, $R^{L1}$ is $C_{1-3}$ alkyl, $R^{L2}$ and $R^{L3}$ and H, and n is 1.

(12-10) The compound or a salt thereof in which L is a bond, $C_{1-3}$ alkylene or C=O.

(12-11) The compound or a salt thereof in which L is a bond.

Regarding another embodiment of L, the compound or a salt thereof in which L is a bond or $C_{1-3}$ alkylene. In one embodiment, the compound or a salt thereof in which L is a bond or C=O. In one embodiment, the compound or a salt thereof in which L is $C_{1-3}$ alkylene. In one embodiment, the compound or a salt thereof in which L is C=O.

(13-1) The compound or a salt thereof in which Z is NH or 5-membered heteroarenediyl containing one to four hetero atoms selected from oxygen, sulfur and nitrogen.

(13-2) The compound or a salt thereof in which Z is NH or a group selected from the group consisting of the formula (V), the formula (X), the formula (XI) and the formula (XII) below.

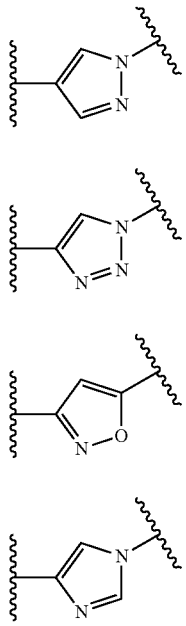

(13-3) The compound or a salt thereof in which Z is NH or a group selected from the group consisting of the formula (V)-1, the formula (X)-1, the formula (XI)-1 and the formula (XII)-1 below.

[Chem. 25]

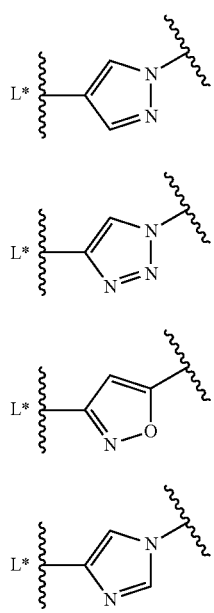

(In the formulae, L* represents linking to L.)

(13-4) The compound or a salt thereof in which Z is NH or a group selected from the group consisting of the formula (X), the formula (XI) and the formula (XII) below.

[Chem. 26]

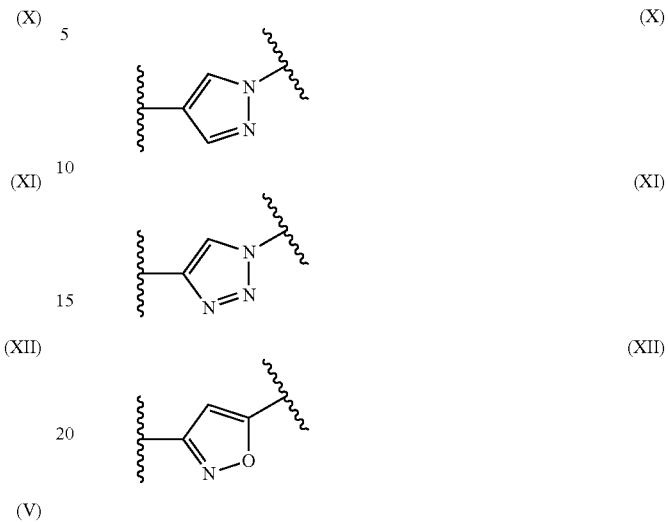

(13-5) The compound or a salt thereof in which Z is NH or a group selected from the group consisting of the formula (X)-1, the formula (XI)-1 and the formula (XII)-1 below.

[Chem. 27]

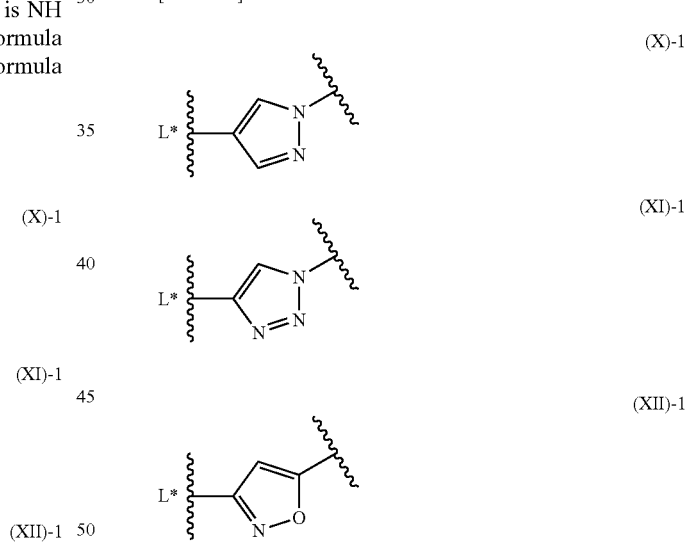

(In the formulae, L* represents linking to L.)

(13-6) The compound or a salt thereof in which Z is NH or a group selected from the group consisting of the formula (X) and the formula (XI) below.

[Chem. 28]

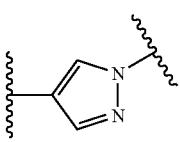

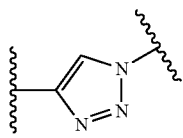

(13-7) The compound or a salt thereof in which Z is NH or a group selected from the group consisting of the formula (X)-1 and the formula (XI)-1 below.

[Chem. 29]

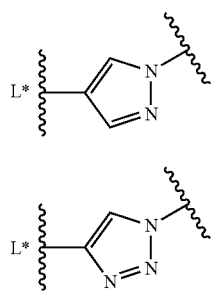

(In the formulae, L* represents linking to L.)

(13-8) The compound or a salt thereof in which Z is a group selected from the group consisting of the formula (X) and the formula (XI).

(13-9) The compound or a salt thereof in which Z is a group selected from the group consisting of the formula (X)-1 and the formula (XI)-1.

(13-10) The compound or a salt thereof in which Z is NH.

(13-11) The compound or a salt thereof in which Z is the formula (XI).

[Chem. 30]

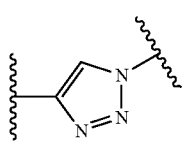

(13-12) The compound or a salt thereof in which Z is the formula (XI)-1.

[Chem. 31]

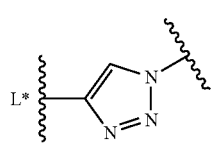

(In the formula, L* represents linking to L.)

Regarding another embodiment of Z, the compound or a salt thereof in which Z is a group selected from the group consisting of the formula (X), the formula (XI) and the formula (XII). In one embodiment, the compound or a salt thereof in which Z is a group selected from the group consisting of the formula (X)-1, the formula (XI)-1 and the formula (XII)-1. In one embodiment, the compound or a salt thereof in which Z is the formula (XI) or the formula (XII). In one embodiment, the compound or a salt thereof in which Z is the formula (XI)-1 or the formula (XII)-1. In one embodiment, the compound or a salt thereof in which Z is the formula (X). In one embodiment, the compound or a salt thereof in which Z is the formula (X)-1. In one embodiment, the compound or a salt thereof in which Z is the formula (XII). In one embodiment, the compound or a salt thereof in which Z is the formula (XII)-1.

(14-1) The compound or a salt thereof in which Y-L-Z is the following formula (XIII).

[Chem. 32]

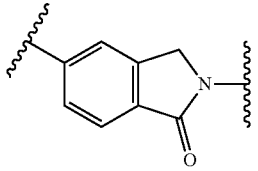

(14-2) The compound or a salt thereof in which Y-L-Z is the following formula (XIII)-1.

[Chem. 33]

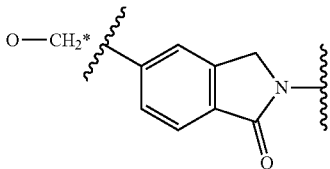

(In the formula, O—CH$_2$* represents linking to the carbon in O—CH$_2$.)

(15) The compound or a salt thereof which is a combination of any compatible two or more of the embodiments described in (1-1) to (14-2) above.

Specific examples of the combination described in (15) above include the following embodiments.

(16-1) The compound of the formula (I) or a salt thereof which is the combination of the embodiments of (1-1), (2-1), (3-1), (4-1), (5-1), (6-1), (7-1), (8-1), (10-1), (11-1), (12-1) and (13-1) above or the combination of the embodiments of (1-1), (2-1), (3-1), (4-1), (5-1), (6-1), (7-1), (8-1), (10-1) and (14-1).

(16-2) The compound of the formula (I) or a salt thereof which is the combination of the embodiments of (1-1), (2-1), (3-2), (4-1), (5-1), (6-1), (7-1), (8-1), (10-1), (11-1), (12-2) and (13-2) above or the combination of the embodiments of (1-1), (2-1), (3-2), (4-1), (5-1), (6-1), (7-1), (8-1), (10-1) and (14-1).

(16-3) The compound or a salt thereof in which the formula (I) is the formula (Ia) and which is the combination of the embodiments of (1-2), (2-1), (3-3), (4-2), (5-2), (6-2), (9), (10-2), (11-1), (12-2) and (13-2) above or the combination of the embodiments of (1-2), (2-1), (3-3), (4-2), (5-2), (6-2), (9), (10-2) and (14-1).

(16-3-i) The compound or a salt thereof in which the formula (I) is the formula (Ia) and which is the combination of the embodiments of (1-2), (2-1), (3-3), (4-2), (5-2), (6-2), (7-5), (8-2), (10-2), (11-1), (12-2) and (13-2) above or the combination of the embodiments of (1-2), (2-1), (3-3), (4-2), (5-2), (6-2), (7-5), (8-2), (10-2) and (14-1).

(16-3-ii) The compound or a salt thereof in which the formula (I) is the formula (Ia) and which is the combination of the embodiments of (1-2), (2-1), (3-3), (4-2), (5-2), (6-2), (7-2), (8-3), (10-2), (11-1), (12-2) and (13-2) above or the combination of the embodiments of (1-2), (2-1), (3-3), (4-2), (5-2), (6-2), (7-2), (8-3), (10-2) and (14-1).

(16-4) The compound or a salt thereof in which the formula (I) is the formula (Ia) and which is the combination of the embodiments of (1-2), (2-2), (3-3), (4-3), (5-2), (6-2), (9), (10-3), (11-1), (12-4) and (13-2) above or the combination of the embodiments of (1-2), (2-2), (3-3), (4-3), (5-2), (6-2), (9), (10-3) and (14-1).

(16-4-i) The compound or a salt thereof in which the formula (I) is the formula (Ia) and which is the combination of the embodiments of (1-2), (2-2), (3-3), (4-3), (5-2), (6-2), (7-5), (8-2), (10-3), (11-1), (12-4) and (13-2) above or the combination of the embodiments of (1-2), (2-2), (3-3), (4-3), (5-2), (6-2), (7-5), (8-2), (10-3) and (14-1).

(16-4-ii) The compound or a salt thereof in which the formula (I) is the formula (Ia) and which is the combination of the embodiments of (1-2), (2-2), (3-3), (4-3), (5-2), (6-2), (7-2), (8-3), (10-3), (11-1), (12-4) and (13-2) above or the combination of the embodiments of (1-2), (2-2), (3-3), (4-3), (5-2), (6-2), (7-2), (8-3), (10-3) and (14-1).

(16-5) The compound or a salt thereof in which the formula (I) is the formula (Ia) and which is the combination of the embodiments of (1-2), (2-2), (3-3), (4-3), (5-2), (6-2), (7-2), (8-3), (10-3), (11-1), (12-4) and (13-2) above.

(16-6) The compound or a salt thereof in which the formula (I) is the formula (Ib) and which is the combination of the embodiments of (1-3), (2-3), (3-3), (4-4), (5-3), (6-3), (7-3), (10-4), (11-2), (12-10) and (13-4) above or the combination of the embodiments of (1-3), (2-3), (3-3), (4-4), (5-3), (6-3), (7-3), (10-4) and (14-1).

(16-7) The compound or a salt thereof in which the formula (I) is the formula (Ia) and which is the combination of the embodiments of (1-3), (2-4), (3-3), (4-6), (5-4), (6-3), (7-4), (8-4), (10-3), (11-1), (12-6) and (13-6) above.

(16-8) The compound or a salt thereof in which the formula (I) is the formula (Ia) and which is the combination of the embodiments of (1-3), (2-4), (3-3), (4-6), (5-4), (6-3), (7-4), (8-4), (10-3), (11-1), (12-7) and (13-7) above.

(16-9) The compound or a salt thereof in which the formula (I) is the formula (Ia) and which is the combination of the embodiments of (1-3), (2-4), (3-3), (4-6), (5-4), (6-3), (7-4), (8-4), (10-3), (11-1), (12-8) and (13-10) above or the combination of the embodiments of (1-3), (2-4), (3-3), (4-6), (5-4), (6-3), (7-4), (8-4), (10-3), (11-1), (12-11) and (13-8).

(16-10) The compound or a salt thereof in which the formula (I) is the formula (Ia), $R^1$ is the formula (IIa), $R^{1a}$ is F, $R^2$ is cyclopropyl, $R^3$ is the formula (IV), $R^4$ is $C_{1-6}$ alkyl optionally substituted with $OCH_3$, tetrahydropyranyl or piperidinyl optionally substituted with $C_{1-3}$ alkyl optionally substituted with F, $R^5$ is isopropyl, $R^{6a}$ is H, $R^{6b}$ is $C_{1-3}$ alkyl optionally substituted with OH, $R^7$ is a group selected from the group consisting of the formula (VI), the formula (VII), the formula (VIII) and the formula (IX), $R^{7a}$ is $C_{1-3}$ alkyl optionally substituted with OH, $W^1$ is CH, $W^2$ is CH, X is O, Y is phenylene optionally substituted with F, L is a bond, and Z is the formula (XI).

(16-11) The compound or a salt thereof in which the formula (I) is the formula (Ia), $R^1$ is the formula (IIa), $R^{1a}$ is F, $R^2$ is cyclopropyl, $R^3$ is the formula (IV), $R^4$ is $C_{1-6}$ alkyl optionally substituted with $OCH_3$, tetrahydropyranyl or piperidinyl optionally substituted with difluoroethyl, $R^5$ is isopropyl, $R^{6a}$ is H, $R^{6b}$ is $C_{1-3}$ alkyl optionally substituted with OH, $R^7$ is a group selected from the group consisting of the formula (VI), the formula (VII), the formula (VIII) and the formula (IX), $R^{7a}$ is $C_{1-3}$ alkyl optionally substituted with OH, $W^1$ is CH, $W^2$ is CH, X is O, Y is phenylene optionally substituted with F, L is a bond, and Z is the formula (XI).

(16-12) The compound or a salt thereof in which the formula (I) is the formula (Ia), $R^1$ is the formula (IIa), $R^{1a}$ is F, $R^2$ is cyclopropyl, $R^3$ is the formula (IV), $R^4$ is $C_{1-6}$ alkyl optionally substituted with $OCH_3$, tetrahydropyranyl or piperidinyl optionally substituted with difluoroethyl, $R^5$ is isopropyl, $R^{6a}$ is H, $R^{6b}$ is $C_{1-3}$ alkyl optionally substituted with OH, $R^7$ is a group selected from the group consisting of the formula (VI), the formula (VII), the formula (VIII) and the formula (IX), $R^{7a}$ is $C_{1-3}$ alkyl optionally substituted with OH, $W^1$ is CH, $W^2$ is CH, X is O, Y is phenylene optionally substituted with F, L is a bond, and Z is the formula (XI)-1.

(16-13) The compound or a salt thereof in which the formula (I) is the formula (Ib), $R^1$ is the formula (IIa), $R^{1a}$ is F, $R^2$ is cyclopropyl, $R^3$ is the formula (IV), $R^4$ is tetrahydropyranyl or optionally substituted piperidinyl, $R^5$ is isopropyl, $R^{6a}$ is H, $R^{6b}$ is $C_{1-3}$ alkyl optionally substituted with OH, $R^7$ is the formula (VI), (VIII) or (IX), $R^{7a}$ is $C_{1-3}$ alkyl optionally substituted with OH, X is O, Y is phenylene, L is a bond, and Z is the formula (XI).

(16-14) The compound or a salt thereof in which the formula (I) is the formula (Ib), $R^1$ is the formula (IIa), $R^{1a}$ is F, $R^2$ is cyclopropyl, $R^3$ is the formula (IV), $R^4$ is tetrahydropyranyl, $R^5$ is isopropyl, $R^{6a}$ is H, $R^{6b}$ is $C_{1-3}$ alkyl optionally substituted with OH, $R^7$ is the formula (VI) or (VIII), $R^{7a}$ is $C_{1-3}$ alkyl, X is O, Y is 1,4-phenylene, L is a bond, and Z is the formula (XI)-1.

Examples of specific compounds included in the present invention include the following compounds in one embodiment.

A compound or a salt thereof selected from the group consisting of (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-2-{[1-(2,2-difluoroethyl)piperidin-4-yl]oxy}-7-(6-fluoro-5-methyl-1H-indazol-4-yl)quinazolin-8-yl}oxy)methyl]phenyl}-1H-1,2,3-triazol-1- yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide, (4R)-1-{(2S)-2-[4-(4-{[(6-cyclopropyl-4-[(1S,4S)-2,5-diazabicyclo[2.2.1]heptan-2-yl]-7-(6-fluoro-5-methyl-1H-indazol-4-yl)-2-{[(2R,3R)-3-methoxybutan-2-yl]oxy}quinazolin-8-yl)oxy]methyl}phenyl)-1H-1,2,3-triazol-1-yl]-3-methylbutanoyl}-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide and (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl)phenyl]ethyl}-L-prolinamide.

Examples of specific compounds included in the present invention include the following compounds in one embodiment.

A compound or a salt thereof selected from the group consisting of (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-2-{[1-(2,2-difluoroethyl)piperidin-4-yl]oxy}-7-(6-fluoro-5-methyl-1H-indazol-4-yl)quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide, (4R)-1-[(2S)-2-{4-[4-({[(7M)-6-cyclopropyl-4-[(1S,4S)-2,5-diazabicyclo[2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl)phenyl]-1H-1,2,3-triazol-1-yl}-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide and (4R)-1-[(2S)-2-(4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl)phenyl]ethyl}-L-prolinamide.

Examples of specific compounds included in the present invention include the following compounds in one embodiment.

A compound or a salt thereof selected from the group consisting of (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8- yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-2-{[1-(2,2-difluoroethyl)piperidin-4-yl]oxy}-7-(6-fluoro-5-methyl-1H-indazol-4-yl)quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide, (4R)-1-[(2S)-2-{4-[4-({[(7P)-6-cyclopropyl-4-[(1S,4S)-2,5-diazabicyclo[2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl)phenyl]-1H-1,2,3-triazol-1-yl}-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide and (4R)-1-[(2S)-2-(4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl)phenyl]ethyl}-L-prolinamide.

Examples of specific compounds included in the present invention include the following compounds in one embodiment.

A compound or a salt thereof selected from the group consisting of (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-2-{[1-(2,2-difluoroethyl)piperidin-4-yl]oxy}-7-(6-fluoro-5-methyl-1H-indazol-4-yl)quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide, (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl)phenyl]ethyl}-L-prolinamide and (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl)phenyl]-2-hydroxyethyl}-4-hydroxy-L-prolinamide.

The compound of the formula (I) may have tautomers or geometrical isomers depending on the type of the substituent. In this specification, the compound of the formula (I) is sometimes described only as one of isomers, but the present invention includes isomers other than the above one and includes separated isomers or mixtures thereof.

In addition, the compound of the formula (I) may have an asymmetric carbon atom or an axial chirality and may have diastereomers based on them. The present invention includes separated diastereomers of the compound of the formula (I) or mixtures thereof.

Furthermore, the present invention includes pharmaceutically acceptable prodrugs of the compound represented by the formula (I). A pharmaceutically acceptable prodrug is a compound having a group that can be converted into an amino group, a hydroxy group, a carboxyl group or the like by solvolysis or under physiological conditions. Examples of groups to form a prodrug include groups described in Prog. Med., 1985, 5, p. 2157-2161 or in "Iyakuhin no Kaihatsu (development of pharmaceuticals)", Vol. 7, Bunshi-sekkei (molecular design), Hirokawa Shoten, 1990, p. 163-198.

In addition, the salt of the compound of the formula (I) is a pharmaceutically acceptable salt of the compound of the formula (I) and may be an acid addition salt or a salt formed with a base depending on the type of the substituent. Examples thereof include salts shown in P. Heinrich Stahl, Handbook of Pharmaceutical Salts Properties, Selection, and Use, Wiley-VCH, 2008. Specific examples include an acid addition salt with an inorganic acid, such as hydrochloric acid, hydrobromic acid, hydroiodic acid, sulfuric acid, nitric acid or phosphoric acid, or with an organic acid, such as formic acid, acetic acid, propionic acid, oxalic acid, malonic acid, succinic acid, fumaric acid, maleic acid, lactic acid, malic acid, mandelic acid, tartaric acid, dibenzoiltartaric acid, ditoluoyltartaric acid, citric acid, methanesulfonic acid, ethanesulfonic acid, benzenesulfonic acid, p-toluenesulfonic acid, aspartic acid or glutamic acid, a salt with an inorganic metal, such as sodium, potassium, magnesium, calcium or aluminum, a salt with an organic base, such as methylamine, ethylamine or ethanolamine, a salt with various amino acids and amino acid derivatives, such as acetylleucine, lysine or ornithine, an ammonium salt and the like.

Furthermore, the present invention also includes various hydrates, solvates and crystal polymorphism substances of the compound of the formula (I) and a salt thereof.

The present invention also includes all the compounds of the formula (I) or salts thereof which are labeled with one or more pharmaceutically acceptable radioactive or non-radioactive isotopes. Examples of suitable isotopes used for isotopic labeling of the compound of the present invention include isotopes of hydrogen ($^{2}$H, $^{3}$H and the like), carbon ($^{11}$C, $^{13}$C, $^{14}$C and the like), nitrogen ($^{13}$N, $^{15}$N and the like), oxygen ($^{15}$O, $^{17}$O, $^{18}$O and the like), fluorine ($^{18}$F and the like), chlorine ($^{36}$Cl and the like), iodine ($^{123}$I, $^{125}$I and the like) and sulfur ($^{35}$S and the like).

The isotope-labeled compound of the invention of the present application can be used for research and the like such as research on tissue distribution of drugs and/or substrates. For example, radioactive isotopes such as tritium (H) and carbon 14 ($^{14}$C) can be used for this purpose due to the easiness of labeling and the convenience of detection.

Substitution by a heavier isotope, for example, substitution of hydrogen by deuterium ($^{2}$H), is therapeutically advantageous through the improvement of metabolic stability in some cases (for example, increase in the in vivo half-life, decrease in the required dose or decrease in the interaction between drugs).

Substitution by a positron-emitting isotope ($^{11}$C, $^{18}$F, $^{15}$O, $^{13}$N or the like) can be used in a positron emission tomography (PET) test for testing occupancy of a substrate receptor.

The isotope-labeled compound of the present invention can be generally produced by a conventional method known to a person skilled in the art or by the same production methods as in the Examples or the Production Examples and the like using suitable reagents which are labeled with an isotope in place of unlabeled reagents.

(Production Method)

The compound of the formula (I) and a salt thereof can be produced by applying various known synthetic methods using characteristics based on the basic structure or the type of substituent thereof. Here, depending on the type of functional group, it is sometimes effective as a production technique to substitute the functional group with an appropriate protective group (a group that can be easily converted to the functional group) in the process from a raw material to an intermediate. Examples of the protective group include protective groups described in P. G. M. Wuts and T. W. Greene, "Greene's Protective Groups in Organic Synthesis", 5th edition, John Wiley & Sons Inc., 2014 and the like, and a group appropriately selected from the protective groups is used depending on the reaction conditions. In such a method, a reaction is carried out with the protective group introduced, and then the protective group is removed, as required, whereby a desired compound can be obtained.

In addition, a prodrug of the compound of the formula (I) can be produced by introducing a special group in a process from a raw material to an intermediate as for the above protective group or by further carrying out a reaction using the compound of the formula (I) obtained. This reaction can be carried out by applying a method known to a parson skilled in the art, such as common esterification, amidation or dehydration.

Typical methods for producing the compound of the formula (I) will be described below. The production methods can also be carried out with reference to a reference attached to the description. Note that the production method of the present invention is not limited to the examples described below.

In this specification, the following abbreviations are sometimes used.

DMF: N,N-dimethylformamide, DMAc: N,N-dimethylacetamide, THF: tetrahydrofuran, MeCN: acetonitrile, MeOH: methanol, EtOH: ethanol, tBuOH: tert-butanol, DOX: 1,4-dioxane, DMSO: dimethyl sulfoxide, TEA: triethylamine, DIPEA: N,N-diisopropylethylamine, tBuOK: potassium tert-butoxide, PdCl$_2$(dppf)·CH$_2$Cl$_2$: [1,1'-bis(diphenylphosphino)ferrocene]palladium(II) dichloride-dichloromethane adduct, Pd/C: palladium on carbon.

(Production Method 1)

[Chem. 34]

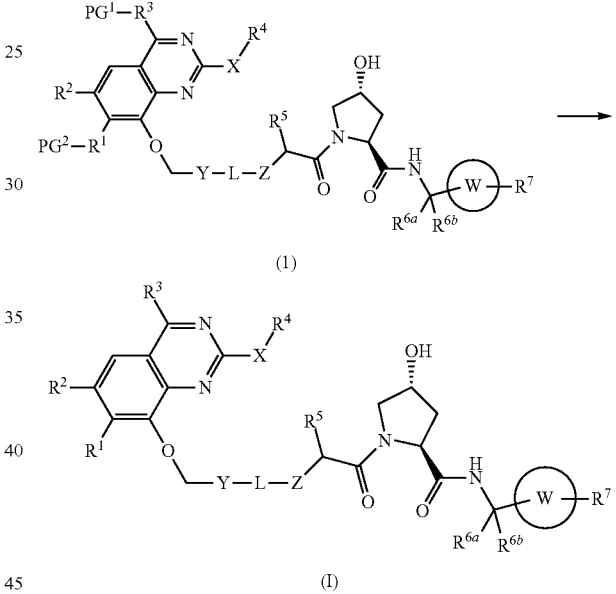

(In the formula, PG$^1$ represents a protective group of NH contained in R$^3$, and PG$^2$ represents a protective group of NH or OH contained in R$^1$ or a hydrogen atom. The same shall apply hereinafter.)

The compound of the formula (I) can be obtained by subjecting a compound (1) to a deprotection reaction. Here, examples of the protective group which can be removed under acidic conditions include a tert-butoxycarbonyl group, a triphenylmethyl group, a tetrahydro-2H-pyran-2-yl group, a methoxymethyl group, a dimethylmethanediyl group, a tert-butylsulfinyl group and the like.

This reaction is performed by stirring, from under cooling to reflux with heat, generally for 0.1 hours to 5 days. Examples of the solvent used here include, but are not particularly limited to, an alcohol, such as MeOH or EtOH, a halogenated hydrocarbon, such as dichloromethane, 1,2-dichloroethane or chloroform, an ether, such as diethyl ether, THF, DOX or dimethoxyethane, DMF, DMSO, MeCN or water and a mixture thereof. Examples of the deprotection reagent include, but are not particularly limited to, acids such as hydrogen chloride (DOX solution), trifluoroacetic acid and methanesulfonic acid.

By selecting a protective group, deprotection can also be performed by a catalytic hydrogenation reaction. Examples of the protective group include a benzyl group, a p-methoxybenzyl group, a benzyloxycarbonyl group and the like. Moreover, deprotection can also be performed with a fluoride ion source such as tetra-n-butylammonium fluoride. Examples of the protective group include a tert-butyl(dimethyl)silyl group, a (trimethylsilyl)ethoxymethyl group and the like. Examples of the protective group which can be removed under basic conditions include an acetyl group, a trifluoroacetyl group, a benzoyl group and the like. Moreover, the deprotection can also be performed in stages by selecting protective groups which can be removed under different deprotection conditions as $PG^1$ and $PG^2$.

For example, the following can be referred as a reference about this reaction.

P. G. M. Wuts and T. W. Greene, "Greene's Protective Groups in Organic Synthesis", 5th edition, John Wiley & Sons Inc., 2014

Note that, when the compound (1) as a raw material has an axial chirality, a stereoisomer which is obtained by once separating the compound (1) may be used for this reaction.

By subjecting the compound of the formula (I) to the following operation as a salt formation reaction, the hydrochloride salt of the compound of the formula (I) can be obtained.

The compound of the formula (I), which is believed to form a salt with hydrogen chloride due to the characteristics of the chemical structure thereof, is dissolved in $CH_2Cl_2$ and MeOH, and after adding hydrogen chloride (4M DOX solution, 10 equivalents) under ice-bath cooling, and the mixture is stirred under ice-bath cooling for 30 minutes. The reaction mixture is concentrated under reduced pressure, and after adding diethyl ether to the resulting residue, the produced solid is collected by filtration and is dried under reduced pressure, thus obtaining the hydrochloride salt of the compound of the formula (I).

By subjecting the hydrochloride salt of the compound of the formula (I) to the following operation as a desalting reaction, the free form of the compound of the formula (I) can be obtained.

The hydrochloride salt of the compound of the formula (I) is purified by ODS column chromatography (MeCN/0.1% aqueous formic acid solution), and after collecting fractions containing the target substance and basifying with saturated aqueous sodium hydrogen carbonate solution, the solution is extracted with $CHCl_3$/MeOH (5/1). The combined organic layer is dried over anhydrous sodium sulfate, and the solution is concentrated under reduced pressure. The resulting solid is washed with diethyl ether and is dried under reduced pressure, thus obtaining the compound of the formula (I).

(Raw Material Synthesis 1)

[Chem. 35]

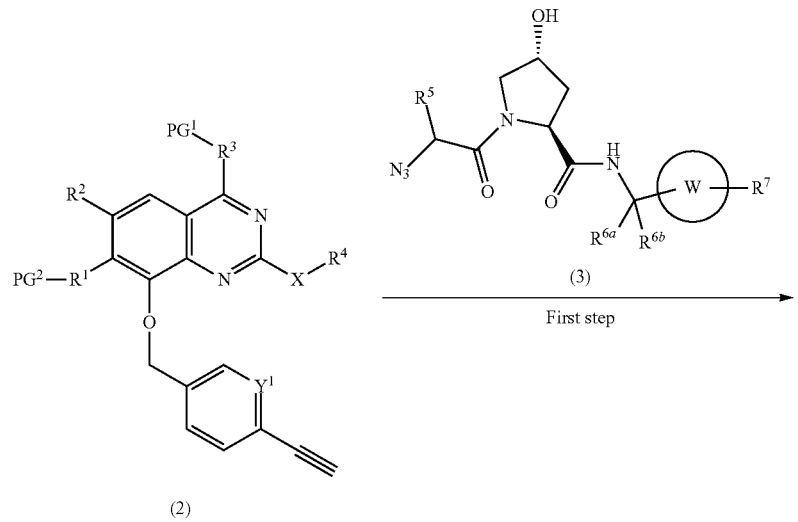

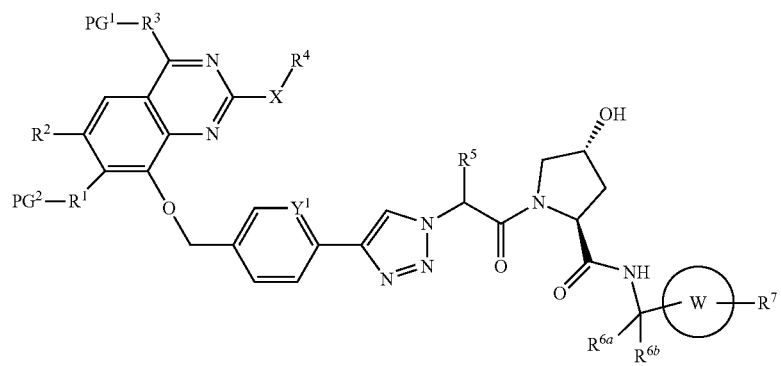

(In the formulae, $Y^1$ represents CH, CF or N. The same shall apply hereinafter.)

The production method is a first method for producing a compound (1)-1 included in the raw material compound (1).

(First Step)

This step is a method for producing the compound (1)-1 by a cycloaddition reaction of a compound (2) and a compound (3).

In this reaction, the compound (2) and the compound (3) are used in an equal amount or with one compound thereof in a larger amount, and the mixture of the compounds is stirred preferably in the presence of a copper salt, further preferably in the presence of a copper salt and a reductant, in a solvent inactive for the reaction or with no solvent, from under cooling to under reflux with heat, preferably at 0° C. to 100° C., generally for 0.1 hours to 5 days. Examples of the solvent used here include, but are not particularly limited to, a halogenated hydrocarbon, such as dichloromethane, 1,2-dichloroethane or chloroform, an aromatic hydrocarbon, such as benzene, toluene or xylene, an ether, such as diethyl ether, THF, DOX or 1,2-dimethoxyethane, DMF, DMSO, ethyl acetate, MeCN, tBuOH, water and a mixture thereof. Examples of the copper salt include CuI, $CuSO_4$, CuOTf and the like. Examples of the reductant include sodium ascorbate and the like. Performing the reaction in the presence of TEA, DIPEA, N-methylmorpholine (NMM), 2,6-lutidine, tris[(1-benzyl-1H-1,2,3-triazol-4-yl)methyl]amine (TBTA) or the like is sometimes advantageous for smoothly promoting the reaction.

REFERENCE

Angew. Chem. Int. Ed. 2002, 41, p. 2596-2599.

Note that this reaction may be performed using a compound obtained by subjecting $PG^2$ of the compound (2) first to a deprotection reaction.

(Raw Material Synthesis 2)

[Chem. 36]

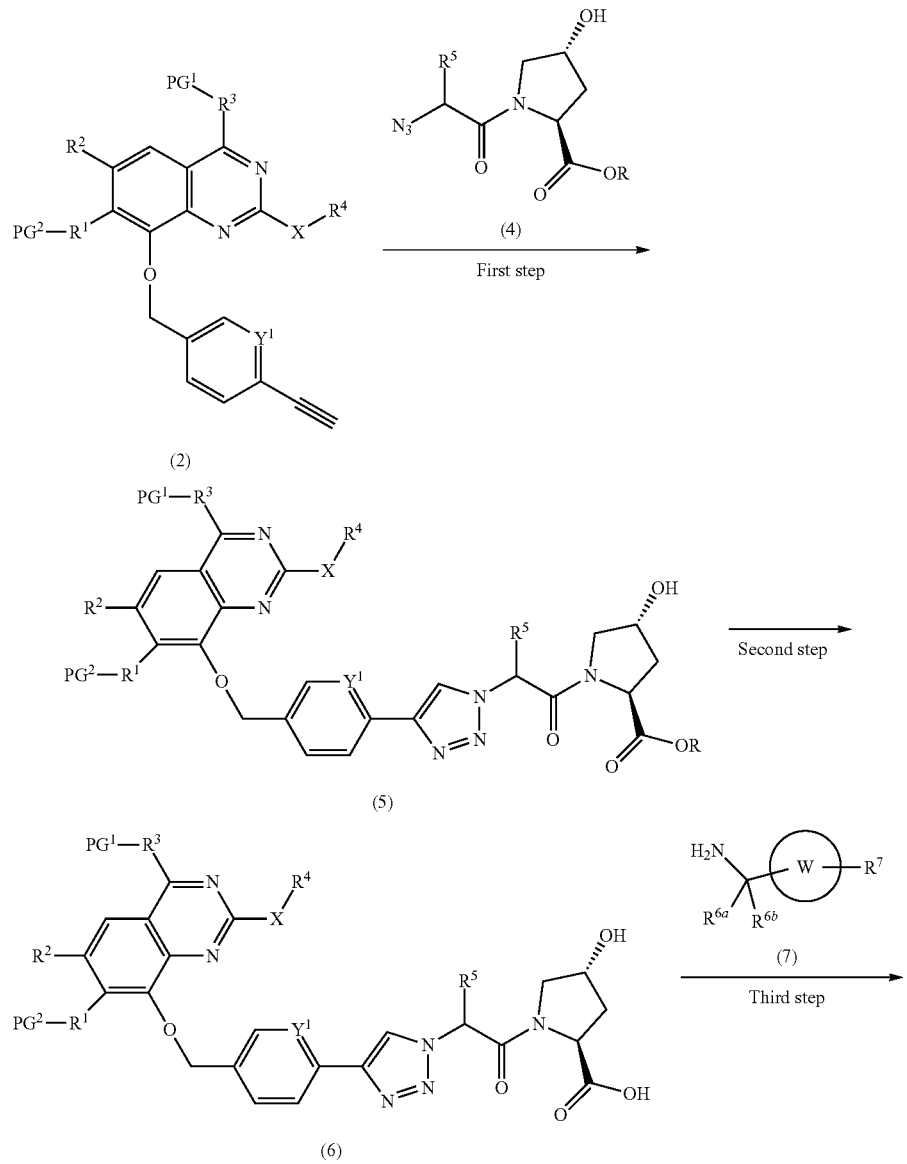

-continued

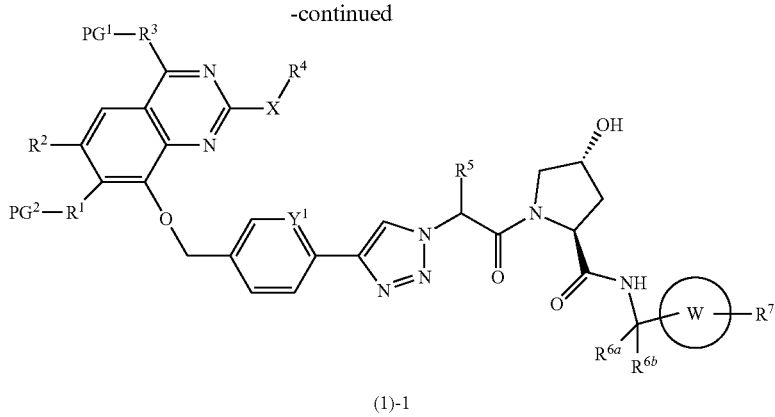

(1)-1

(In the formulae, R represents a $C_{1-3}$ alkyl group. The same shall apply hereinafter.)

This production method is a second method for producing the compound (1)-1 included in the raw material compound (1).

(First Step)

This step is a method for producing a compound (5) by a cycloaddition reaction of the compound (2) and a compound (4).

The reaction conditions are the same as in the first step of the Raw Material Synthesis 1.

(Second Step)

This step is a method for producing a compound (6) by hydrolysis of the compound (5). This reaction is performed by stirring the compound (5) from under cooling to under reflux with heat generally for 0.1 hours to 5 days. Examples of the solvent used here include, but are not particularly limited to, an alcohol, acetone, N,N-dimethylformamide, tetrahydrofuran and the like. In addition, a mixed solvent of the above solvent and water is sometimes suitable for the reaction. Examples of the hydrolysis reagent include, but are not particularly limited to, an aqueous sodium hydroxide solution, an aqueous potassium hydroxide solution, trimethyltin hydroxide and the like.

For example, the following can be referred as a reference about this reaction.

The Chemical Society of Japan, "Jikken Kagaku Koza (Courses in Experimental Chemistry) (5th edition)", Vol. 16 (2005) (Maruzen)

Angew. Chem. Int. Ed. 2005, 44, p. 1378-1382.

(Third Step)

This step is a method for producing the compound (1)-1 by an amidation reaction of the compound (6) and a compound (7).

In this reaction, the compound (6) and the compound (7) are used in an equal amount or with one compound thereof in a larger amount, and the mixture of the compounds is stirred in the presence of a condensing agent, in a solvent inactive for the reaction, from under cooling to under heating, preferably at −20° C. to 60° C., generally for 0.1 hours to 5 days. Examples of the solvent include, but are not particularly limited to, an aromatic hydrocarbon, such as toluene, an ether, such as THF or DOX, a halogenated hydrocarbon, such as dichloromethane, an alcohol, N,N-dimethylformamide, DMSO, ethyl acetate, MeCN and a mixture thereof. Examples of the condensing agent include (benzotriazol-1-yloxy)tripyrrolidinophosphonium hexafluorophosphate (PyBOP), O-(7-azabenzotriazol-1-yl)-N,N,N',N'-tetramethyluronium hexafluorophosphate (HATU), 1-(3-dimethylaminopropyl)-3-ethylcarbodiimide or the hydrochloride thereof, N,N'-dicyclohexylcarbodiimide (DCC), 1,1'-carbonyldiimidazole (CDI), diphenylphosphoryl azide (DPPA) and the like. Use of an additive (for example, 1-hydroxybenzotriazole) is sometimes preferred for the reaction. Performing the reaction in the presence of an organic base, such as TEA, DIPEA or NMM, or an inorganic base, such as potassium carbonate, sodium carbonate or potassium hydroxide, is sometimes advantageous for smoothly promoting the reaction.

Alternatively, a method in which the compound (6) is converted into a reactive derivative, which is then subjected to an acylation reaction, can be used. Examples of the reactive derivative of a carboxylic acid include an acid halogenation product obtained by a reaction with a halogenating agent, such as phosphorus oxychloride or thionyl chloride, a mixed acid anhydride obtained by a reaction with isobutyl chloroformate or the like, an active ester obtained by condensation with 1-hydroxybenzotriazole or the like and the like. The reaction of such a reactive derivative and the compound (7) can be performed in a solvent inactive for the reaction, such as a halogenated hydrocarbon, an aromatic hydrocarbon or an ether, from under cooling to under heating, preferably at −20° C. to 120° C.

REFERENCE

S. R. Sandler and W. Karo, "Organic Functional Group Preparations", 2nd edition, Vol. 1, Academic Press Inc., 1991

The Chemical Society of Japan, "Jikken Kagaku Koza (Courses in Experimental Chemistry) (5th edition)", Vol. 16 (2005) (Maruzen)

(Raw Material Synthesis 3)

[Chem. 37]

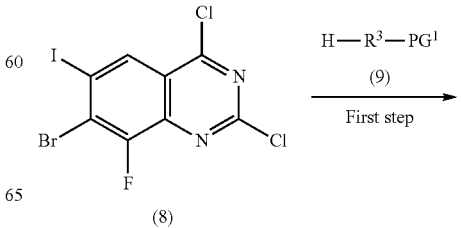

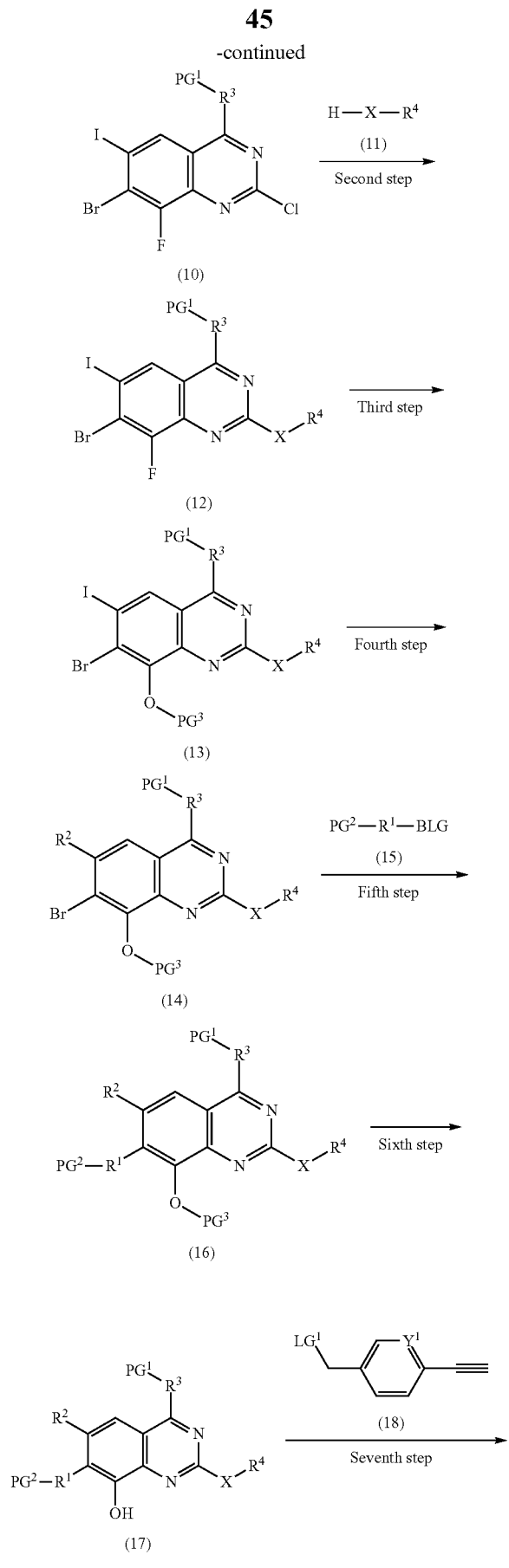

(In the formulae, PG³ represents a protective group of OH, LG¹ represents a leaving group, and BLG represents a boronic acid group, a boronic acid group protected with a protective group of boronic acid such as a boronic acid pinacol ester group or a trifluoroboric acid salt group (hereinafter sometimes described as a boronic acid group or the like). Examples of the leaving group shown here include Cl, Br, a methanesulfonyl group, p-toluenesulfonyl group and the like.)

This production method is a first method for producing a raw material compound (2).

(First Step)

This step is a method for producing a compound (10) by an ipso substitution reaction of a compound (8) and a compound (9).

In this reaction, the compound (8) and the compound (9) are used in an equal amount or with one compound thereof in a larger amount, and the mixture of the compounds is stirred in a solvent inactive for the reaction or with no solvent, from under cooling to under reflux with heat, preferably at 0° C. to 80° C., generally for 0.1 hours to 5 days. Examples of the solvent used here include, but are not particularly limited to, a halogenated hydrocarbon, such as dichloromethane, 1,2-dichloroethane or chloroform, an aromatic hydrocarbon, such as benzene, toluene or xylene, an ether, such as diethyl ether, THF, DOX or 1,2-dimethoxyethane, DMF, DMAc, DMSO, ethyl acetate, MeCN and a mixture thereof. Performing the reaction in the presence of an organic base, such as TEA, DIPEA, N-methylmorpholine (NMM), 1,4-diazabicyclo[2.2.2]octane (DABCO) or tBuOK, or an inorganic base, such as sodium hydride, potassium carbonate, sodium carbonate or cesium carbonate, is sometimes advantageous for smoothly promoting the reaction.

Moreover, the compound (10) can be produced by a catalytic hydrogenation reaction of the compound obtained by a Mizoroki-Heck reaction of the compound (8) and the compound (9).

(Second Step)

This step is a method for producing a compound (12) by an ipso substitution reaction of the compound (10) and a compound (11).

The reaction conditions are the same as in the first step of the Raw Material Synthesis 3.

Moreover, the compound (12) can be produced by the Negishi coupling of a compound in which a hydrogen atom of the compound (11) is converted to halogen and the compound (10).

(Third Step)

This step is a method for producing a compound (13) by an ipso substitution reaction of the compound (12) and $PG^3$-OH.

Examples of the $PG^3$-OH used here include benzyl alcohol and p-methoxybenzyl alcohol.

The reaction conditions are the same as in the first step of the Raw Material Synthesis 3.

(Fourth Step)

This step is a method for producing a compound (14) by a Suzuki-Miyaura coupling reaction of the compound (13) and a boronic acid derivative composed of a $R^2$-boronic acid group or the like. Examples of the boronic acid group or the like used here include, but are not particularly limited to, a boronic acid group, a boronic acid ester group, a boronic acid pinacol ester group, a triol borate salt group and a trifluoroboric acid salt group.

In this reaction, the compound (13) and the boronic acid derivative composed of the $R^2$-boronic acid group or the like are used in an equal amount or with one compound thereof in a larger amount, and the mixture of the compounds is stirred in a solvent inactive for the reaction, in the presence of a base and a palladium catalyst, from at room temperature to under reflux with heat, preferably at 20° C. to 140° C., generally for 0.1 hours to 5 days. Examples of the solvent used here include, but are not particularly limited to, a halogenated hydrocarbon, such as dichloromethane, 1,2-dichloroethane or chloroform, an aromatic hydrocarbon, such as benzene, toluene or xylene, an ether, such as diethyl ether, THF, DOX or 1,2-dimethoxyethane, an alcohol, such as MeOH, EtOH, isopropyl alcohol, butanol or amyl alcohol, DMF, DMSO, MeCN, 1,3-dimethylimidazolidin-2-one, water and a mixture thereof. Examples of the base include inorganic bases, such as tripotassium phosphate, sodium carbonate, potassium carbonate and sodium hydroxide. Examples of the palladium catalyst include tetrakis(triphenylphosphine)palladium, bis(triphenylphosphine)palladium(II) dichloride, [1,1'-bis(diphenylphosphino)ferrocene]palladium(II) dichloride·dichloromethane additive, (1E,4E)-1,5-diphenylpenta-1,4-dien-3-one/palladium (3:2), (2-dicyclohexylphosphino-2',6'-diisopropoxy-1,1'-biphenyl)[2-(2'-amino-1,1'-biphenyl)]palladium(II) methanesulfonate, palladium(II) acetate and the like. Performing the reaction in the presence of a ligand, such as dicyclohexyl(2',6'-dimethoxybiphenyl-2-yl)phosphine, dicyclohexyl(2',6'-diisopropoxy-[1,1'-biphenyl]-2-yl)phosphine or 1,1'-bis(diphenylphosphino)ferrocene, is sometimes advantageous for smoothly promoting the reaction. In addition, heating the mixture by microwave irradiation is sometimes advantageous for smoothly promoting the reaction.

REFERENCE

J. Am. Chem. Soc., 2005, 127, p. 4685-4696
Org. Lett. 2011, 13, p. 3948-3951
Org. Lett. 2012, 14, p. 1278-1281

When $R^2$ is hydrogen atom, the compound (14) can be produced by a catalytic hydrogenation reaction of the compound (13).

(Fifth Step)

This step is a method for producing a compound (16) by a Suzuki-Miyaura coupling reaction of the compound (14) and a compound (15).

The reaction conditions are the same as in the fourth step of the Raw Material Synthesis 3.

When the compound (16) has an axial chirality, the compound (16) is obtained as a mixture of diastereomers, and each diastereomer can be isolated by separation using a common separation operation, for example, ODS column chromatography or silica gel column chromatography.

(Sixth Step)

This step is a method for producing a compound (17) by deprotection by a catalytic hydrogenation reaction of the compound (16).

This reaction can be performed by stirring the compound (16) under hydrogen atmosphere, from under normal pressure to under increased pressure, in a solvent inactive for the reaction, such as MeOH, EtOH or ethyl acetate, in the presence of a metal catalyst, from under cooling to under heating, preferably at room temperature, for 1 hour to 5 days. As the metal catalyst, a palladium catalyst, such as Pd/C or palladium black, a platinum catalyst, such as a platinum plate or platinum oxide, a nickel catalyst, such as reduced nickel or Raney nickel, or the like is used.

(Seventh Step)

This step is a method for producing the compound (2) by a reaction of the compound (17) and a compound (18).

This reaction is performed by reacting a mixture of the compound (17) and the compound (18) in an equal amount or with one compound thereof in a larger amount in the presence of a base, in a solvent inactive for the reaction, from under cooling to under reflux with heat, preferably at 0° C. to 80° C., generally for 0.1 hours to 5 days. The solvent used here is not particularly limited, and examples thereof include an aromatic hydrocarbon, such as benzene, toluene or xylene, an alcohol, such as MeOH or EtOH, an ether, such as diethyl ether, THF, DOX or 1,2-dimethoxyethane, a halogenated hydrocarbon, such as dichloromethane, 1,2-dichloroethane or chloroform, DMF, DMSO, ethyl acetate, MeCN and a mixture thereof. Examples of the base include, but are not particularly limited to, an organic base, for example, such as TEA, DIPEA, 1,8-diazabicyclo[5.4.0]-7-undecene, n-butyllithium or tBuOK, and an inorganic base, such as sodium hydroxide, sodium carbonate, potassium carbonate, cesium carbonate or sodium hydride. Performing the reaction in the presence of a phase transfer catalyst, such as tetra-n-butylammonium chloride, is sometimes advantageous.

For example, the following can be referred as a reference about this reaction.

The Chemical Society of Japan, "Jikken Kagaku Koza (Courses in Experimental Chemistry)", 5th edition, Vol. 14, Maruzen, 2005

The compound (2) sometimes has an axial chirality and is obtained as a mixture of diastereomers, and each diastereomer can be isolated by subjecting the compound (2) in which $PG^2$ is a protective group or a compound obtained by subjecting the compound (2) to a deprotection reaction to separation using a common separation operation, for example, ODS column chromatography or silica gel column chromatography.

The reaction conditions for the deprotection reaction used here are the same as in the step described in the Production Method 1.

The compound (18) in which $LG^1$ is halogen can be produced by halogenating a compound in which the moiety corresponding to $LG^1$ is a hydroxy group. Examples of the halogenating agent used here include, but are not particularly limited to, for example, thionyl chloride, phosphorus oxychloride, hydrobromic acid, phosphorus tribromide and the like.

For example, the following can be referred as a reference about this reaction.

The Chemical Society of Japan, "Jikken Kagaku Koza (Courses in Experimental Chemistry)" (5th edition), Vol. 13, Maruzen, 2005

The compound (18) in which $LG^1$ is a sulfonyl group can be produced by sulfonylation of a compound in which the moiety corresponding to $LG^1$ is a hydroxy group in the presence of a base. Examples of the sulfonylating reagent used here include, but are not particularly limited to, for example, methanesulfonylchloride, p-toluenesulfonylchloride, methanesulfonic anhydride and the like. Examples of the base include, but are not particularly limited to, for example, TEA, DIPEA, pyridine, tetramethylethylenediamine and the like.

For example, the following can be referred as a reference about this reaction.

Synthesis 1999, 9, p. 1633-1636

(Raw Material Synthesis 4)

[Chem. 38]

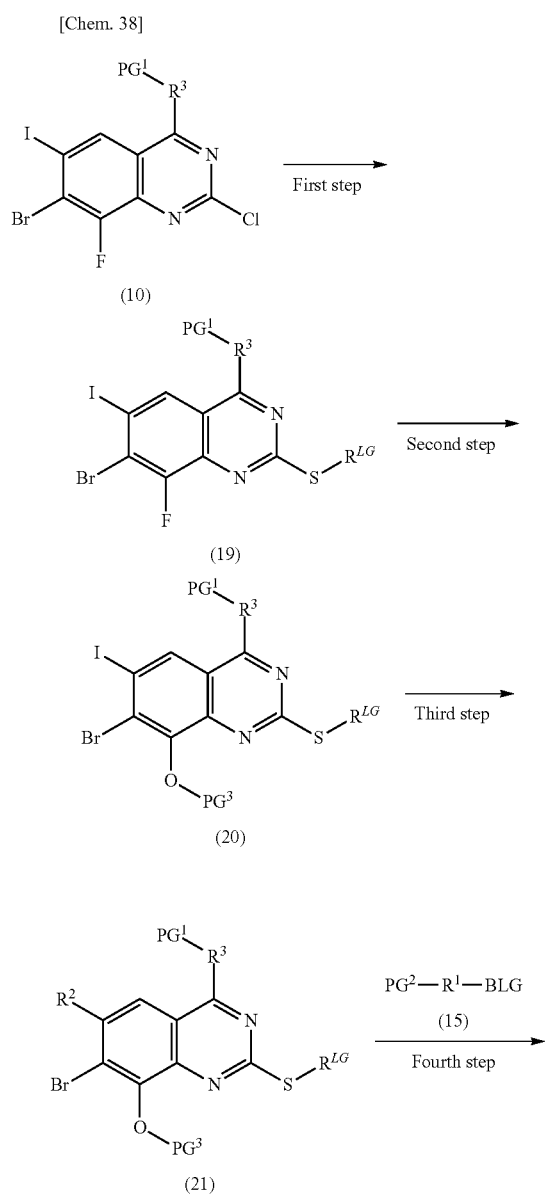

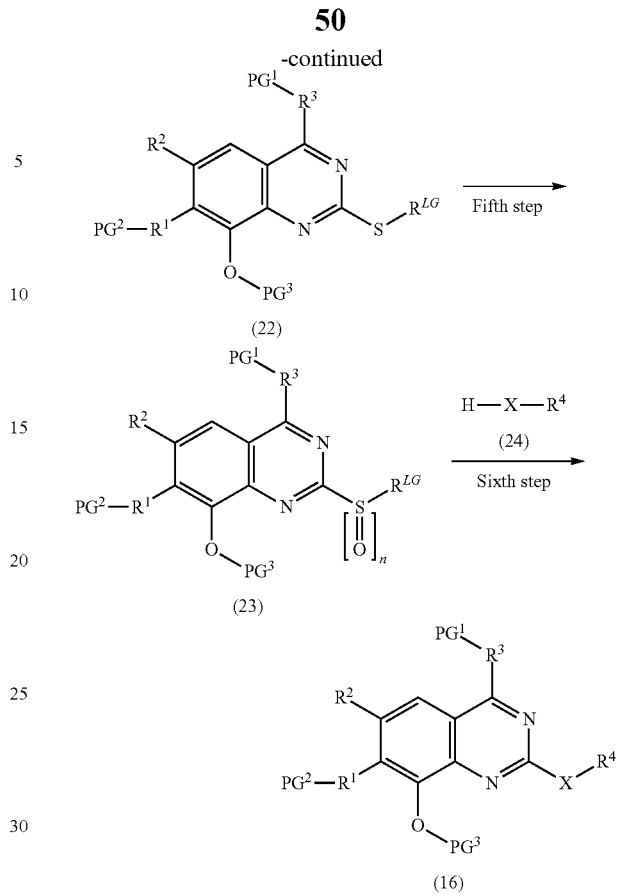

(In the formulae, $R^{LG}$ represents a $C_{1-12}$ alkyl group, and n represents 1 or 2.)

This production method is a second method for producing the raw material compound (16).

(First Step)

This step is a method for producing a compound (19) by an ipso substitution reaction of the compound (10) and $R^{LG}$—SH. Examples of the $R^{LG}$-SH used here include $C_{1-12}$ alkylthiols, for example, ethanethiol and dodecanethiol.

The reaction conditions are the same as in the first step of the Raw Material Synthesis 3.

(Second Step)

This step is a method for producing a compound (20) by an ipso substitution reaction of the compound (19) and $PG^3$-OH. Examples of the $PG^3$-OH used here include benzyl alcohol and p-methoxybenzyl alcohol.

The reaction conditions are the same as in the first step of the Raw Material Synthesis 3.

(Third Step)

This step is a method for producing a compound (21) by a Suzuki-Miyaura coupling reaction of the compound (20) and a boronic acid derivative composed of a $R^2$-boronic acid group or the like.

The reaction conditions are the same as in the fourth step of the Raw Material Synthesis 3.

When $R^2$ is hydrogen atom, the compound (21) can be produced by a catalytic hydrogenation reaction of the compound (20).

(Fourth Step)

This step is a method for producing a compound (22) by a Suzuki-Miyaura coupling reaction of the compound (21) and the compound (15).

The reaction conditions are the same as in the fourth step of the Raw Material Synthesis 3.

(Fifth Step)

This step is a method for producing a compound (23) by an oxidation reaction of the compound (22).

In this reaction, the compound (22) is treated with an oxidant in an equal amount or an excess amount in a solvent inactive for the reaction, from under cooling to under heating, preferably at −20° C. to 80° C., generally for 0.1 hours to 3 days. In this reaction, oxidation with m-chloroperbenzoic acid, perbenzoic acid, peracetic acid, sodium hypochlorite or hydrogen peroxide is suitably used. Examples of the solvent include an aromatic hydrocarbon, an ether, a halogenated hydrocarbon such as dichloromethane, DMF, DMSO, ethyl acetate, MeCN and a mixture thereof. Other examples of the oxidant include cumene hydroperoxide, Oxone, active manganese dioxide, chromic acid, potassium permanganate, sodium periodate and the like.

REFERENCE

The Chemical Society of Japan, "Jikken Kagaku Koza (Courses in Experimental Chemistry)", 5th edition, Vol. 17, Maruzen, 2005

(Sixth Step)

This step is a method for producing the compound (16) by an ipso substitution reaction of the compound (23) and a compound (24).

The reaction conditions are the same as in the first step of the Raw Material Synthesis 3.

When the compound (16) has an axial chirality, the compound (16) is obtained as a mixture of diastereomers, and each diastereomer can be isolated by separation using a common separation operation, for example, ODS column chromatography or silica gel column chromatography.

(Raw Material Synthesis 5)

[Chem. 39]

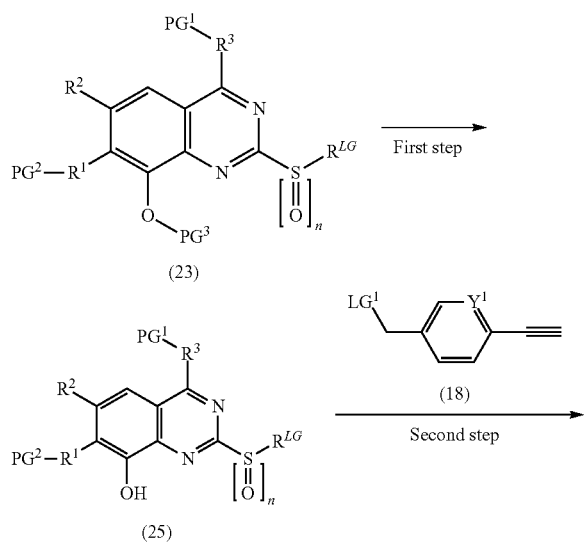

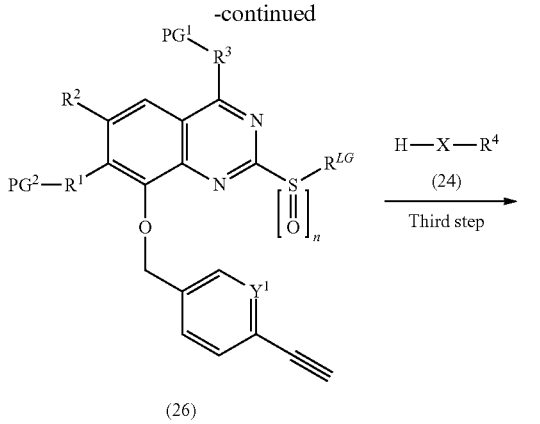

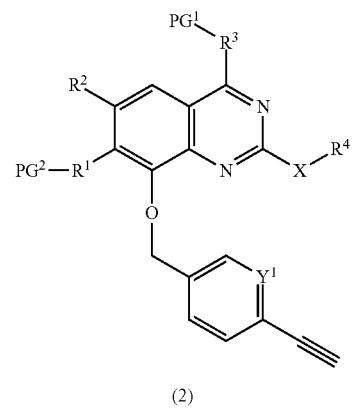

This production method is a second method for producing the raw material compound (2).

(First Step)

This step is a method for producing a compound (25) by deprotection by a catalytic hydrogenation reaction of the compound (23).

The reaction conditions are the same as in the sixth step of the Raw Material Synthesis 3.

(Second Step)

This step is a method for producing a compound (26) by a reaction of the compound (25) and the compound (18).

The reaction conditions are the same as in the seventh step of the Raw Material Synthesis 3.

(Third Step)

This step is a method for producing the compound (2) by an ipso substitution reaction of the compound (26) and the compound (24).

The reaction conditions are the same as in the first step of the Raw Material Synthesis 3.

The compound (2) sometimes has an axial chirality and is obtained as a mixture of diastereomers, and each diastereomer can be isolated by subjecting the compound (2) in which $PG^2$ is a protective group or a compound obtained by subjecting the compound (2) to a deprotection reaction to separation using a common separation operation, for example, ODS column chromatography or silica gel column chromatography.

The reaction conditions for the deprotection reaction used here are the same as in the step described in the Production Method 1.

(Raw Material Synthesis 6)

[Chem. 40]

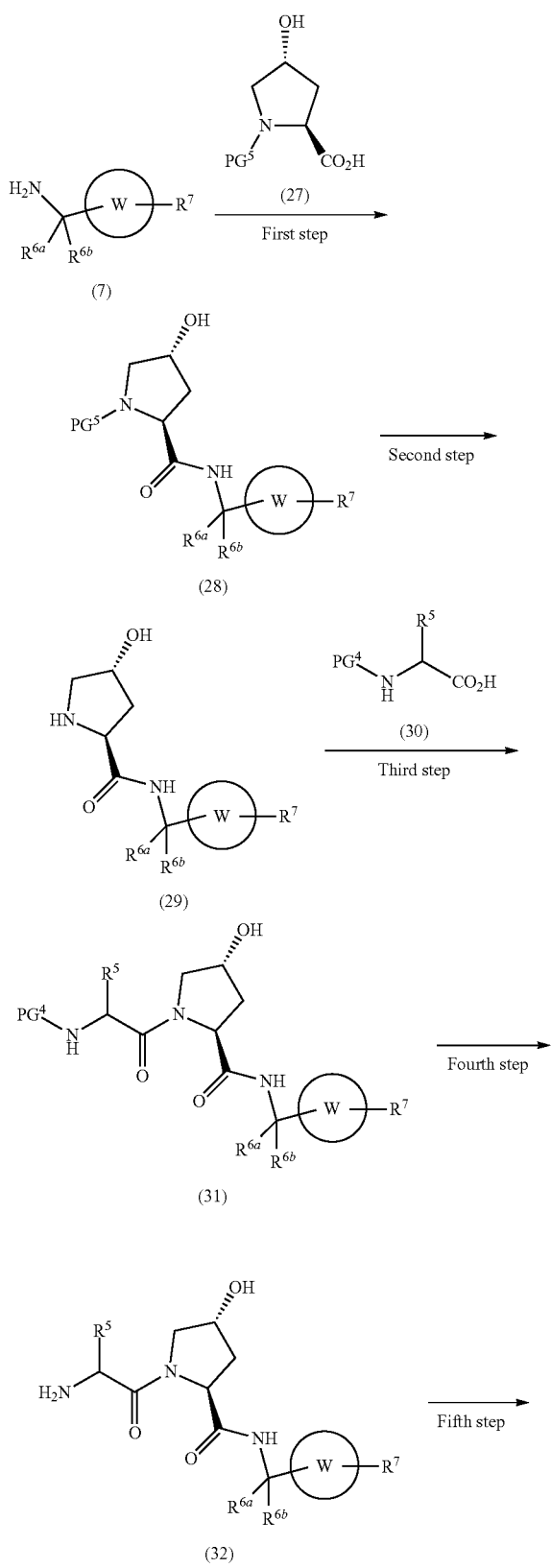

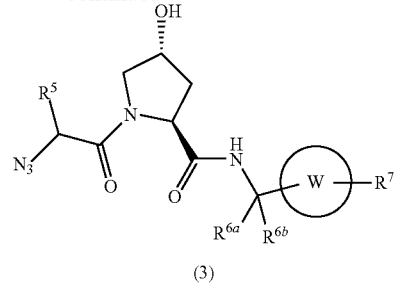

(In the formulae, $PG^4$ and $PG^5$ represent a protective group.)

This production method is a method for producing the raw material compound (3).

(First Step)

This step is a method for producing a compound (28) by an amidation reaction of the compound (7) and a compound (27).

The reaction conditions are the same as in the third step of the Raw Material Synthesis 2.

(Second Step)

This step is a method for producing a compound (29) by subjecting the compound (28) to a deprotection reaction.

The reaction conditions are the same as in the step described in the Production Method 1.

(Third Step)

This step is a method for producing a compound (31) by an amidation reaction of the compound (29) and a compound (30).

The reaction conditions are the same as in the third step of the Raw Material Synthesis 2.

(Fourth Step)

This step is a method for producing a compound (32) by subjecting the compound (31) to a deprotection reaction.

The reaction conditions are the same as in the step described in the Production Method 1.

(Fifth Step)

This step is a method for producing the compound (3) by a reaction of the compound (32) and a diazo-transfer reagent.

In this reaction, the compound (32) is treated with the diazo-transfer reagent in an equal amount or an excess amount in a solvent inactive for the reaction, from under cooling to under heating, preferably at 0° C. to 50° C., generally for 0.1 hours to 3 days. Examples of the diazo-transfer reagent include, but are not particularly limited to, for example trifluoromethanesulfonyl azide, imidazole-1-sulfonyl azide or a salt thereof, 2-azido-1,3-dimethylimidazolinium hexafluorophosphate (ADMP) and the like. Performing the reaction in the presence of an organic base, such as TEA, 4-dimethylaminopyridine (DMAP) or 2,6-lutidine, and a catalytic amount of a copper salt, such as $CuSO_4$, is sometimes advantageous. Examples of the solvent include a halogenated hydrocarbon, such as THF or dichloromethane, MeCN, an alcohol, water and a mixture thereof.

REFERENCE
J. Org. Chem. 2012, 77, p. 1760-1764
Nature 2019, 574, p. 86-89
Org. Biomol. Chem. 2014, 12, p. 4397-4406
(Raw Material Synthesis 7)
[Chem. 41]
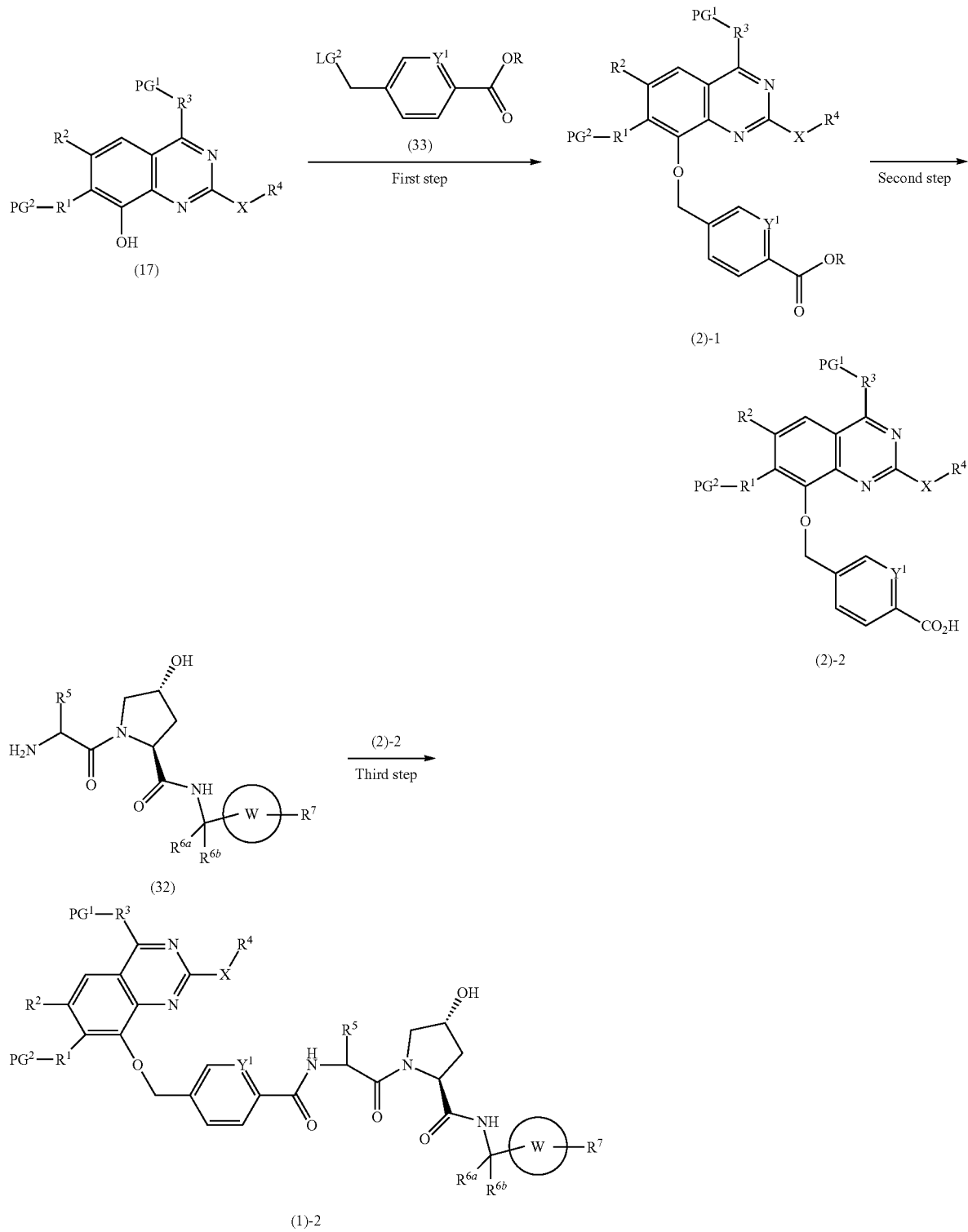

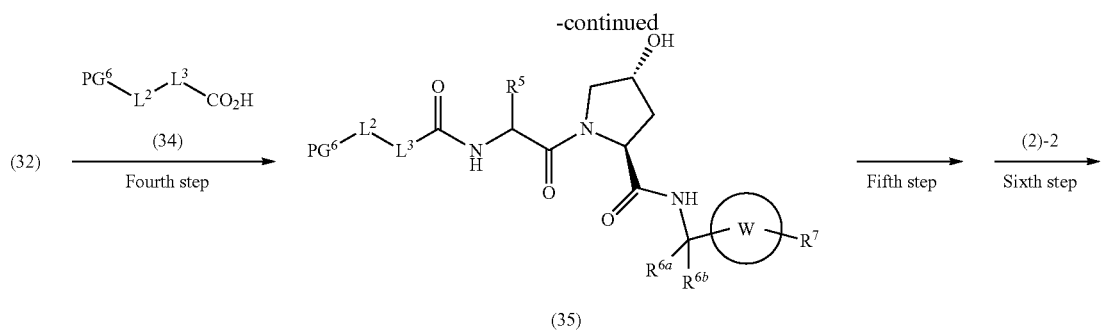

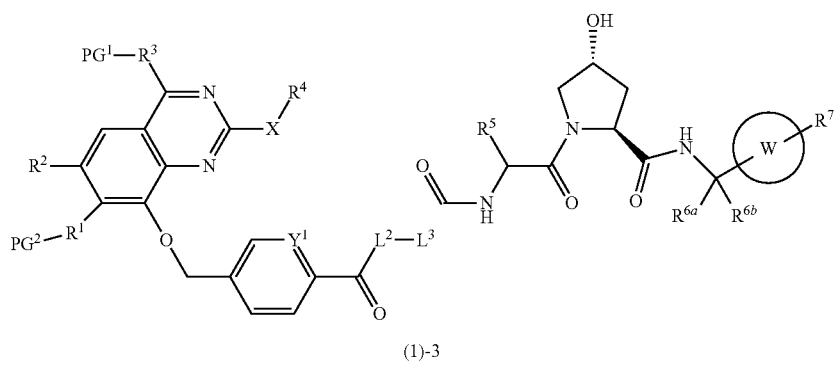

(In the formulae, $LG^2$ represents a leaving group, and $PG^6$ represents a protective group of NH.)

This production method is a method for producing a raw material compound (1)-2 or a raw material compound (1)-3 included in the raw material compound (1). Here, a production method in which $L^2$ in the raw material compound (1)-3 is $NR^{L1}$, pyrrolidinediyl, piperidinediyl or piperazinediyl is shown.

(First Step)

This step is a method for producing a compound (2)-1 by a reaction of the compound (17) and a compound (33).

The reaction conditions are the same as in the seventh step of the Raw Material Synthesis 3.

(Second Step)

This step is a method for producing a compound (2)-2 by hydrolysis of the compound (2)-1.

The reaction conditions are the same as in the second step of the Raw Material Synthesis 2.

(Third Step)

This step is a method for producing the compound (1)-2 by an amidation reaction of the compound (32) and the compound (2)-2.

The reaction conditions are the same as in the third step of the Raw Material Synthesis 2.

(Fourth Step)

This step is a method for producing a compound (35) by an amidation reaction of the compound (32) and a compound (34).

The reaction conditions are the same as in the third step of the Raw Material Synthesis 2.

(Fifth Step and Sixth Step)

The steps are a method for producing the compound (1)-3 by an amidation reaction of a compound obtained by a deprotection reaction of the compound (35) and the compound (2)-2.

The reaction conditions for the deprotection reaction are the same as in the step described in Production Method 1.

The reaction conditions for the amidation reaction are the same as in the third step of the Raw Material Synthesis 2.

(Raw Material Synthesis 8)

[Chem. 42]

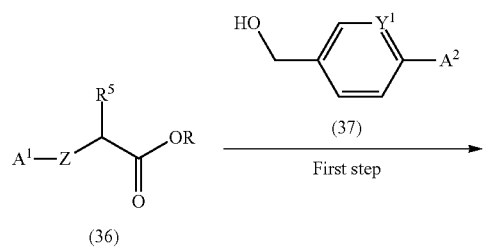

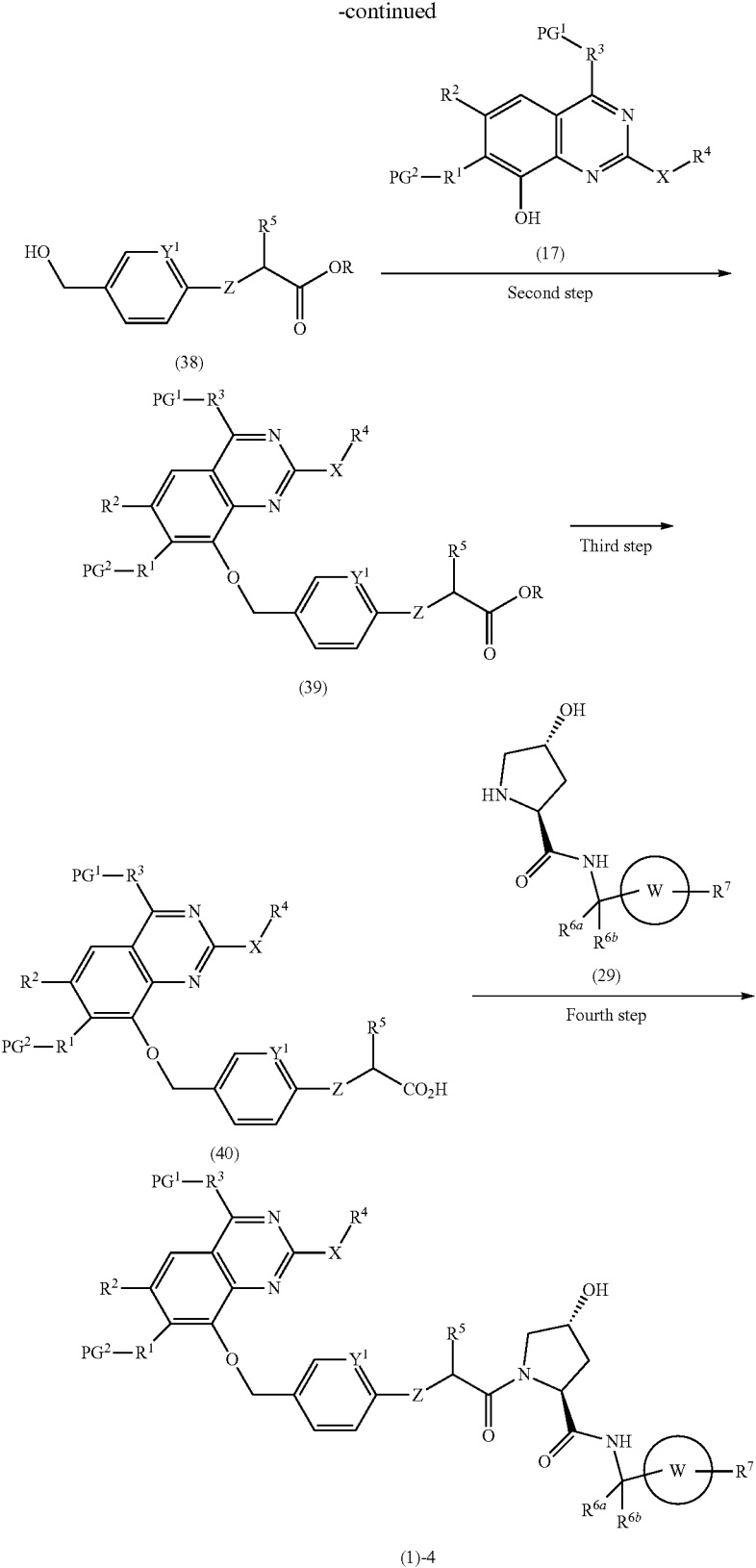
(In the formulae, when Z is NH, $A^1$ represents hydrogen atom, and $A^2$ represents halogen. When Z is 5-membered heteroarenediyl containing one to four hetero atoms selected from oxygen, sulfur and nitrogen, $A^2$ represents a boronic acid group or the like when $A^1$ is a group selected from the group consisting of Cl, Br and I, and $A^2$ represents a group selected from the group consisting of Cl, Br and I when $A^1$ is a boronic acid group or the like.)

This production method is a method for producing a raw material compound (1)-4.

(First Step)

This step is a method for producing a compound (38) by an ipso reaction or a Buchwald-Hartwig amination reaction of a compound (36) and a compound (37) when Z is NH.

(Fourth Step)

This step is a method for producing the compound (1)-4 by an amidation reaction of the compound (40) and the compound (29).

The reaction conditions are the same as in the third step of the Raw Material Synthesis 2.

(Raw Material Synthesis 9)

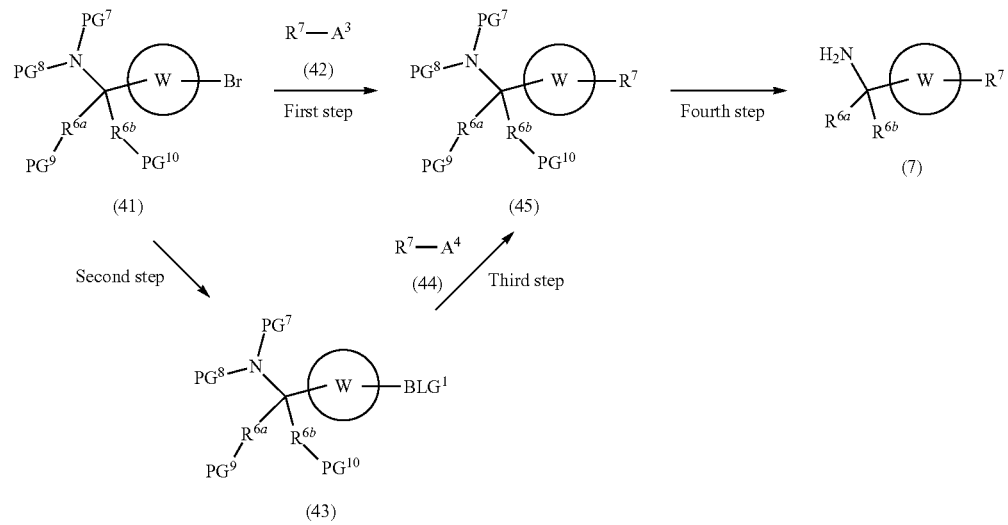

[Chem. 43]

The reaction conditions for the ipso reaction are the same as in the first step of the Raw Material Synthesis 3.

For example, the following can be referred as a reference about the Buchwald-Hartwig amination reaction.
J. Am. Chem. Soc., 2020, 142, p. 15027-15037

This step is a method for producing the compound (38) by a Suzuki-Miyaura coupling reaction of the compound (36) and the compound (37) when Z is 5-membered heteroaryl containing one to four hetero atoms selected from oxygen, sulfur and nitrogen.

The reaction conditions are the same as in the fourth step of the Raw Material Synthesis 3.

For example, the following can be referred as a reference about the reaction when Z is the formula (V).
J. Org. Chem., 2000, 65, p. 1516-1524
Chemical Communications 2014, 50, p. 1867-1870
Bioorg. Med. Chem. Lett., 2001, 11, p. 2061-2065

(Second Step)

This step is a method for producing a compound (39) by a reaction of the compound (38) and the compound (17).

The reaction conditions are the same as in the seventh step of the Raw Material Synthesis 3.

In this step, the compound (39) can also be produced by a Mitsunobu reaction of the compound (38) and the compound (17).

For example, the following can be referred as a reference about the Mitsunobu reaction.
Chem. Asian J. 2007, 2, p. 1340-1355

(Third Step)

This step is a method for producing a compound (40) by hydrolysis of the compound (39).

The reaction conditions are the same as in the second step of the Raw Material Synthesis 2.

(In the formulae, $PG^7$ represents a protective group, $PG^8$, $PG^9$ and $PG^{10}$, which are the same as or different, represent hydrogen atom or a protective group, $A^3$ represents hydrogen atom, a carboxyl group, a boronic acid group or the like, $A^4$ represents hydrogen atom or a group selected from the group consisting of Cl, Br and I, and $BLG^1$ represents a boronic acid group or the like.)

This production method is a method for producing the raw material compound (7) when $R^7$ is a group selected from the group consisting of the formula (VI), the formula (VII), the formula (VIII), the formula (IX), the formula (XX), the formula (XXI), the formula (XXII), the formula (XXIII) and the formula (XXIV).

(First Step)

This step is a method for producing a compound (45) by a Mizoroki-Heck reaction of a compound (42) in which $R^7$ is the formula (VI) when $A^3$ is hydrogen atom and a compound (41).

In this reaction, the compound (42) and the compound (41) are used in an equal amount or with one compound thereof in a larger amount, and the mixture of the compounds is stirred in a solvent inactive for the reaction, in the presence of a base and a palladium catalyst, from at room temperature to under reflux with heat, preferably at 20° C. to 140° C., generally for 0.1 hours to 5 days. Examples of the solvent used here include, but are not particularly limited to, an ether, such as diethyl ether, THF, DOX or 1,2-dimethoxyethane, DMF, DMAc, DMSO, MeCN, 1,3-dimethylimidazolidin-2-one, ethyl acetate, water and a mixture thereof. Examples of the base include a base, such as tripotassium phosphate, sodium carbonate, potassium carbonate and potassium acetate. Examples of the palladium catalyst include tetrakis(triphenylphosphine)palladium, bis(triphenylphosphine)palladium(II) dichloride, [1,1'-bis(diphenylphosphino)ferrocene]palladium(II) dichloride·dichloromethane additive, (1E,4E)-1,5-diphenylpenta-1,4-dien-3-one/palladium (3:2), (2-dicyclohexylphosphino-2',6'-diisopropoxy-1,1'-biphenyl)[2-(2'-amino-1,1'-biphenyl)]palladium(II) methanesulfonate, palladium(II) acetate and the like. In addition, heating the mixture by microwave irradiation is sometimes advantageous for smoothly promoting the reaction.

For example, the following can be referred as a reference about the reaction.
Synthesis 2020, 52, p. 2521-2527
PNAS 2016, 113, p. 7124-7129

Alternatively, this step is, for example, a method for producing the compound (45) by an Ullmann reaction of the compound (42) which is a group selected from the group consisting of the formula (IX), the formula (XX), the formula (XXI), the formula (XXII) and the formula (XXIV) and the compound (41).

For example, the following can be referred as a reference about the reaction.
Angew. Chem. Int. Ed., 2003, 42, p. 5400-5449

This step is a method for producing the compound (45) by a decarbonation coupling reaction of the compound (42) in which $R^7$ is, for example, the formula (VII) when $A^3$ is a carboxyl group and the compound (41).

For example, the following can be referred as a reference about the reaction.
Science, 2006, 313, p. 662-664

This step is a method for producing the compound (45) by a Suzuki-Miyaura coupling reaction of the compound (42) in which $R^7$ is, for example, a group selected from the group consisting of the formula (VI), the formula (VIII) and the formula (XXIII) when $A^3$ is a boronic acid group or the like and the compound (41).

The reaction conditions are the same as in the fourth step of the Raw Material Synthesis 3.
(Second Step)

This step is a method for producing a compound (43) by a reaction for substituting the bromo group of the compound (41) by a boronic acid group or the like.

For example, the following can be referred as a reference about the reaction.
Eur. J. Med. Chem., 2019, 162, p. 407-422
J. Org. Chem. 2020, 85, 16, p. 10966-10972
J. Am. Chem. Soc., 2010, 132, p. 17701-17703
(Third Step)

This step is a method for producing the compound (45) by a Suzuki-Miyaura coupling reaction of a compound (44) and the compound (43) when $A^4$ is a group selected from the group consisting of Cl, Br and I.

The reaction conditions are the same as in the fourth step of the Raw Material Synthesis 3.

This step is a method for producing the compound (45) by a Chan-Lam-Evans Coupling reaction of the compound (44) which is, for example, a group selected from the group consisting of the formula (IX), the formula (XX), the formula (XXI), the formula (XXII) and the formula (XXIV) when $A^4$ is hydrogen atom and the compound (43).

For example, the following can be referred as a reference about the reaction.
Adv. Synth. Catal. 2020, 362, p. 3311-3331.
(Fourth Step)

This step is a method for producing the compound (7) by subjecting the compound (45) to a deprotection reaction.

The reaction conditions are the same as in the step described in the Production Method 1.

The compound of the formula (I) is isolated and purified as a free compound, a salt, hydrate, solvate or crystal polymorphous substance thereof or a substance in the amorphous solid form. A salt of the compound of the formula (I) can also be produced by subjecting the compound to a salt formation reaction which is an ordinary method.

The isolation and purification are performed by applying a common chemical operation, such as extraction, fractional crystallization or various types of fraction chromatography.

Various types of isomers can be produced by selecting an appropriate raw material compound or can be separated using a difference in physiochemical properties between the isomers. For example, an optical isomer can be obtained by a general optical resolution method of a racemate (for example, fractional crystallization for inducing a racemate to a diastereomer salt with an optically active base or acid, chromatography using a chiral column or the like or the like) and can also be produced from an appropriate optically active raw material compound.

In addition, the compound of the formula (I) or an intermediate thereof sometimes has an axial chirality and is obtained as a mixture of diastereomers, and each diastereomer can be isolated by separation using a common separation operation, for example, octadecylsilyl (ODS) column chromatography or silica gel column chromatography.

The pharmacological activities of the compounds of the formula (I) were confirmed by the following tests.

Test Example 1-1: Evaluation of KRAS Degradation Action on Human G12D Mutant KRAS-Positive Pancreatic Cancer Line AsPC-1

The KRAS degradation action of test compounds was evaluated by measuring the expression levels of KRAS G12D by a sandwich ELISA method.

AsPC-1 cells (ATCC, CRL-1682) were seeded at 90 µL per well on a 96-well plate (from IWAKI) to give $1.8 \times 10^4$ cells per well. As for the cell culture conditions, RPMI 1640 medium (from Merck) containing 10% fetal bovine serum (from Cytiva) was used in the presence of 5% $CO_2$ at 37° C.

The next day, the test compounds (10 points having final concentrations in the range of M to 0.3 nM) were diluted 100-fold with a fresh medium and were added at 10 µL per well. The same treatments were each applied to 4 wells. In addition, in production of the sandwich ELISA plate, a capture antibody (anti-KRAS antibody, from LS Bio) mixed in Phosphate Buffered Saline [PBS; from FUJIFILM Wako Pure Chemical Corporation] in 1,000-fold dilution was added at 20 µL per well to a Maxisorp 384-well plate (from Thermo Scientific), and after attaching a seal, the plate was allowed to stand at 4° C. overnight.

After 24 hours of the test compound treatment, the culture supernatant was discarded. Immediately, a cytolytic solution (produced by adding, to a RIPA buffer [from Thermo Scientific], a Halt Protease Phosphatese Inhibitor Cocktail [from Thermo Scientific] and Benzonase Nuclease [from Merck] in amounts of 1/100 and 1/500, respectively) was added at 50 µL per well, and the cells were lysed. Then, equally treated 4 wells were combined to prepare a cell lysate sample of 200 µL in total. For KRAS detection, the Maxisorp 384-well plate which had been treated with the capture antibody since the previous day was washed (twice with 25 µL each) with 0.05% Tween-20-containing PBS (from Thermo Scientific; 20×PBS Tween-20 was diluted 20-fold with ion exchange water and used) and was treated with a blocking solution (Intercept Blocking Buffer; from LI-COR Biosciences) for 60 minutes, and then, the cell lysate samples were added at 20 µL per well. For f-actin detection, the cell lysate samples were added as they were at 20 µL per well to the Maxisorp 384-well plate, and after attaching a seal, the plate was allowed to stand at 4° C. overnight.

The next day, after washing the KRAS detection plate with 0.05% Tween-20-containing PBS, an anti-Ras (G12D mutant specific) antibody (from Cell Signaling Technology) diluted 1,000-fold with a blocking solution was added at 20 µL per well as a detection antibody, and the plate was allowed to stand for 5 hours at room temperature. Then, the plate was centrifuged to remove the supernatant (using a centrifugal dehydrator machine, the supernatant was removed by the same method hereinafter) and was washed with 0.05% Tween-20-containing PBS. Then, an anti-Rabbit IgG IRP-linked antibody (from Cell Signaling Technology) diluted 1,000-fold with a blocking solution was added at 20 µL per well as a secondary antibody, and the plate was allowed to stand for 1 hour at room temperature. The plate was centrifuged to remove the supernatant and was washed with 0.05% Tween-20-containing PBS. Then, a BM chemiluminescent ELISA substrate (from Merck) was added at 20 µL per well, and the amounts of luminescence were measured with 2103 EnVision (from PerkinElmer). In addition, the f-actin detection plate was washed with 0.05% Tween-20-containing PBS and was treated with a blocking solution for 60 minutes, and then, an anti-β-actin antibody (from Abcam) diluted 1,000-fold with a blocking solution was added at 20 µL per well as a detection antibody. The plate was allowed to stand for 5 hours at room temperature. Then, the plate was centrifuged to remove the supernatant and washed with 0.05% Tween-20-containing PBS, and then, an anti-Mouse IgG HIRP-linked antibody (from Cell Signaling Technology) diluted 1,000-fold with a blocking solution was added at 20 µL per well as a secondary antibody. The plate was allowed to stand for 1 hour at room temperature. Then, the plate was centrifuged to remove the supernatant and was washed with 0.05% Tween-20-containing PBS. Then, a BM chemiluminescent ELISA substrate was added at 20 µL per well, and the amounts of luminescence were measured with EnVision.

With the signaling value at the time of addition of DMSO corrected with the amount of β-actin taken as 100% and with the signaling value at the time of addition of 10 µM of the compound of Example No. 7 taken as 0%, the 50% degradation values ($DC_{50}$) of the amounts of KRAS were calculated by Sigmoid-Emax model nonlinear regression analysis. The molecular weights of the test compounds were calculated as the molecular weights of the dihydrochloride for Example No. 22, the trihydrochlorides for Example Nos. 2-7, 9-12 and 14-18, the tetrahydrochloride for Example No. 19, the pentahydrochloride for Example No. 21 and the free forms forming no salt for the remaining Example Nos.

The results for some test compounds of the formula (I) are shown in Table 1.

TABLE 1

| Ex | $DC_{50}$ (nM) |
|---|---|
| 1 | 123 |
| 2 | 598 |
| 3 | 140 |
| 4 | 897 |
| 5 | 153 |
| 6 | 103 |
| 7 | 46 |
| 8 | 37 |

TABLE 1-continued

| Ex | $DC_{50}$ (nM) |
|---|---|
| 9 | 77 |
| 10 | 124 |
| 11 | 178 |
| 12 | 136 |
| 13 | 151 |
| 14 | 221 |
| 15 | 95 |
| 16 | 188 |
| 17 | 92 |
| 18 | 74 |
| 19 | 139 |
| 20 | 100 |
| 21 | 72 |
| 22 | 62 |
| 23 | 34 |
| 24 | 103 |
| 25 | 44 |
| 26 | 24 |
| 27 | 55 |
| 28 | 45 |
| 29 | 33 |

Test Example 1-2: Evaluation of KRAS Degradation Action on Human G12D Mutant KRAS-Positive Pancreatic Cancer Line AsPC-1

The KRAS degradation action of test compounds was evaluated by measuring the expression levels of KRAS G12D by Cell ELISA.

AsPC-1 cells were seeded at 20 µL per well on a 384-well plate (from Greiner bio-one) to give $2.0 \times 10^4$ cells per well. As for the cell culture conditions, a RPMI 1640 medium containing 10% fetal bovine serum was used in the presence of 5% $CO_2$ at 37° C.

The next day, the test compounds (10 points having final concentrations in the range of M to 0.3 nM), the compound of Example No. 26 (Example No. 8 for Example Nos. 74 and 75) of a final concentration of 10 µM as a positive control and DMSO, which was the solvent for the test compounds, as a negative control were diluted 500-fold with a fresh medium and were added at 20 µL per well. The cells were cultured overnight.

The next day, the culture supernatant was removed, and 4% paraformaldehyde phosphate buffer (from FUJIFILM Wako Pure Chemical Corporation) was added at 20 µL per well. The plate was allowed to stand for 30 minutes at room temperature to thus immobilize the cells. Then, the supernatant was removed, and 0.1% Triton X-100 (from Amersham Biosciences)-containing PBS was added at 20 µL per well. After allowing to stand for 10 minutes at room temperature, the supernatant was removed. PBS was added at 25 µL per well, and the supernatant was removed to thus wash each well. The washing was performed twice in total. Next, the supernatant was removed, and 0.5% sodium dodecyl sulfate (SDS; from Invitrogen)-containing PBS was added at 20 µL per well. After allowing to stand at room temperature for 10 minutes, the supernatant was removed by centrifugation (using a centrifugal dehydrator machine, the supernatant was removed by the same method hereinafter). PBS was added at 25 µL per well, and the supernatant was removed to thus wash each well. The washing was performed twice in total. The supernatant was removed by centrifugation, and a blocking solution (Intercept Blocking Buffer) was added at 20 µL per well. After allowing to stand for 30 minutes at room temperature, the supernatant was removed by centrifugation, and a solution obtained by diluting an anti-Ras (G12D Mutant Specific) antibody and an anti-β-actin antibody 1,000-fold with a blocking solution was added at 20 µL per well as a primary antibody. The plate was allowed to stand overnight at 4° C.

The next day, the plate was centrifuged to remove the supernatant. PBS was added at L per well, and the supernatant was removed to thus wash each well. The washing was performed twice in total. The supernatant was removed by centrifugation, and a solution obtained by diluting Donkey anti-Mouse IgG H&L (IRDye 680RD) (from Li-COR Biosciences) and Goat anti-Rabbit IgG H&L (IRDye 800CW) (from Li-COR Biosciences) 1,000-fold with a blocking solution was added at 20 µL per well as a secondary antibody. After allowing to stand for 1 hour at room temperature, the supernatant was removed. PBS was added at 25 µL per well, and the supernatant was removed to thus wash each well. The washing was performed twice in total. After removing the supernatant by centrifuging the plate, the plate was dried as it was with air at room temperature for 2 hours or more, and the 700-nm and 800-nm fluorescent signals were measured with Aerius (from LI-COR Biosciences).

With the signaling value at the time of addition of DMSO corrected with the signaling value of β-actin taken as 100% and with the signaling value at the time of addition of 10 µM of the compound of Example No. 26 taken as 0%, the 50% degradation values ($DC_{50}$) of the amounts of KRAS were calculated by Sigmoid-Emax model nonlinear regression analysis. The molecular weights of the test compounds were calculated as the molecular weights of the trihydrochloride for Example No. 30, the tetrahydrochloride for Example No. 46 and the free forms forming no salt for the remaining Example Nos. The results for some test compounds of the formula (I) are shown in Table 2.

TABLE 2

| Ex | $DC_{50}$ (nM) |
|---|---|
| 30 | 157 |
| 31 | 138 |
| 32 | 139 |
| 33 | 30 |
| 34 | 24 |
| 35 | 84 |
| 36 | 17 |
| 37 | 25 |
| 38 | 53 |
| 39 | 6 |
| 40 | 5 |
| 41 | 9 |
| 42 | 6 |
| 43 | 10 |
| 44 | 111 |
| 45 | 15 |
| 46 | 37 |
| 47 | 13 |
| 48 | 4 |
| 49 | 15 |
| 50 | 11 |
| 51 | 11 |
| 52 | 10 |
| 53 | 8 |
| 54 | 8 |
| 55 | 24 |
| 75 | 5886 |
| 57 | 134 |
| 58 | 37 |
| 59 | 45 |
| 60 | 102 |
| 61 | 21 |
| 62 | 10 |
| 63 | 70 |
| 64 | 48 |

TABLE 2-continued

| Ex | $DC_{50}$ (nM) |
|---|---|
| 65 | 14 |
| 66 | 250 |
| 67 | 840 |
| 68 | 1393 |
| 69 | 31 |
| 70 | 14 |
| 71 | 35 |
| 72 | 16 |
| 73 | 134 |
| 74 | 1000 |

Test Example 2: Evaluation of ERK Phosphorylation Inhibition Action on Human G12D Mutant KRAS-Positive Pancreatic Cancer Line AsPC-1

The ERK phosphorylation inhibition action of test compounds was evaluated by measuring phosphorylation of the 202th threonine (Thr202) and the 204th tyrosine (Tyr204) of ERK located downstream of the KRAS signal by Cell ELISA.

AsPC-1 cells were seeded on a 384-well plate (from Greiner bio-one) at 36 µL/well to give $2.0 \times 10^4$ cells per well. As for the cell culture conditions, a RPMI 1640 medium containing 10% fetal bovine serum was used in the presence of 5% $CO_2$ at 37° C.

The next day, the test compounds (6 points having final concentrations in the range of M to 3.0 nM), trametinib (MEK inhibitor) of a final concentration of 1 µM as a positive control and DMSO, which was the solvent for the test compounds, as a negative control were diluted 100-fold with a fresh medium and were added at 4 µL per well. The cells were then cultured for 24 hours. After culturing, a 30% glyoxal solution (40% glyoxal [from Nacalai Tesque] was diluted with PBS) was quickly added at 30 µL per well, and the plate was allowed to stand for 90 minutes at room temperature to thus immobilize the cells. Then, the plate was centrifuged to remove the supernatant (using a centrifugal dehydrator machine, the supernatant was removed by the same method hereinafter), and 0.1% Triton X-100-containing PBS was added at 20 µL per well. After allowing to stand for 10 minutes at room temperature, the supernatant was removed by centrifugation, and the same operation was further repeated. Next, 0.5% SDS-containing PBS was added at 20 µL per well, and after allowing to stand at room temperature for 30 minutes, the supernatant was removed by centrifugation. Subsequently, a blocking solution (Intercept Blocking Buffer) was added at 20 µL per well, and the plate was allowed to stand for 1 hour at room temperature. The supernatant was removed by centrifugation, and an ERK (Thr202/Tyr204) phosphorylation antibody (Phospho-p44/42 MAPK (Erk 1/2) (Thr202/Tyr204) (D13.14.4E) XP Rabbit mAb; from Cell Signaling Technology) diluted 2,500-fold with a blocking solution was added at 10 or 15 µL per well as a primary antibody. The plate was allowed to stand at 4° C. overnight.

The next day, the plate was centrifuged to remove the supernatant. 0.05% Tween-20-containing PBS was added at 50 µL per well, and the supernatant was removed by centrifugation to thus wash each well. The washing was performed three times in total. After washing, Goat anti-Rabbit IgG H&L (IRDye 800CW) diluted 1,000-fold with a blocking solution was added at 15 µL per well as a secondary antibody, and the plate was allowed to stand for 1 hour at room temperature. The plate was centrifuged to remove the supernatant, and each well was washed three times with 0.05% Tween-20-containing PBS in the same manner as after the primary antibody reaction. After removing the supernatant by centrifuging the plate, the plate was dried as it was with air at room temperature for 3 hours or more, and the 800-nm fluorescent signals were measured with Aerius.

With the signaling value at the time of addition of DMSO taken as 100% and with the signaling value at the time of addition of 1 μM trametinib taken as 0%, the 50% inhibition values ($IC_{50}$) were calculated by Sigmoid-Emax model nonlinear regression analysis. The molecular weights of the test compounds were calculated as the molecular weights of the dihydrochloride for Example No. 22, the trihydrochlorides for Example Nos. 2-7, 9-12, 14-18 and 30, the tetrahydrochlorides for Example Nos. 19 and 46, the pentahydrochloride for Example No. 21 and the free forms forming no salt for the remaining Example Nos. The results for some test compounds of the formula (I) are shown in Table 3.

TABLE 3

| Ex | $IC_{50}$ (nM) | Ex | $IC_{50}$ (nM) | Ex | $IC_{50}$ (nM) |
|---|---|---|---|---|---|
| 1 | 89 | 11 | 39 | 21 | 19 |
| 2 | 779 | 12 | 37 | 22 | 12 |
| 3 | 62 | 13 | 29 | 23 | 10 |
| 4 | 522 | 14 | 63 | 24 | 25 |
| 5 | 97 | 15 | 22 | 25 | 15 |
| 6 | 58 | 16 | 67 | 26 | 8 |
| 7 | 17 | 17 | 36 | 27 | 27 |
| 8 | 15 | 18 | 28 | 28 | 12 |
| 9 | 18 | 19 | 51 | 29 | 15 |
| 10 | 26 | 20 | 36 | | |
| 30 | 185 | 45 | 11 | 60 | 50 |
| 31 | 194 | 46 | 22 | 61 | 24 |
| 32 | 92 | 47 | 18 | 62 | 15 |
| 33 | 32 | 48 | 8 | 63 | 72 |
| 34 | 26 | 49 | 21 | 64 | 80 |
| 35 | 55 | 50 | 10 | 65 | 11 |
| 36 | 31 | 51 | 14 | 66 | 114 |
| 37 | 18 | 52 | 11 | 67 | 758 |
| 38 | 28 | 53 | 10 | 68 | 2209 |
| 39 | 6 | 54 | 18 | 69 | 17 |
| 40 | 7 | 55 | 38 | 70 | 12 |
| 41 | 17 | | | 71 | 38 |
| 42 | 22 | 57 | 65 | 72 | 16 |
| 43 | 11 | 58 | 25 | 73 | 133 |
| 44 | 95 | 59 | 26 | | |

Test Example 3: Evaluation of Non-Anchorage-Dependent Cell Growth Inhibition Action on Human G12D Mutant KRAS-Positive Pancreatic Cancer Line AsPC-1

The non-anchorage-dependent cell growth inhibition action of test compounds was evaluated by spheroid 3D cell culture.

AsPC-1 cells were seeded on a low-cell-adhesive round bottom 384-well plate (PrimeSurface: from Sumitomo Bakelite) at 36 μL/well to give $5 \times 10^2$ cells per well. The cell culture was performed under the same conditions as in the Test Example 2.

The next day, the test compounds (6 points having final concentrations in the range of 10 μM to 3.0 nM) and DMSO, which was the solvent for the test compounds, as a negative control were diluted 100-fold with a fresh medium and were added at 4 μL per well. After culturing in the presence of 500 $CO_2$ at 37° C. for 6 days, CellTiter Glo 2.0 (from Promega) was added at 20 μL per well. After stirring with a plate mixer (from FINEPCR) at normal temperature for 1 hour, the luminescent signals were measured with ARVO X3 (from PerkinElmer).

With the signaling value in treatment with DMSO taken as 10000 and with the signaling value in the medium alone without cells taken as 000, the 500% inhibition values ($IC_{50}$) were calculated by Sigmoid-Emax model nonlinear regression analysis. The molecular weights of the test compounds were calculated as the molecular weights of the dihydrochloride for Example No. 22, the trihydrochlorides for Example Nos. 2-7, 9-12, 14-18 and 30, the tetrahydrochlorides for Example Nos. 19 and 46, the pentahydrochloride for Example No. 21 and the free forms forming no salt for the remaining Example Nos. The results for some test compounds of the formula (I) are shown in Table 4.

TABLE 4

| Ex | $IC_{50}$ (nM) | Ex | $IC_{50}$ (nM) | Ex | $IC_{50}$ (nM) |
|---|---|---|---|---|---|
| 1 | 190 | 11 | 128 | 21 | 47 |
| 2 | 1412 | 12 | 112 | 22 | 27 |
| 3 | 108 | 13 | 74 | 23 | 21 |
| 4 | 670 | 14 | 153 | 24 | 55 |
| 5 | 169 | 15 | 64 | 25 | 66 |
| 6 | 100 | 16 | 185 | 26 | 20 |
| 7 | 31 | 17 | 104 | 27 | 103 |
| 8 | 23 | 18 | 70 | 28 | 37 |
| 9 | 96 | 19 | 138 | 29 | 42 |
| 10 | 114 | 20 | 79 | | |
| 30 | 323 | 45 | 20 | 60 | 127 |
| 31 | 321 | 46 | 56 | 61 | 61 |
| 32 | 186 | 47 | 22 | 62 | 34 |
| 33 | 42 | 48 | 20 | 63 | 133 |
| 34 | 33 | 49 | 46 | 64 | 245 |
| 35 | 43 | 50 | 21 | 65 | 45 |
| 36 | 24 | 51 | 27 | 66 | 360 |
| 37 | 19 | 52 | 31 | 67 | 975 |
| 38 | 27 | 53 | 23 | 68 | 1627 |
| 39 | 18 | 54 | 24 | 69 | 64 |
| 40 | 20 | 55 | 76 | 70 | 21 |
| 41 | 31 | | | 71 | 51 |
| 42 | 46 | 57 | 90 | 72 | 26 |
| 43 | 16 | 58 | 80 | 73 | 112 |
| 44 | 266 | 59 | 70 | | |

Test Example 4: Evaluation of Anti-Tumor Activity in Human KRAS G12D Mutant-Positive PK-59 Pancreatic Cancer Cell Line-Derived Xenograft Mice PK-59 cells (RIKEN BRC, RCB 1901) were cultured using a RPMI 1640 medium containing 10% fetal bovine serum in the presence of 5% $CO_2$ at 37° C. The PK-59 cells were collected and suspended in PBS, and after adding an equal amount of Matrigel (from Becton, Dickinson and Company), the cell suspension prepared at $1.0 \times 10^7$ to $2.0 \times 10^7$ cells/mL was subcutaneously inoculated in a volume of 100 μL in 4- to 6-week-old male nude mice (CAnN.Cg-Foxn1$^{nu}$/CrlCrlj (nu/nu), from Charles River Laboratories Japan). About two weeks after the inoculation, the mice were divided into groups so that all the groups had approximately the same tumor volume and body weight, and administration of test compounds was started on the next day. The study was conducted for 5 mice each of a vehicle group and test compound administration groups. The compounds of Example 8, Example 48 and Example 70 were dissolved in a solvent containing ethanol (from FUJIFILM Wako Pure Chemical Corporation), a 5% glucose solution (from Otsuka Pharmaceutical), 1M hydrochloric acid (from Kanto Chemical Co., Inc.), an aqueous 50% (2-hydroxypropyl)-β-cyclodextrin (HP-βCD) solution (from ROQUETTE), HCO-40 (from Nikko Chemicals Co., Ltd.) and an aqueous 1M sodium hydroxide solution (from Kanto Chemical Co., Inc.) at a liquid amount ratio of 4:84.4:1.1:1:9:0.5. The compounds of Example 22 and Example 26 were dissolved in a solvent containing propylene glycol (from FUJIFILM Wako Pure Chemical Corporation), Tween80 (from Nacalai Tesque) and Otsuka normal saline (from Otsuka Pharmaceutical) at a liquid amount ratio of 6.7:3.3:90. The compound of Example 39 was dissolved in a solvent containing propylene glycol, ethanol, an aqueous 50% HP-βCD solution, HCO-40 and a 5% glucose solution at a liquid amount ratio of 10:8:10:10:62. The test compounds dissolved in the respective solvents or the solvents were administered into tail vein. The administration was performed twice with an interval of once a week. The tumor sizes and the body weights were measured twice a week. The tumor volumes were calculated using the following equation.

[Tumor volume $(mm^3)$]=[Major axis of tumor $(mm)$]×[Minor axis of tumor $(mm)$]$^2$×0.5

The tumor growth inhibitions (%) by the test compounds were calculated with the tumor volumes of the test compound administration groups on the previous day of the start of the administration taken as 100% inhibition and the tumor volumes of the vehicle groups two weeks after the initial administration taken as 0% inhibition. In addition, when the tumor volume of a test compound administration group was smaller than the tumor volume on the previous day of the start of the administration, the tumor regression (%) by the test compound was calculated with the tumor volume on the previous day of the start of the administration taken as 0% regression and with the tumor volume 0 taken as 100% regression. The molecular weights of the test compounds were calculated as the molecular weights of the dihydrochloride for Example No. 22 and the free forms forming no salt for the remaining Example Nos. The results for some test compounds of the formula (I) are shown in Table 5.

TABLE 5

| Ex | Dose (mg/kg) | Anti-Tumor Activity Two Weeks After Initial Administration |
|---|---|---|
| 8 | 10 | 98% inhibition |
| 22 | 10 | 93% inhibition |
| 26 | 10 | 94% inhibition |
| 39 | 10 | 13% regression |
| 48 | 10 | 32% regression |
| 70 | 10 | 42% regression |

Test Example 5: Evaluation of Inhibition Action on KRAS G12D/SOS/c-Raf Complex Formation Using human recombinant KRAS G12D, SOS and c-Raf proteins, the inhibition action of test compounds on the formation of the complex of the proteins was examined by the time-resolved fluorescence resonance energy transfer (TR-FRET) method.

Biotinylated AviTag-KRAS G12D (amino acid region of 1-185, GDP) (2.5 µL; 400 nM) and test compounds dissolved in an assay buffer (50 mM HEPES, 150 mM NaCl, 5 mM $MgCl_2$, 0.05% Tween 20, pH7.0) were added to a 384-well plate (from Corning) in a liquid volume of 2.5 µL at 40,000 nM to 40 nM. Son of Sevenless (SOS) (amino acid region of 564-1049, 2.5 µL; 1.3 µM) and c-Raf (amino acid region of 51-131) GST (2.5 µL; 130 nM) containing GTP (from Sigma-Aldrich; 2 µM) were added to the plate, and the plate was allowed to stand for 1 hour at room temperature. Then, a mixture liquid (10 µL) of LANCE Ulight-anti-GST (from PerkinElmer; 120 nM) and LANCE Eu-W1024 labeled Streptoavidin (from PerkinElmer; 100 ng/mL) was added, and the 620-nm and 665-nm fluorescence intensities were measured using EnVision 2104 (from PerkinElmer) under the conditions of an excitation wavelength of 337 nm. After standardizing the values with the fluorescence intensity at a reference wavelength of 620 nm, the 50% inhibition concentrations ($IC_{50}$) were calculated by Sigmoid-Emax model nonlinear regression analysis with the signaling value of the solvent treatment taken as 0% inhibition and with the signaling value without the addition of GTP taken as 100% inhibition.

As a result of the above tests, G12D mutant KRAS degradation action was observed for some compounds of the formula (I) (Test Example 1-1 and Test Example 1-2). Moreover, G12D mutant KRAS inhibition action was observed (Test Example 5). Furthermore, inhibition action on phosphorylation of ERK located downstream of the KRAS signal was observed for some compounds of the formula (I) (Test Example 2). For some compounds of the formula (I), cell growth inhibition action on a human G12D mutant KRAS-positive pancreatic cancer line was observed (Test Example 3), and anti-tumor action in human G12D mutant KRAS-positive pancreatic cancer line tumor-bearing mice was observed (Test Example 4). Therefore, the compounds of the formula (I) can be used for the treatment of pancreatic cancer, in particular, G12D mutant KRAS-positive pancreatic cancer, and the like.

A pharmaceutical composition that contains one or two or more compounds of the formula (I) or a salt thereof as active ingredients can be prepared by a usually used method using an excipient usually used in the art, namely, a pharmaceutical excipient, a pharmaceutical carrier or the like.

The administration may be either oral administration with a tablet, pill, capsule, granule, powder, liquid or other agent or parenteral administration with an intraarticular, intravenous, intramuscular or other injection, a transmucosal agent, an inhalant or the like.

As a solid composition for oral administration, a tablet, powder, granular or other agent is used. In such a solid composition, one or two or more active ingredients are mixed with at least one inactive excipient. The composition may contain an inactive additive, for example, a lubricant, a disintegrator, a stabilizer or a dissolution aid, according to an ordinary method. A tablet or pill may be coated with a sugar coating or a film soluble in the stomach or intestine, as needed.

Liquid compositions for oral administration include a pharmaceutically acceptable emulsion, solution, suspension, syrup, elixir agent and the like and contain a generally used inactive diluent, for example, purified water or EtOH (ethanol). The liquid composition may contain, in addition to the inactive diluent, an adjuvant, such as a solubilizer, a wetting agent or a suspending agent, a sweetening agent, a flavor, an aromatic or a preservative.

The injection agents for parenteral administration include a sterile aqueous or nonaqueous solution, suspension or emulsion agent. Examples of the aqueous solvent include distilled water for injection or physiological saline. An example of the nonaqueous solvent is an alcohol, such as EtOH. Such a composition may further contain an isotonizing agent, a preservative, a wetting agent, an emulsifier, a dispersant, a stabilizer or a dissolution aid. These are sterilized, for example, by filtration through a bacteria keeping filter, incorporation of a microbicide or irradiation. In addition, such a composition can be produced as a sterile solid composition, which is dissolved or suspended in sterile water or a sterile solvent for injection before use.

The transmucosal agent, such as an inhalant or a transnasal agent, is used in a solid, liquid or semi-solid form and can be produced according to a conventionally known method. For example, a known excipient and in addition, a pH modifier, a preservative, a surfactant, a lubricant, a stabilizer, a thickener or the like may be appropriately added. The administration can be performed using an appropriate device for inhalation or insufflation. For example, the agent can be administered using a known device, such as a metering and administering inhalation device, or an atomizer, as a compound alone or a powder of a mixture formulated, or as a solution or a suspension in combination with a medically acceptable carrier. A dry powder inhaler or the like may be for a single administration or multiple administrations, and dry powder or powder-containing capsule can be used. Alternatively, the agent may be used in a form of a pressurized aerosol spray or the like using an appropriate ejection agent, for example, a suitable gas, such as a chlorofluoroalkane or carbon dioxide.

In the case of a common oral administration, the daily dose is appropriately about 0.001 to 100 mg/kg body weight, preferably 0.1 to 30 mg/kg body weight, further preferably 0.1 to 10 mg/kg body weight, and the dose is given once or is divided into two to four times in a day. In the case of intravenous administration, the daily dose is appropriately about 0.0001 to 10 mg/kg body weight and is given once or is divided into multiple times in a day. In addition, the daily dose of a transmucosal agent is about 0.001 to 100 mg/kg body weight and is given once or is divided into multiple times in a day. The dose is appropriately decided depending on the individual case taking the symptom, age, sex and the like into account.

Depending on the route of administration, dosage form, site of administration and types of excipient and additive, the pharmaceutical composition of the present invention contains 0.01 to 100% by weight, in one embodiment, 0.01 to 50% by weight, of one or more compounds of the formula (I) or salts thereof which are active ingredients.

The compound of the formula (I) can be used in combination with various therapeutic agents or preventive agents for a disease to which the compound of the formula (I) is considered to have an effectiveness. The combination use may be simultaneous administration or separate administration either sequential or with a desired interval. A simultaneous administration preparation may be a formulated agent or may be separately formulated.

EXAMPLES

The production method of the compound of the formula (I) will be described in further detail below based on Examples. Note that the present invention is not to be limited to the compounds described in the following Examples. The production methods of raw material compounds are also shown in the Production Examples. The production method of the compound of the formula (I) is not limited only to the production methods of specific Examples described below, and the compound of the formula (I) can also be produced by a combination of the production methods or a method that is obvious to a person skilled in the art.

Note that, in this specification, a compound is sometimes named using naming software, such as ACD/Name (registered trademark, Advanced Chemistry Development, Inc.).

For the purpose of convenience, the concentration mol/L is shown as M. For example, 1 M aqueous sodium hydroxide solution means an aqueous sodium hydroxide solution of 1 mol/L.

The "amorphous solid form" described in this specification includes both a form showing no peak in the powder X-ray diffraction (XRD) pattern and a form having a low crystallinity.

XRD was measured using Empyrean under the conditions of a vacuum tube of Cu, a tube current of 40 mA, a tube voltage of 45 kV, a step width of 0.013°, a wavelength of 1.5418 Å and a measurement diffraction angle range (2θ) of 2.5 to 40°.

Production Example 1

A mixture of 7-bromo-2,4-dichloro-8-fluoro-6-iodoquinazoline (100 g), DOX (1000 mL) and THF (500 mL) was cooled with ice bath, and then DIPEA (240 mL) and tert-butyl (1S,4S)-2,5-diazabicyclo[2.2.1]heptane-2-carboxylate (48 g) were added. The mixture was stirred at room temperature overnight. Water was added to the reaction mixture, and the mixture was extracted with ethyl acetate. The organic layer was washed with an aqueous sodium chloride solution, was dried over anhydrous magnesium sulfate and was then concentrated under reduced pressure until the total amount of the solution became about 400 mL. A mixed solvent (hexane/ethyl acetate=4/1, 1000 mL) was added to the resulting solution, and the mixture was stirred at room temperature. The precipitated solid was filtered to give tert-butyl (1S,4S)-5-(7-bromo-2-chloro-8-fluoro-6-iodoquinazolin-4-yl)-2,5-diazabicyclo[2.2.1]heptane-2-carboxylate (123 g) as a solid.

Production Example 2

To a mixture of tert-butyl (1S,4S)-5-(7-bromo-2-chloro-8-fluoro-6-iodoquinazolin-4-yl)-2,5-diazabicyclo[2.2.1]heptane-2-carboxylate (30 g), tetrahydro-2H-pyran-4-ol (15.0 mL), DMF (150 mL), THF (100 mL) and DABCO (1.15 g) was added cesium carbonate (50.3 g) with stirring at room temperature, and under an argon atmosphere, the mixture was stirred at room temperature overnight. About 1 kg of ice water was added to the reaction mixture, and the mixture was stirred at room temperature for 6 hours. The precipitated solid was filtered, was washed with water and was dried under reduced pressure overnight, thus obtaining tert-butyl (1S,4S)-5-{7-bromo-8-fluoro-6-iodo-2-[(oxan-4-yl)oxy]quinazolin-4-yl}-2,5-diazabicyclo[2.2.1]heptane-2-carboxylate (32.8 g) as a solid.

Production Example 5

Under argon flow, to a mixture of tert-butyl (1S,4S)-5-{7-bromo-8-fluoro-6-iodo-2-[(oxan-4-yl)oxy]quinazolin-4-yl}-2,5-diazabicyclo[2.2.1]heptane-2-carboxylate (11.9 g), benzyl alcohol (2.37 g) and THF (40 mL) was added tBuOK (2.54 g) under ice-bath cooling, and the mixture was stirred at the same temperature for 1.5 hours. Ice water and saturated aqueous ammonium chloride solution were added to the reaction mixture, and the mixture was extracted with ethyl acetate. The organic layer was dried over anhydrous magnesium sulfate. The solution was concentrated under reduced pressure, and a mixed solvent of hexane/ethyl acetate (6/1) was added to the resulting residue. The mixture was stirred for a while, and the precipitated solid was filtered and was dried, thus obtaining tert-butyl (1S,4S)-5-{8-(benzyloxy)-7-bromo-6-iodo-2-[(oxan-4-yl)oxy]quinazolin-4-yl}-2,5-diazabicyclo[2.2.1]heptane-2-carboxylate (11.8 g) as a solid.

Production Example 8

Under an argon atmosphere, a mixture of tert-butyl (1S,4S)-5-{8-(benzyloxy)-7-bromo-6-iodo-2-[(oxan-4-yl) oxy]quinazolin-4-yl}-2,5-diazabicyclo[2.2.1]heptane-2-carboxylate (5.47 g), MeCN (88 mL), DOX (10 mL), water (22 mL), cyclopropylboronic acid (1.27 g), tripotassium phosphate (5.67 g) and $PdCl_2$ (dppf)·$CH_2Cl_2$ (600 mg) was stirred at 100° C. for 3 hours. After the reaction mixture was allowed to cool to room temperature, the solution was concentrated under reduced pressure. Saturated aqueous sodium chloride solution was added to the resulting residue, and the mixture was extracted with $CHCl_3$. The organic layer was dried over anhydrous magnesium sulfate, and the solution was concentrated under reduced pressure. The resulting residue was purified by silica gel column chromatography (hexane/ethyl acetate), thus obtaining tert-butyl (1S,4S)-5-{8-(benzyloxy)-7-bromo-6-cyclopropyl-2-[(oxan-4-yl) oxy] quinazolin-4-yl}-2,5-diazabicyclo[2.2.1]heptane-2-carboxylate (3.8 g) as a foam-like solid.

Production Example 11A mixture of tert-butyl (1S,4S)-5-{8-(benzyloxy)-7-bromo-6-cyclopropyl-2-[(oxan-4-yl)oxy]quinazolin-4-yl}-2,5-diazabicyclo[2.2.1]heptane-2-carboxylate (3.15 g), 6-fluoro-5-methyl-1-(tetrahydro-2H-pyran-2-yl)-4-(4,4,5,5-tetramethyl-1,3,2-dioxaborolan-2-yl)-1H-indazol (1.92 g), tripotassium phosphate (4.1 g), dicyclohexyl(2',6'-diisopropoxy-[1,1'-biphenyl]-2-yl)phosphine (0.12 g), (2-dicyclohexylphosphino-2',6'-diisopropoxy-1,1'-biphenyl)[2-(2'-amino-1,1'-biphenyl)]palladium(II) methanesulfonate (0.2 g), DOX (40 mL) and water (8 mL) was degassed and substituted with argon with stirring at room temperature, and then, the mixture was stirred at 100° C. for 2.5 hours under an argon atmosphere. Water (about 150 mL) was added to the reaction mixture cooled to room temperature, and the mixture was extracted with ethyl acetate. After the organic layer was dried over anhydrous magnesium sulfate, the insoluble materials were removed by filtration, and the filtrate was concentrated under reduced pressure. The resulting residue was purified by silica gel column chromatography (basic silica gel, hexane/ethyl acetate), and fractions respectively containing (1) a low-polar diastereomeric mixture (peak-1 and peak-2; peak-1 and peak-2 had the same axial chirality) and (2) a high-polar diastereomeric mixture (peak-3 and peak-4; peak-3 and peak-4 had the same axial chirality) were obtained. Of these fractions, the fractions containing the low-polar diastereomeric mixture (peak-1 and peak-2, the same axial chirality) were collected, thus obtaining tert-butyl (1S,4S)-5-{8-(benzyloxy)-6-cyclopropyl-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (1.42 g) as a foam-like solid. In addition, the fractions containing the high-polar diastereomeric mixture (peak-3 and peak-4, the same axial chirality) were collected, thus obtaining tert-butyl (1S,4S)-5-{8-(benzyloxy)-6-cyclopropyl-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (1.37 g) as a foam-like solid. The low-polar diastereomeric mixture was used for the subsequent reaction.

Production Example 14

To a MeOH (200 mL) solution of tert-butyl (1S,4S)-5-{8-(benzyloxy)-6-cyclopropyl-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (10 g) which was the low-polar diastereomeric mixture obtained in Production Example 11 was added 10% Pd/C (50% water content, 2 g), and the reaction mixture was stirred under hydrogen atmosphere at room temperature for 2 hours. The resulting reaction mixture was filtered through celite pad and was washed with MeOH. The filtrate was concentrated under reduced pressure, and the resulting residue was purified by silica gel column chromatography (hexane/ethyl acetate), thus obtaining tert-butyl (1S,4S)-5-{6-cyclopropyl-7-[6-fluoro-5-methyl-1-(oxan-2-yl)-1H-indazol-4-yl]-8-hydroxy-2-[(oxan-4-yl)oxy]quinazolin-4-yl}-2,5-diazabicyclo[2.2.1]heptane-2-carboxylate (8.11 g) as a foam-like solid.

Production Example 22

To a mixture of tert-butyl (1S,4S)-5-{6-cyclopropyl-7-[6-fluoro-5-methyl-1-(oxan-2-yl)-1H-indazol-4-yl]-8-hydroxy-2-[(oxan-4-yl)oxy]quinazolin-4-yl}-2,5-diazabicyclo[2.2.1]heptane-2-carboxylate (7.48 g), DMF (70 mL) and 1-(chloromethyl)-4-ethynylbenzene (1.9 g) was added cesium carbonate (6.2 g) with stirring at room temperature, and the mixture was stirred under an argon atmosphere at 60° C. for 2 hours. To the reaction mixture which was allowed to cool to room temperature, ice water and saturated aqueous ammonium chloride solution were added, and the mixture was extracted with ethyl acetate. The organic layer was washed with saturated aqueous sodium chloride solution and was dried over anhydrous magnesium sulfate. Then, the insoluble materials were removed by filtration, and the filtrate was concentrated under reduced pressure. The resulting residue was purified by silica gel column chromatography (basic silica gel, hexane/ethyl acetate), and the resulting solid was filtered to give tert-butyl (1S,4S)-5-{6-cyclopropyl-8-[(4-ethynylphenyl)methoxy]-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (8.12 g) as a foam-like solid.

Production Example 32

To a $CH_2Cl_2$ (13 mL) solution of tert-butyl (1S,4S)-5-{8-(benzyloxy)-6-cyclopropyl-2-(dodecylsulfanyl)-7-[6-fluoro-5-methyl-1-(oxan-2-yl)-1H-indazol-4-yl]quinazolin-4-yl}-2,5-diazabicyclo[2.2.1]heptane-2-carboxylate (1.3 g) was added m-chloroperbenzoic acid (about 30% water content, 358 mg) under ice-bath cooling, and the mixture was stirred at the same temperature for 2 hours. Under ice-bath cooling, 10% aqueous sodium thiosulfate solution and saturated aqueous sodium hydrogen carbonate solution were added to the reaction mixture. The aqueous layer and the organic layer were separated, and the resulting aqueous layer was extracted with ethyl acetate. The resulting organic layers were mixed and were dried over anhydrous magnesium sulfate. The resulting solution was concentrated under reduced pressure, thus obtaining tert-butyl (1S,4S)-5-{8-(benzyloxy)-6-cyclopropyl-2-(dodecane-1-sulfinyl)-7-[6-fluoro-5-methyl-1-(oxan-2-yl)-1H-indazol-4-yl]quinazolin-4-yl}-2,5-diazabicyclo[2.2.1]heptane-2-carboxylate (1.32 g) as an oil.

Production Example 34

To a mixture of tert-butyl (1S,4S)-5-{8-(benzyloxy)-6-cyclopropyl-2-(dodecane-1-sulfinyl)-7-[6-fluoro-5-methyl-1-(oxan-2-yl)-1H-indazol-4-yl]quinazolin-4-yl}-2,5-diazabicyclo[2.2.1]heptane-2-carboxylate (1.32 g), DMAc (15 mL) and 4-ethyl-3-hydroxypyridine (525 mg) were added cesium carbonate (1.9 g) and DABCO (160 mg) at room temperature, and under nitrogen atmosphere, the mixture was stirred at 80° C. for 2 hours and at 100° C. for 2 hours. After the mixture was allowed to cool to room temperature, water was added to the reaction mixture, and the mixture was extracted with ethyl acetate. The organic layer was washed with water and saturated aqueous sodium chloride solution and was then dried over anhydrous sodium sulfate, and the solution was concentrated under reduced pressure. The resulting residue was purified by silica gel column chromatography (hexane/ethyl acetate), thus obtaining tert-butyl (1S,4S)-5-{8-(benzyloxy)-6-cyclopropyl-2-[(4-ethylpyridin-3-yl)oxy]-7-[6-fluoro-5-methyl-1-(oxan-2-yl)-1H-indazol-4-yl]quinazolin-4-yl}-2,5-diazabicyclo[2.2.1]heptane-2-carboxylate (774 mg) as an oil.

Production Example 36

To a mixture of tert-butyl (1S,4S)-5-{8-(benzyloxy)-6-cyclopropyl-2-(ethylsulfanyl)-7-[6-fluoro-5-methyl-1-(oxan-2-yl)-1H-indazol-4-yl]quinazolin-4-yl}-2,5-diazabicyclo[2.2.1]heptane-2-carboxylate (10 g) and CH$_2$Cl$_2$ (150 mL) was added m-chloroperbenzoic acid (about 30% water content, 3.3 g) under ice-bath cooling, and the mixture was stirred at the same temperature for 3 hours. Under ice-bath cooling, saturated aqueous sodium thiosulfate solution and saturated aqueous sodium hydrogen carbonate solution were added to the reaction mixture, and the mixture was stirred for a while. The aqueous layer and the organic layer were separated, and the resulting aqueous layer was extracted with CH$_2$Cl$_2$. The resulting organic layers were mixed and were dried over anhydrous magnesium sulfate. The drying agent was removed by filtration, and the resulting solution was concentrated under reduced pressure, thus obtaining an oxidized compound as a foam-like solid. The resulting foam-like solid was dissolved in THE (100 mL), and 2-(trimethylsilyl)ethyl 4-hydroxypiperidine-1-carboxylate (4.17 g) and tBuOK (2.2 g) were added under an argon atmosphere under cooling in an ice/MeOH bath. The mixture was stirred at room temperature for 30 minutes. Saturated aqueous ammonium chloride solution, water and ethyl acetate were added under ice cooling, and the aqueous layer was extracted with ethyl acetate, and the combined organic layer was washed with water and saturated aqueous sodium chloride solution and was dried over anhydrous magnesium sulfate. After separating the drying agent by filtration, the filtrate was concentrated under reduced pressure. The residue was purified by silica gel column chromatography (basic silica gel, hexane/ethyl acetate), and fractions respectively containing (1) a low-polar diastereomeric mixture (peak-1 and peak-2; peak-1 and peak-2 had the same axial chirality) and (2) a high-polar diastereomeric mixture (peak-3 and peak-4; peak-3 and peak-4 had the same axial chirality) were obtained. Of these fractions, the fractions containing the low-polar diastereomeric mixture (peak-1 and peak-2, the same axial chirality) was collected, thus obtaining tert-butyl (1S,4S)-5-{8-(benzyloxy)-6-cyclopropyl-7-[6-fluoro-5-methyl-1-(oxan-2-yl)-1H-indazol-4-yl]-2-[(1-{[2-(trimethylsilyl)ethoxy]carbonyl}piperidin-4-yl)oxy]quinazolin-4-yl}-2,5-diazabicyclo[2.2.1]heptane-2-carboxylate (3.77 g) as an oil. In addition, the fractions containing the high-polar diastereomeric mixture (peak-3 and peak-4, the same axial chirality) was collected, thus obtaining tert-butyl (1S,4S)-5-{8-(benzyloxy)-6-cyclopropyl-7-[6-fluoro-5-methyl-1-(oxan-2-yl)-1H-indazol-4-yl]-2-[(1-{[2-(trimethylsilyl)ethoxy]carbonyl}piperidin-4-yl)oxy]quinazolin-4-yl}-2,5-diazabicyclo[2.2.1]heptane-2-carboxylate (1.75 g) as a solid. The low-polar diastereomeric mixture was used for the subsequent reaction.

Production Example 37

Under an argon atmosphere, to a mixture of tert-butyl (1S,4S)-5-{8-(benzyloxy)-6-cyclopropyl-2-(ethanesulfinyl)-7-[6-fluoro-5-methyl-1-(oxan-2-yl)-1H-indazol-4-yl]quinazolin-4-yl}-2,5-diazabicyclo[2.2.1]heptane-2-carboxylate (935 mg), (3S)-oxolan-3-ol (163 μL) and THE (10 mL) was added tBuOK (269 mg) under cooling in an ice/MeOH bath, and the mixture was stirred at room temperature for 3 hours. Saturated aqueous ammonium chloride solution was added under ice-bath cooling, and the mixture was extracted twice with ethyl acetate. The combined organic layer was washed with water and saturated aqueous sodium chloride solution and was dried over anhydrous magnesium sulfate. The drying agent was removed by filtration, and the filtrate was concentrated under reduced pressure. The resulting residue was purified by silica gel column chromatography (hexane/ethyl acetate), and fractions respectively containing (1) a low-polar diastereomeric mixture (peak-1 and peak-2; peak-1 and peak-2 had the same axial chirality) and (2) a high-polar diastereomeric mixture (peak-3 and peak-4; peak-3 and peak-4 had the same axial chirality) were obtained. Of these fractions, the fractions containing the low-polar diastereomeric mixture (peak-1 and peak-2, the same axial chirality) was collected, thus obtaining tert-butyl (1S,4S)-5-[8-(benzyloxy)-6-cyclopropyl-7-[6-fluoro-5-methyl-1-(oxan-2-yl)-1H-indazol-4-yl]-2-{[(3S)-oxolan-3-yl]oxy}quinazolin-4-yl]-2,5-diazabicyclo[2.2.1]heptane-2-carboxylate (346 mg) as a solid. In addition, the fractions containing the high-polar diastereomeric mixture (peak-3 and peak-4, the same axial chirality) was collected, thus obtaining tert-butyl (1S,4S)-5-[8-(benzyloxy)-6-cyclopropyl-7-[6-fluoro-5-methyl-1-(oxan-2-yl)-1H-indazol-4-yl]-2-{[(3S)-oxolan-3-yl]oxy}quinazolin-4-yl]-2,5-diazabicyclo[2.2.1]heptane-2-carboxylate (329 mg) as a solid. The low-polar diastereomeric mixture was used for the subsequent reaction.

Production Example 40

To a mixture of tert-butyl (1S,4S)-5-{6-cyclopropyl-8-[(4-ethynylphenyl)methoxy]-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (4.24 g), (4R)-1-[(2S)-2-azido-3-methylbutanoyl]-4-hydroxy-N-{(1R)-2-hydroxy-1-[4-(4-methyl-1,3-thiazol-5-yl)phenyl]ethyl}-L-prolinamide (2.30 g), sodium ascorbate (1.45 g), tert-butyl alcohol (35 mL), THF (35 mL) and water (35 mL) was added anhydrous copper(II) sulfate (389 mg) at room temperature, and the mixture was stirred at room temperature for 2.5 hours. Ethyl acetate and water were added, and the aqueous layer was extracted with ethyl acetate, and the combined organic layer was washed with saturated aqueous sodium chloride solution and was dried over anhydrous sodium sulfate. The insoluble materials were removed by filtration, and the filtrate was concentrated under reduced pressure. The residue was purified by silica gel column chromatography (CHCl$_3$/MeOH), thus obtaining tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1- oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (5.62 g) as a solid.

Production Example 51

Under an argon atmosphere, to a mixture of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-[(1-{[2-(trimethylsilyl)ethoxy]carbonyl}piperidin-4-yl)oxy]quinazolin-4-yl}-2,5-diazabicyclo[2.2.1]heptane-2-carboxylate (1.1 g), THF (22 mL) and tetra-n-butylammonium fluoride (1M THF solution, 2.57 mL) was added acetic acid (90 μL) at room temperature, and the mixture was stirred at 60° C. for 15 hours. After the mixture was allowed to cool to room temperature, ethyl acetate and saturated aqueous ammonium chloride solution were added, and the mixture was separated into layers. The aqueous layer was extracted with ethyl acetate/methanol (10/1), and the combined organic layer was washed with saturated aqueous sodium chloride solution and was dried over anhydrous sodium sulfate. The insoluble materials were removed by filtration, and the filtrate was concentrated under reduced pressure. The residue was purified by silica gel column chromatography (basic silica gel, CHCl$_3$/MeOH), thus obtaining tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-[(piperidin-4-yl)oxy]quinazolin-4-yl}-2,5-diazabicyclo[2.2.1]heptane-2-carboxylate (951 mg) as a solid.

Production Example 52

To a mixture of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-[(piperidin-4-yl)oxy]quinazolin-4-yl}-2,5-diazabicyclo[2.2.1]heptane-2-carboxylate (250 mg), oxetan-3-one (43 mg) and CH$_2$Cl$_2$ (3 mL) was added sodium triacetoxyborohydride (122 mg) at room temperature, and the mixture was stirred at room temperature for 16 hours. Saturated aqueous sodium hydrogen carbonate solution was added, and the mixture was stirred at room temperature for 10 minutes. The mixture was extracted with CHCl$_3$/MeOH (5/1), and the combined organic layer was dried over anhydrous sodium sulfate. The insoluble materials were removed by filtration, and the filtrate was concentrated under reduced pressure. The residue was purified by silica gel column chromatography (CHCl$_3$/MeOH), thus obtaining tert-butyl (1S,4S)-5-(6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-{[1-(oxetan-3-yl)piperidin-4-yl]oxy}quinazolin-4-yl)-2,5-diazabicyclo[2.2.1]heptane-2-carboxylate (220 mg) as a solid.

Production Example 53

To a mixture of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-[(piperidin-4-yl)oxy]quinazolin-4-yl}-2,5-diazabicyclo[2.2.1]heptane-2-carboxylate (250 mg), 2,2-difluoroethyl trifluoromethanesulfonate (124 mg) and MeCN (3 mL) was added DIPEA (99 μL) at room temperature, and the mixture was stirred at room temperature for 16 hours. The mixture was concentrated under reduced pressure, and the residue was purified by silica gel column chromatography (CHCl$_3$/MeOH), thus obtaining tert-butyl (1S,4S)-5-(6-cyclopropyl-2-{[1-(2,2-difluoroethyl)piperidin-4-yl]oxy}-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}quinazolin-4-yl)-2,5-diazabicyclo[2.2.1]heptane-2-carboxylate (196 mg) as a solid.

Production Example 54

To a CH$_2$Cl$_2$ (12 mL) solution of methyl (2S)-2-[5-(hydroxymethyl)-1-oxo-1,3-dihydro-2H-isoindol-2-yl]-3-methylbutanoate (190 mg) was added thionyl chloride (500 μL) under an argon atmosphere under ice-bath cooling, and the mixture was stirred at the same temperature for 2 hours. The reaction mixture was concentrated under reduced pressure, and to the resulting residue, DMF (7 mL), tert-butyl (1S,4S)-5-{6-cyclopropyl-7-[6-fluoro-5-methyl-1-(oxan-2-yl)-1H-indazol-4-yl]-8-hydroxy-2-[(oxan-4-yl)oxy]quinazolin-4-yl}-2,5-diazabicyclo[2.2.1]heptane-2-carboxylate (450 mg) and cesium carbonate (260 mg) were added under ice-bath cooling. The mixture was stirred at 60° C. overnight under an argon atmosphere. The reaction solution was filtered through celite pad, and the residue on the celite pad was washed with ethyl acetate. The filtrate was concentrated under reduced pressure, and the resulting residue was purified by silica gel column chromatography (basic silica gel, hexane/ethyl acetate), thus obtaining tert-butyl (1S,4S)-5-{6-cyclopropyl-7-[6-fluoro-5-methyl-1-(oxan-2-yl)-1H-indazol-4-yl]-8-({2-[(2S)-1-methoxy-3-methyl-1-oxobutan-2-yl]-1-oxo-2,3-dihydro-1H-isoindol-5-yl}methoxy)-2-[(oxan-4-yl)oxy]quinazolin-4-yl}-2,5-diazabicyclo[2.2.1]heptane-2-carboxylate (670 mg) as a foam-like solid.

Production Example 56

To a MeOH (7 mL) solution of tert-butyl (1S,4S)-5-{6-cyclopropyl-7-[6-fluoro-5-methyl-1-(oxan-2-yl)-1H-indazol-4-yl]-8-({2-[(2S)-1-methoxy-3-methyl-1-oxobutan-2-yl]-1-oxo-2,3-dihydro-1H-isoindol-5-yl}methoxy)-2-[(oxan-4-yl)oxy]quinazolin-4-yl}-2,5-diazabicyclo[2.2.1]heptane-2-carboxylate (670 mg) was added aqueous sodium hydroxide solution (1 M, 2.5 mL) under ice-bath cooling, and the mixture was stirred for 3 days at room temperature. Under ice-bath cooling, hydrochloric acid (1M, 2.5 mL) was added to neutralize the mixture. Then, CHCl$_3$ and water were added to divide the mixture into layers, and the aqueous layer was extracted with CHCl$_3$. The combined organic layer was dried over anhydrous sodium sulfate. Then, the insoluble materials were removed by filtration, and the filtrate was concentrated under reduced pressure. The resulting residue was purified by silica gel column chromatography (CHCl$_3$/MeOH) and then was again purified by silica gel column chromatography (basic silica gel, CHCl$_3$/MeOH), thus obtaining (2S)-2-{5-[({4-[(1S,4S)-5-

(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]-1-oxo-1,3-dihydro-2H-isoindol-2-yl}-3-methylbutanoic acid (372 mg) as a foam-like solid.

Production Example 61

To a 1, 2-dichloroethane (60 mL) solution of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-(methoxycarbonyl)pyrrolidin-1-yl]-3-methyl-1-oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (3.97 g) was added trimethyltin (IV) hydroxide (3.35 g) at room temperature, and the mixture was stirred at 80° C. for 18 hours. After the mixture was allowed to cool to room temperature, hydrochloric acid (1M, 60 mL) was added, and the mixture was extracted with CHCl$_3$/MeOH (9/1). The organic layer was washed with 1M hydrochloric acid and was dried over anhydrous sodium sulfate. The insoluble materials were removed by filtration, and the filtrate was concentrated under reduced pressure. The residue was purified by silica gel column chromatography (CHCl$_3$/MeOH), thus obtaining (4R)-1-[(2S)-2-(4-{4-[({4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]phenyl}-1H-1,2,3-triazol-1-yl)-3-methylbutanoyl]-4-hydroxy-L-proline (3.26 g) as a solid.

Production Example 63

To a mixture of (4R)-1-[(2S)-2-(4-{4-[({4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]phenyl}-1H-1,2,3-triazol-1-yl)-3-methylbutanoyl]-4-hydroxy-L-proline (150 mg), 3-{4-[(1R)-1-amino-2-hydroxyethyl]phenyl}-1,3-oxazolidin-2-one hydrochloride (60 mg), DIPEA (70 μL) and DMF (3 mL) was added HATU (70 mg) under ice-bath cooling, and the mixture was stirred under ice-bath cooling for 1 hour. Water, saturated aqueous sodium chloride solution and ethyl acetate were added to the mixture, and the aqueous layer was extracted with ethyl acetate, and the combined organic layer was washed with water and saturated aqueous sodium chloride solution and was dried over anhydrous magnesium sulfate. The insoluble materials were removed by filtration, and the filtrate was concentrated under reduced pressure. The residue was purified by silica gel column chromatography (CHCl$_3$/MeOH), thus obtaining tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(2-oxo-1,3-oxazolidin-3-yl)phenyl]ethyl}carbamoyl)pyrrolidin-1-yl]-3-methyl-1-oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (173 mg) as a solid.

Production Example 66

A mixture of tert-butyl (1S,4S)-5-{8-(benzyloxy)-7-bromo-6-cyclopropyl-2-[(oxan-4-yl)oxy]quinazolin-4-yl}-2,5-diazabicyclo[2.2.1]heptane-2-carboxylate (6.5 g), 4,4,4',4',5,5,5',5'-octamethyl-2,2'-bi-1,3,2-dioxaborolane (7.6 g), triphenylphosphine (0.53 g), potassium acetate (4.9 g), DOX (120 mL) and palladium acetate (0.23 g) was degassed, was substituted with argon gas and was stirred at 115° C. overnight. The reaction solution which was allowed to cool to room temperature was filtered through celite pad while washing the celite pad with a small amount of dioxane, and the filtrate was concentrated under reduced pressure. The residue was purified by silica gel column chromatography (hexane/ethyl acetate), thus obtaining tert-butyl (1S,4S)-5-[8-(benzyloxy)-6-cyclopropyl-2-[(oxan-4-yl)oxy]-7-(4,4,5,5-tetramethyl-1,3,2-dioxaborolan-2-yl)quinazolin-4-yl]-2,5-diazabicyclo[2.2.1]heptane-2-carboxylate (5.47 g) as a foam-like solid.

Production Example 67

Tert-butyl (1S,4S)-5-[8-(benzyloxy)-6-cyclopropyl-2-[(oxan-4-yl)oxy]-7-(4,4,5,5-tetramethyl-1,3,2-dioxaborolan-2-yl)quinazolin-4-yl]-2,5-diazabicyclo[2.2.1]heptane-2-carboxylate (1.52 g), (3-bromo-5-fluoro-4-methylphenoxy)(tert-butyl)di(methyl)silane (0.84 g), tripotassium phosphate (1.85 g), dicyclohexyl(2',6'-diisopropoxy-[1,1'-biphenyl]-2-yl)phosphine (0.15 g), (2-dicyclohexylphosphino-2',6'-diisopropoxy-1,1'-biphenyl)[2-(2'-amino-1,1'-biphenyl)]palladium(II) methanesulfonate (0.27 g), DOX (20 mL) and water (4 mL) were sequentially added, and while stirring the mixture at room temperature, degassing/argon gas substitution operation was performed. Then, the mixture was stirred under an argon atmosphere at 90° C. for 5 hours. The mixture was further stirred at 100° C. for 7 hours. The reaction solution which was allowed to cool to room temperature was diluted with water and extracted with ethyl acetate. The organic layer was dried over anhydrous magnesium sulfate, and the solution was concentrated under reduced pressure. The resulting residue was purified by silica gel column chromatography (basic silica gel, hexane/ethyl acetate), thus obtaining fractions respectively containing (1) a low-polarity diastereomer (peak-1) and (2) a high-polarity diastereomer (peak-2). Of these fractions, the fractions containing the low-polar diastereomer (peak-1) were collected, thus obtaining tert-butyl (1S,4S)-5-{8-(benzyloxy)-6-cyclopropyl-7-(3-fluoro-5-hydroxy-2-methylphenyl)-2-[(oxan-4-yl)oxy]quinazolin-4-yl}-2,5-diazabicyclo[2.2.1]heptane-2-carboxylate (580 mg) as a foam-like solid. In addition, the fractions containing the high-polar diastereomer (peak-2) were collected, thus obtaining tert-butyl (1S,4S)-5-{8-(benzyloxy)-6-cyclopropyl-7-(3-fluoro-5-hydroxy-2-methylphenyl)-2-[(oxan-4-yl)oxy]quinazolin-4-yl}-2,5-diazabicyclo[2.2.1]heptane-2-carboxylate (360 mg) as a foam-like solid. The low-polar diastereomer was used for the subsequent reaction.

Production Example 68

Under nitrogen atmosphere, to a DMF (5 mL) solution of tert-butyl (1S,4S)-5-{8-(benzyloxy)-6-cyclopropyl-7-(3-fluoro-5-hydroxy-2-methylphenyl)-2-[(oxan-4-yl)oxy]quinazolin-4-yl}-2,5-diazabicyclo[2.2.1]heptane-2-carboxylate (250 mg) were added cesium carbonate (180 mg) and chloro(methoxy)methane (35 μL) under ice-bath cooling, and the mixture was stirred at room temperature for 15 hours.

Under ice-bath cooling, cesium carbonate (260 mg) and chloro(methoxy)methane (50 μL) were added, and the mixture was further stirred at room temperature for 2 hours. The reaction mixture was diluted with ethyl acetate, and water and saturated aqueous sodium chloride solution were added to wash the mixture. After the organic layer was dried over anhydrous magnesium sulfate, the insoluble materials were removed by filtration, and the filtrate was concentrated under reduced pressure.

The resulting residue was purified by silica gel column chromatography (hexane/ethyl acetate), thus obtaining tert-butyl (1S,4S)-5-{8-(benzyloxy)-6-cyclopropyl-7-[3-fluoro-5-(methoxymethoxy)-2-methylphenyl]-2-[(oxan-4-yl)oxy]quinazolin-4-yl}-2,5-diazabicyclo[2.2.1]heptane-2-carboxylate (186 mg) as an oil.

Production Example 69

Under an argon atmosphere, to a mixture of tert-butyl N-[(1R)-1-(4-bromophenyl)-2-hydroxyethyl]carbamate (4.43 g), 1-ethyl-5-(4,4,5,5-tetramethyl-1,3,2-dioxaborolan-2-yl)-1H-pyrazole (4.67 g), potassium carbonate (3.87 g), DOX (80 mL) and water (8 mL) was added $PdCl_2(dppf) \cdot CH_2Cl_2$ (1.14 g), and the mixture was stirred at 100° C. for 16 hours. After the mixture was allowed to cool to room temperature, ethyl acetate was added, and the mixture was filtered through celite pad and was concentrated under reduced pressure. The residue was purified by silica gel column chromatography (basic silica gel, hexane/ethyl acetate), thus obtaining tert-butyl {(1R)-1-[4-(1-ethyl-1H-pyrazol-5-yl)phenyl]-2-hydroxyethyl}carbamate (3.74 g) as a solid.

Production Example 71

To a solution in $CH_2Cl_2$ (25 mL) and MeOH (25 mL) of tert-butyl {(1R)-1-[4-(1-ethyl-1H-pyrazol-5-yl)phenyl]-2-hydroxyethyl}carbamate (3.34 g), hydrogen chloride (4M DOX solution, 25.6 mL) was added at −20 to −10° C., and the mixture was stirred at room temperature for 5 hours. The reaction mixture was concentrated under reduced pressure, thus obtaining (2R)-2-amino-2-[4-(1-ethyl-1H-pyrazol-5-yl)phenyl]ethan-1-ol n hydrochloride (3.06 g) as a solid.

Production Example 73

To a mixture of (2R)-2-amino-2-[4-(1-ethyl-1H-pyrazol-5-yl)phenyl]ethan-1-ol n hydrochloride (3.43 g), (4R)-1-(tert-butoxycarbonyl)-4-hydroxy-L-proline (2.81 g) and DMF (40 mL) was added DIPEA (7.8 mL) under ice-bath cooling, and then HATU (4.5 g) was added portionwise under ice-bath cooling. The mixture was stirred for 1 hour under ice-bath cooling and for 1 hour at room temperature. Under ice-bath cooling, water, saturated aqueous sodium chloride solution and ethyl acetate were added, and the aqueous layer was extracted with ethyl acetate and then was extracted with ethyl acetate/isopropyl alcohol (9/1). The organic layer was washed with saturated aqueous sodium chloride solution and was dried over anhydrous magnesium sulfate. The insoluble materials were removed by filtration, and the filtrate was concentrated under reduced pressure. The residue was purified by silica gel column chromatography ($CHCl_3$/MeOH), thus obtaining tert-butyl (2S,4R)-2-({(1R)-1-[4-(1-ethyl-1H-pyrazol-5-yl)phenyl]-2-hydroxyethyl}carbamoyl)-4-hydroxypyrrolidine-1-carboxylate (5.01 g) as an oil.

Production Example 76

To a solution in $CH_2Cl_2$ (35 mL) and MeOH (30 mL) of tert-butyl (2S,4R)-2-({(1R)-1-[4-(1-ethyl-1H-pyrazol-5-yl)phenyl]-2-hydroxyethyl}carbamoyl)-4-hydroxypyrrolidine-1-carboxylate (5.01 g) was added hydrogen chloride (4M DOX solution, 28 mL) at −20 to −10° C., and the mixture was stirred at room temperature for 5 hours. The reaction mixture was concentrated under reduced pressure, thus obtaining (4R)-N-{(1R)-1-[4-(1-ethyl-1H-pyrazol-5-yl)phenyl]-2-hydroxyethyl}-4-hydroxy-L-prolinamide n hydrochloride (4.71 g) as a solid.

Production Example 79

To a mixture of (4R)-4-hydroxy-N-{(1R)-2-hydroxy-1-[4-(4-methyl-1,3-thiazol-5-yl)phenyl]ethyl}-L-prolinamide n hydrochloride (3.81 g), N-(tert-butoxycarbonyl)-L-valine (2.16 g) and DMF (45 mL) was added DIPEA (6.2 mL), and then HATU (3.61 g) was added portionwise under ice-bath cooling. The mixture was stirred for 1 hour under ice-bath cooling and for 1 hour at room temperature. Under ice-bath cooling, water, saturated aqueous sodium chloride solution and ethyl acetate were added, and the aqueous layer was extracted with ethyl acetate and then was extracted with ethyl acetate/isopropyl alcohol (9/1). The combined organic layer was washed with saturated aqueous sodium chloride solution and was dried over anhydrous sodium sulfate. The insoluble materials were removed by filtration, and the filtrate was concentrated under reduced pressure. The residue was purified by silica gel column chromatography ($CHCl_3$/MeOH), thus obtaining N-(tert-butoxycarbonyl)-L-valyl-(4R)-4-hydroxy-N-{(1R)-2-hydroxy-1-[4-(4-methyl-1,3-thiazol-5-yl)phenyl]ethyl}-L-prolinamide (4.43 g) as a solid.

Production Example 83

To a solution in $CH_2Cl_2$ (35 mL) and MeOH (35 mL) of N-(tert-butoxycarbonyl)-L-valyl-(4R)-4-hydroxy-N-{(1R)-2-hydroxy-1-[4-(4-methyl-1,3-thiazol-5-yl)phenyl]ethyl}-L-prolinamide (4.43 g) was added hydrogen chloride (4M DOX solution, 20 mL) under cooling at −20 to −15° C., and the mixture was stirred at room temperature for 6 hours. The reaction mixture was concentrated under reduced pressure, thus obtaining L-valyl-(4R)-4-hydroxy-N-{(1R)-2-hydroxy-1-[4-(4-methyl-1,3-thiazol-5-yl)phenyl]ethyl}-L-prolinamide n hydrochloride (4.21 g) as a solid.

Production Example 88

To a mixture of L-valyl-(4R)-4-hydroxy-N-{(1R)-2-hydroxy-1-[4-(4-methyl-1,3-thiazol-5-yl)phenyl]ethyl}-L-prolinamide n hydrochloride (1.71 g), TEA (3.2 mL), THF (20 mL) and MeCN (20 mL) was added a MeCN (5 mL) solution of 2-azido-1,3-dimethylimidazolinium hexafluorophosphate (1.06 g) dropwise slowly over 10 minutes or more under ice-bath cooling, and the mixture was stirred under ice-bath cooling for 5 hours. Water, saturated aqueous sodium chloride solution and ethyl acetate were added, and the aqueous layer was extracted with ethyl acetate, and the combined organic layer was dried over anhydrous sodium sulfate. The insoluble materials were removed by filtration, and the filtrate was concentrated under reduced pressure. The residue was purified by silica gel column chromatography ($CHCl_3$/MeOH), thus obtaining (4R)-1-[(2S)-2-azido-3-methylbutanoyl]-4-hydroxy-N-{(1R)-2-hydroxy-1-[4-(4-methyl-1,3-thiazol-5-yl)phenyl]ethyl}-L-prolinamide (1.07 g) as a solid.

Production Example 93

To a mixture of L-valine methyl ester hydrochloride (1.96 g), MeCN (45 mL) and DIPEA (5 mL) was added methyl 4-bromo-2-(bromomethyl)benzoate (3.00 g) under water-bath cooling, and the temperature was slowly increased to 80° C. The mixture was stirred at 80° C. for 2 days. After the mixture was allowed to cool to room temperature, ethyl acetate and water were added, and the mixture was extracted with ethyl acetate. The combined organic layer was washed with saturated aqueous sodium chloride solution and was dried over anhydrous sodium sulfate. The insoluble materials were removed by filtration, and the filtrate was concentrated under reduced pressure. The residue was purified by silica gel column chromatography (CHCl$_3$/ethyl acetate), thus obtaining methyl (2S)-2-(5-bromo-1-oxo-1,3-dihydro-2H-isoindol-2-yl)-3-methylbutanoate (2.86 g) as a solid.

Production Example 94

Under an argon atmosphere, to a mixture of methyl (2S)-2-(5-bromo-1-oxo-1,3-dihydro-2H-isoindol-2-yl)-3-methylbutanoate (600 mg), potassium (2-trimethylsilyl)-ethoxymethyltrifluoroborate (876 mg), dicyclohexyl(2',6'-dimethoxybiphenyl-2-yl)phosphine (151 mg), sodium carbonate (390 mg), DOX (9 mL) and water (1.8 mL), was added palladium acetate (41 mg) at room temperature, and under microwave irradiation, the mixture was stirred at 130° C. for 4 hours. After the mixture was allowed to cool to room temperature, ethyl acetate was added. Then, the mixture was filtered through celite pad, and the celite pad was washed with ethyl acetate. Water was added to the resulting filtrate to divide the mixture into layers, and the organic layer was washed with saturated aqueous sodium chloride solution. After the organic layer was dried over anhydrous sodium sulfate, the insoluble materials were removed by filtration, and the filtrate was concentrated under reduced pressure. The resulting residue was purified by silica gel column chromatography (basic silica gel, hexane/ethyl acetate), thus obtaining a coupling reaction product (600 mg). To a CH$_2$Cl$_2$ (4.2 mL) solution of the resulting coupling reaction product, trifluoroacetic acid (2.1 mL) was added under ice-bath cooling, and the mixture was stirred at room temperature for 2 hours. The mixture was concentrated under reduced pressure, and the resulting residue was purified by silica gel column chromatography (basic silica gel, hexane/ethyl acetate), thus obtaining methyl (2S)-2-[5-(hydroxymethyl)-1-oxo-1,3-dihydro-2H-isoindol-2-yl]-3-methylbutanoate (190 mg) as a solid.

Production Example 95

Under an argon atmosphere, to a mixture of ethyl 3-methyl-2-[4-(4,4,5,5-tetramethyl-1,3,2-dioxaborolan-2-yl)-1H-pyrazol-1-yl]butanoate (190 mg), 4-bromobenzyl alcohol (100 mg), PdCl$_2$(dppf)·CH$_2$Cl$_2$ (45 mg) and tripotassium phosphate (227 mg) were added DOX (2 mL) and water (0.4 mL), and the mixture was stirred at 100° C. for 12 hours. The reaction mixture was cooled to room temperature and was then filtered through celite pad, and the celite pad was washed with ethyl acetate. The filtrate was diluted with ethyl acetate, then was washed with water and saturated aqueous sodium chloride solution and was then dried over anhydrous magnesium sulfate. The insoluble materials were removed by filtration, and the filtrate was concentrated under reduced pressure. The resulting residue was purified by silica gel column chromatography (hexane/ethyl acetate), thus obtaining ethyl 2-{4-[4-(hydroxymethyl)phenyl]-1H-pyrazol-1-yl}-3-methylbutanoate (157 mg) as an oil.

Production Example 96

Under an argon atmosphere, to a THF (80 mL) solution of 2,2,6,6-tetramethylpyperidine (4.4 mL) was added n-butyl-lithium (1.57 M hexane solution, 15.2 mL) dropwise under cooling with a dry ice-MeOH bath (−78° C.), and the mixture was stirred under ice-bath cooling for 1 hour. While cooling the reaction mixture with a dry ice-MeOH bath, a THF (20 mL) solution of (3-bromo-5-fluorophenoxy)(tert-butyl)di(methyl)silane (5.21 g) was added, and the mixture was stirred at the same temperature for 1 hour. Methyl iodide (2.2 mL) was added dropwise to the reaction mixture, and the mixture was stirred at the same temperature for 1 hour. To the reaction mixture, saturated aqueous ammonium chloride solution was added, and the mixture was stirred while increasing the temperature to room temperature. Ethyl acetate was added to the reaction mixture to extract the reaction mixture, and the organic layer was washed with saturated aqueous sodium chloride solution and was then dried over anhydrous sodium sulfate. The insoluble materials were removed by filtration, and the filtrate was concentrated under reduced pressure. The resulting residue was purified by silica gel column chromatography (hexane/ethyl acetate), thus obtaining (3-bromo-5-fluoro-4-methylphenoxy)(tert-butyl)di(methyl)silane (5.13 g) as an oil.

Production Example 97

To a mixture of tert-butyl N-[(1R)-1-(4-bromophenyl)-2-hydroxyethyl]carbamate (500 mg), N-methyl-2-nitrobenzene sulfonamide (376 mg), tri-n-butylphosphine (0.51 mL) and THF (7 mL) was added 1,1'-azobis(N,N-dimethylformamide) (353 mg) portionwise under ice-bath cooling, and the mixture was stirred at room temperature for 8 hours. The mixture was diluted with ethyl acetate and was washed with saturated aqueous sodium hydrogen carbonate solution, water and saturated aqueous sodium chloride solution and was then dried over anhydrous magnesium sulfate. The insoluble materials were removed by filtration, and the filtrate was concentrated under reduced pressure. The residue was purified by silica gel chromatography (hexane/ethyl acetate), thus obtaining tert-butyl {(1R)-1-(4-bromophenyl)-2-[methyl(2-nitrobenzene-1-sulfonyl)amino]ethyl}carbamate (667 mg) as a solid.

Production Example 98

Under an argon atmosphere, to a mixture of tert-butyl {(1R)-1-(4-bromophenyl)-2-[methyl(2-nitrobenzene-1-sulfonyl)amino]ethyl}carbamate (665 mg), 4-methyl-1,3-thiazole (235 μL), potassium acetate (253 mg) and DMAc (13 mL) was added palladium acetate (29 mg), and the mixture was stirred at 100° C. for 16 hours. After the mixture was allowed to cool to room temperature, ethyl acetate and water were added, and the insoluble materials were filtered through celite pad. The filtrate was divided into layers, and the aqueous layer was extracted with ethyl acetate. The combined organic layer was washed with water and saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining tert-butyl {(1R)-2-[methyl(2-nitrobenzene-1-sulfonyl)amino]-1-[4-(4-methyl-1,3-thiazol-5-yl)phenyl]ethyl}carbamate (268 mg) as a solid.

Production Example 99

Under an argon atmosphere, to a mixture of tert-butyl {(1R)-2-[methyl(2-nitrobenzene-1-sulfonyl)amino]-1-[4-(4-methyl-1,3-thiazol-5-yl)phenyl]ethyl}carbamate (130 mg), potassium carbonate (84 mg) and DMF (1.3 mL) was added 4-tert-butylbenzenethiol (82 μL) at room temperature, and the mixture was stirred at room temperature for 3 hours. Ethyl acetate and water were added, and the aqueous layer was extracted with ethyl acetate, and the combined organic layer was washed with water and saturated aqueous sodium chloride solution and was dried over anhydrous sodium sulfate. The insoluble materials were removed by filtration, and the filtrate was concentrated under reduced pressure. The residue was purified by silica gel column chromatography (CHCl$_3$/MeOH), thus obtaining tert-butyl {(1R)-2-(methylamino)-1-[4-(4-methyl-1,3-thiazol-5-yl)phenyl]ethyl}carbamate (60 mg) as an oil.

Production Example 100

To a mixture of tert-butyl {(1R)-2-(methylamino)-1-[4-(4-methyl-1,3-thiazol-5-yl)phenyl]ethyl}carbamate (55 mg) and THF (1 mL) was added formaldehyde (37% aqueous solution, 26 μL) under ice-bath cooling, and the mixture was stirred under the same conditions for 10 minutes. Sodium triacetoxyborohydride (67 mg) was added thereto, and the mixture was stirred at room temperature for 1 hour. CHCl$_3$ was added to dilute the mixture, and then saturated aqueous sodium hydrogen carbonate solution was added. The mixture was stirred for a while, and the aqueous layer was extracted with CHCl$_3$/MeOH (5/1), and the combined organic layer was dried over anhydrous sodium sulfate. The insoluble materials were removed by filtration, and the filtrate was concentrated under reduced pressure, thus obtaining tert-butyl {(1R)-2-(dimethylamino)-1-[4-(4-methyl-1,3-thiazol-5-yl)phenyl]ethyl}carbamate (75 mg) as an oil.

Production Example 102

A mixture of tert-butyl N-[(1R)-1-(4-bromophenyl)-2-hydroxyethyl]carbamate (2.04 g), 4,4,4',4',5,5,5',5'-octamethyl-2,2'-bi-1,3,2-dioxaborolane (2.05 g), potassium acetate (1.91 g), DOX (40 mL) and bis(triphenylphosphine) palladium(II) dichloride (460 mg) was stirred under an argon atmosphere at 100° C. overnight. The reaction solution which was allowed to cool to room temperature was diluted with ethyl acetate, and the mixture was filtered through celite pad. The filtrate was washed with water and saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining tert-butyl {(1R)-2-hydroxy-1-[4-(4,4,5,5-tetramethyl-1,3,2-dioxaborolan-2-yl)phenyl]ethyl}carbamate (3.21 g) as an oil.

Production Example 103

Under an argon atmosphere, to a mixture of tert-butyl {(1R)-2-hydroxy-1-[4-(4,4,5,5-tetramethyl-1,3,2-dioxaborolan-2-yl)phenyl]ethyl}carbamate (3.21 g), 5-bromo-1,3-thiazol-4-carboxylic acid methyl ester (2.6 g), tripotassium phosphate (3.8 g), dicyclohexyl(2',6'-dimethoxybiphenyl-2-yl)phosphine (730 mg), DOX (30 mL) and water (6 mL) was added palladium acetate (200 mg) at room temperature, and the mixture was stirred at 100° C. for 3 hours. After the mixture was allowed to cool to room temperature, ethyl acetate was added, and the mixture was washed with water and saturated aqueous sodium chloride solution. After the organic layer was dried over anhydrous magnesium sulfate, the insoluble materials were removed by filtration, and the filtrate was concentrated under reduced pressure. The resulting residue was purified by silica gel column chromatography (hexane/ethyl acetate), thus obtaining methyl 5-(4-{(1R)-1-[(tert-butoxycarbonyl)amino]-2-hydroxyethyl}phenyl)-1,3-thiazol-4-carboxylate (1.48 g) as a solid.

Production Example 104

Under nitrogen atmosphere, to a CH$_2$Cl$_2$ (20 mL) solution of methyl 5-(4-{(1R)-1-[(tert-butoxycarbonyl)amino]-2-hydroxyethyl}phenyl)-1,3-thiazol-4-carboxylate (1.01 g) was added diisobutylaluminum hydride (1M toluene solution, 11 mL) dropwise under ice-bath cooling, and the mixture was stirred under ice-bath cooling for 1 hour. Under ice-bath cooling, the reaction was quenched with MeOH, and 10% aqueous sodium potassium tartrate solution (60 mL) and CHCl$_3$ were added. The mixture was stirred overnight. The mixture was divided into layers, and the aqueous layer was extracted with CHCl$_3$. The organic layer was dried over anhydrous sodium sulfate. The insoluble materials were removed by filtration, and the filtrate was concentrated under reduced pressure. The residue was dissolved in MeOH (10 mL), and sodium borohydride (350 mg) was added under ice-bath cooling. The mixture was stirred under ice-bath cooling for 1 hour. Water was added, and the mixture was extracted with CHCl$_3$. The organic layer was dried over anhydrous sodium sulfate. The insoluble materials were removed by filtration, and the filtrate was concentrated under reduced pressure. The residue was purified by silica gel column chromatography (CHCl$_3$/MeOH), thus obtaining tert-butyl [(1R)-2-hydroxy-1-{4-[4-(hydroxymethyl)-1,3-thiazol-5-yl]phenyl}ethyl]carbamate (588 mg) as a solid.

Production Example 106

To a mixture of tert-butyl N-[(1R)-1-(4-bromophenyl)-2-hydroxyethyl]carbamate (1 g), 2,2-dimethoxypropane (3.3 mL) and acetone (15 mL) was added a boron trifluoride-diethyl ether complex (26 μL), and the mixture was stirred at room temperature for 1 hour. TEA (66 μL) was added, and the mixture was stirred at room temperature for 10 minutes. The mixture was concentrated under reduced pressure, and the residue was purified by silica gel column chromatography (hexane/ethyl acetate), thus obtaining tert-butyl (4R)-4-(4-bromophenyl)-2,2-dimethyl-1,3-oxazolidine-3-carboxylate (1.09 g) as a solid.

Production Example 107

To a DOX (1.69 mL) solution of tert-butyl (4R)-4-(4-bromophenyl)-2,2-dimethyl-1,3-oxazolidine-3-carboxylate (300 mg) and 1,3-oxazolidin-2-one (183 mg) were added copper(I) iodide (32 mg), racemic-(1R,2R)-cyclohexane-1,2-diamine (20 μL) and potassium carbonate (290 mg) at room temperature. Under microwave irradiation, the mixture was stirred for 2 hours at 140° C. and for 1 hour at 150° C. Ethyl acetate and water were added, and the mixture was filtered through celite pad. The filtrate was concentrated under reduced pressure, and the residue was purified by silica gel column chromatography (hexane/ethyl acetate), thus obtaining tert-butyl (4R)-2,2-dimethyl-4-[4-(2-oxo-1,3-oxazolidin-3-yl)phenyl]-1,3-oxazolidine-3-carboxylate (120 mg) as a solid.

Production Example 109

To a THF (27 mL) solution of 1-(4-bromophenyl)-2-fluoroethanone (2.7 g) and (S)-2-methylpropane-2-sulfinamide (3.03 g) was added tetraisopropyl orthotitanate (11.1 g), and the mixture was stirred at 40° C. for 12 hours. Under ice-bath cooling (0-5° C.), a $BH_3$-THF complex (1 M THF solution, 18.4 mL) was added, and the mixture was stirred for 2 hours. After the reaction was quenched with water, the mixture was filtered through celite pad. The filtrate was extracted with ethyl acetate. The organic layer was washed with saturated aqueous sodium chloride solution and was dried over anhydrous sodium sulfate. Then, the insoluble materials were separated by filtration, and the solution was concentrated under reduced pressure. The resulting residue was purified by silica gel column chromatography (petroleum ether/ethyl acetate), thus obtaining (S)-N-[(1R)-1-(4-bromophenyl)-2-fluoroethyl]-2-methylpropane-2-sulfinamide (3.2 g) as an oil.

Production Example 156

Under nitrogen atmosphere, DIPEA (200 µL) was added to a $CH_2Cl_2$ (2 mL) solution of (4-ethynyl-3-fluorophenyl)methanol (110 mg) under ice-bath cooling, and then methanesulfonyl chloride (80 µL) was added. After the reaction mixture was stirred at room temperature overnight, water was added, and the mixture was extracted with $CHCl_3$. The organic layer was washed with water and saturated aqueous sodium chloride solution and was dried over anhydrous magnesium sulfate. The insoluble materials were removed by filtration, and the filtrate was concentrated under reduced pressure, thus obtaining 4-(chloromethyl)-1-ethynyl-2-fluorobenzene (122 mg) as an oil.

Production Example 189

To a mixture of tert-butyl (1S,4S)-5-{6-cyclopropyl-8-[(4-ethynylphenyl)methoxy]-7-(6-fluoro-5-methyl-1H-indazol-4-yl)-2-[(2-hydroxyethyl)amino]quinazolin-4-yl}-2,5-diazabicyclo[2.2.1]heptane-2-carboxylate (49 mg), tBuOH (0.5 mL), THF (0.5 mL) and water (0.5 mL), (4R)-1-[(2S)-2-azido-3-methylbutanoyl]-4-hydroxy-N-{(1R)-2-hydroxy-1-[4-(4-methyl-1,3-thiazol-5-yl)phenyl]ethyl}-L-prolinamide (33 mg), copper(I) iodide (7 mg) and sodium ascorbate (21 mg) were added at room temperature, and the mixture was stirred at 50° C. for 3 hours. Ice, 2% aqueous disodium ethylenediamine tetraacetate solution and saturated aqueous sodium chloride solution were poured into the reaction container, and the mixture was extracted with $CH_2Cl_2$ three times. The combined organic layer was dried over anhydrous magnesium sulfate. The insoluble materials were removed by filtration, and the residue obtained by concentration under reduced pressure was purified by silica gel column chromatography (basic silica gel, $CHCl_3$/MeOH), thus obtaining tert-butyl (1S,4S)-5-[6-cyclopropyl-7-(6-fluoro-5-methyl-1H-indazol-4-yl)-2-[(2-hydroxyethyl)amino]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}quinazolin-4-yl]-2,5-diazabicyclo[2.2.1]heptane-2-carboxylate (62 mg) as a solid.

Production Example 238

Under an argon atmosphere, bis(tri-tert-butylphosphine)palladium(0) (18 mg) was added to a mixture of 4-methyl-1,3-oxazole-5-carboxylic acid (178 mg), tetra-n-butylammonium chloride (195 mg), tert-butyl (4R)-4-(4-bromophenyl)-2,2-dimethyl-1,3-oxazolidine-3-carboxylate (250 mg), cesium carbonate (344 mg) and DMF (2.5 mL), and under microwave irradiation, the mixture was stirred at 170° C. for 30 minutes. The mixture was cooled to room temperature and was then diluted with ethyl acetate, and the insoluble materials were removed by filtration through celite pad. The filtrate was washed with water and saturated aqueous sodium chloride solution and was dried over anhydrous magnesium sulfate. The insoluble materials were removed by filtration, and the filtrate was concentrated under reduced pressure. The resulting residue was purified by silica gel column chromatography ($CHCl_3$/MeOH), thus obtaining tert-butyl (4R)-2,2-dimethyl-4-[4-(4-methyl-1,3-oxazol-5-yl)phenyl]-1,3-oxazolidine-3-carboxylate (215 mg) as a solid.

Production Example 239

In DMSO (10 mL), tert-butyl (4R)-4-(4-bromophenyl)-2,2-dimethyl-1,3-oxazolidine-3-carboxylate (858 mg), 2-methyl-1H-imidazole (500 mg), copper(I) iodide (95 mg), quinolin-8-ol (138 mg) and potassium carbonate (670 mg) were suspended, and under an argon atmosphere, under microwave irradiation, the suspension was reacted at 150° C. for 3 hours. After cooling to room temperature, ethyl acetate and water were added, and the mixture was extracted with ethyl acetate twice. The combined organic layer was washed with saturated aqueous sodium chloride solution and was then dried over anhydrous magnesium sulfate. The insoluble materials were removed by filtration, and the filtrate was concentrated under reduced pressure. The resulting residue was purified by silica gel column chromatography (basic silica gel, hexane/ethyl acetate), thus obtaining tert-butyl (4R)-2,2-dimethyl-4-[4-(2-methyl-1H-imidazol-1-yl)phenyl]-1,3-oxazolidine-3-carboxylate (500 mg) as an oil.

Production Example 245

To a mixture of 4-bromo-6-fluoro-1H-indazole (235 g), TEA (183 mL) and $CH_2Cl_2$ (1880 mL) was added 1,1',1"-(chloromethanetriyl)tribenzene (335 g) at room temperature, and the mixture was stirred at 25° C. for 16 hours. The reaction mixture was poured into ice water (1.5 L), and the organic layer and the aqueous layer were separated. The aqueous layer was extracted with $CH_2Cl_2$ (400 mL) three times. The combined organic layer was dried over anhydrous sodium sulfate. Then, the insoluble materials were removed by filtration, and the filtrate was concentrated under reduced pressure. Petroleum ether (550 mL) was added to the resulting residue for trituration (0° C., 2 hours), and then 4-bromo-6-fluoro-2-(triphenylmethyl)-2H-indazole (508.98 g) was obtained as a solid by collecting by filtration and drying under reduced pressure.

Production Example 246

To a mixture of 4-bromo-6-fluoro-2-(triphenylmethyl)-2H-indazole (100 g) and 2-methyltetrahydrofuran (1000 mL) was added lithium diisopropylamide (2 M THF solution, 214.28 mL) at −78° C. under nitrogen atmosphere, and the mixture was stirred at −78° C. for 2.5 hours. Methyl iodide (26.68 mL) was added at −78° C., and the mixture was stirred at 25° C. for 2.5 hours. Water (2000 mL) was added to quench the reaction, and the mixture was extracted with ethyl acetate (800 mL) twice. The combined organic layer was dried over anhydrous sodium sulfate. Then, the insoluble materials were removed by filtration, and the filtrate was concentrated under reduced pressure. Ethyl acetate (50 mL)/petroleum ether (50 mL) were added to the resulting residue for trituration, and then 4-bromo-6-fluoro-5-methyl-2-(triphenylmethyl)-2H-indazole (81 g) was obtained as a solid by collecting by filtration and drying under reduced pressure.

Production Example 247

To a mixture of 4-bromo-6-fluoro-5-methyl-2-(triphenylmethyl)-2H-indazole (100 g), 4,4,4',4',5,5,5',5'-octamethyl-2,2'-bi-1,3,2-dioxaborolane (61.42 g), triphenylphosphine (10.57 g), potassium acetate (59.34 g) and DOX (1000 mL) was added palladium acetate (4.52 g) under nitrogen atmosphere at room temperature. After the reaction mixture was degassed and filled with nitrogen gas three times each, the mixture was stirred at 100° C. for 12 hours under nitrogen atmosphere. After cooling, water (1500 mL) was added, and the mixture was extracted with ethyl acetate (900 mL) three times. The combined organic layer was dried over anhydrous sodium sulfate, and then the insoluble materials were removed by filtration. Activated carbon (50 g) was added to the resulting solution, and the solution was stirred at 20° C. for 1 hour and filtered while washing with ethyl acetate (50 ml) three times. The filtrate was concentrated. Methanol (200 mL) was added to the resulting residue for trituration, and 6-fluoro-5-methyl-4-(4,4,5,5-tetramethyl-1,3,2-dioxaborolan-2-yl)-2-(triphenylmethyl)-2H-indazole (110 g) was obtained as a solid by collecting by filtration and drying under reduced pressure.

Production Example 248

Tert-butyl (1S,4S)-5-{8-(benzyloxy)-6-cyclopropyl-2-(ethanesulfonyl)-7-[6-fluoro-5-methyl-2-(triphenylmethyl)-2H-indazol-4-yl]quinazolin-4-yl}-2,5-diazabicyclo[2.2.1]heptane-2-carboxylate (350 mg), 2-aminoethanol (1 mL) and N-methyl-2-pyrrolidone (2 mL) were mixed and reacted at 130° C. for 30 minutes under microwave irradiation. The reaction solution was diluted with ice water and saturated aqueous ammonium chloride solution and extracted with ethyl acetate twice. The combined organic layer was washed with saturated aqueous sodium chloride solution and was then dried over anhydrous magnesium sulfate. The insoluble materials were removed by filtration, and the residue obtained by concentrating the filtrate under reduced pressure was purified by silica gel column chromatography (basic silica gel, hexane/ethyl acetate), thus obtaining tert-butyl (1S,4S)-5-{8-(benzyloxy)-6-cyclopropyl-7-[6-fluoro-5-methyl-2-(triphenylmethyl)-2H-indazol-4-yl]-2-[(2-hydroxyethyl)amino]quinazolin-4-yl}-2,5-diazabicyclo[2.2.1]heptane-2-carboxylate (198 mg) as a solid.

Production Example 249

Dehydrated THF (2 mL) was added to tert-butyl (1S,4S)-5-(6-cyclopropyl-8-[(4-ethynylphenyl)methoxy]-7-[6-fluoro-5-methyl-1-(oxan-2-yl)-1H-indazol-4-yl]-2-{[(2R,3R)-3-hydroxybutan-2-yl]oxy}quinazolin-4-yl)-2,5-diazabicyclo[2.2.1]heptane-2-carboxylate (75 mg), and after sodium hydride (55% mineral oil dispersion, 20 mg) was added with stirring under cooling in an ice-methanol bath under an argon gas atmosphere, the mixture was stirred for 1 hour at room temperature. The reaction container was placed again in an ice-methanol bath, and methyl iodide (20 μL) was added with stirring under cooling. Then the mixture was stirred overnight at room temperature under an argon atmosphere. Ice and saturated aqueous ammonium chloride solution were poured into the reaction container, and the mixture was extracted with ethyl acetate twice. The collected organic layer was washed with saturated aqueous sodium chloride solution and was then dried over anhydrous magnesium sulfate. The solvent was removed under reduced pressure, and the resulting residue was purified by silica gel column chromatography (hexane/ethyl acetate), thus obtaining tert-butyl (1S,4S)-5-(6-cyclopropyl-8-[(4-ethynylphenyl)methoxy]-7-[6-fluoro-5-methyl-1-(oxan-2-yl)-1H-indazol-4-yl]-2-{[(2R,3R)-3-methoxybutan-2-yl]oxy}quinazolin-4-yl)-2,5-diazabicyclo[2.2.1]heptane-2-carboxylate (74 mg) as a foam-like solid.

Production Example 252

MeOH (3 mL) was added to tert-butyl (1S,4S)-5-{6-cyclopropyl-8-[(4-ethynylphenyl)methoxy]-7-[6-fluoro-5-methyl-2-(triphenylmethyl)-2H-indazol-4-yl]-2-[(2S)-2-methoxypropoxy]quinazolin-4-yl}-2,5-diazabicyclo[2.2.1]heptane-2-carboxylate (211 mg), and 4-methylbenzene-1-sulfonic acid monohydrate (48 mg) was added at room temperature with stirring. Then, the mixture was stirred at room temperature for 1 hour under an argon atmosphere. Ice and saturated aqueous sodium hydrogen carbonate solution were added to the reaction container, and the mixture was extracted with ethyl acetate twice. The combined organic layer was washed with saturated aqueous sodium chloride solution and was dried over anhydrous magnesium sulfate. The insoluble materials were removed by filtration, and the filtrate was concentrated under reduced pressure. The resulting residue was purified by silica gel column chromatography (basic silica gel, hexane/ethyl acetate), thus obtaining tert-butyl (1S,4S)-5-{6-cyclopropyl-8-[(4-ethynylphenyl)methoxy]-7-(6-fluoro-5-methyl-1H-indazol-4-yl)-2-[(2S)-2-methoxypropoxy]quinazolin-4-yl}-2,5-diazabicyclo[2.2.1]heptane-2-carboxylate (87 mg) which was a low-polar diastereomer as a solid and tert-butyl (1S,4S)-5-{6-cyclopropyl-8-[(4-ethynylphenyl)methoxy]-7-(6-fluoro-5-methyl-1H-indazol-4-yl)-2-[(2S)-2-methoxypropoxy]quinazolin-4-yl}-2,5-diazabicyclo[2.2.1]heptane-2-carboxylate (59 mg) which was a high-polar diastereomer as a solid. The low-polar diastereomer was used for the subsequent reaction.

Production Example 281

DMF (25 mL) and triethylamine (3 mL) were added to (3R)-pyrrolidin-3-ol (1.7 g), and 1-({[2-(trimethylsilyl)ethoxy]carbonyl}oxy)pyrrolidine-2,5-dione (4.5 g) was added portionwise under an argon atmosphere with stirring under cooling in an ice/methanol bath. Then, the mixture was stirred for 2 hours under cooling at the same temperature under an argon atmosphere. Ice water was added to the reaction mixture to dilute the reaction mixture, and the mixture was extracted with ethyl acetate twice. The combined organic layer was sequentially washed with 1 M hydrochloric acid/ice water (1/1), water, saturated aqueous sodium hydrogen carbonate solution and saturated aqueous sodium chloride solution and was dried over anhydrous magnesium sulfate. The insoluble materials were removed by filtration, and the filtrate was concentrated under reduced pressure, thus obtaining 2-(trimethylsilyl)ethyl (3R)-3-hydroxypyrrolidine-1-carboxylate (3.6 g) as an oil.

In the same manner as in the production methods of the Production Examples described above, the compounds shown in Table 6 to Table 101 presented later were produced. In addition, the production method, the structure and the physiochemical data of the compound of each Production Example are shown in Table 6 to Table 101.

Example 8

To a mixture of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (5.61 g) and $CH_2Cl_2$ (60 mL) was added trifluoroacetic acid (27 mL) under cooling (internal temperature: −5° C. or lower), and then the mixture was stirred at room temperature for 2 hours. The resulting reaction mixture was concentrated under reduced pressure, and saturated aqueous sodium hydrogen carbonate solution was added to the residue. The mixture was extracted three times with $CHCl_3$/MeOH (5/1), and then, the combined organic layer was dried over anhydrous sodium sulfate. The solution was concentrated under reduced pressure, and the resulting crude product was purified by ODS column chromatography (MeCN/0.1% aqueous formic acid solution). Saturated aqueous sodium hydrogen carbonate solution was added to fractions containing the target compound, and the mixture was extracted three times with $CHCl_3$/MeOH (5/1). The combined organic layer was dried over anhydrous sodium sulfate, and the solution was concentrated under reduced pressure. The residue was purified by silica gel column chromatography (basic silica gel, $CHCl_3$/MeOH), thus obtaining a product. Isopropyl acetate (70 mL) was added to the resulting product, and the mixture was stirred at 80° C. for 10 minutes and was stirred at room temperature overnight. Hexane (70 mL) was added, and the mixture was stirred at room temperature for 1 hour. Then, the resulting solid was filtered and was washed with isopropyl acetate/hexane (1/1) and was then dried under reduced pressure at 40° C. overnight, thus obtaining (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide (3.01 g) as a solid.

Example 7

After (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide (1.04 g) was dissolved in $CH_2Cl_2$ (9 mL) and MeOH (9 mL), hydrogen chloride (4M DOX solution, 3 mL) was added under ice-bath cooling. The mixture was stirred under ice-bath cooling for 30 minutes. The reaction mixture was concentrated under reduced pressure, and diethyl ether was added to the resulting residue. The precipitated solid was filtered and was dried under reduced pressure, thus obtaining (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide n hydrochloride (1.04 g) as a solid.

Example 20

To a mixture of tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-({(1R)-2-hydroxy-1-[4-(2-oxo-1,3-oxazolidin-3-yl)phenyl]ethyl}carbamoyl)pyrrolidin-1-yl]-3-methyl-1-oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (170 mg), $CH_2Cl_2$ (2 mL) and MeOH (2 mL) was added hydrogen chloride (4M DOX solution, 0.988 mL) under ice-bath cooling, and the mixture was stirred at room temperature for 3 hours. The mixture was concentrated under reduced pressure, and $CHCl_3$ and saturated aqueous sodium hydrogen carbonate solution were added. The mixture was stirred for a while, and then, the aqueous layer was separated. The aqueous layer was extracted with $CHCl_3$/MeOH (5/1), and the combined organic layer was dried over anhydrous sodium sulfate. The insoluble materials were removed by filtration, and then the filtrate was concentrated under reduced pressure. The residue was purified by silica gel column chromatography (basic silica gel, $CHCl_3$/MeOH) and was then purified by ODS column chromatography (MeCN/0.1% aqueous formic acid solution). A fractions containing the target compound were collected, and the collected solution was basified with saturated aqueous sodium hydrogen carbonate solution and was then extracted twice with $CHCl_3$/MeOH (5/1). The combined organic layer was dried over anhydrous sodium sulfate. The insoluble materials were removed by filtration, and then the filtrate was concentrated under reduced pressure. The resulting solid was washed with diethyl ether and was dried under reduced pressure, thus obtaining (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl)phenyl]ethyl}-L-prolinamide (74 mg) as a solid.

Example 18

Under nitrogen atmosphere, to a mixture of (4R)-1-[(2S)-2-(4-{4-[({4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]phenyl}-1H-1,2,3-triazol-1-yl)-3-methylbutanoyl]-4-hydroxy-L-proline (65 mg), (2R)-2-amino-2-{4-[4-(hydroxymethyl)-1,3-thiazol-5-yl]phenyl}ethan-1-ol n hydrochloride (25 mg) and DMF (1 mL) were sequentially added DIPEA (50 μL) and HATU (35 mg) under ice-bath cooling, and the mixture was stirred at room temperature for 1 hour. Water was added, and the mixture was extracted with ethyl acetate. The organic layer was washed with water and saturated aqueous sodium chloride solution and was then dried over anhydrous sodium sulfate. The insoluble materials were removed by filtration, and the filtrate was concentrated under reduced pressure. The resulting residue was purified by silica gel column chromatography (CHCl₃/MeOH), thus obtaining tert-butyl (1S,4S)-5-{6-cyclopropyl-7-[6-fluoro-5-methyl-1-(oxan-2-yl)-1H-indazol-4-yl]-8-{[4-(1-{(2S)-1-[(2S,4R)-4-hydroxy-2-{[((1R)-2-hydroxy-1-{4-[4-(hydroxymethyl)-1,3-thiazol-5-yl]phenyl}ethyl]carbamoyl}pyrrolidin-1-yl]-3-methyl-1-oxobutan-2-yl}-1H-1,2,3-triazol-4-yl)phenyl]methoxy}-2-[(oxan-4-yl)oxy]quinazolin-4-yl}-2,5-diazabicyclo[2.2.1]heptane-2-carboxylate (59 mg). Subsequently, the resulting compound was dissolved in CH₂Cl₂ (0.5 mL) and MeOH (0.5 mL), and hydrogen chloride (4M DOX solution, 0.5 mL) was added under ice-bath cooling. The mixture was stirred at room temperature for 2 hours and was then concentrated under reduced pressure. Diethyl ether was added to the resulting residue, and the precipitated solid was filtered, was washed with diethyl ether and was then dried under reduced pressure, thus obtaining (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide n hydrochloride (43 mg) as a solid.

Example 49

Under nitrogen atmosphere, methanesulfonic acid (100 μL) was added to an EtOH solution (2 mL) of tert-butyl (1S,4S)-5-(6-cyclopropyl-8-{[3-fluoro-4-(1-{(2S)-1-[(2S,4R)-4-hydroxy-2-({(1R)-2-hydroxy-1-[4-(4-methyl-1,3-thiazol-5-yl)phenyl]ethyl}carbamoyl)pyrrolidin-1-yl]-3-methyl-1-oxobutan-2-yl}-1H-1,2,3-triazol-4-yl)phenyl]methoxy}-7-[6-fluoro-5-methyl-1-(oxan-2-yl)-1H-indazol-4-yl]-2-[(oxan-4-yl)oxy]quinazolin-4-yl)-2,5-diazabicyclo[2.2.1]heptane-2-carboxylate (158 mg) at room temperature. The mixture was stirred at 50° C. for 16 hours and was then concentrated under reduced pressure. The residue was separated and purified by ODS column chromatography (MeCN/0.1% aqueous formic acid solution). Aqueous 5% sodium hydrogen carbonate solution was added to fractions containing the target compound, and the mixture was extracted twice with CHCl₃/MeOH (9/1). The combined organic layer was dried over anhydrous sodium sulfate, and the solution was concentrated under reduced pressure. EtOH was added to the residue to dissolve the residue, and the mixture was concentrated under reduced pressure. The operation was performed twice. Diethyl ether was added, and the resulting solid was filtered, was washed with diethyl ether and was then dried under reduced pressure, thus obtaining (4R)-1-[(2S)-2-(4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl)phenyl]ethyl}-L-prolinamide (50 mg) as a solid.

In the same manner as in the production methods of the Examples described above, the Example compounds shown in Table 102 to Table 126 presented later were produced. In addition, the production method and the physiochemical data of the compound of each Example are shown in Table 127 to Table 131 presented later.

In the tables presented below, the following abbreviations are sometimes used.

PEx: Production Example No., Ex: Example No., PSyn: Production Example No. produced in the same method, Syn: Example No. produced in the same method (for example, Syn: 8 represents that it was produced by the same method as for Example 8, and Syn: 18# represents that a hydrochloride salt produced and obtained by the same method as for Example 18 was subjected to the desalting reaction described in Production Method 1), Str: chemical structural formula (a compound with "*" in the chemical structural formula represents that the compound is single structure with regard to the axial chirality or central chirality), n HCl: n hydrochloride (the compound with Production Example No. shows that the compound is monohydrochloride to trihydrochloride, and the compound with Example No. shows that the compound is monohydrochloride to pentahydrochloride), DAT: physiochemical data, ESI+: m/z value in mass spectrometry (ionization method ESI, $[M+H]^+$ unless otherwise specified), ESI−: m/z value in mass spectrometry (ionization method ESI, $[M-H]^-$ unless otherwise specified), NMR: δ value (ppm) of peak in ¹H-NMR (500 MHz) in DMSO-d₆, NMR (100° C.): δ value (ppm) of peak in ¹H-NMR (500 MHz) in DMSO-d₆ at 100° C., s: singlet (spectrum), d: doublet (spectrum), dd: double doublet (spectrum), t: triplet (spectrum), q: quartet (spectrum), m: multiplet (spectrum), br: broad (spectrum) (example: br s).

TABLE 6

| PEx | PSyn | Str | DAT |
|---|---|---|---|
| 1 | 1 | [structure] | ESI+: 583.1, 585.1 |

TABLE 6-continued
| PEx | PSyn | Str | DAT |
|---|---|---|---|
| 2 | 2 | 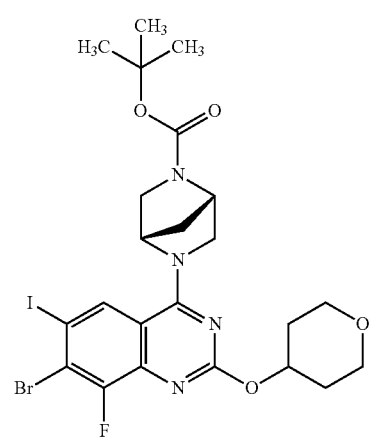 [SMILES: CC(C)(C)OC(=O)N1C[C@@H]2C[C@H]1CN2c1nc(OC2CCOCC2)nc2c(F)c(Br)c(I)cc12] | ESI+: 651.0 |
| 3 | 2 | 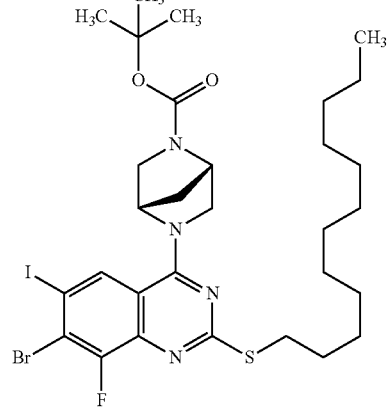 | ESI+: 751.3 |
TABLE 7
| PEx | PSyn | Str | DAT |
|---|---|---|---|
| 4 | 2 | 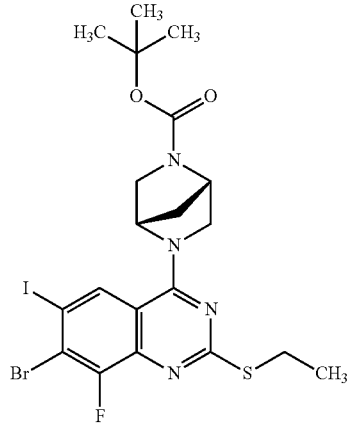 [SMILES: CCSc1nc(N2C[C@@H]3C[C@H]2CN3C(=O)OC(C)(C)C)c2cc(I)c(Br)c(F)c2n1] | ESI+: 610.9 |
| 5 | 5 | 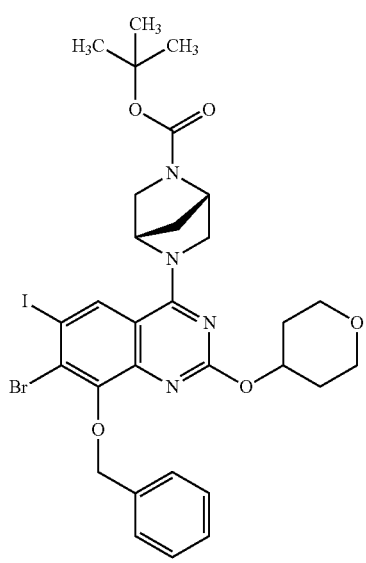 [SMILES: CC(C)(C)OC(=O)N1C[C@@H]2C[C@H]1CN2c1nc(OC2CCOCC2)nc2c(OCc3ccccc3)c(Br)c(I)cc12] | ESI+: 739.2 |

TABLE 8
| PEx | PSyn | Str | DAT |
|---|---|---|---|
| 6 | 5 | 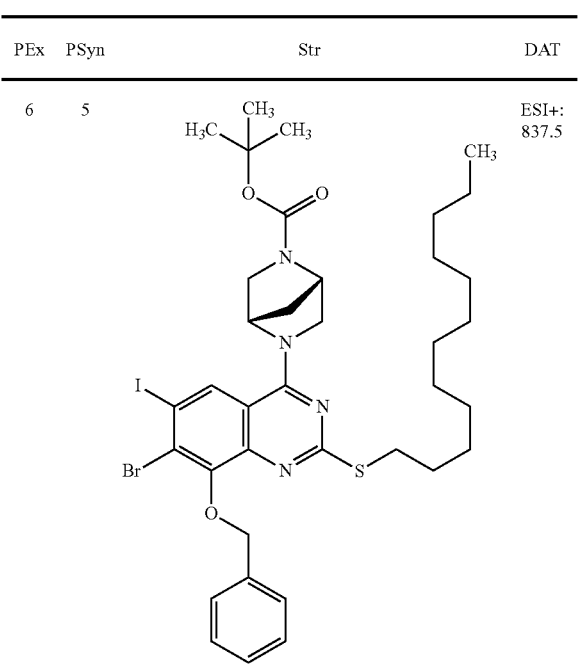 | ESI+: 837.5 |
| 7 | 5 | 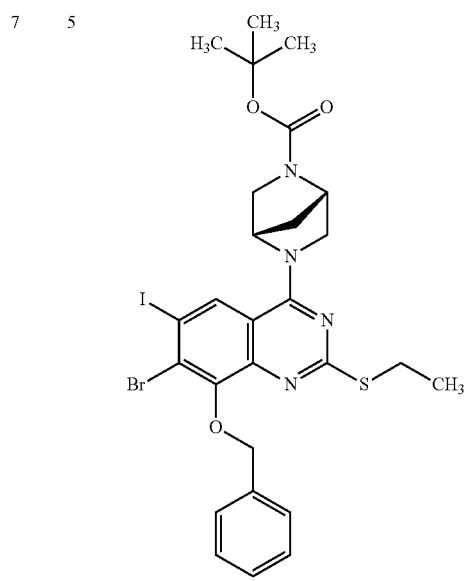 | ESI+: 698.9 |
TABLE 9
| PEx | PSyn | Str | DAT |
|---|---|---|---|
| 8 | 8 | 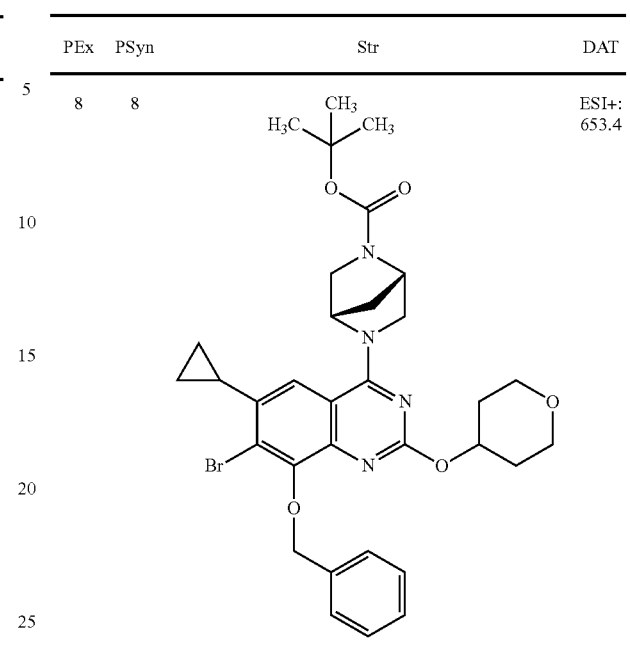 | ESI+: 653.4 |
| 9 | 8 | 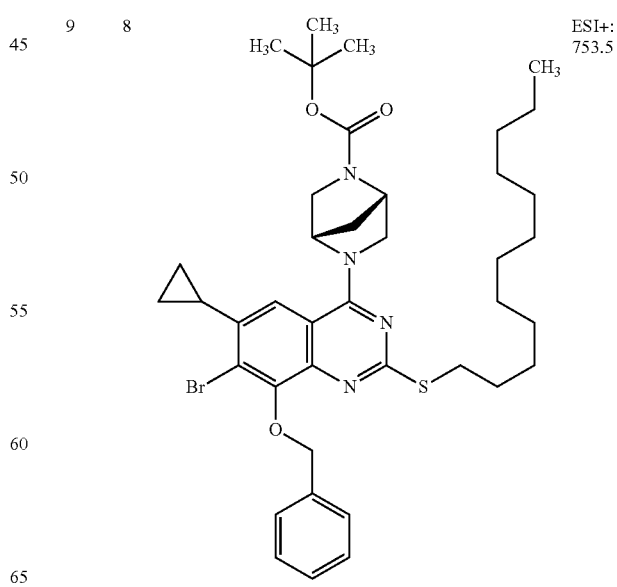 | ESI+: 753.5 |

TABLE 10
| PEx | PSyn | Str | DAT |
|---|---|---|---|
| 10 | 8 | 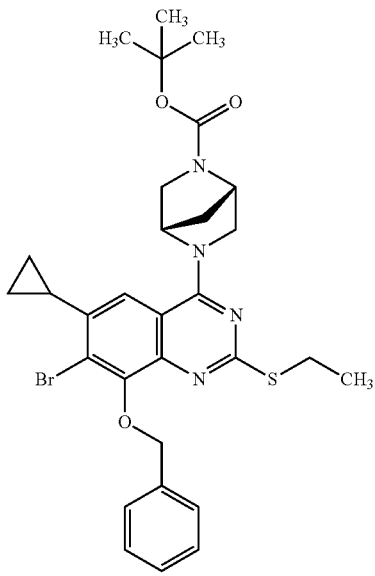 [SMILES: CCSc1nc(N2C[C@@H]3C[C@H]2CN3C(=O)OC(C)(C)C)c2cc(C3CC3)c(Br)c(OCc3ccccc3)c2n1] | ESI+: 613.3 |
| 11 | 11 | 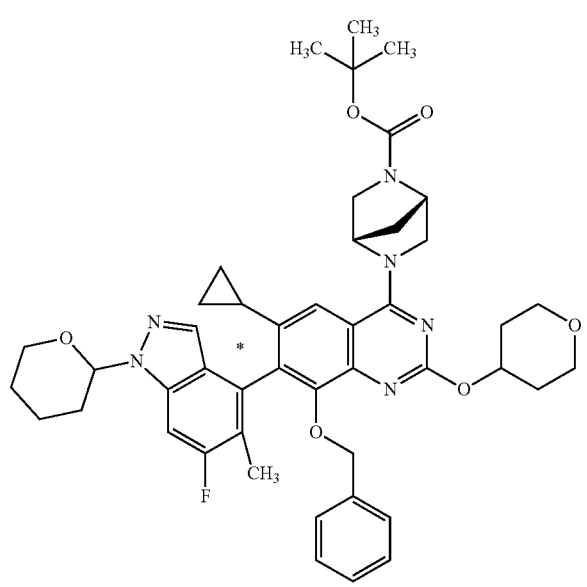 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccccc1] | ESI+: 805.6 |

TABLE 11
| PEx | PSyn | Str | DAT |
|---|---|---|---|
| 12 | 11 | 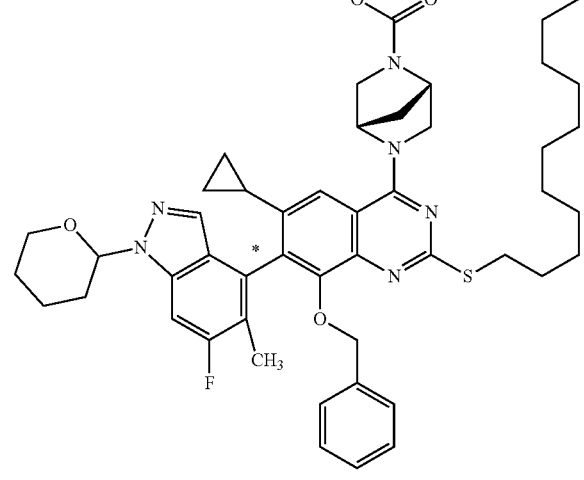 | ESI+: 905.5 |
| 13 | 11 | 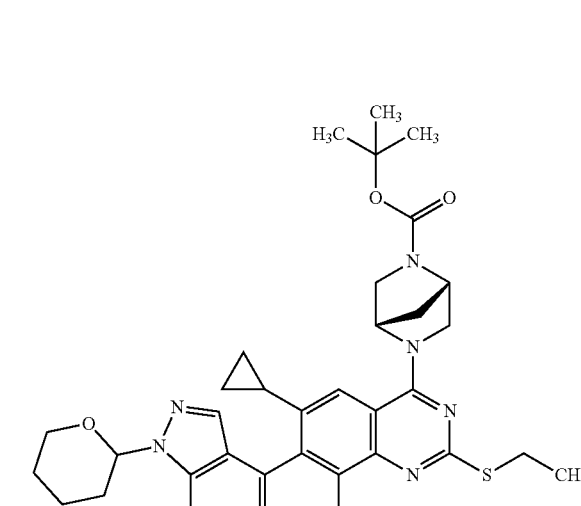 | ESI+: 765.4 |

TABLE 12
| PEx | PSyn | Str | DAT |
|---|---|---|---|
| 14 | 14 | 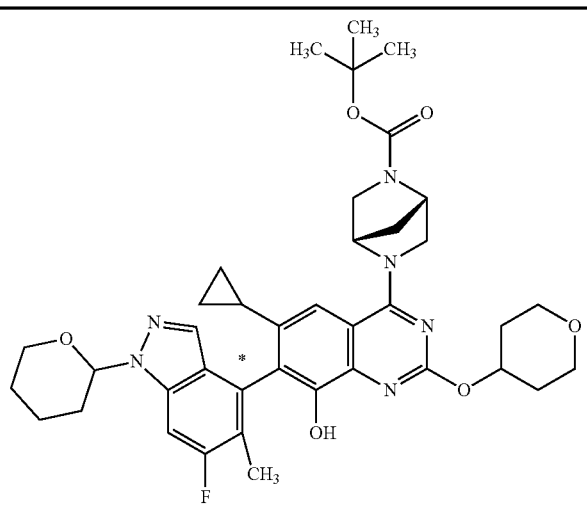 | ESI+: 715.4 |
| 15 | 14 | 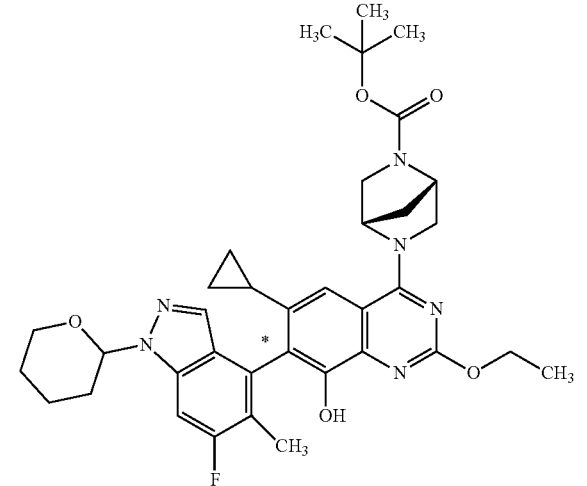 [SMILES: CCOc1nc(N2C[C@@H]3C[C@H]2CN3C(=O)OC(C)(C)C)c2cc(C3CC3)c(-c3c(C)c(F)cc4c3cnn4C3CCCCO3)c(O)c2n1] | ESI+: 659.4 |
TABLE 13
| PEx | PSyn | Str | DAT |
|---|---|---|---|
| 16 | 14 | 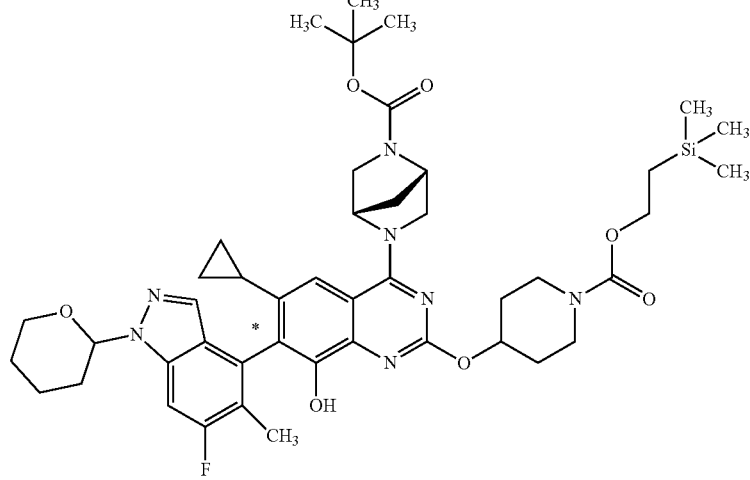 | ESI+: 858.7 |

TABLE 13-continued

| PEx | PSyn | Str | DAT |
|-----|------|-----|-----|
| 17 | 14 | | ESI+: 701.4 |
| 18 | 14 | | ESI+: 701.4 |

TABLE 14

| PEx | PSyn | Str | DAT |
|-----|------|-----|-----|
| 19 | 14 | | ESI+: 687.4 |

TABLE 14-continued
| PEx | PSyn | Str | DAT |
|---|---|---|---|
| 20 | 14 | 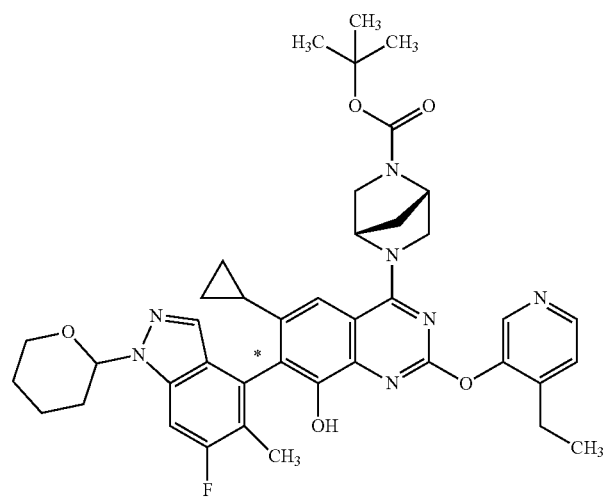 [SMILES: CCc1ccncc1Oc1nc(N2C[C@@H]3C[C@H]2CN3C(=O)OC(C)(C)C)c2cc(C3CC3)c(-c3c(C)c(F)cc4c3cnn4C3CCCCO3)c(O)c2n1] | ESI+: 736.5 |
| 21 | 14 | 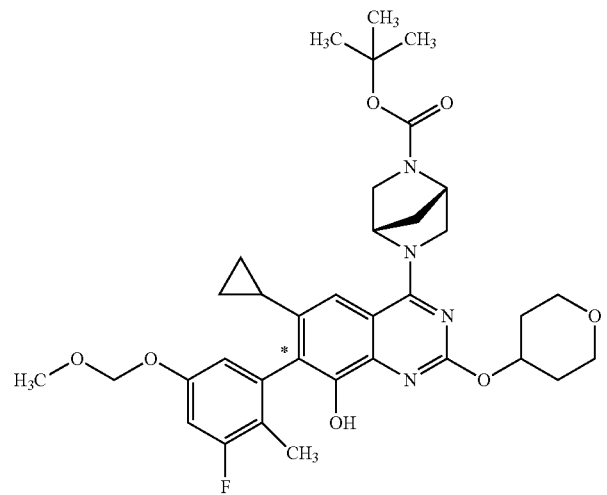 [SMILES: COCOc1cc(F)c(C)c(-c2c(C3CC3)cc3c(N4C[C@@H]5C[C@H]4CN5C(=O)OC(C)(C)C)nc(OC4CCOCC4)nc3c2O)c1] | ESI+: 651.6 |

TABLE 15
| PEx | PSyn | Str | DAT |
|---|---|---|---|
| 22 | 22 | 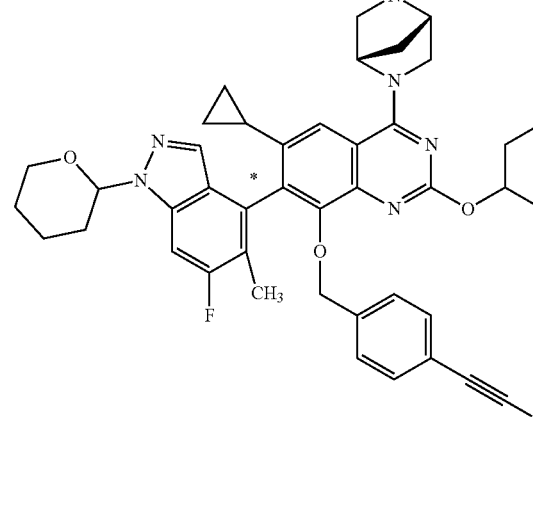 | ESI+: 829.5 |
| 23 | 22 | 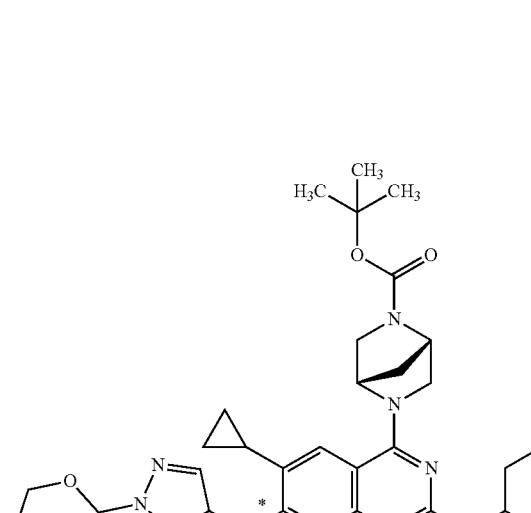 | ESI+: 863.6 |

TABLE 16

| PEx | PSyn | Str | DAT |
|---|---|---|---|
| 24 | 22 | | ESI+: 864.5 |
| 25 | 22 | | ESI+: 807.6 |

TABLE 17
| PEx | PSyn | Str | DAT |
|---|---|---|---|
| 26 | 22 | 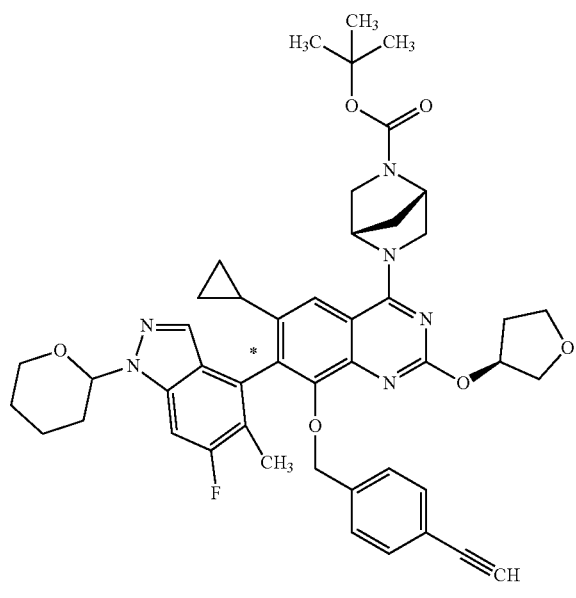 [SMILES: C#Cc1ccc(COc2c(-c3c(C)c(F)cc4c3cnn4C3CCCCO3)c(C3CC3)cc3c(N4C[C@@H]5C[C@H]4CN5C(=O)OC(C)(C)C)nc(O[C@H]4CCOC4)nc23)cc1] | ESI+: 815.7 |
| 27 | 22 | 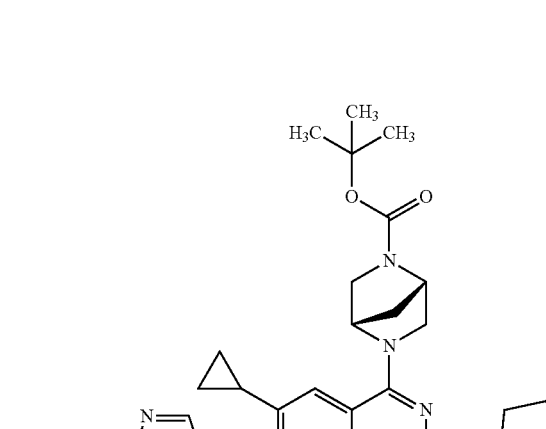 | ESI+: 815.4 |

TABLE 18
| PEx | PSyn | Str | DAT |
|---|---|---|---|
| 28 | 22 | 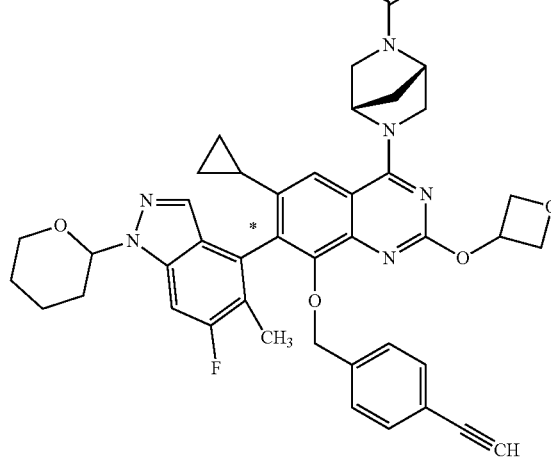 | ESI+: 801.4 |
| 29 | 22 | 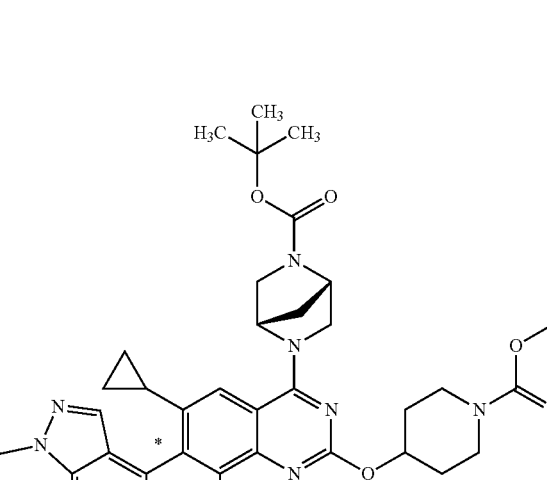 | ESI+: 972.8 |

TABLE 19
| PEx | PSyn | Str | DAT |
|---|---|---|---|
| 30 | 22 | 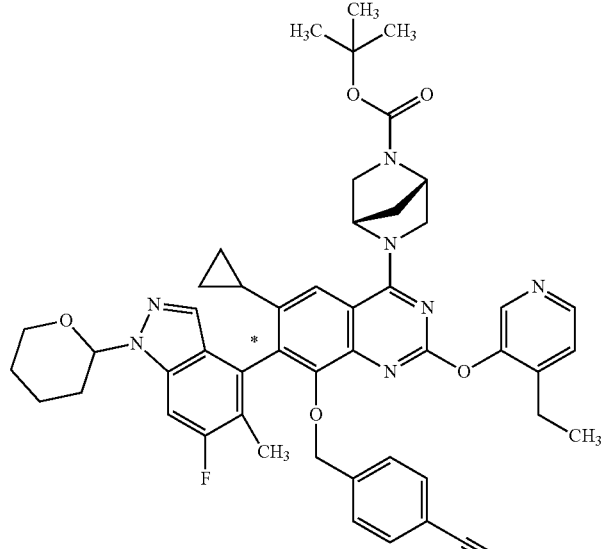 | ESI+: 850.4 |
| 31 | 22 | 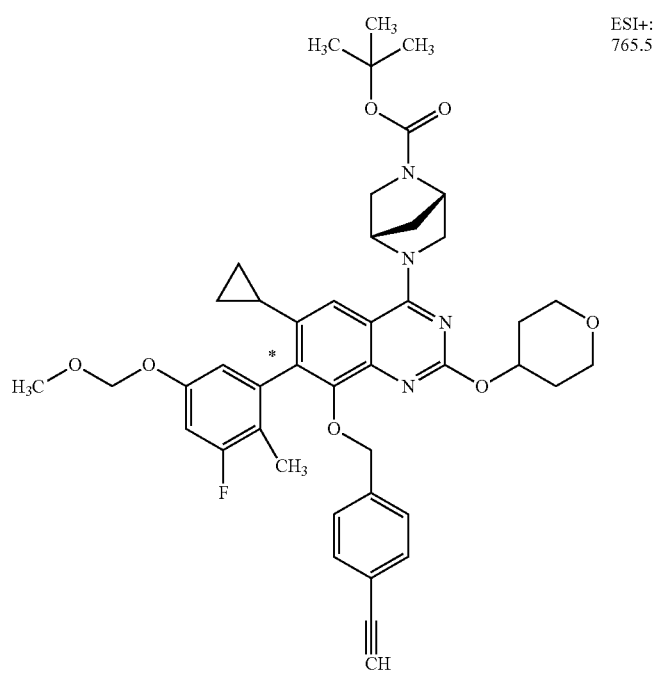 | ESI+: 765.5 |

TABLE 20
| PEx | PSyn | Str | DAT |
|---|---|---|---|
| 32 | 32 | 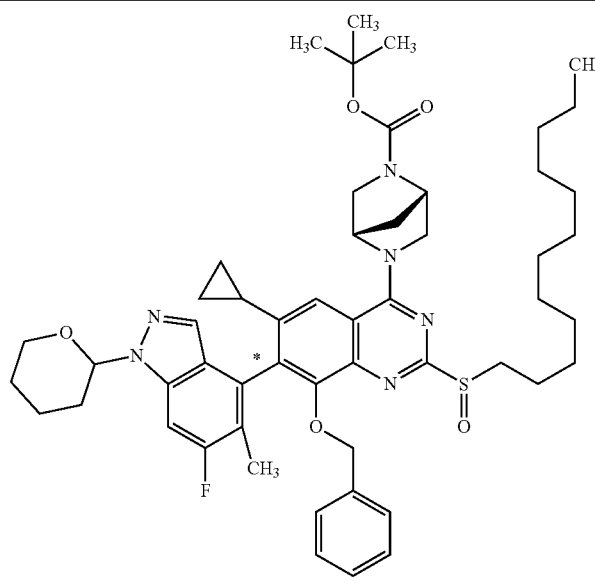 | ESI+: 921.4 |
| 33 | 32 | 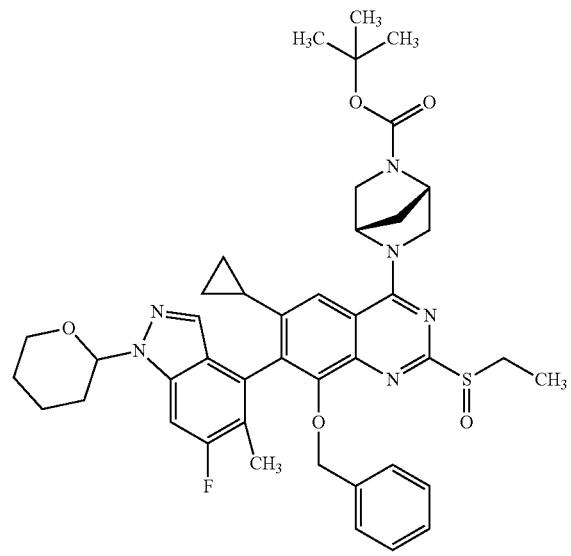 [SMILES: CCS(=O)c1nc(N2C[C@@H]3C[C@H]2CN3C(=O)OC(C)(C)C)c2cc(C3CC3)c(-c3c(C)c(F)cc4c3cnn4C3CCCCO3)c(OCc3ccccc3)c2n1] | ESI+: 781.4 |

123
TABLE 21
| PEx | PSyn | Str | DAT |
|---|---|---|---|
| 34 | 34 | 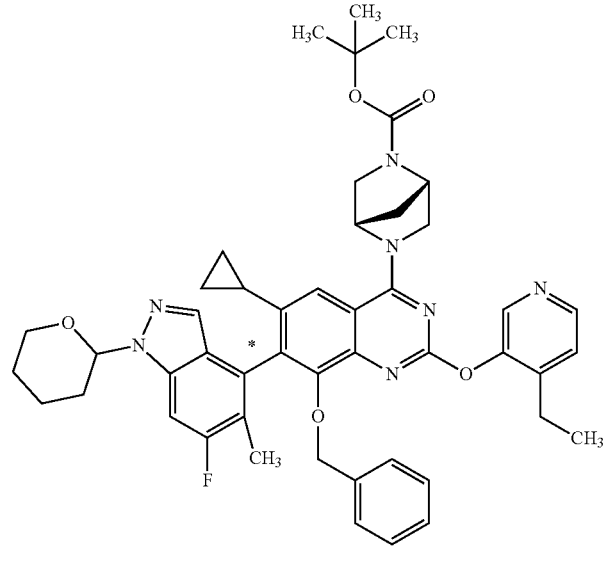 [SMILES: CCc1ccncc1Oc1nc(N2C[C@@H]3C[C@H]2CN3C(=O)OC(C)(C)C)c2cc(C3CC3)c(-c3c(C)c(F)cc4c3cnn4C3CCCCO3)c(OCc3ccccc3)c2n1] | ESI+: 826.5 |
| 35 | 34 | 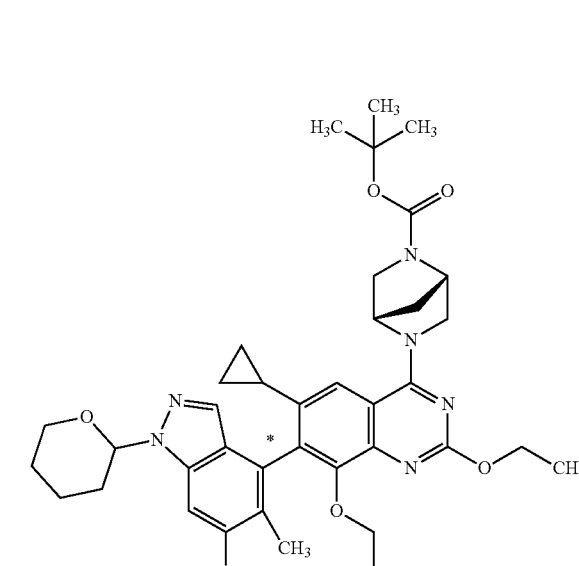 | ESI+: 749.5 |

TABLE 22

| PEx | PSyn | Str | DAT |
|---|---|---|---|
| 36 | 36 | | ESI+: 948.5 |
| 37 | 37 | | ESI+: 791.4 |

TABLE 23
| PEx | PSyn | Str | DAT |
|---|---|---|---|
| 38 | 37 | 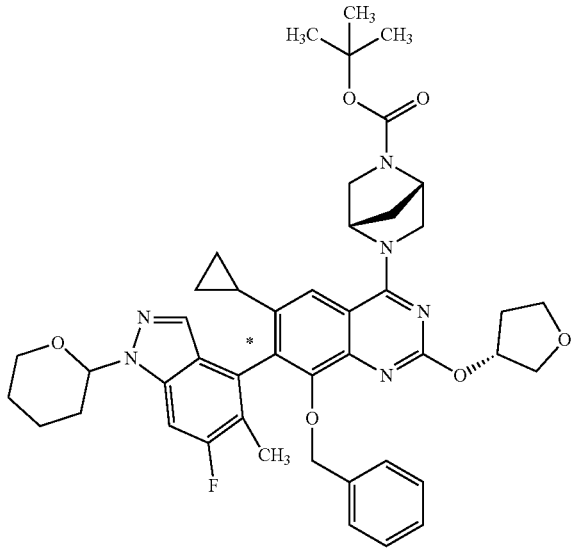 [SMILES: Cc1c(F)cc2c(cnn2C2CCCCO2)c1-c1c(C2CC2)cc2c(N3C[C@@H]4C[C@H]3CN4C(=O)OC(C)(C)C)nc(O[C@@H]3CCOC3)nc2c1OCc1ccccc1] | ESI+: 791.4 |
| 39 | 37 | 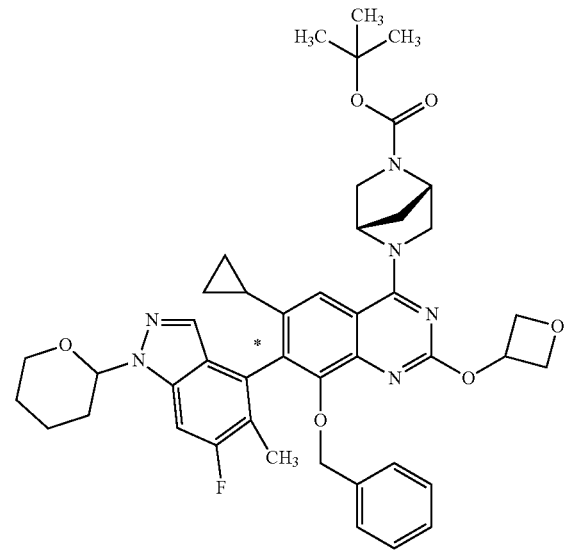 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3COC3)nc2c1OCc1ccccc1] | ESI+: 777.4 |

TABLE 24
| PEx | PSyn | Str | DAT |
|---|---|---|---|
| 40 | 40 | 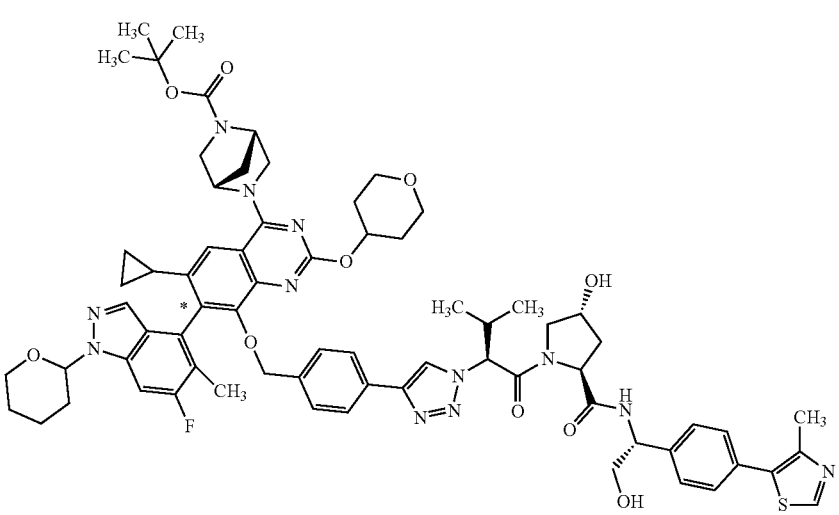 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCOCC6)nc45)cc3)nn2)cc1] | ESI+: 1301.3 |
| 41 | 40 | 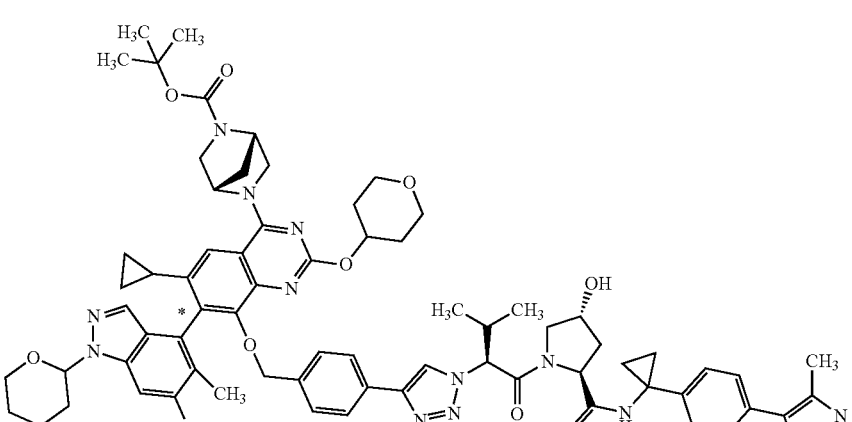 | ESI+: 1297.5 |

TABLE 25
| PEx | PSyn | Str | DAT |
|---|---|---|---|
| 42 | 40 | 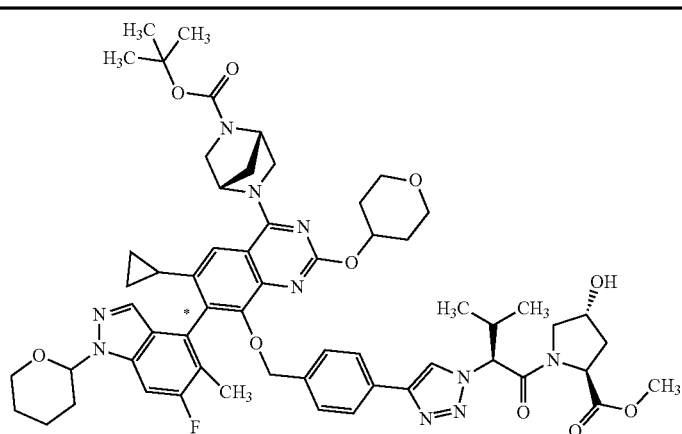 | ESI+: 1099.4 |
| 43 | 40 | 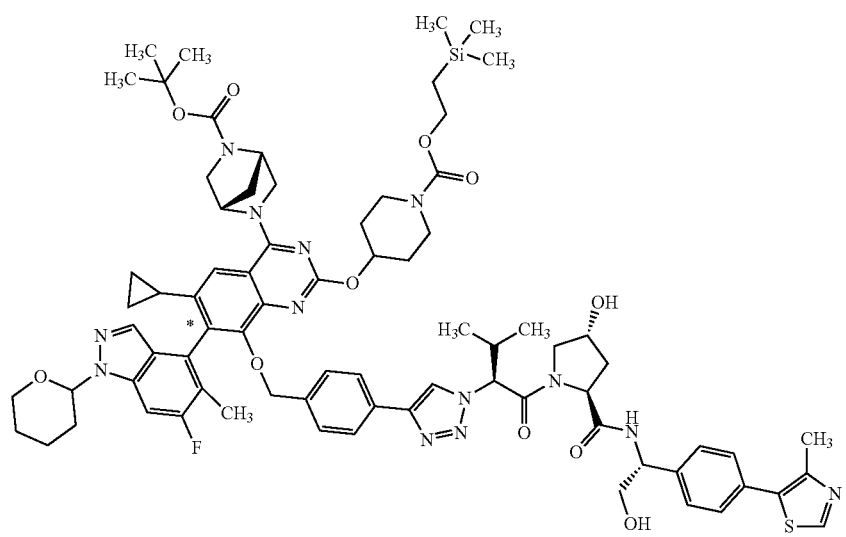 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCN(C(=O)OCC[Si](C)(C)C)CC6)nc45)cc3)nn2)cc1] | ESI+: 1444.5 |

TABLE 26

| PEx | PSyn | Str | DAT |
|---|---|---|---|
| 44 | 40 | | ESI+: 1298.4 |
| 45 | 40 | | ESI+: 1284.4 |

TABLE 27

| PEx | PSyn | Str | DAT |
|---|---|---|---|
| 46 | 40 | | ESI+: 1287.3 |
| 47 | 40 | | ESI+: 1287.4 |

TABLE 28
| PEx | PSyn | Str | DAT |
|---|---|---|---|
| 48 | 40 | 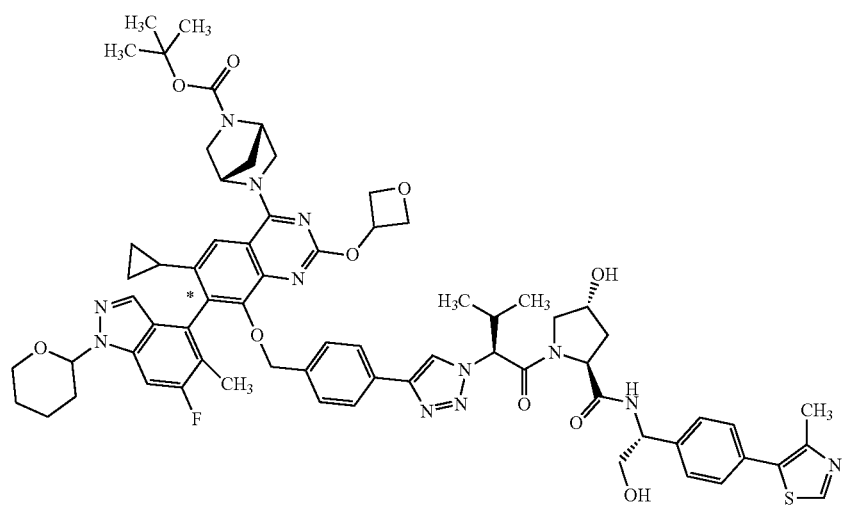 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6COC6)nc45)cc3)nn2)cc1] | ESI+: 1274.0 |
| 49 | 40 | 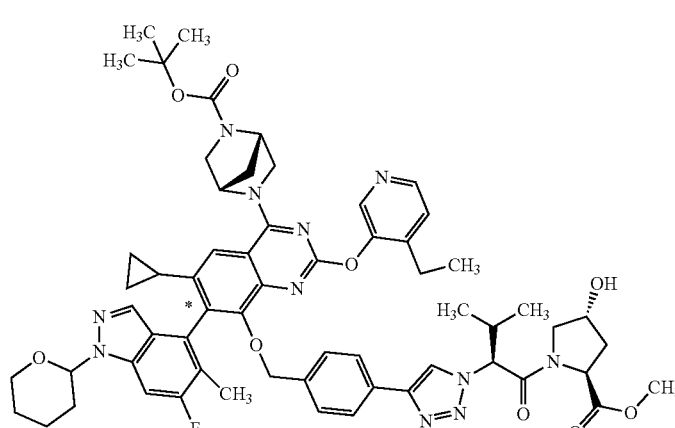 | ESI+: 1142.5 [M + Na]+ |

TABLE 29

| PEx | PSyn | Str | DAT |
|---|---|---|---|
| 50 | 40 | | ESI+: 1237.5 |
| 51 | 51 | | ESI+: 1300.8 |

TABLE 30

| PEx | PSyn | Str | DAT |
|---|---|---|---|
| 52 | 52 | | ESI+: 1356.5 |
| 53 | 53 | | ESI+: 1364.4 |

TABLE 31
| PEx | PSyn | Str | DAT |
|---|---|---|---|
| 54 | 54 | 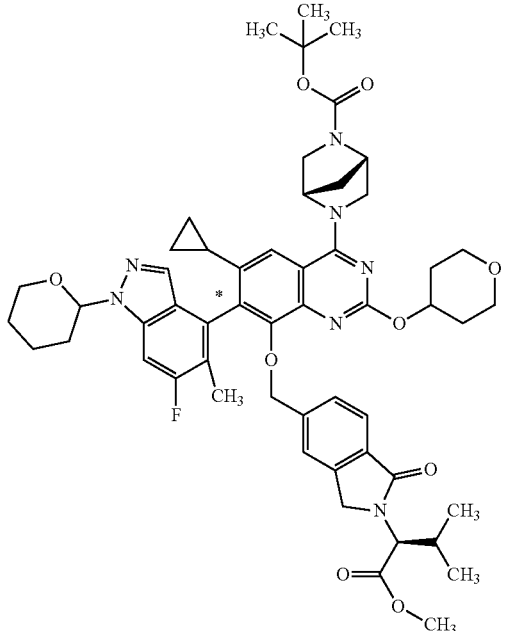 [SMILES: COC(=O)[C@H](C(C)C)N1Cc2cc(COc3c(-c4c(C)c(F)cc5c4cnn5C4CCCCO4)c(C4CC4)cc4c(N5C[C@@H]6C[C@H]5CN6C(=O)OC(C)(C)C)nc(OC5CCOCC5)nc34)ccc2C1=O] | ESI+: 974.4 |
| 55 | 54 | 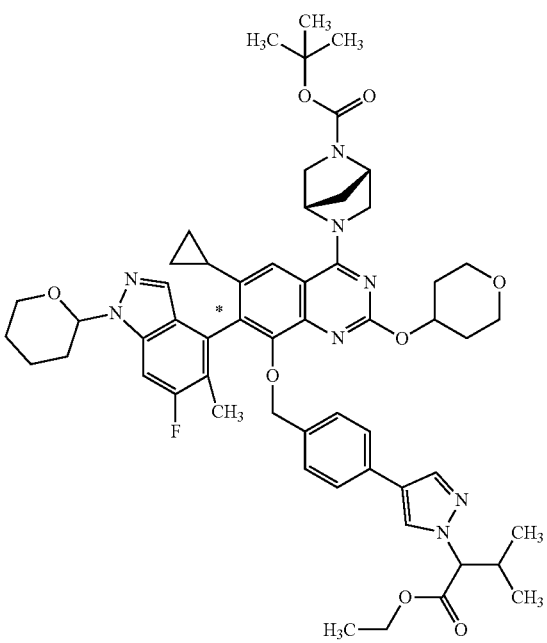 [SMILES: CCOC(=O)C(C(C)C)n1cc(-c2ccc(COc3c(-c4c(C)c(F)cc5c4cnn5C4CCCCO4)c(C4CC4)cc4c(N5C[C@@H]6C[C@H]5CN6C(=O)OC(C)(C)C)nc(OC5CCOCC5)nc34)cc2)cn1] | ESI+: 999.5 |

TABLE 32
| PEx | PSyn | Str | DAT |
|---|---|---|---|
| 56 | 56 | 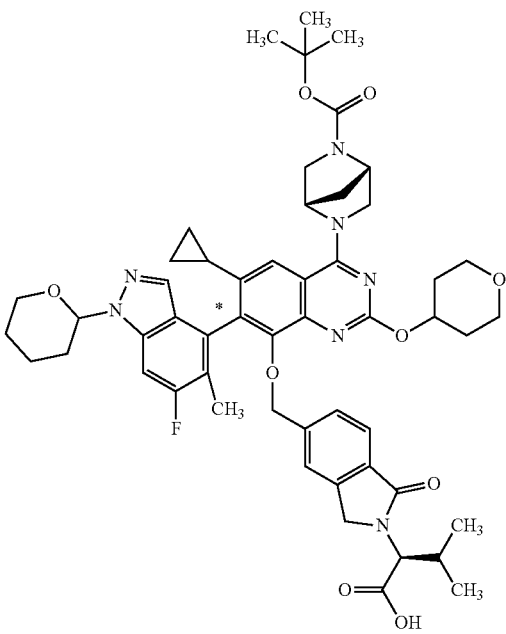 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc2c(c1)CN([C@H](C(=O)O)C(C)C)C2=O] | ESI+: 960.5 |
| 57 | 56 | 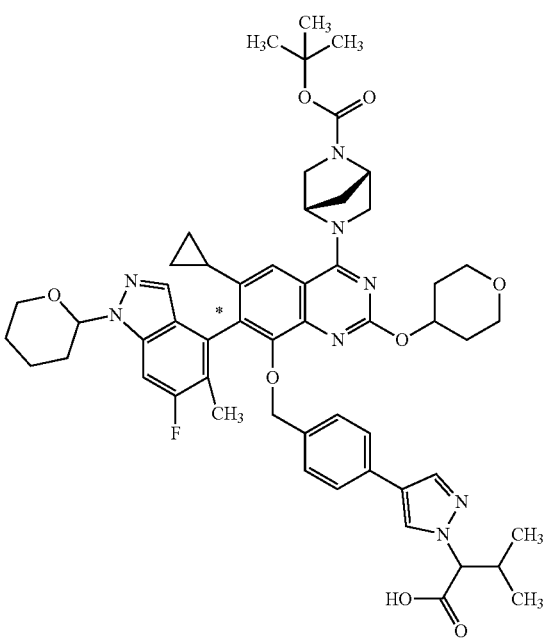 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(-c2cnn(C(C(=O)O)C(C)C)c2)cc1] | ESI−: 969.7 |

TABLE 33

| PEx | PSyn | Str | DAT |
|---|---|---|---|
| 58 | 56 | | ESI+: 849.5 |
| 59 | 56 | | ESI+: 850.4 |

TABLE 34
| PEx | PSyn | Str | DAT |
|---|---|---|---|
| 60 | 56 | 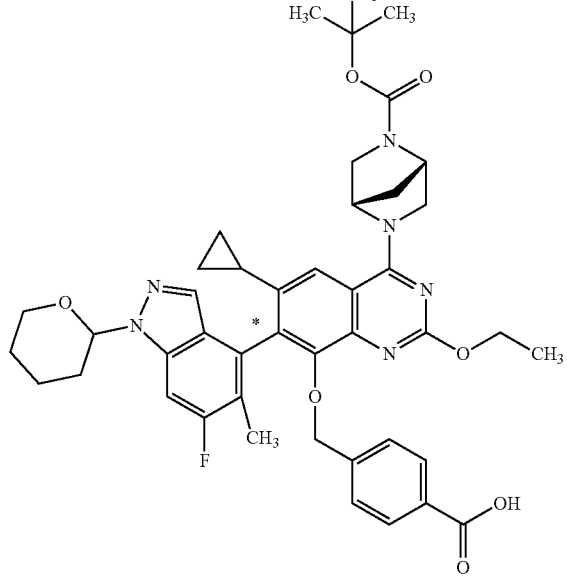 | ESI+: 793.7 |
| 61 | 61 | 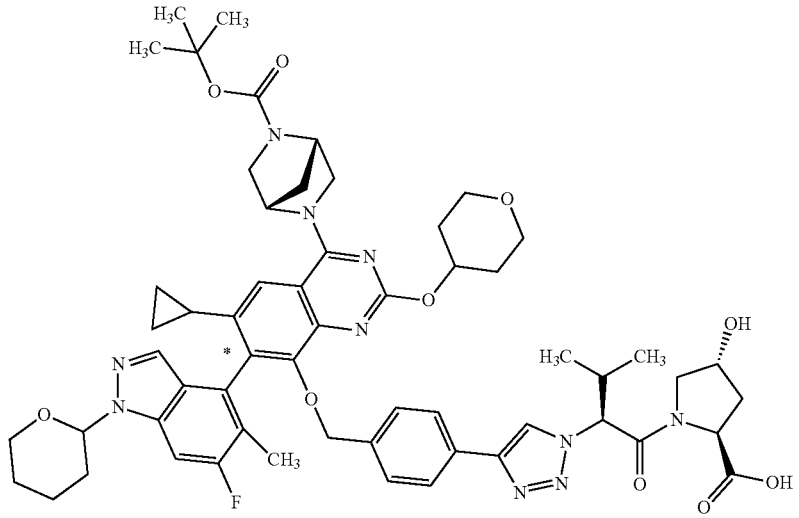 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(-c2cn([C@H](C(=O)N3C[C@H](O)C[C@H]3C(=O)O)C(C)C)nn2)cc1] | ESI−: 1083.6 |

TABLE 35
| PEx | PSyn | Str | DAT |
|---|---|---|---|
| 62 | 61 | 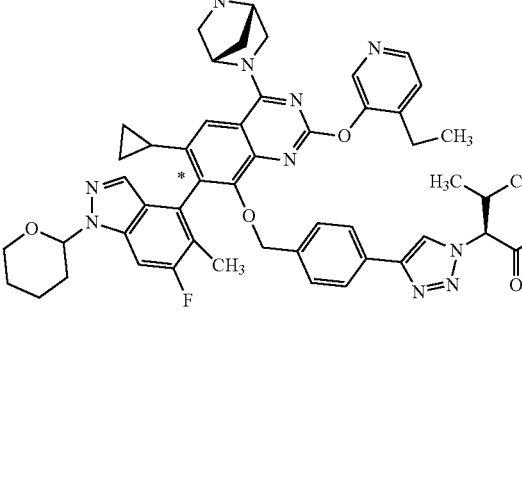 | ESI−: 1104.5 |
| 63 | 63 | 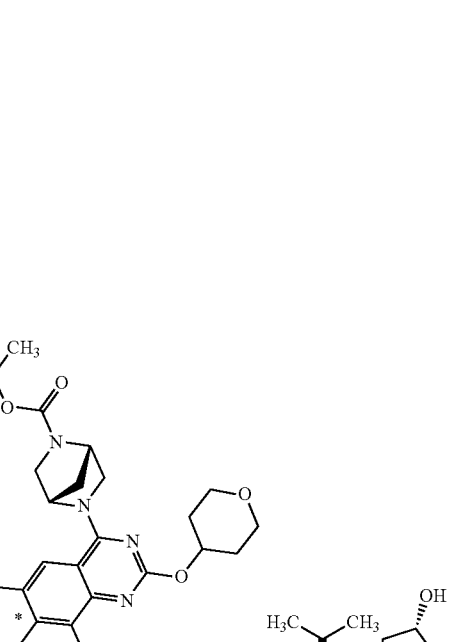 | ESI+: 1289.9 |

TABLE 36

| PEx | PSyn | Str | DAT |
|---|---|---|---|
| 64 | 63 | (structure) | ESI+: 1222.8 |
| 65 | 63 | (structure) | ESI+: 1329.2 |

TABLE 37
| PEx | PSyn | Str | DAT |
|---|---|---|---|
| 66 | 66 | | ESI+: 699.5 |
| 67 | 67 | | ESI+: 697.6 |
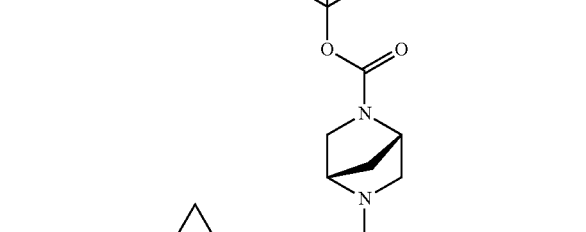

TABLE 37-continued

| PEx | PSyn | Str | DAT |
|---|---|---|---|
| 68 | 68 | | ESI+: 741.7 |

TABLE 38

| PEx | PSyn | Str | DAT |
|---|---|---|---|
| 69 | 69 | | ESI+: 332.2 |
| 70 | 69 | | ESI+: 318.2 |
| 71 | 71 | | ESI+: 232.2 |

TABLE 38-continued

| PEx | PSyn | Str | DAT |
|---|---|---|---|
| 72 | 71 | | ESI+: 218.1 |
| 73 | 73 | | ESI+: 445.3 |

TABLE 39

| PEx | PSyn | Str | DAT |
|---|---|---|---|
| 74 | 73 | | ESI+: 444.4 |
| 75 | 73 | | ESI+: 431.3 |
| 76 | 76 | | ESI+: 345.2 |

TABLE 39-continued
| PEx | PSyn | Str | DAT |
|---|---|---|---|
| 77 | 76 | 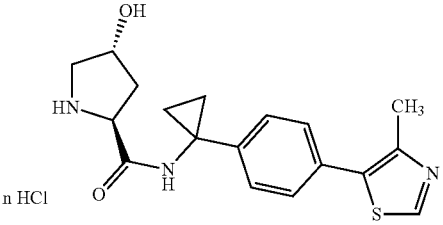 [SMILES: Cc1ncsc1-c1ccc(C2(NC(=O)[C@@H]3C[C@@H](O)CN3)CC2)cc1] | ESI+: 344.3 |
TABLE 40
| PEx | PSyn | Str | DAT |
|---|---|---|---|
| 78 | 76 | 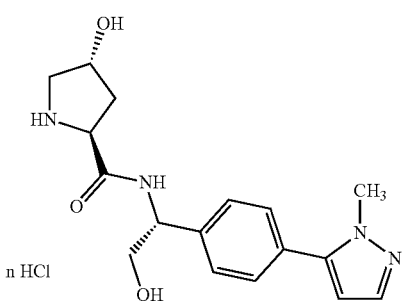 [SMILES: Cn1nccc1-c1ccc([C@H](CO)NC(=O)[C@@H]2C[C@@H](O)CN2)cc1] | ESI+: 331.2 |
| 79 | 79 | 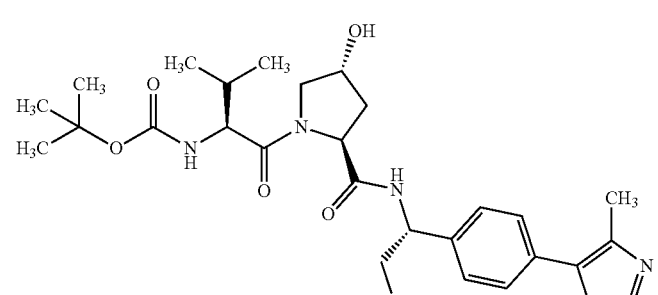 | ESI+: 547.4 |
| 80 | 79 | 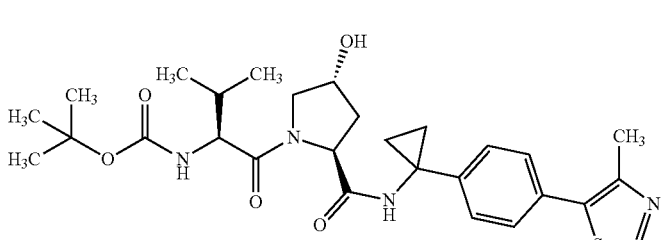 | ESI+: 565.4 [M + Na]+ |
| 81 | 79 | 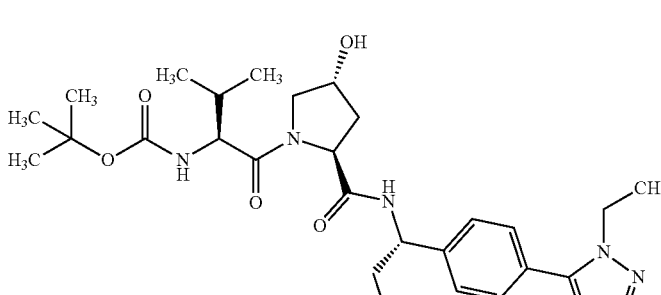 | ESI+: 544.3 |

TABLE 41
| PEx | PSyn | Str | DAT |
|---|---|---|---|
| 82 | 79 | 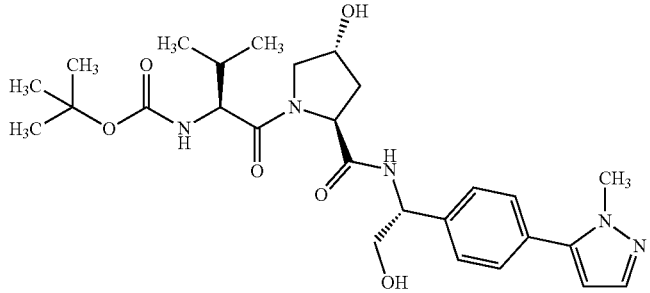 [SMILES: CC(C)[C@H](NC(=O)OC(C)(C)C)C(=O)N1C[C@H](O)C[C@H]1C(=O)N[C@@H](CO)c1ccc(-c2ccnn2C)cc1] | ESI+: 530.4 |
| 83 | 83 | 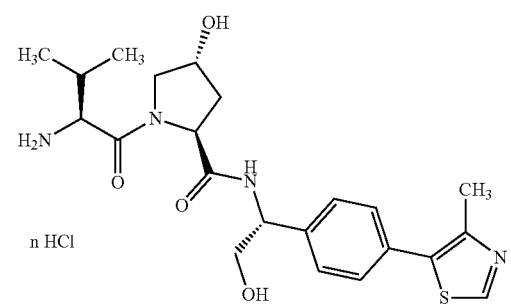 [SMILES: Cc1ncsc1-c1ccc([C@H](CO)NC(=O)[C@@H]2C[C@@H](O)CN2C(=O)[C@@H](N)C(C)C)cc1] n HCl | ESI+: 447.3 |
| 84 | 83 | 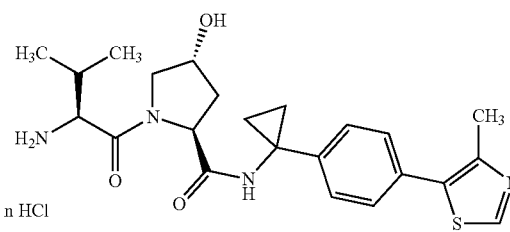 n HCl | ESI+: 443.4 |
| 85 | 83 | 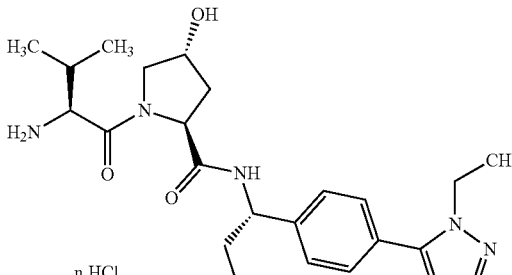 n HCl | ESI+: 444.3 |
TABLE 42
| PEx | PSyn | Str | DAT |
|---|---|---|---|
| 86 | 83 | 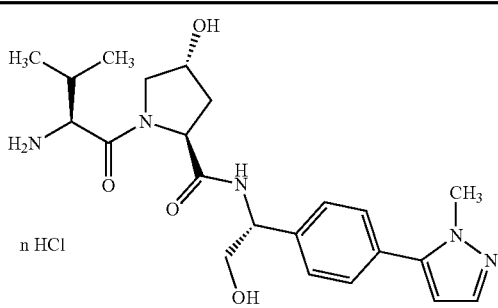 n HCl | ESI+: 430.3 |

TABLE 42-continued
| PEx | PSyn | Str | DAT |
|---|---|---|---|
| 87 | 83 | 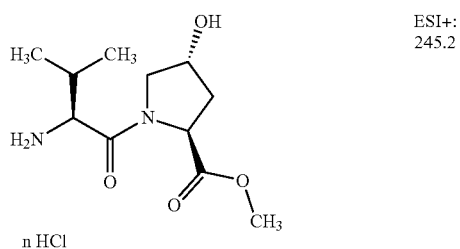 n HCl | ESI+: 245.2 |
| 88 | 88 | 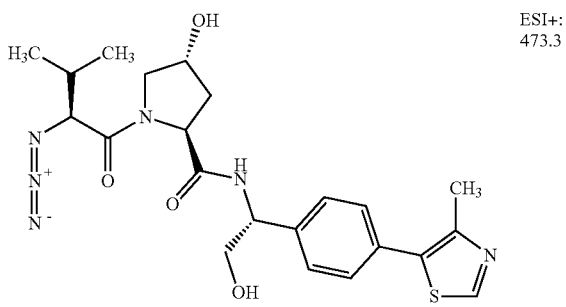 | ESI+: 473.3 |
| 89 | 88 | 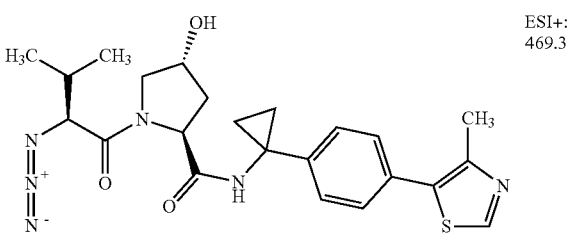 | ESI+: 469.3 |
| 90 | 88 | 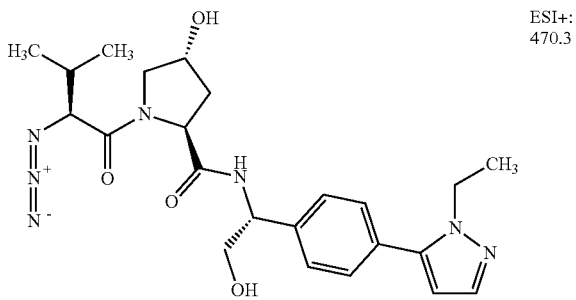 | ESI+: 470.3 |
TABLE 43
| PEx | PSyn | Str | DAT |
|---|---|---|---|
| 91 | 88 | 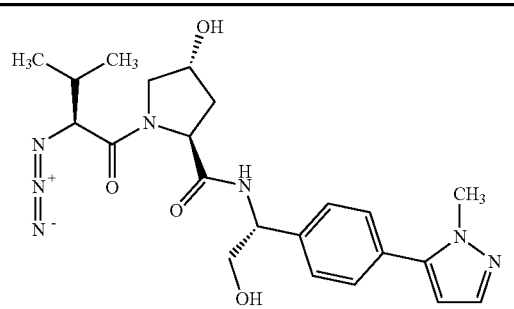 | ESI+: 456.3 |

TABLE 43-continued

| PEx | PSyn | Str | DAT |
|---|---|---|---|
| 92 | 88 | | ESI+: 271.2 |
| 93 | 93 | | ESI+: 328.0 |
| 94 | 94 | | ESI+: 278.1 |
| 95 | 95 | | ESI+: 303.2 |

TABLE 44

| PEx | PSyn | Str | DAT |
|---|---|---|---|
| 96 | 96 | | ESI+: 319.1 |

TABLE 44-continued
| PEx | PSyn | Str | DAT |
|---|---|---|---|
| 97 | 97 | 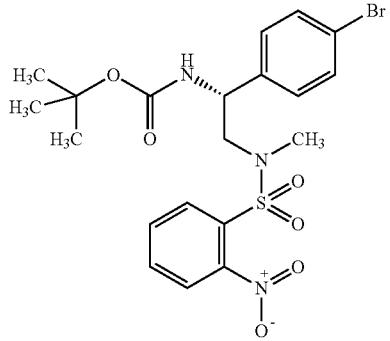 | ESI+: 536.2, 538.2 [M + Na]+ |
| 98 | 98 | 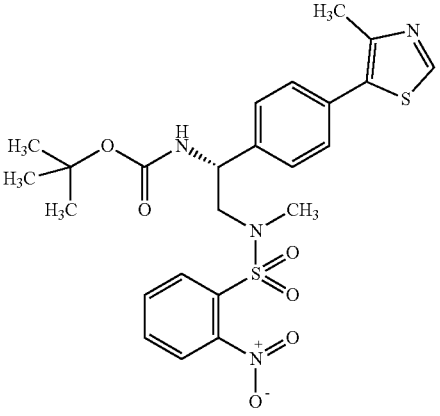 | ESI+: 533.2 |
| 99 | 99 | 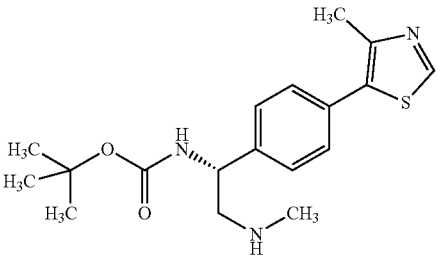 [SMILES: CNC[C@H](NC(=O)OC(C)(C)C)c1ccc(-c2scnc2C)cc1] | ESI+: 348.2 |
| 100 | 100 | 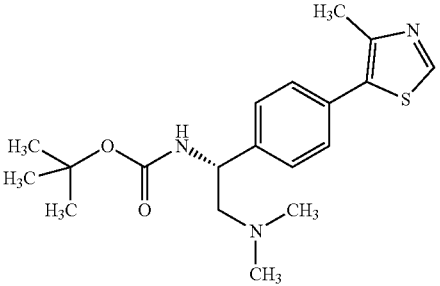 [SMILES: Cc1ncsc1-c1ccc([C@H](CN(C)C)NC(=O)OC(C)(C)C)cc1] | ESI+: 362.2 |

TABLE 45
| PEx | PSyn | Str | DAT |
|---|---|---|---|
| 101 | 71 | 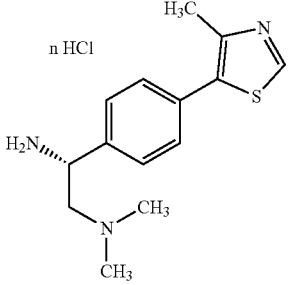 [SMILES: Cc1ncsc1-c1ccc([C@@H](N)CN(C)C)cc1] | ESI+: 262.2 |
| 102 | 102 | 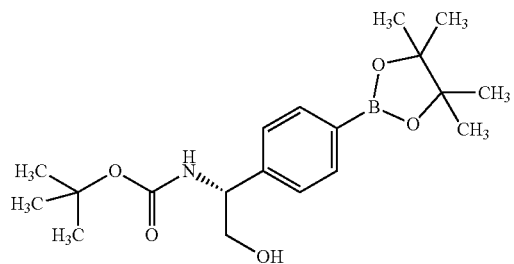 [SMILES: CC(C)(C)OC(=O)N[C@@H](CO)c1ccc(B2OC(C)(C)C(C)(C)O2)cc1] | ESI+: 386.3 [M + Na]+ |
| 103 | 103 | 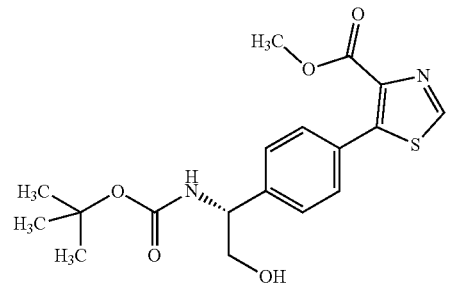 [SMILES: COC(=O)c1ncsc1-c1ccc([C@H](CO)NC(=O)OC(C)(C)C)cc1] | ESI+: 379.3 |
| 104 | 104 | 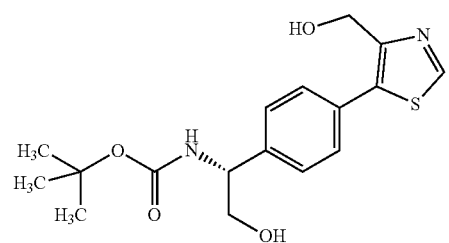 [SMILES: CC(C)(C)OC(=O)N[C@@H](CO)c1ccc(-c2scnc2CO)cc1] | ESI+: 351.2 |
| 105 | 71 | 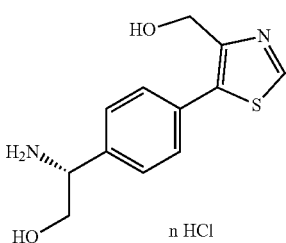 [SMILES: N[C@@H](CO)c1ccc(-c2scnc2CO)cc1] | ESI+: 251.1 |

TABLE 46
| PEx | PSyn | Str | DAT |
|---|---|---|---|
| 106 | 106 | 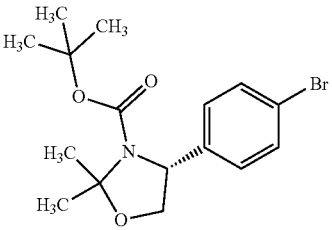 [SMILES: CC(C)(C)OC(=O)N1[C@H](c2ccc(Br)cc2)COC1(C)C] | ESI+: 378.2 [M + Na]+ |
| 107 | 107 | 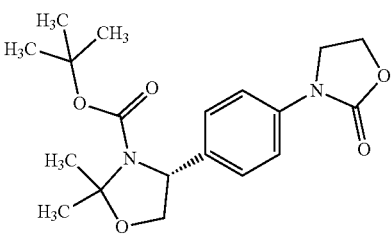 [SMILES: CC(C)(C)OC(=O)N1[C@H](c2ccc(N3CCOC3=O)cc2)COC1(C)C] | ESI+: 385.2 [M + Na]+ |
| 108 | 71 | 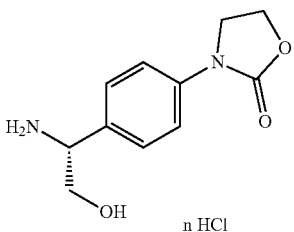 [SMILES: N[C@@H](CO)c1ccc(N2CCOC2=O)cc1] n HCl | ESI+: 245.1 [M + Na]+ |
| 109 | 109 | 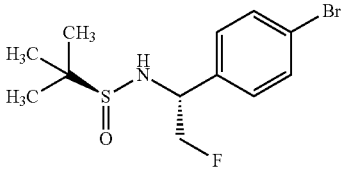 [SMILES: CC(C)(C)[S@](=O)N[C@@H](CF)c1ccc(Br)cc1] | ESI+: 323.9 |
| 110 | 98 | 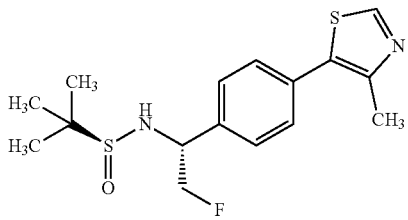 [SMILES: Cc1ncsc1-c1ccc([C@H](CF)N[S@@](=O)C(C)(C)C)cc1] | ESI+: 341.2 |
| 111 | 71 | 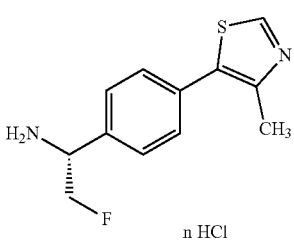 [SMILES: Cc1ncsc1-c1ccc([C@@H](N)CF)cc1] n HCl | ESI+: 237.3 |

TABLE 47
| PEx | PSyn | Str | DAT |
|---|---|---|---|
| 112 | 11 | 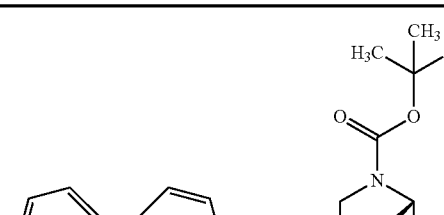 | ESI+: 923.3 |
| 113 | 32 | 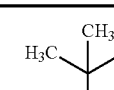 | ESI+: 939.3 |

TABLE 47-continued
| PEx | PSyn | Str | DAT |
|---|---|---|---|
| 114 | 32 | 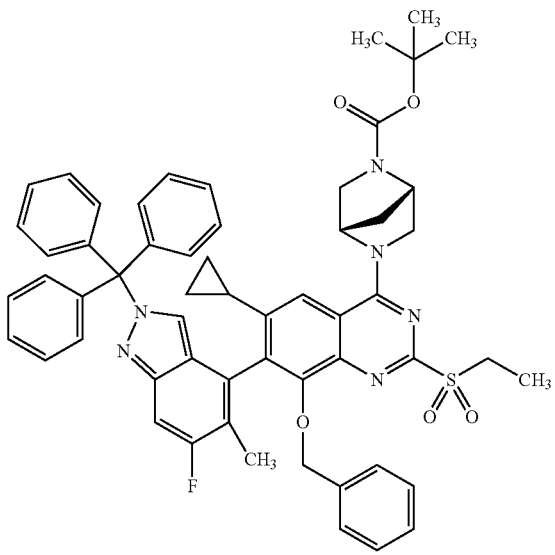 [SMILES: CCS(=O)(=O)c1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccccc3)c2n1] | ESI+: 955.2 |
TABLE 48
| PEx | PSyn | Str | DAT |
|---|---|---|---|
| 115 | 32 | 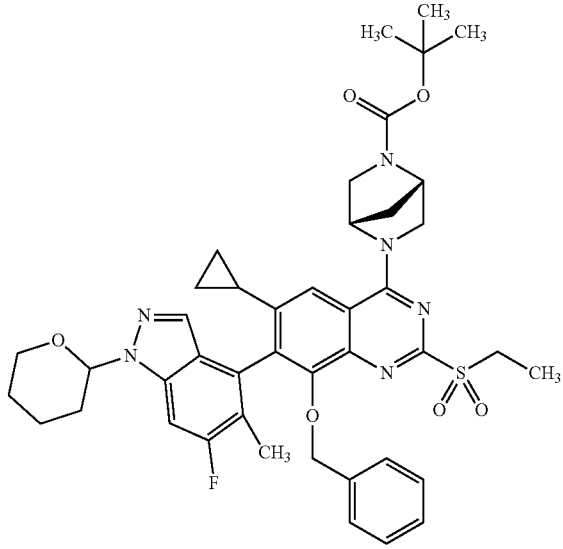 [SMILES: CCS(=O)(=O)c1nc(N2C[C@@H]3C[C@H]2CN3C(=O)OC(C)(C)C)c2cc(C3CC3)c(-c3c(C)c(F)cc4c3cnn4C3CCCCO3)c(OCc3ccccc3)c2n1] | ESI+: 797.4 |

TABLE 48-continued
| PEx | PSyn | Str | DAT |
|---|---|---|---|
| 116 | 36 | 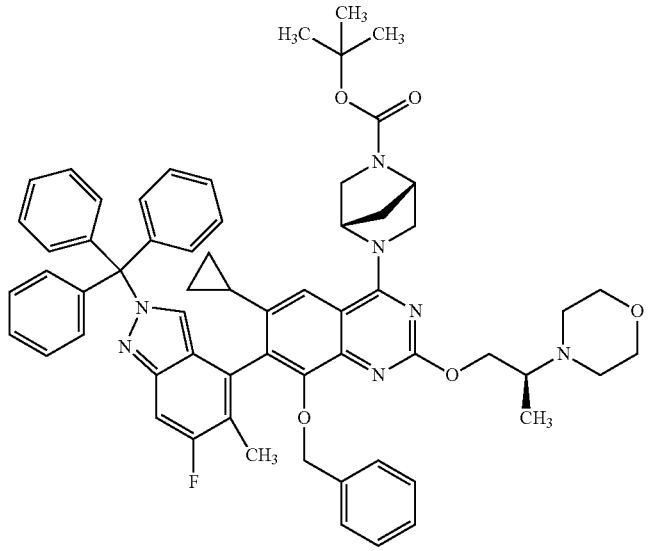 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H](C)N3CCOCC3)nc2c1OCc1ccccc1] | ESI+: 1006.5 |
| 117 | 36 | 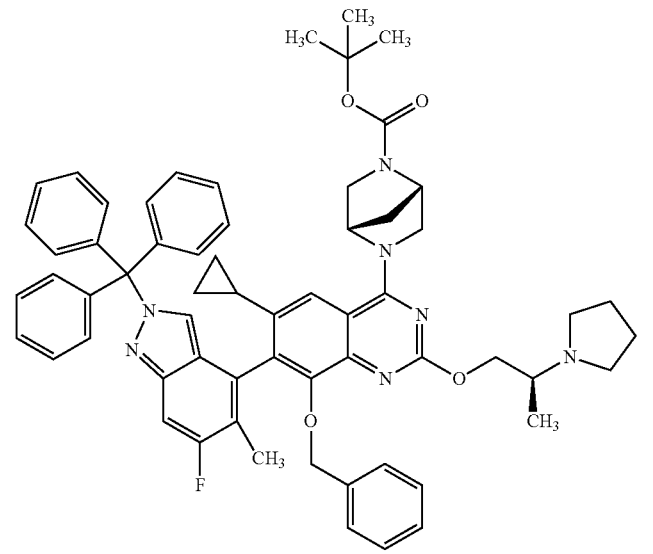 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H](C)N3CCCC3)nc2c1OCc1ccccc1] | ESI+: 990.5 |

TABLE 49
| PEx | PSyn | Str | DAT |
|---|---|---|---|
| 118 | 36 | 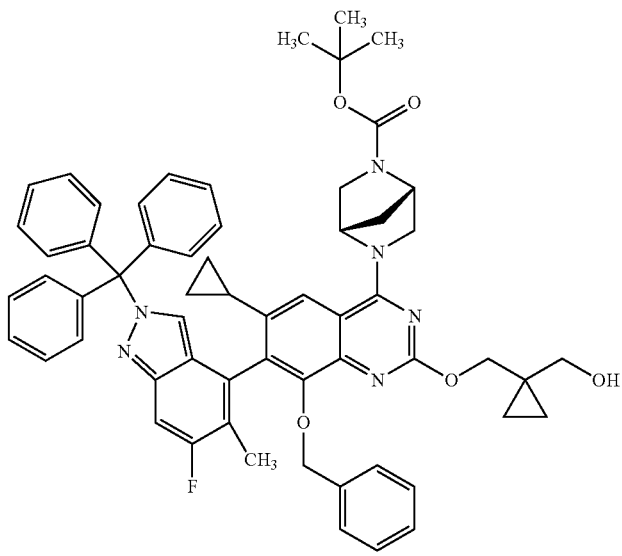 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OCC3(CO)CC3)nc2c1OCc1ccccc1] | ESI+: 963.8 |
| 119 | 36 | 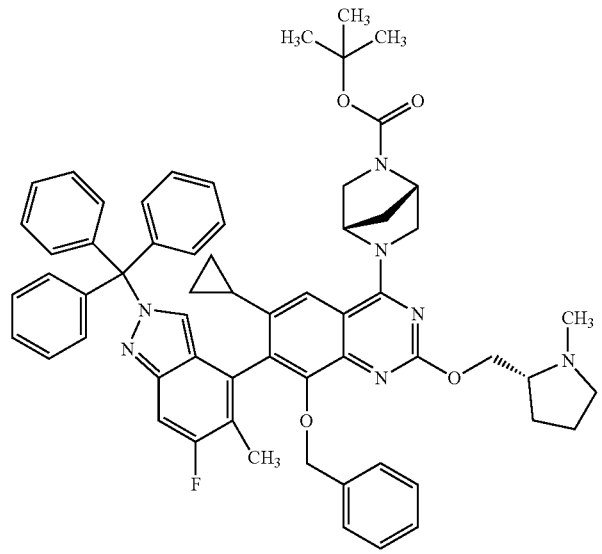 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H]3CCCN3C)nc2c1OCc1ccccc1] | ESI+: 976.8 |

TABLE 49-continued
| PEx | PSyn | Str | DAT |
|---|---|---|---|
| 120 | 36 | | ESI+: 976.4 |
TABLE 50
| PEx | PSyn | Str | DAT |
|---|---|---|---|
| 121 | 36 | | ESI+: 1036.8 |
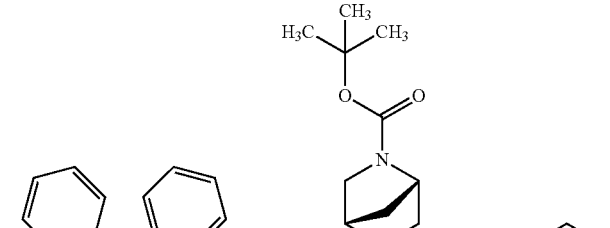

TABLE 50-continued
| PEx | PSyn | Str | DAT |
|---|---|---|---|
| 122 | 36 | 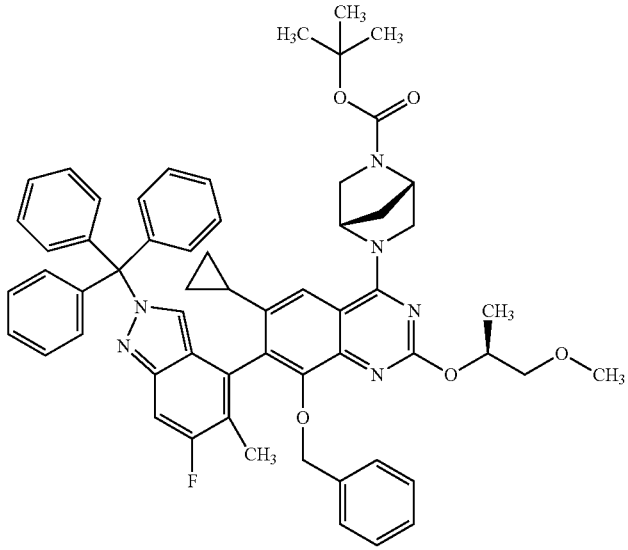 [SMILES: COC[C@H](C)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccccc3)c2n1] | ESI+: 951.7 |
| 123 | 36 | 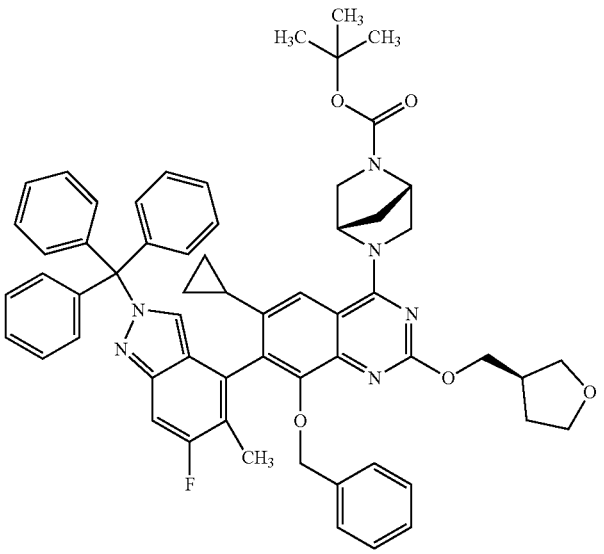 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@@H]3CCOC3)nc2c1OCc1ccccc1] | ESI+: 963.4 |

TABLE 51
| PEx | PSyn | Str | DAT |
|---|---|---|---|
| 124 | 36 | 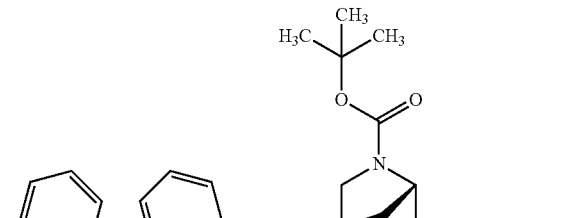 | ESI+: 963.3 |
| 125 | 36 | | ESI+: 951.8 |

TABLE 51-continued
| PEx | PSyn | Str | DAT |
|---|---|---|---|
| 126 | 36 | 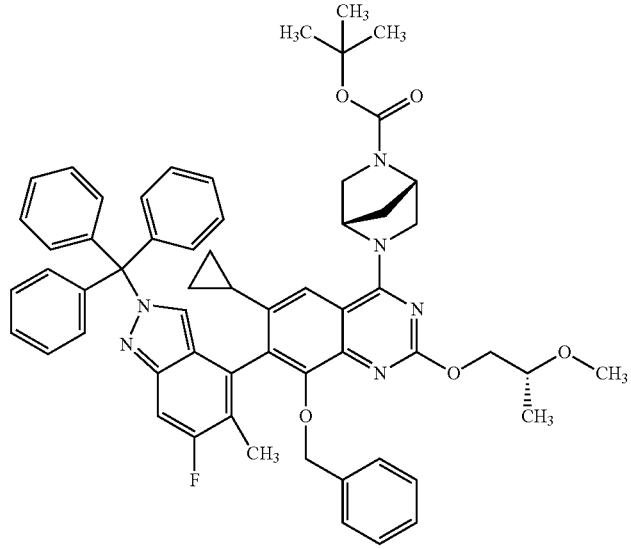 [SMILES: CO[C@H](C)COc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccccc3)c2n1] | ESI+: 951.7 |
TABLE 52
| PEx | PSyn | Str | DAT |
|---|---|---|---|
| 127 | 36 | 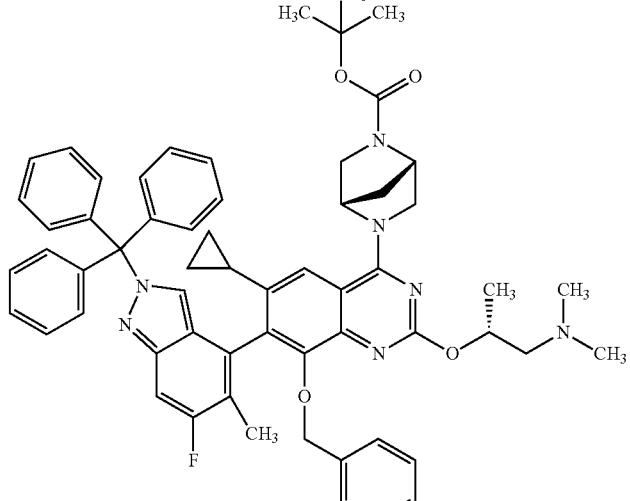 | ESI+: 964.8 |

TABLE 52-continued
| PEx | PSyn | Str | DAT |
|---|---|---|---|
| 128 | 36 | 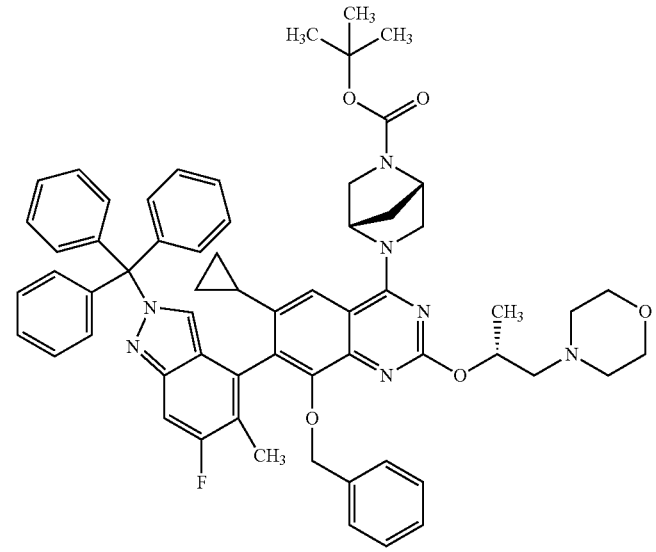 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(O[C@H](C)CN3CCOCC3)nc2c1OCc1ccccc1] | ESI+: 1006.9 |
| 129 | 36 | 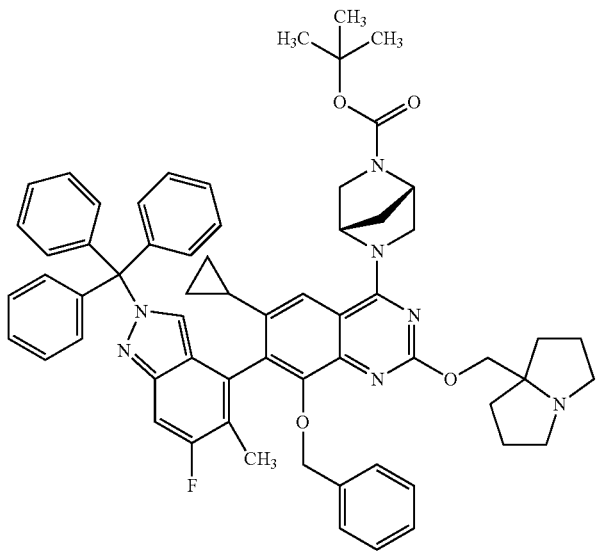 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OCC34CCCN3CCC4)nc2c1OCc1ccccc1] | ESI+: 1002.7 |

TABLE 53
| PEx | PSyn | Str | DAT |
|---|---|---|---|
| 130 | 36 | 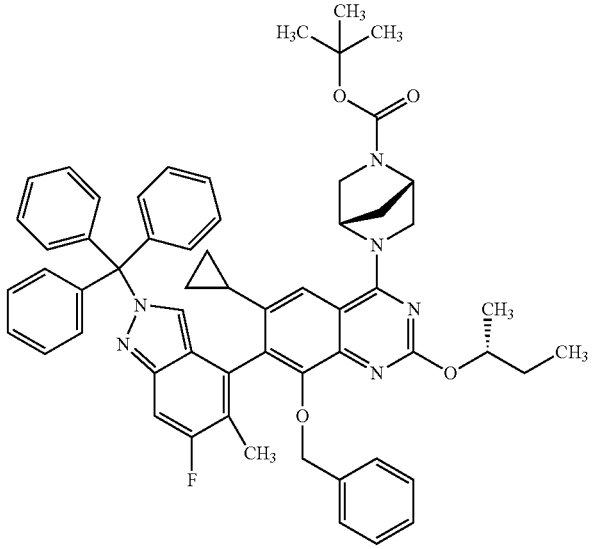 [SMILES: CC[C@@H](C)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccccc3)c2n1] | ESI+: 935.3 |
| 131 | 36 | 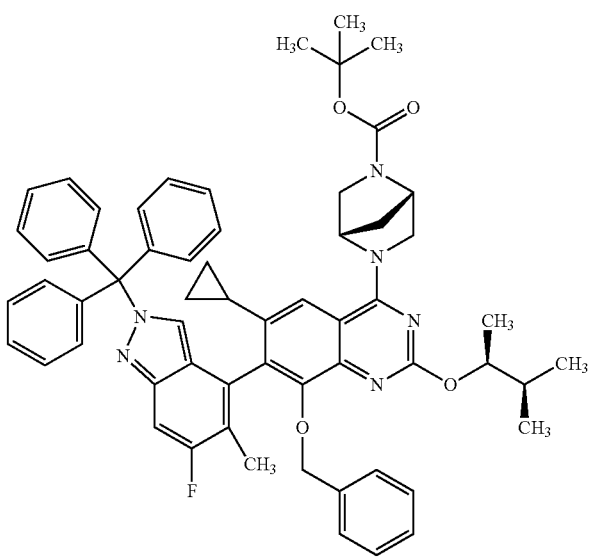 | ESI+: 951.3 |

TABLE 53-continued
| PEx | PSyn | Str | DAT |
|---|---|---|---|
| 132 | 36 | 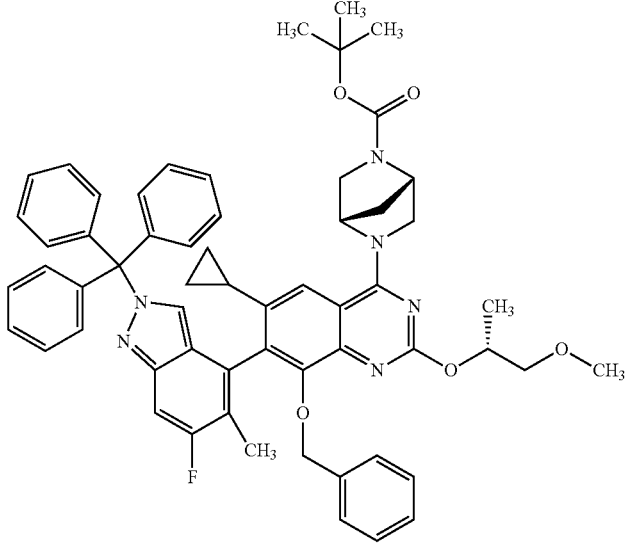 [SMILES: COC[C@@H](C)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccccc3)c2n1] | ESI+: 951.4 |
TABLE 54
| PEx | PSyn | Str | DAT |
|---|---|---|---|
| 133 | 14 | 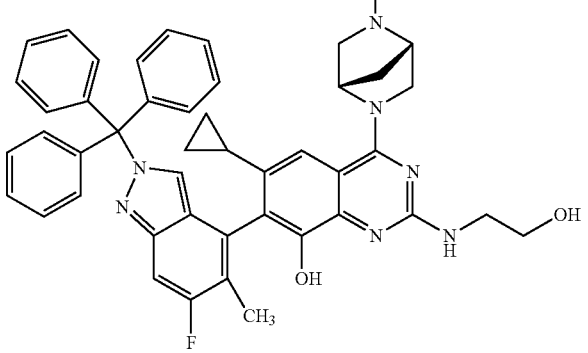 | ESI+: 832.5 |

TABLE 54-continued
| PEx | PSyn | Str | DAT |
|---|---|---|---|
| 134 | 14 | 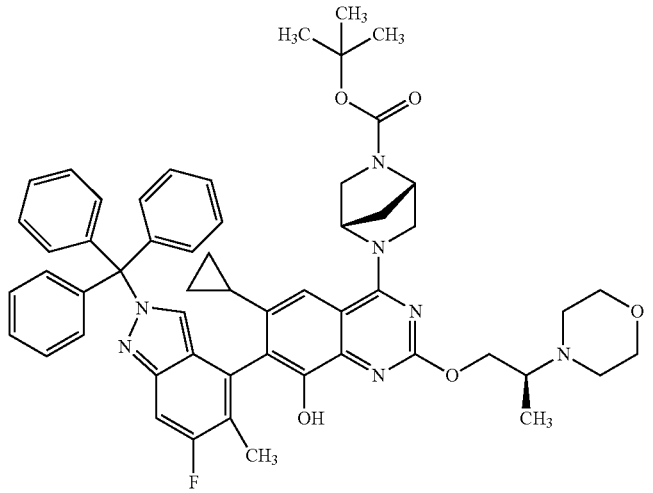 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H](C)N3CCOCC3)nc2c1O] | ESI+: 916.8 |
| 135 | 14 | 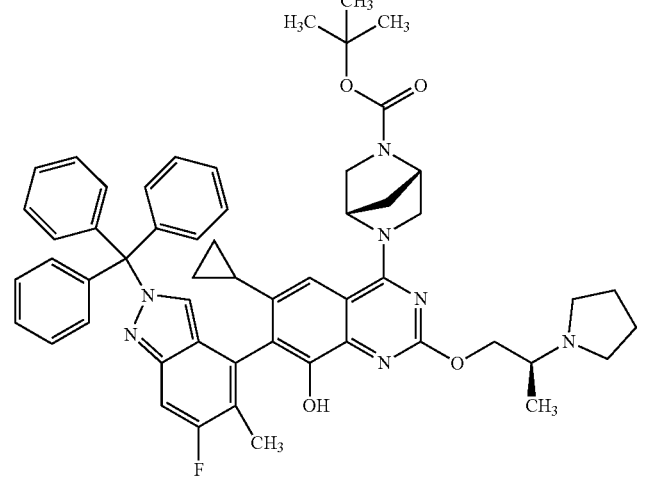 | ESI+: 900.7 |

TABLE 55
| PEx | PSyn | Str | DAT |
|---|---|---|---|
| 136 | 14 | 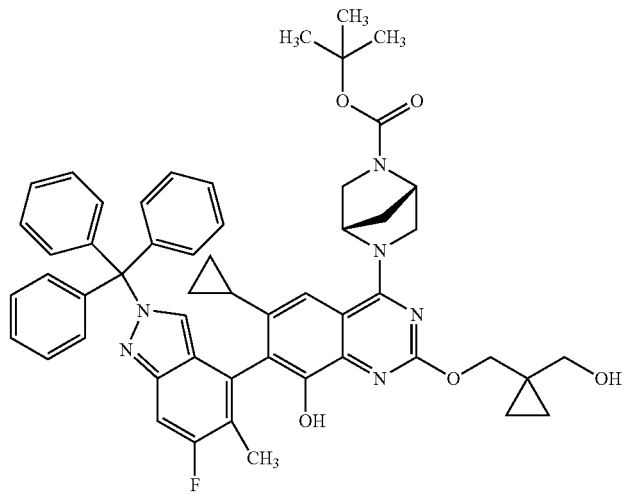 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OCC3(CO)CC3)nc2c1O] | ESI+: 873.7 |
| 137 | 14 | 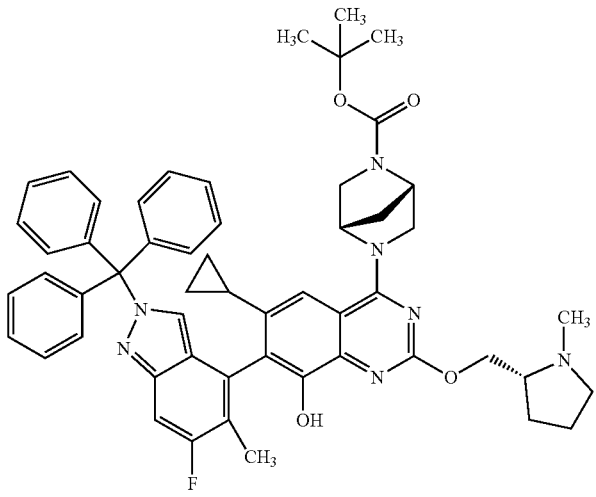 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H]3CCCN3C)nc2c1O] | ESI+: 886.9 |
| 138 | 14 | 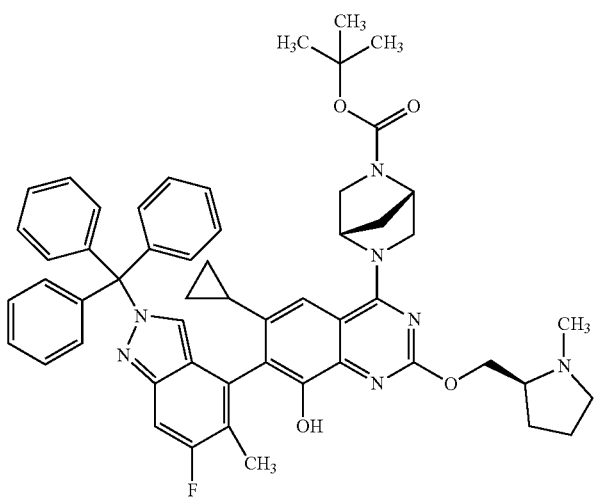 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@@H]3CCCN3C)nc2c1O] | ESI+: 886.4 |

TABLE 56
| PEx | PSyn | Str | DAT |
|---|---|---|---|
| 139 | 14 | 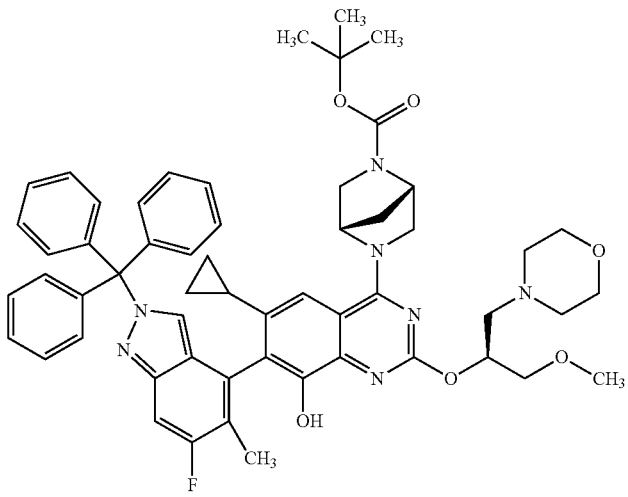 [SMILES: COC[C@H](CN1CCOCC1)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O)c2n1] | ESI+: 946.8 |
| 140 | 14 | 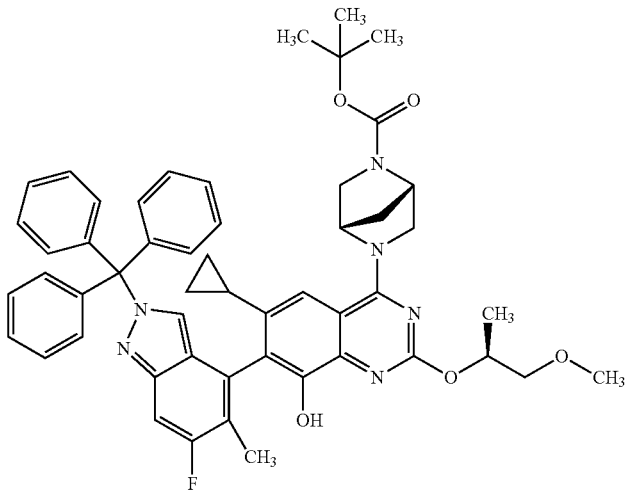 [SMILES: COC[C@H](C)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O)c2n1] | ESI+: 861.7 |
| 141 | 14 | 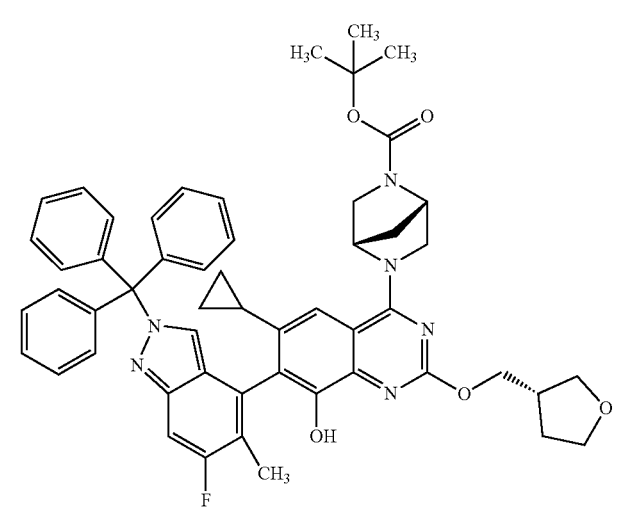 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OC[C@H]3CCOC3)nc2c1O] | ESI+: 873.3 |

TABLE 57
| PEx | PSyn | Str | DAT |
|---|---|---|---|
| 142 | 14 | 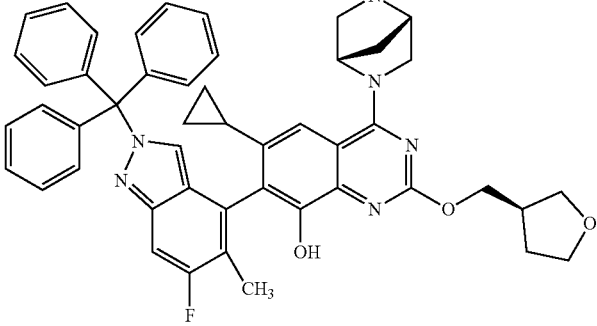 | ESI+: 873.4 |
| 143 | 14 | 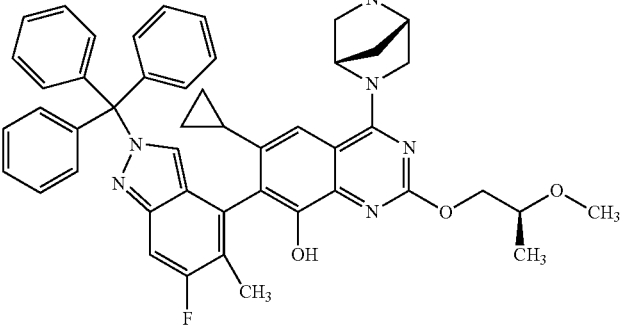 | ESI+: 861.7 |
| 144 | 14 | 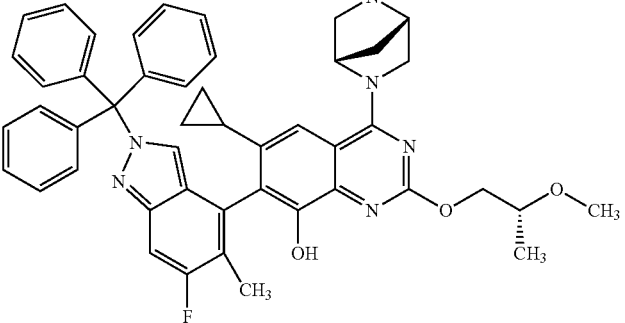 | ESI+: 861.7 |

TABLE 58
| PEx | PSyn | Str | DAT |
|---|---|---|---|
| 145 | 14 | 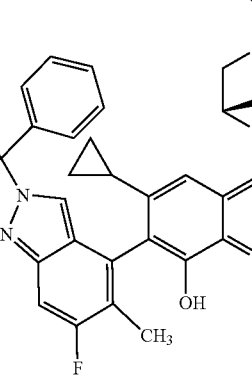 | ESI−: 863.4 |
| 146 | 14 | 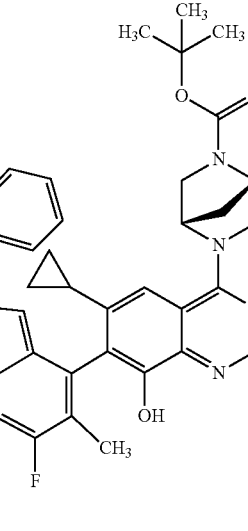 | ESI+: 874.4 |
| 147 | 14 | 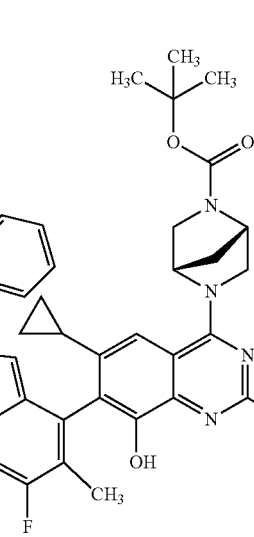 | ESI+: 916.4 |

TABLE 59
| PEx | PSyn | Str | DAT |
|---|---|---|---|
| 148 | 14 | 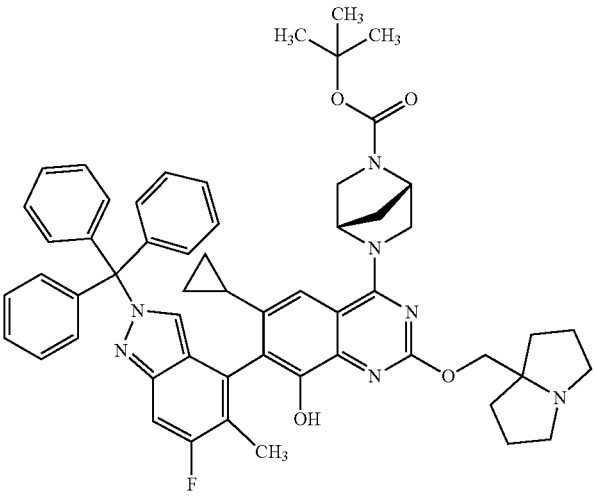 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(OCC34CCCN3CCC4)nc2c1O] | ESI+: 912.4 |
| 149 | 14 | 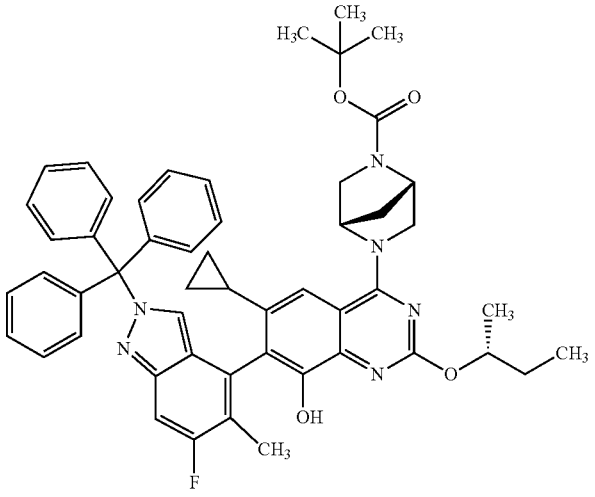 [SMILES: CC[C@@H](C)Oc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O)c2n1] | ESI+: 845.4 |
| 150 | 14 | 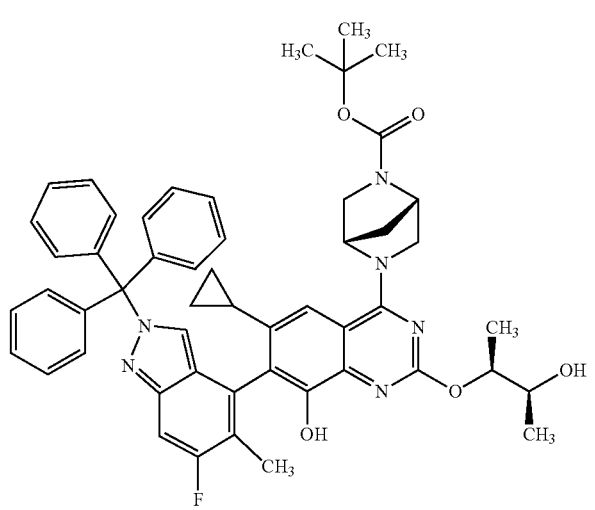 [SMILES: Cc1c(F)cc2nn(C(c3ccccc3)(c3ccccc3)c3ccccc3)cc2c1-c1c(C2CC2)cc2c(N3C[C@@H]4C[C@H]3CN4C(=O)OC(C)(C)C)nc(O[C@@H](C)[C@H](C)O)nc2c1O] | ESI+: 861.4 |

TABLE 60
| PEx | PSyn | Str | DAT |
|---|---|---|---|
| 151 | 14 | 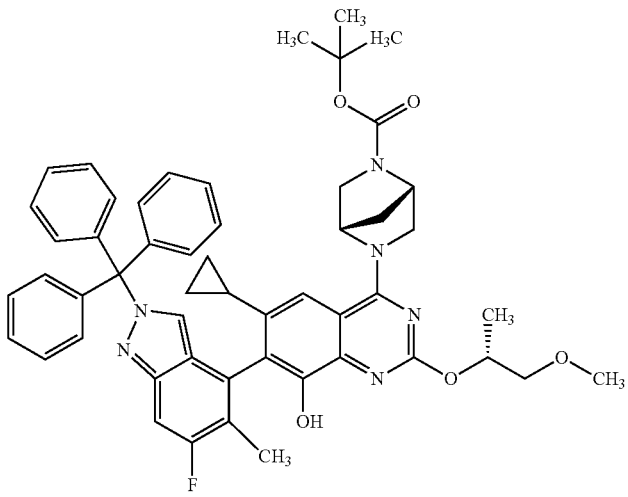 | ESI+: 861.7 |
| 152 | 14 | 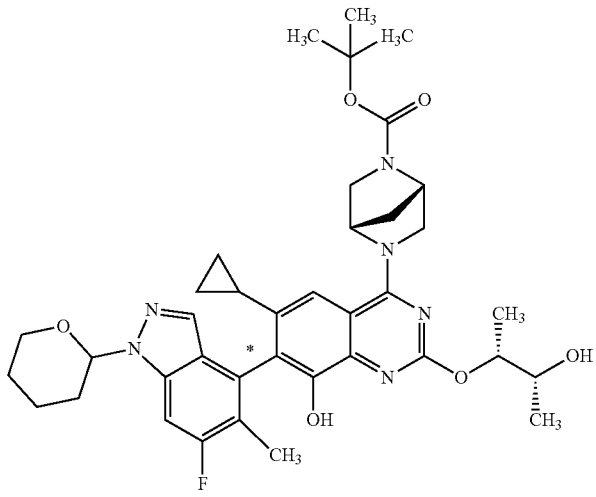 | ESI+: 703.5 |
| 153 | 14 | 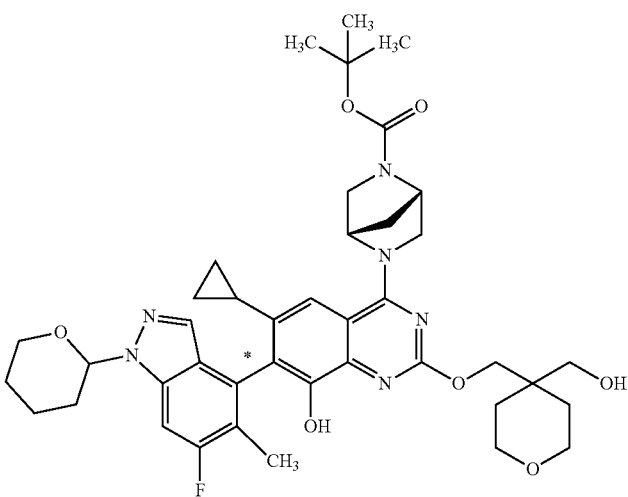 | ESI+: 759.4 |

TABLE 61

| PEx | PSyn | Str | DAT |
|---|---|---|---|
| 154 | 14 | | ESI+: 844.5 |
| 155 | 14 | | ESI+: 844.8 |
| 156 | 156 | | EI: 168.0 [M]+ NMR: 4.54 (1H, s), 4.79 (2H, s), 7.31 (1H, dd), 7.41 (1H, dd), 7.57 (1H, t) |

TABLE 62

| PEx | PSyn | Str | DAT |
|-----|------|-----|-----|
| 157 | 22 | | ESI+: 946.7 |
| 158 | 22 | | ESI+: 1030.5 |

TABLE 62-continued
| PEx | PSyn | Str | DAT |
|---|---|---|---|
| 159 | 22 | 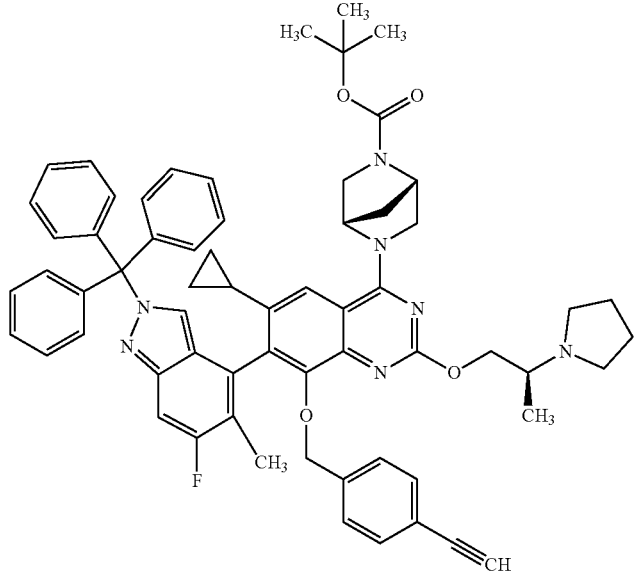 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OC[C@H](C)N4CCCC4)nc23)cc1] | ESI+: 1014.8 |
TABLE 63
| PEx | PSyn | Str | DAT |
|---|---|---|---|
| 160 | 22 | 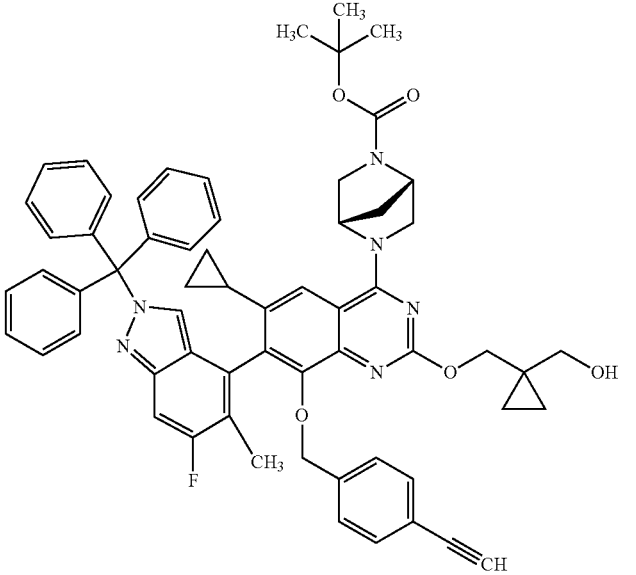 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OCC4(CO)CC4)nc23)cc1] | ESI+: 987.4 |

TABLE 63-continued
| PEx | PSyn | Str | DAT |
|---|---|---|---|
| 161 | 22 | 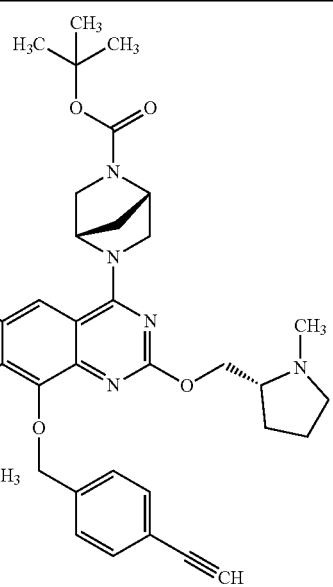 | ESI+: 1001.7 |
| 162 | 22 | 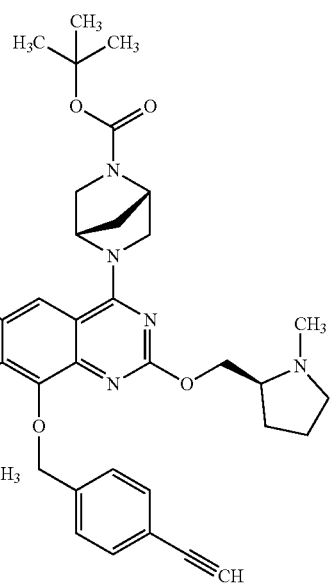 | ESI+: 1000.8 |

TABLE 64
| PEx | PSyn | Str | DAT |
|---|---|---|---|
| 163 | 22 | 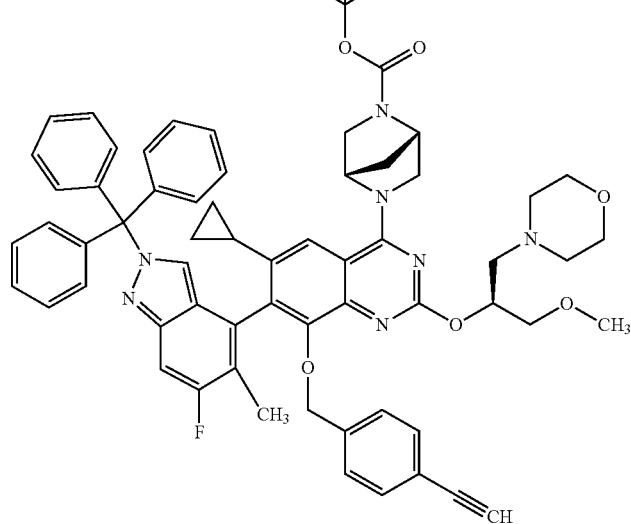 | ESI+: 1060.4 |
| 164 | 22 | 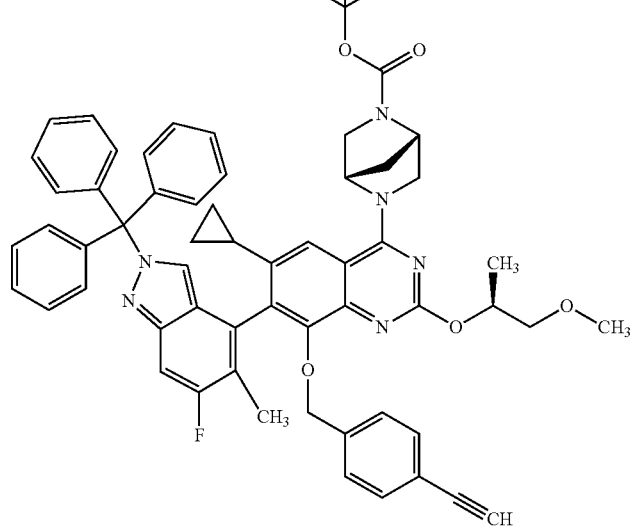 | ESI+: 975.4 |

TABLE 64-continued
| PEx | PSyn | Str | DAT |
|---|---|---|---|
| 165 | 22 | 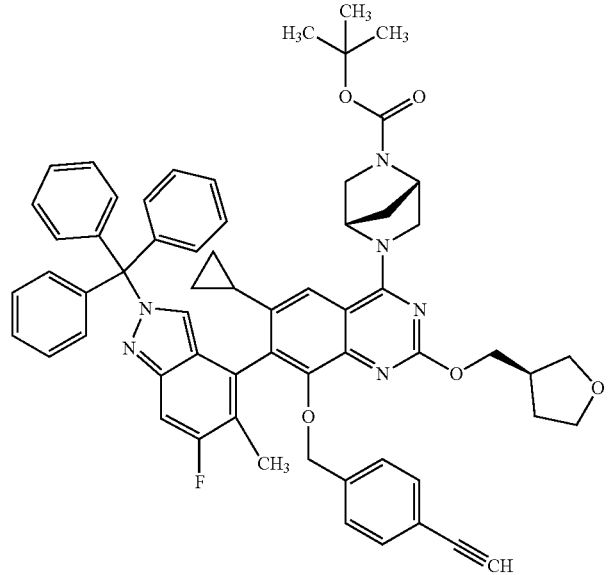 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OC[C@@H]4CCOC4)nc23)cc1] | ESI+: 987.5 |
TABLE 65
| PEx | PSyn | Str | DAT |
|---|---|---|---|
| 166 | 22 | 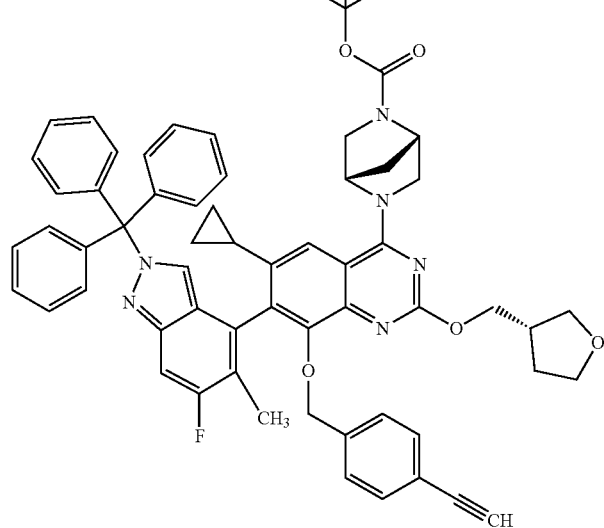 | ESI+: 987.4 |

TABLE 65-continued
| PEx | PSyn | Str | DAT |
|---|---|---|---|
| 167 | 22 | 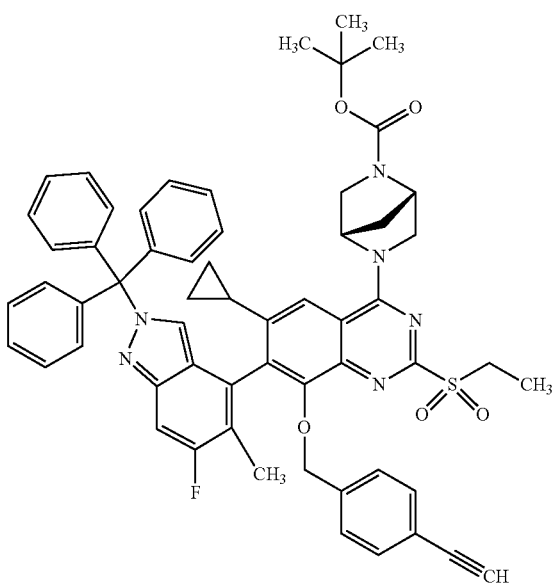 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(S(=O)(=O)CC)nc23)cc1] | ESI+: 979.2 |
| 168 | 22 | 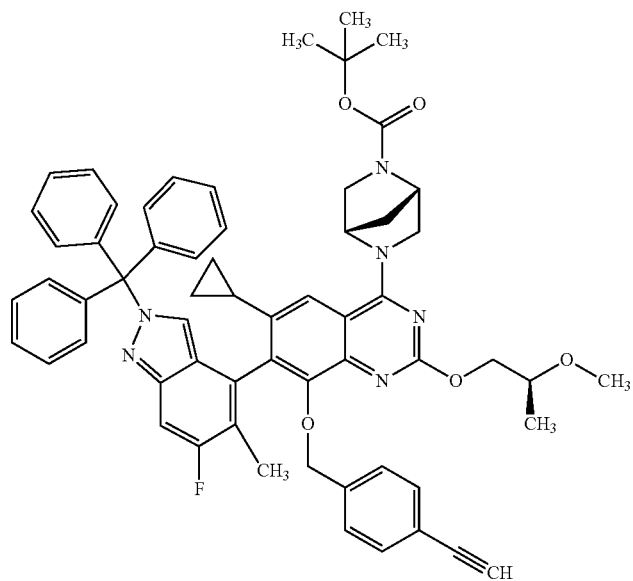 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OC[C@H](C)OC)nc23)cc1] | ESI+: 975.7 |

TABLE 66
| PEx | PSyn | Str | DAT |
|---|---|---|---|
| 169 | 22 | 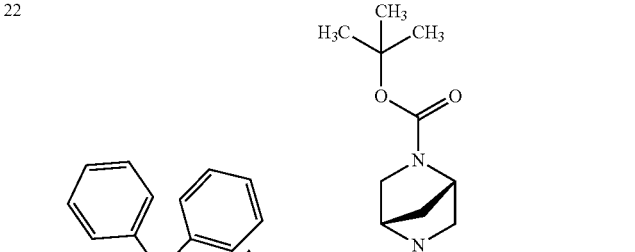 | ESI+: 975.6 |
| 170 | 22 | | ESI+: 847.4 |

TABLE 66-continued
| PEx | PSyn | Str | DAT |
|---|---|---|---|
| 171 | 22 | 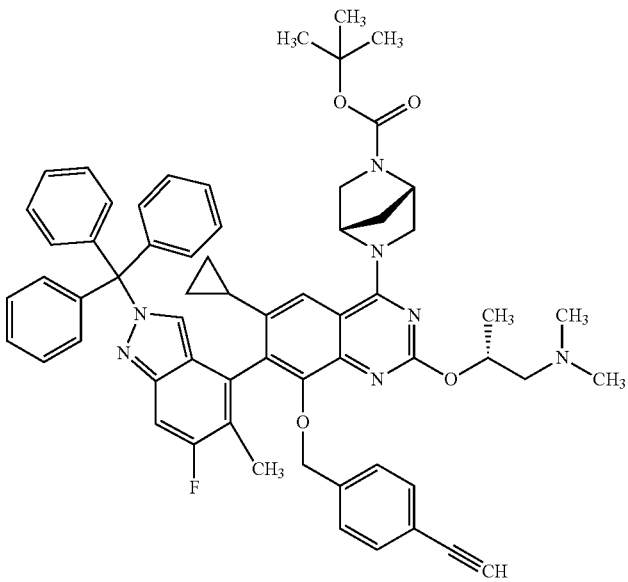 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(O[C@H](C)CN(C)C)nc23)cc1] | ESI+: 988.5 |
TABLE 67
| PEx | PSyn | Str | DAT |
|---|---|---|---|
| 172 | 22 | 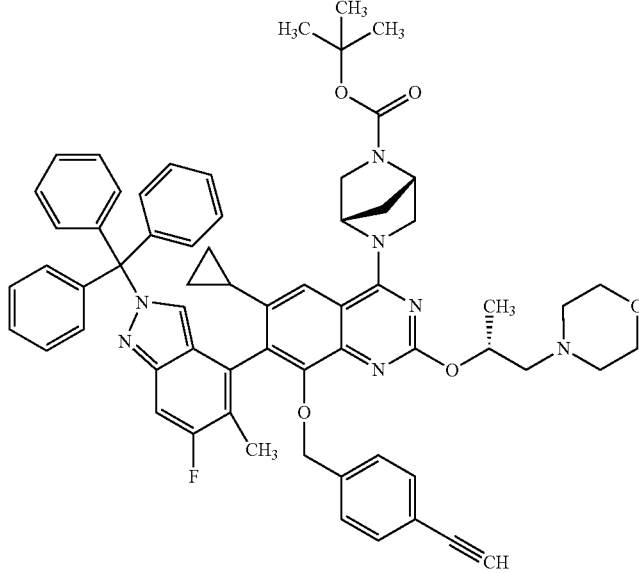 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(O[C@H](C)CN4CCOCC4)nc23)cc1] | ESI+: 1030.3 |

TABLE 67-continued
| PEx | PSyn | Str | DAT |
|---|---|---|---|
| 173 | 22 | 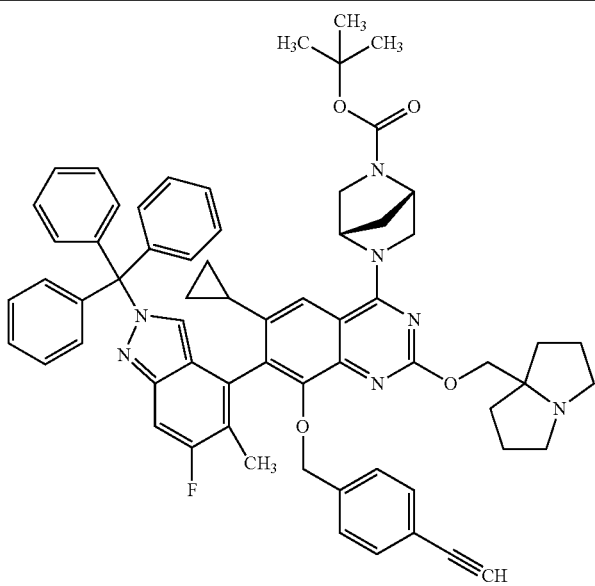 | ESI+: 1026.3 |
| 174 | 22 | 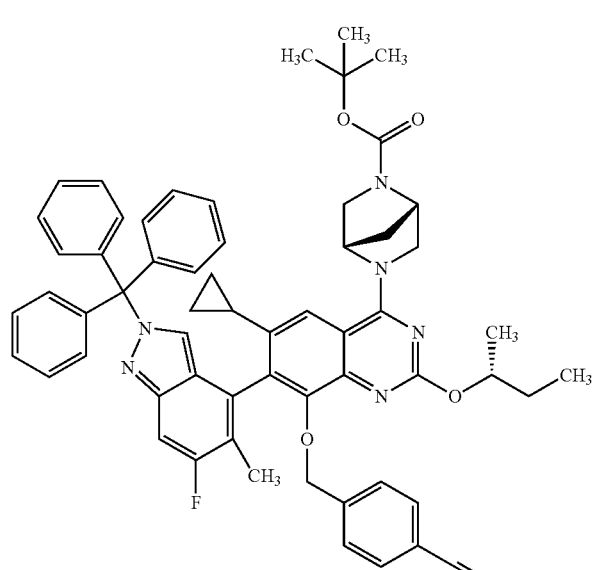 | ESI+: 959.4 |

TABLE 68
| PEx | PSyn | Str | DAT |
|---|---|---|---|
| 175 | 22 | 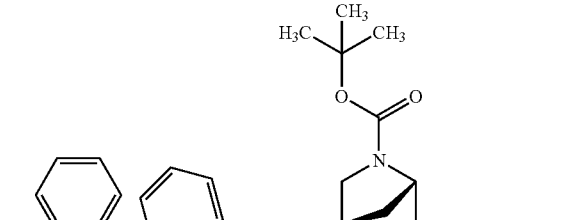 | ESI+: 975.3 |
| 176 | 22 | | ESI+: 975.3 |

TABLE 68-continued
| PEx | PSyn | Str | DAT |
|---|---|---|---|
| 177 | 22 | 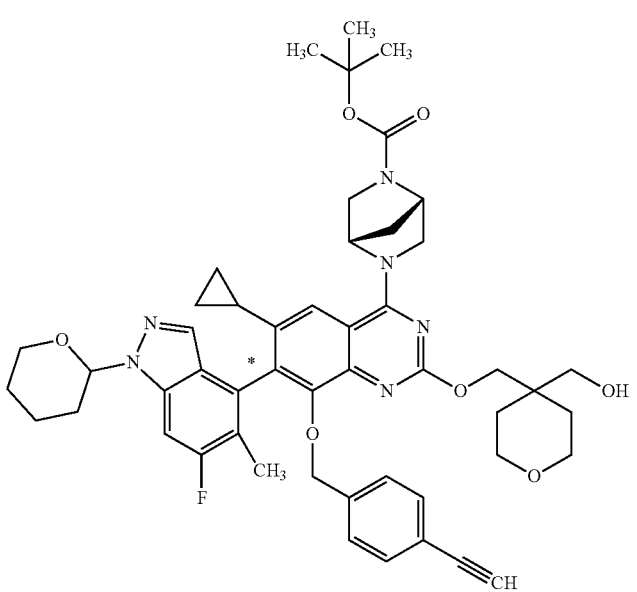 [SMILES: C#Cc1ccc(COc2c(-c3c(C)c(F)cc4c3cnn4C3CCCCO3)c(C3CC3)cc3c(N4C[C@@H]5C[C@H]4CN5C(=O)OC(C)(C)C)nc(OCC4(CO)CCOCC4)nc23)cc1] | ESI+: 873.7 |
TABLE 69
| PEx | PSyn | Str | DAT |
|---|---|---|---|
| 178 | 22 | 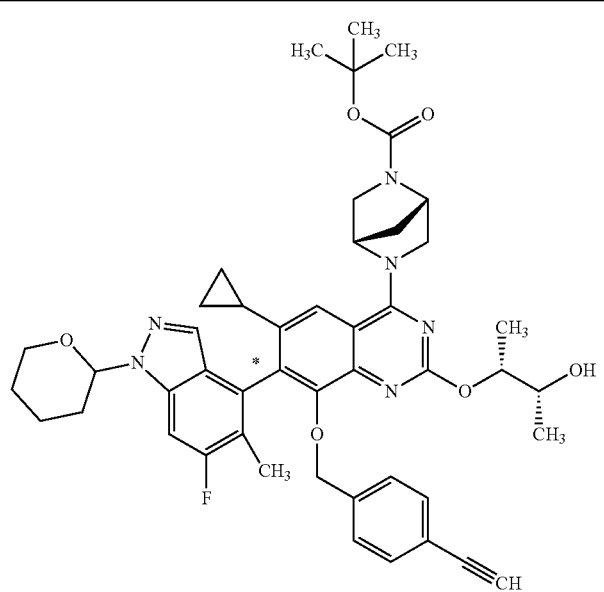 | ESI+: 817.4 |

TABLE 69-continued
| PEx | PSyn | Str | DAT |
|---|---|---|---|
| 179 | 22 | 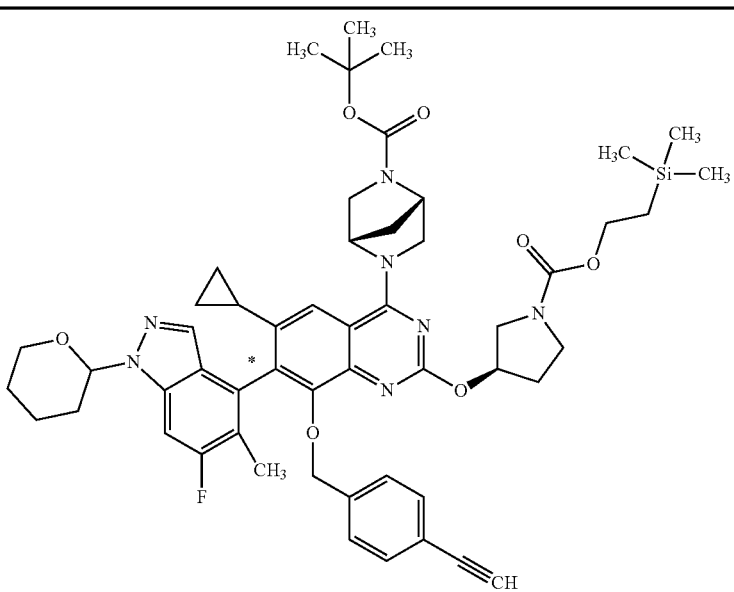 | ESI+: 958.4 |
| 180 | 22 | 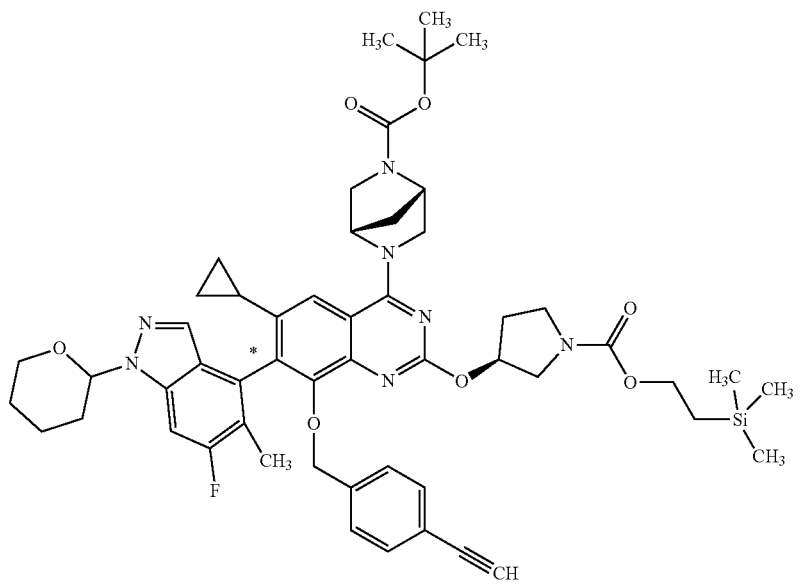 [SMILES: C#Cc1ccc(COc2c(-c3c(C)c(F)cc4c3cnn4C3CCCCO3)c(C3CC3)cc3c(N4C[C@@H]5C[C@H]4CN5C(=O)OC(C)(C)C)nc(O[C@H]4CCN(C(=O)OCC[Si](C)(C)C)C4)nc23)cc1] | ESI+: 958.4 |
TABLE 70
| PEx | PSyn | Str | DAT |
|---|---|---|---|
| 181 | 98 | 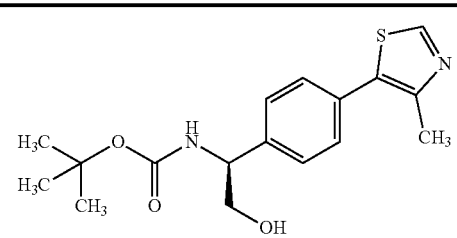 | ESI+: 335.2 |

TABLE 70-continued
| PEx | PSyn | Str | DAT |
|---|---|---|---|
| 182 | 71 | 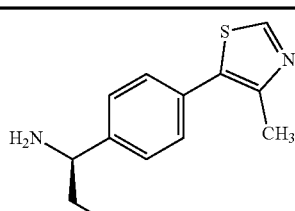 | ESI+: 235.1 |
| 183 | 37 | 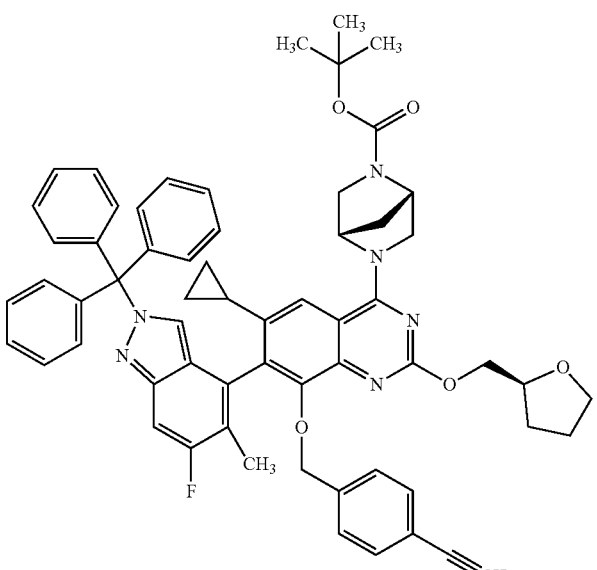 | ESI+: 987.7 |
TABLE 71
| PEx | PSyn | Str | DAT |
|---|---|---|---|
| 184 | 37 | 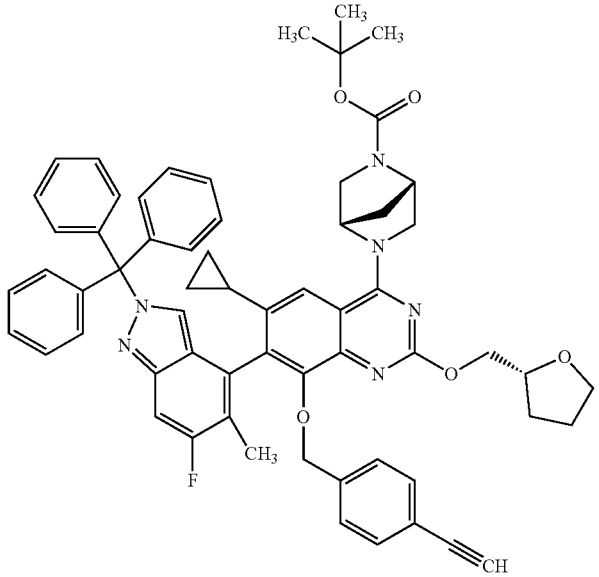 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OC[C@H]4CCCO4)nc23)cc1] | ESI+: 987.4 |

TABLE 71-continued
| PEx | PSyn | Str | DAT |
|---|---|---|---|
| 185 | 37 | 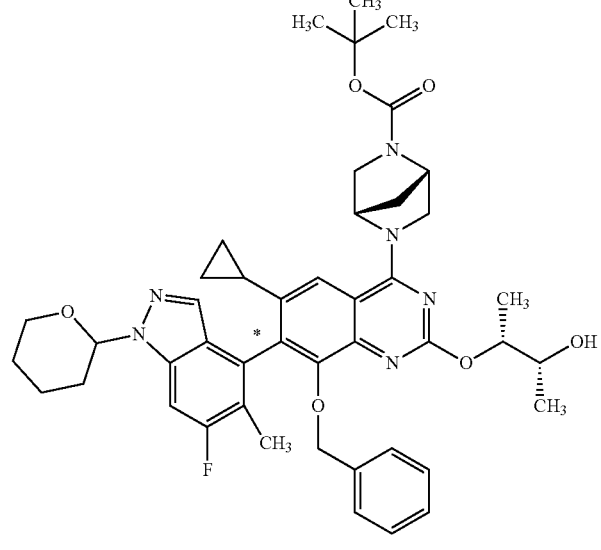 | ESI+: 793.4 |
| 186 | 37 | 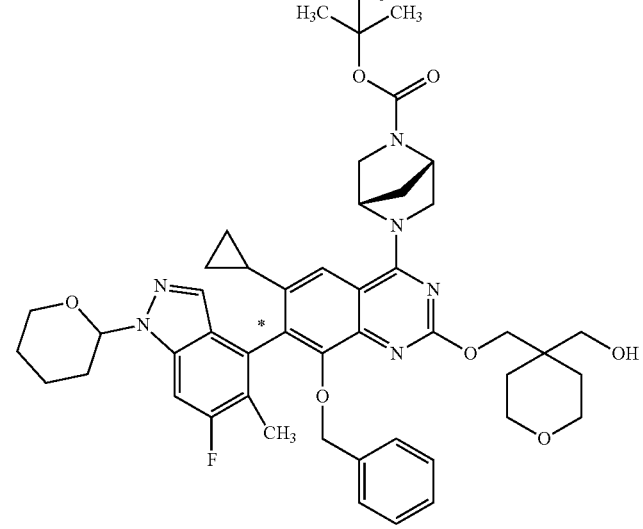 | ESI+: 849.4 |

TABLE 72
| PEx | PSyn | Str | DAT |
|---|---|---|---|
| 187 | 37 | 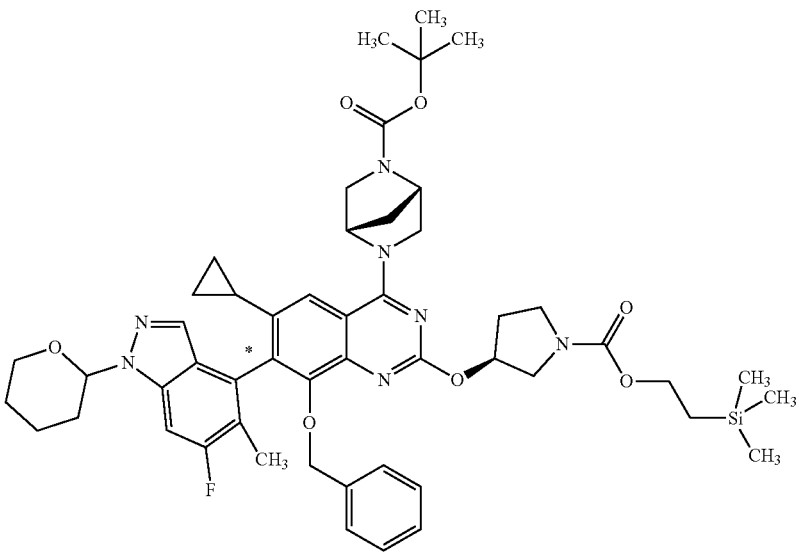 [SMILES: Cc1c(F)cc2c(cnn2C2CCCCO2)c1-c1c(C2CC2)cc2c(N3C[C@@H]4C[C@H]3CN4C(=O)OC(C)(C)C)nc(O[C@H]3CCN(C(=O)OCC[Si](C)(C)C)C3)nc2c1OCc1ccccc1] | ESI+: 934.4 |
| 188 | 37 | 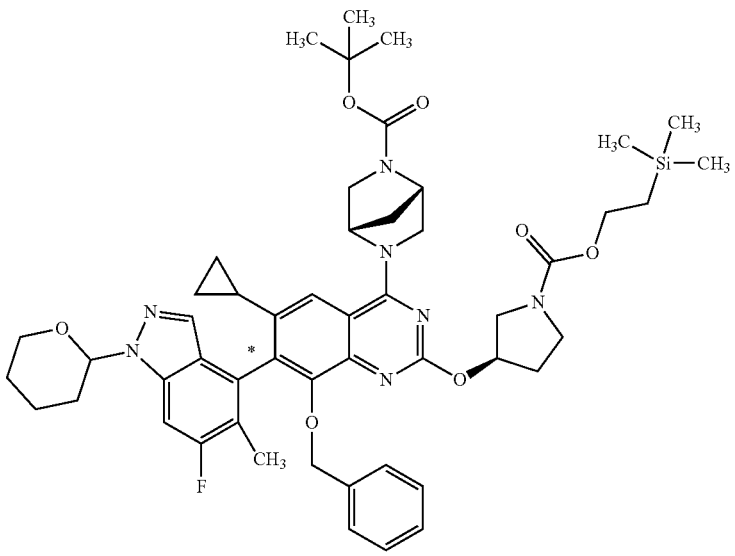 [SMILES: Cc1c(F)cc2c(cnn2C2CCCCO2)c1-c1c(C2CC2)cc2c(N3C[C@@H]4C[C@H]3CN4C(=O)OC(C)(C)C)nc(O[C@@H]3CCN(C(=O)OCC[Si](C)(C)C)C3)nc2c1OCc1ccccc1] | ESI+: 934.4 |
| 189 | 189 | 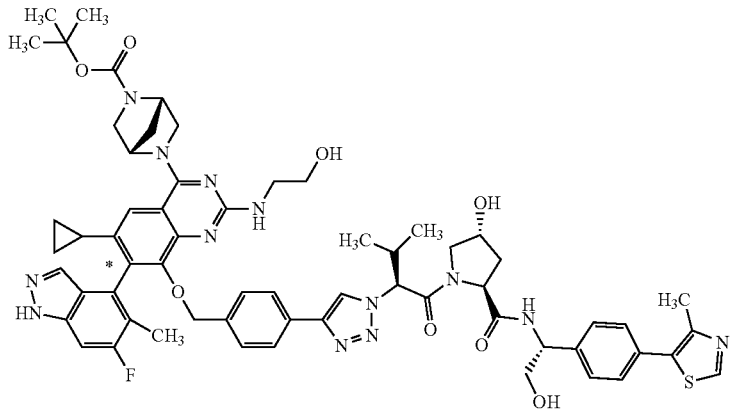 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(NCCO)nc45)cc3)nn2)cc1] | ESI+: 1176.7 |

TABLE 73
| PEx | PSyn | Str | DAT |
|---|---|---|---|
| 190 | 189 | 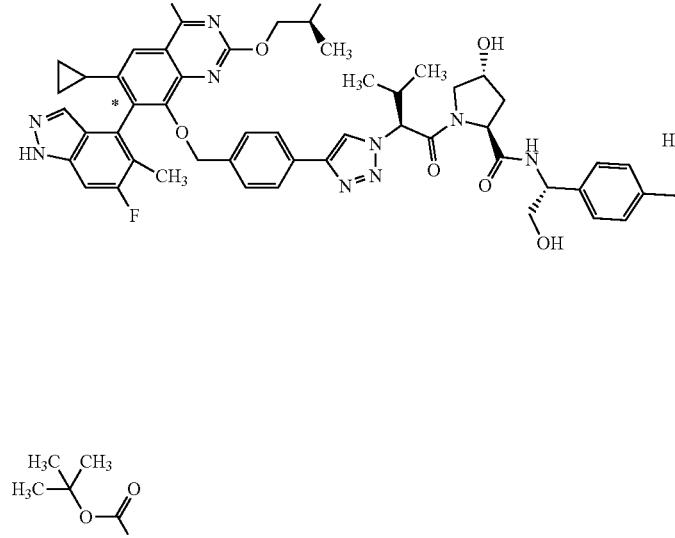 | ESI+: 1260.9 |
| 191 | 189 | 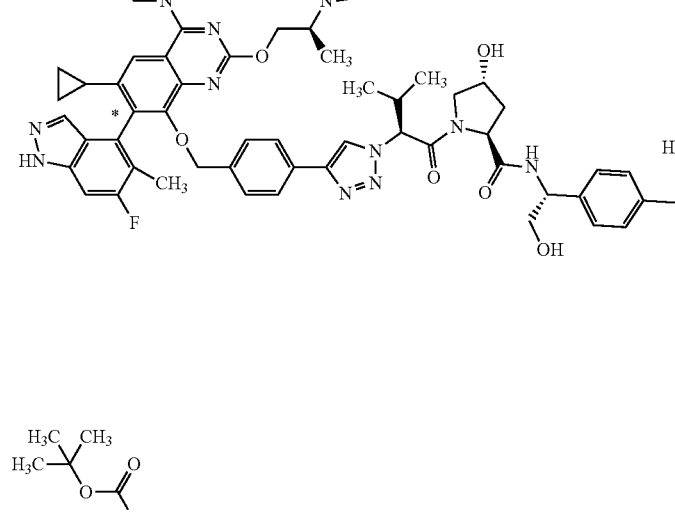 | ESI+: 1245.1 |
| 192 | 189 | 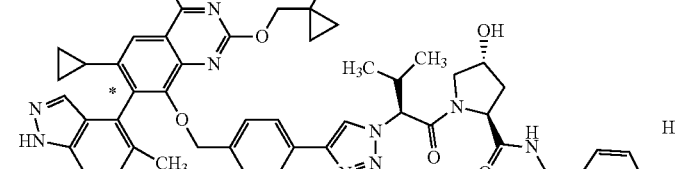 | ESI+: 1231.2 |

TABLE 74
| PEx | PSyn | Str | DAT |
|---|---|---|---|
| 193 | 189 | 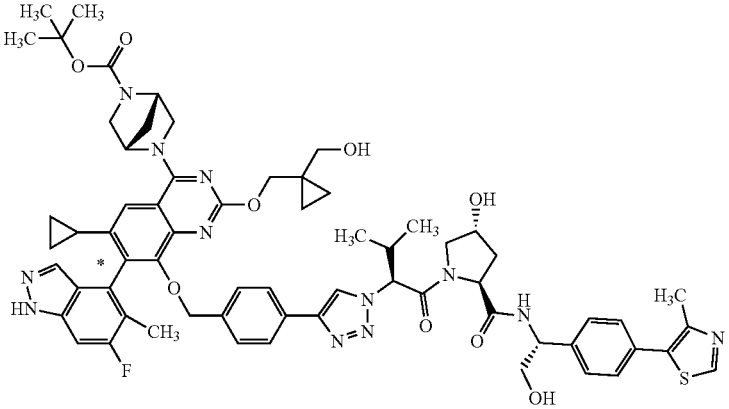 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OCC6(CO)CC6)nc45)cc3)nn2)cc1] | ESI+: 1217.3 |
| 194 | 189 | 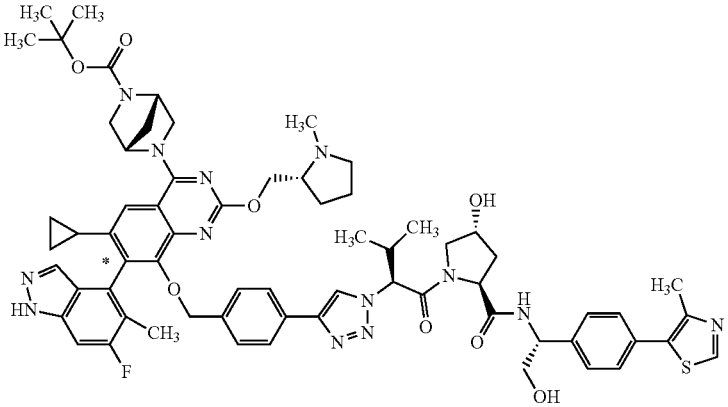 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OC[C@H]6CCCN6C)nc45)cc3)nn2)cc1] | ESI+: 1230.4 |
| 195 | 189 | 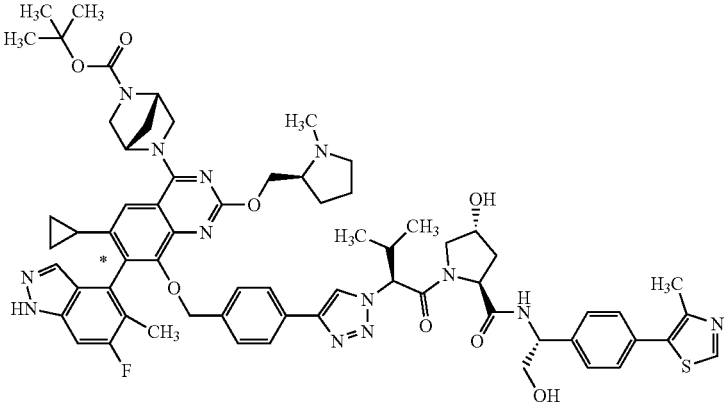 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OC[C@@H]6CCCN6C)nc45)cc3)nn2)cc1] | ESI+: 1231.5 |

TABLE 75
| PEx | PSyn | Str | DAT |
|---|---|---|---|
| 196 | 189 | 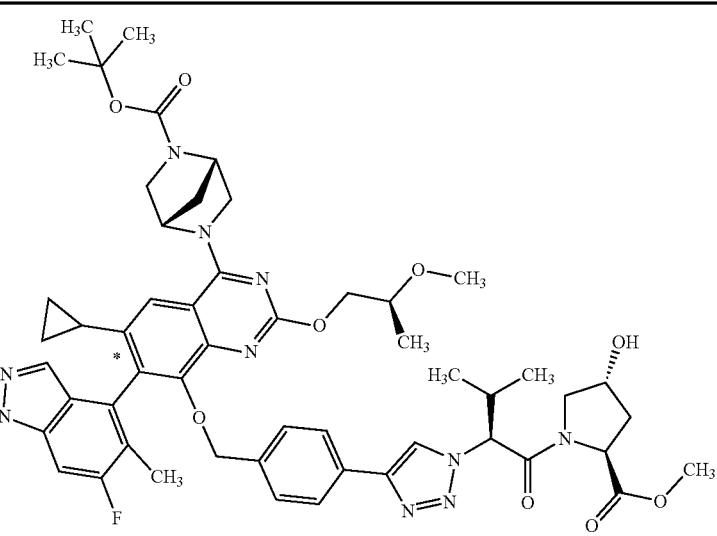 | ESI+: 1003.7 |
| 197 | 189 | 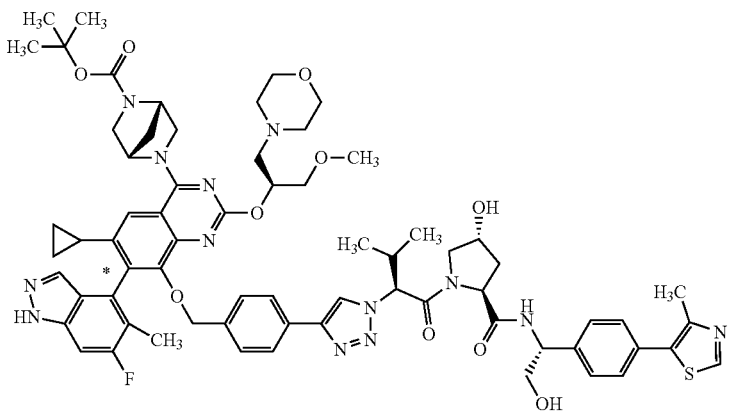 [SMILES: COC[C@H](CN1CCOCC1)Oc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1290.4 |
| 198 | 189 | 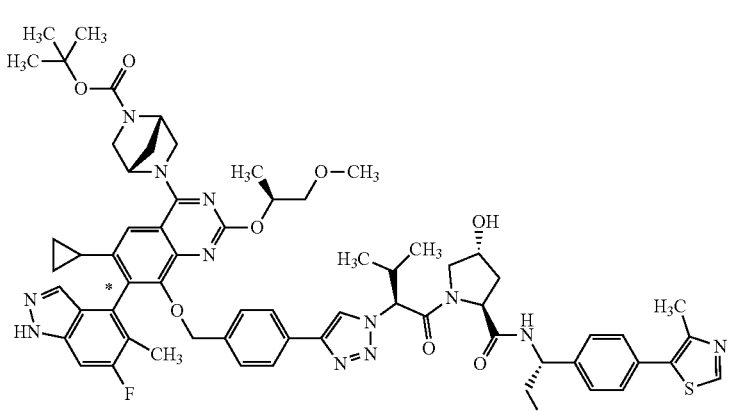 | ESI+: 1205.3 |

TABLE 76
| PEx | PSyn | Str | DAT |
|---|---|---|---|
| 199 | 189 | 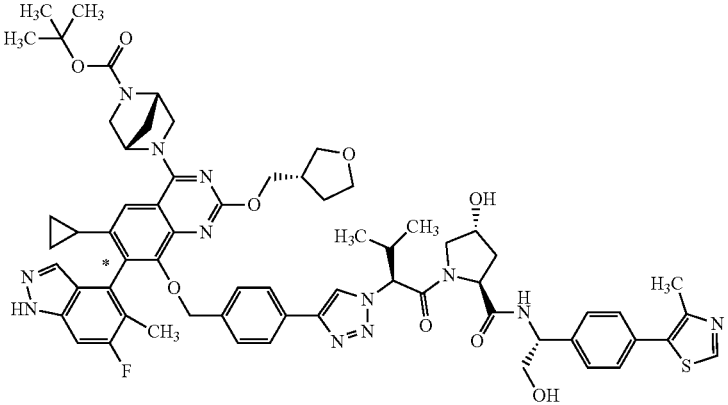 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OC[C@H]6CCOC6)nc45)cc3)nn2)cc1] | ESI+: 1217.4 |
| 200 | 189 | 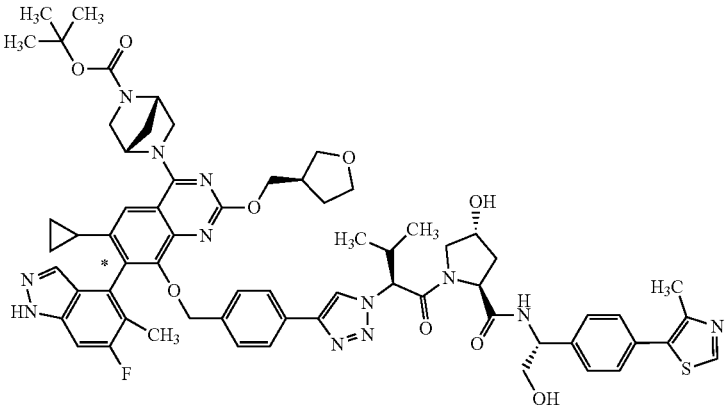 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OC[C@@H]6CCOC6)nc45)cc3)nn2)cc1] | ESI+: 1217.3 |
| 201 | 189 | 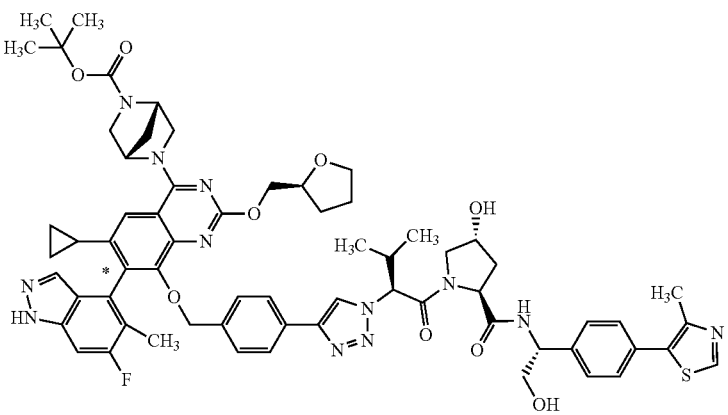 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OC[C@@H]6CCCO6)nc45)cc3)nn2)cc1] | ESI+: 1217.2 |

TABLE 77
| PEx | PSyn | Str | DAT |
|---|---|---|---|
| 202 | 189 | 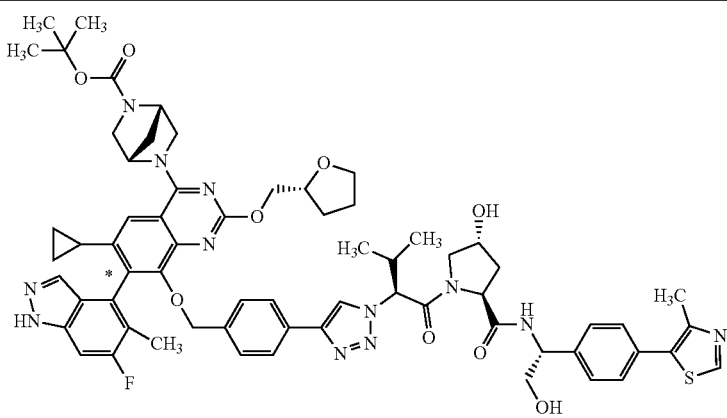 | ESI+: 1217.4 |
| 203 | 189 | 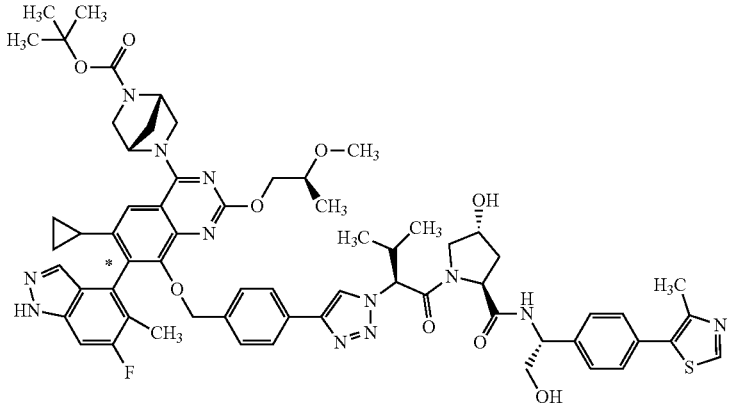 [SMILES: CO[C@@H](C)COc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1205.4 |
| 204 | 189 | 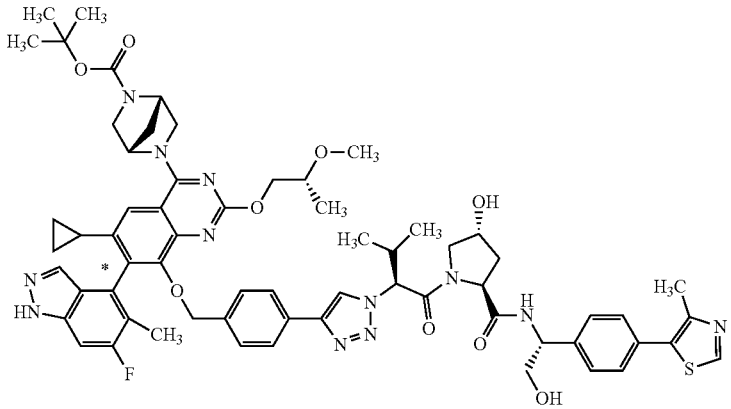 [SMILES: CO[C@H](C)COc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1205.5 |

TABLE 78
| PEx | PSyn | Str | DAT |
|---|---|---|---|
| 205 | 40 | 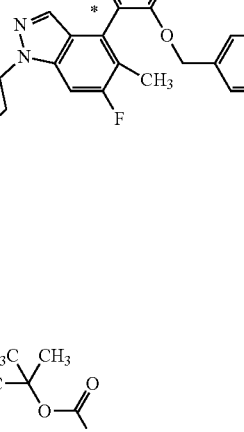 | ESI+: 1319.9 |
| 206 | 189 | 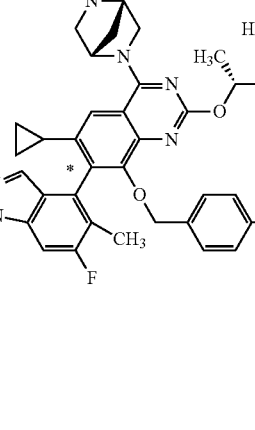 | ESI+: 1218.3 |
| 207 | 189 | 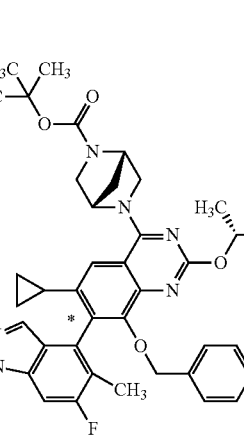 | ESI+: 1261.4 |

TABLE 79
| PEx | PSyn | Str | DAT |
|---|---|---|---|
| 208 | 189 | 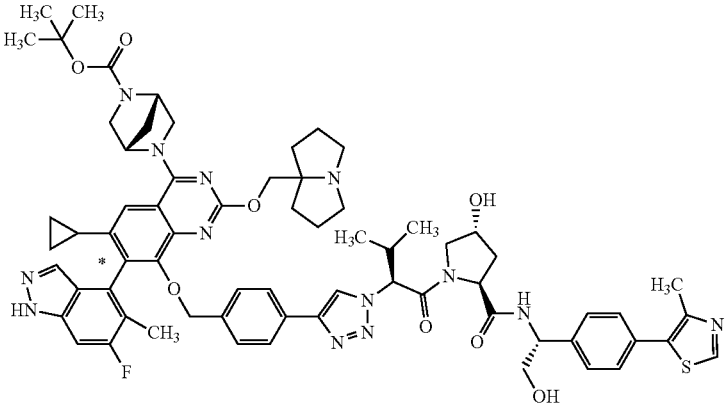 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(OCC67CCCN6CCC7)nc45)cc3)nn2)cc1] | ESI+: 1256.3 |
| 209 | 189 | 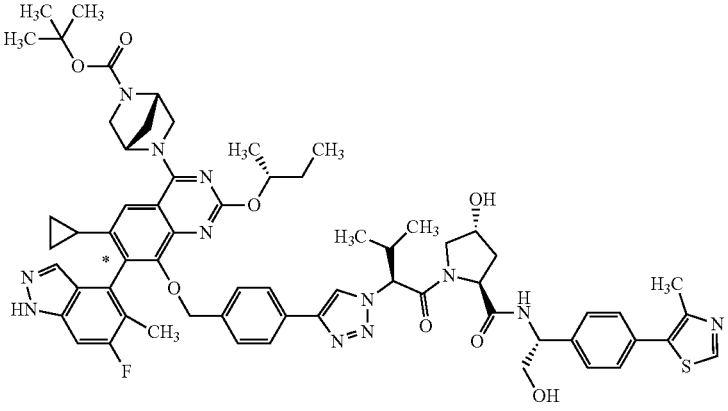 [SMILES: CC[C@@H](C)Oc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1189.1 |
| 210 | 189 | 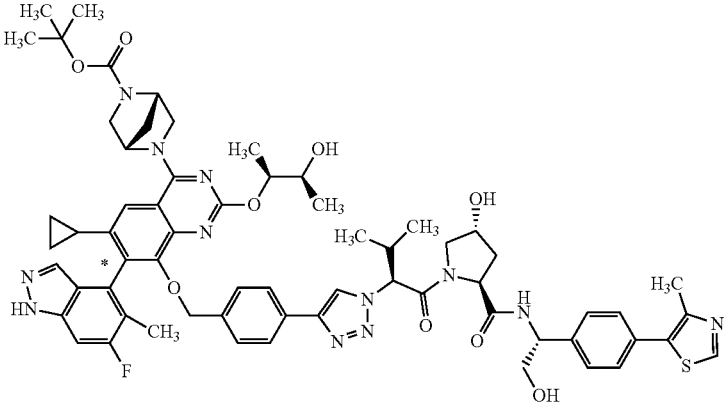 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7C(=O)OC(C)(C)C)nc(O[C@@H](C)[C@H](C)O)nc45)cc3)nn2)cc1] | ESI+: 1205.2 |

TABLE 80
| PEx | PSyn | Str | DAT |
|---|---|---|---|
| 211 | 189 | 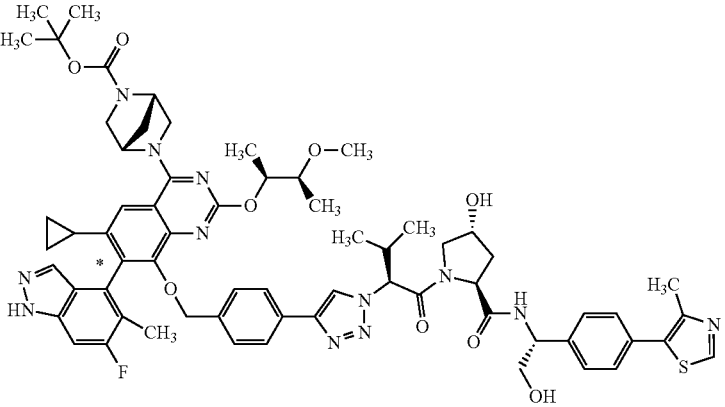 [SMILES: CO[C@@H](C)[C@H](C)Oc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1219.9 |
| 212 | 189 | 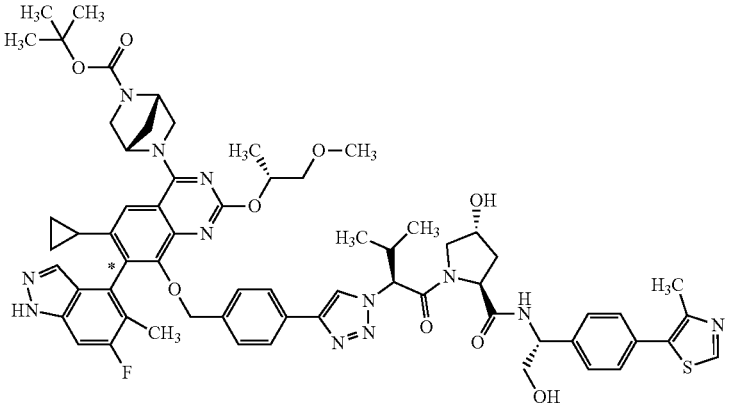 [SMILES: COC[C@@H](C)Oc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] | ESI+: 1205.2 |
| 213 | 40 | 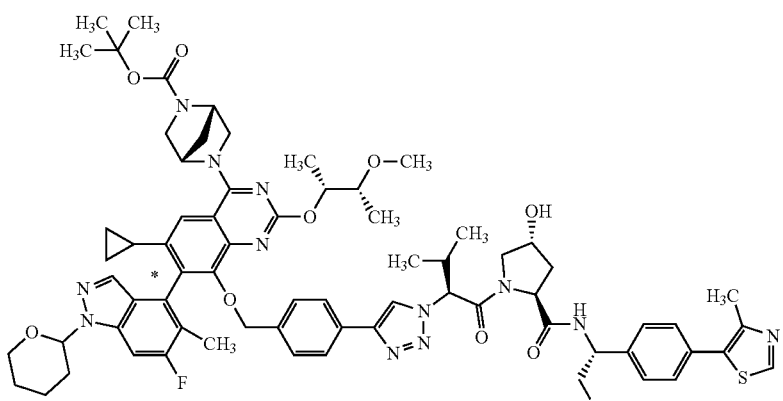 | ESI+: 1304.3 |

TABLE 81
| PEx | PSyn | Str | DAT |
|---|---|---|---|
| 214 | 189 | 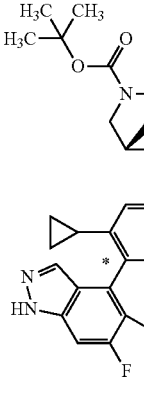 | ESI−: 1215.6 |
| 215 | 40 | 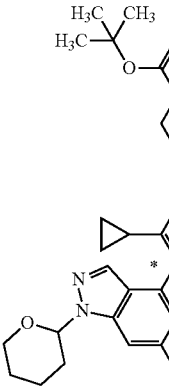 | ESI+: 1345.2 |
| 216 | 40 | 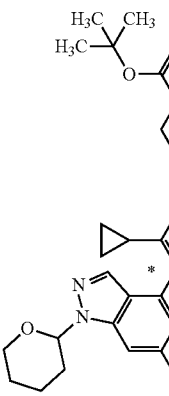 | ESI+: 1289.2 |

TABLE 82
| PEx | PSyn | Str | DAT |
|---|---|---|---|
| 217 | 40 | 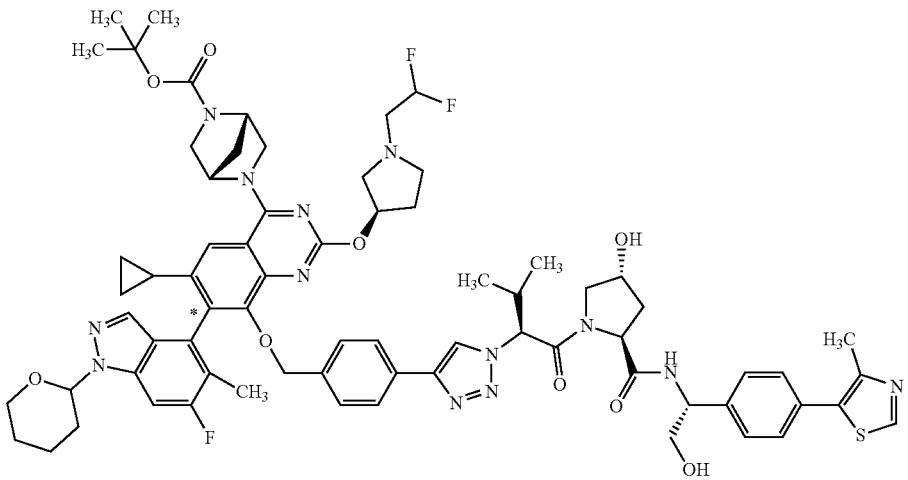 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(O[C@@H]6CCN(CC(F)F)C6)nc45)cc3)nn2)cc1] | ESI+: 1351.9 |
| 218 | 40 | 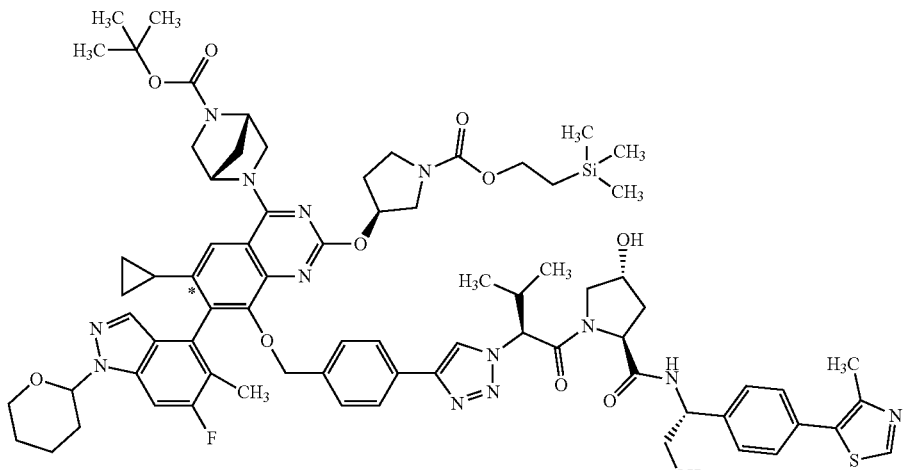 | ESI+: 1430.6 |
| 219 | 51 | 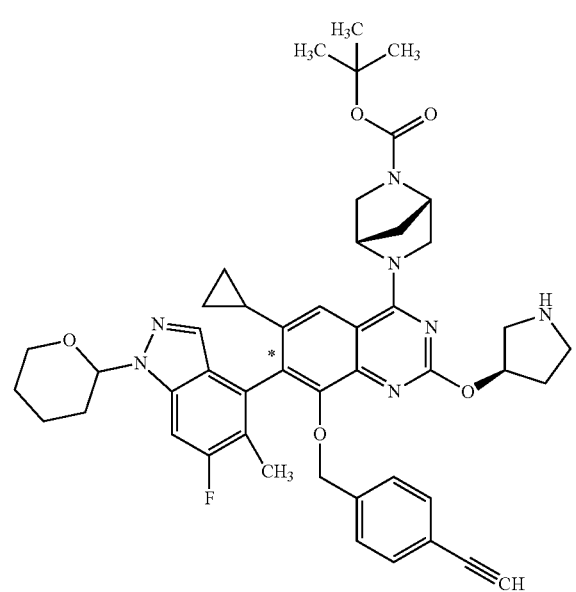 [SMILES: C#Cc1ccc(COc2c(-c3c(C)c(F)cc4c3cnn4C3CCCCO3)c(C3CC3)cc3c(N4C[C@@H]5C[C@H]4CN5C(=O)OC(C)(C)C)nc(O[C@@H]4CCNC4)nc23)cc1] | ESI+: 814.5 |

TABLE 83
| PEx | PSyn | Str | DAT |
|---|---|---|---|
| 220 | 51 | 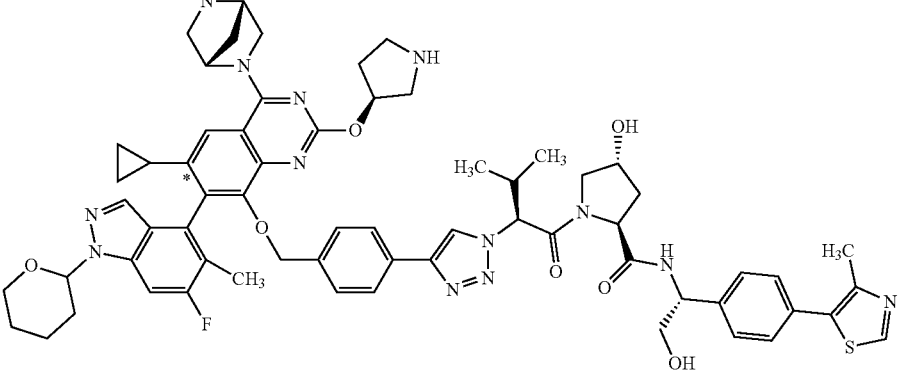 | ESI+: 1286.9 |
| 221 | 53 | 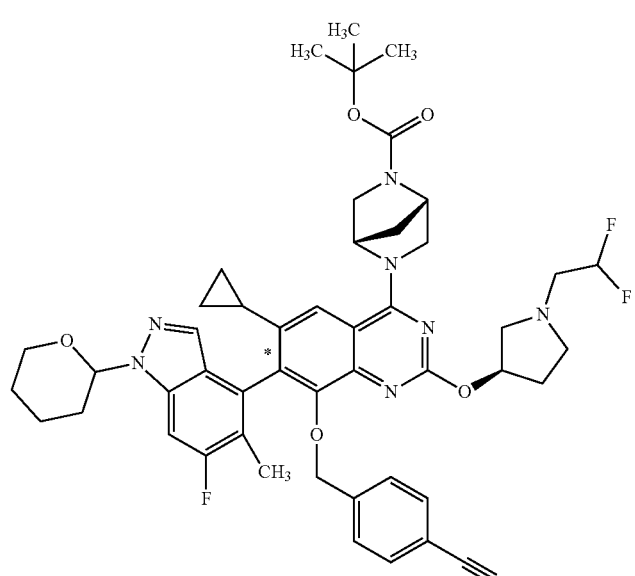 | ESI+: 878.4 |
| 222 | 53 | 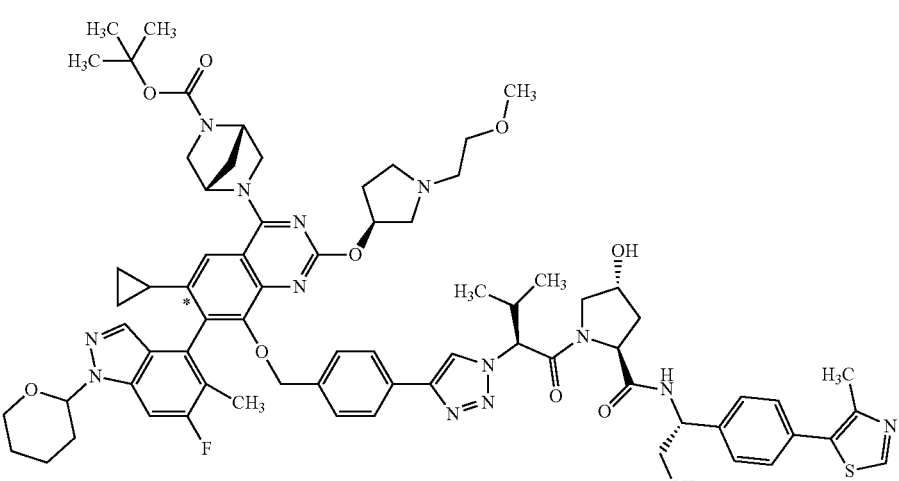 | ESI+: 1367.2 [M + Na]+ |

//
TABLE 84
| PEx | PSyn | Str | DAT |
|---|---|---|---|
| 223 | 53 | 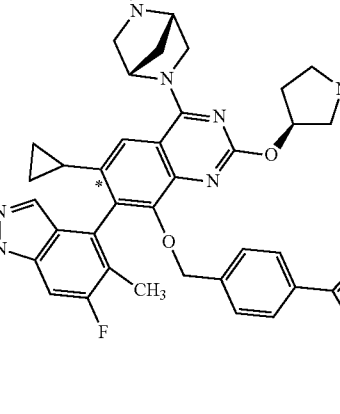 | ESI+: 1373.3 [M + Na]+ |
| 224 | 53 | 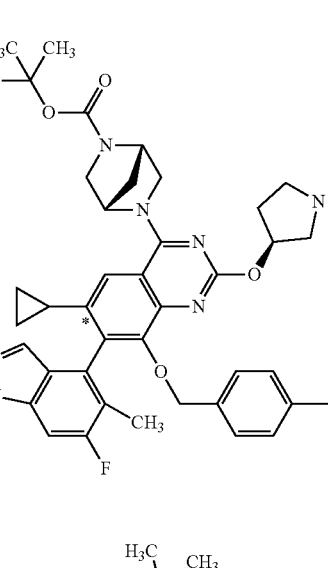 | ESI+: 1352.2 [M + Na]+ |
| 225 | 61 | 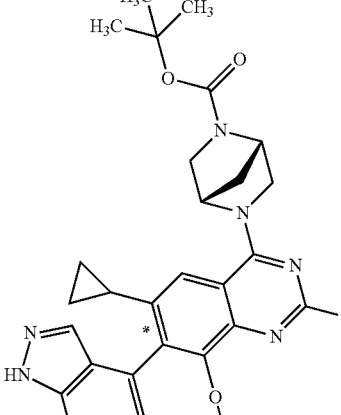 | ESI+: 989.5 |

TABLE 85
| PEx | PSyn | Str | DAT |
|---|---|---|---|
| 226 | 63 | 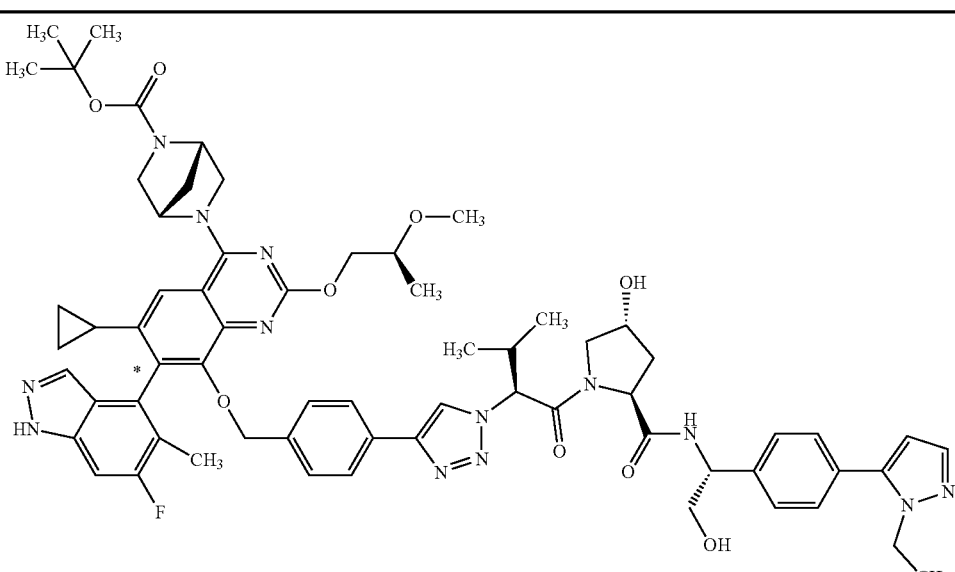 | ESI+: 1203.5 |
| 227 | 63 | 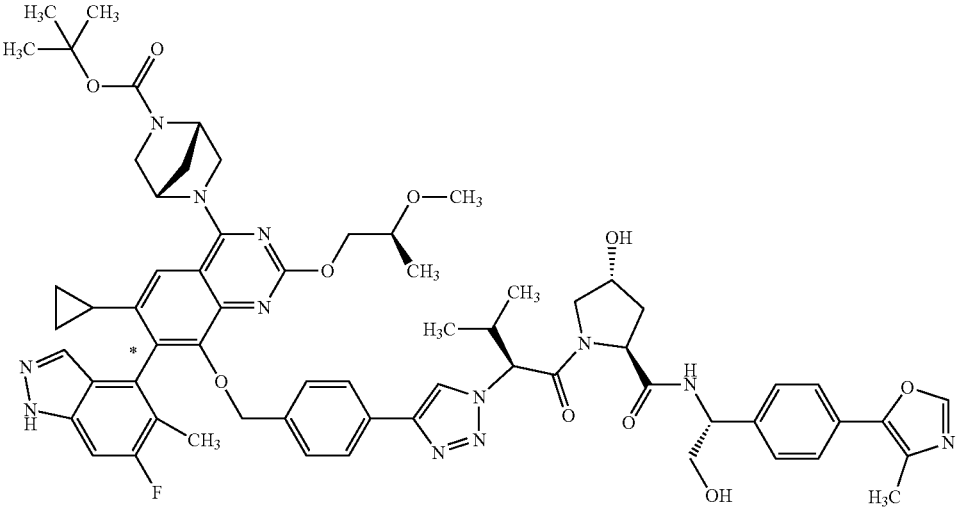 [SMILES: CO[C@@H](C)COc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6ocnc6C)cc5)C(C)C)nn4)cc3)c2n1] | ESI+: 1189.8 |
| 228 | 63 | 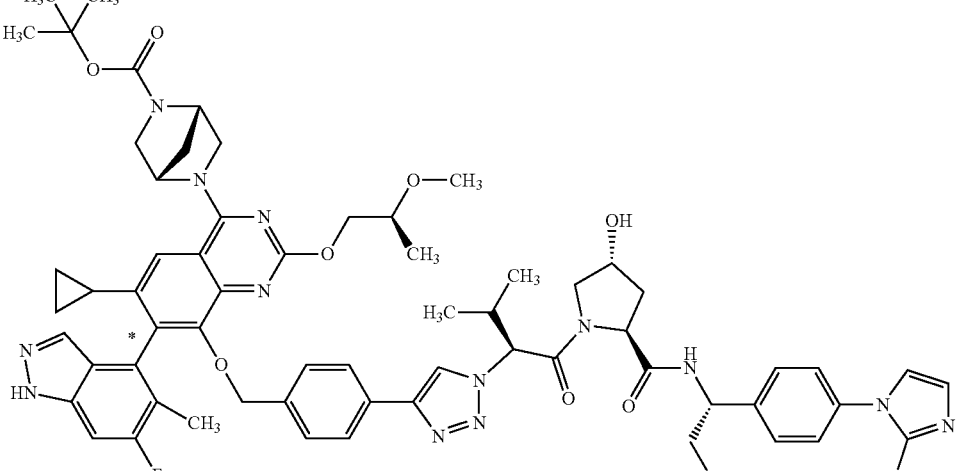 | ESI+: 1188.9 |

TABLE 86
| PEx | PSyn | Str | DAT |
|---|---|---|---|
| 229 | 63 | 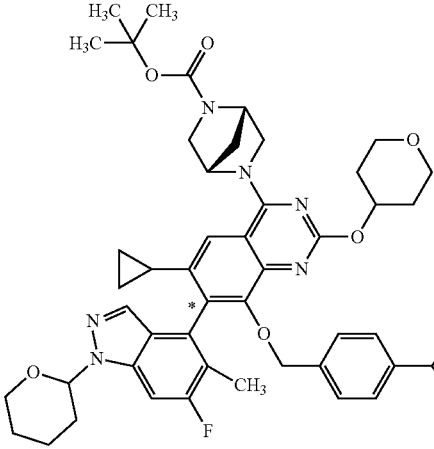 | ESI+: 1285.1 |
| 230 | 63 | 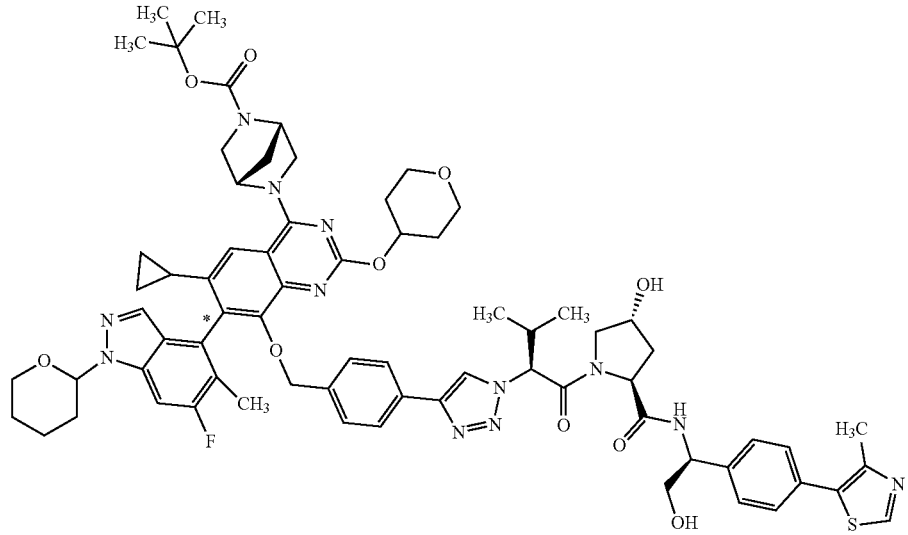 [SMILES: Cc1ncsc1-c1ccc([C@@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCOCC6)nc45)cc3)nn2)cc1] | ESI+: 1301.9 |
| 231 | 63 | 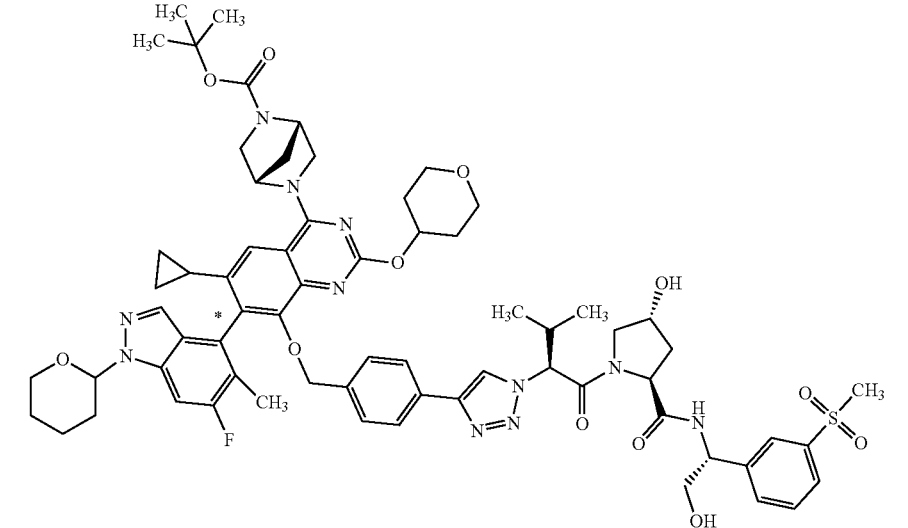 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(-c2cn([C@H](C(=O)N3C[C@H](O)C[C@H]3C(=O)N[C@@H](CO)c3cccc(S(C)(=O)=O)c3)C(C)C)nn2)cc1] | ESI+: 1283.0 |

TABLE 87
| PEx | PSyn | Str | DAT |
|---|---|---|---|
| 232 | 63 | 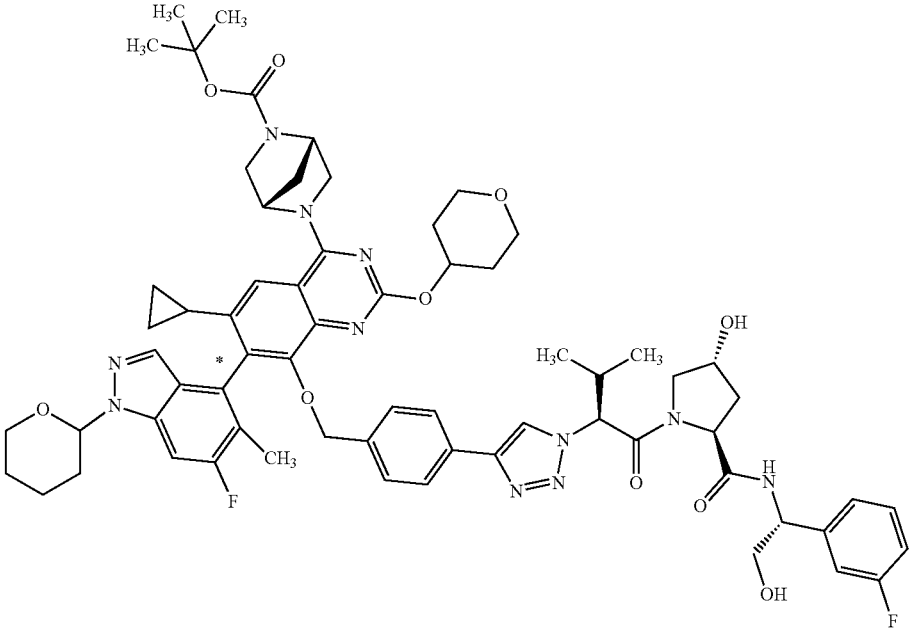 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(-c2cn([C@H](C(=O)N3C[C@H](O)C[C@H]3C(=O)N[C@@H](CO)c3cccc(F)c3)C(C)C)nn2)cc1] | ESI+: 1222.6 |
| 233 | 63 | 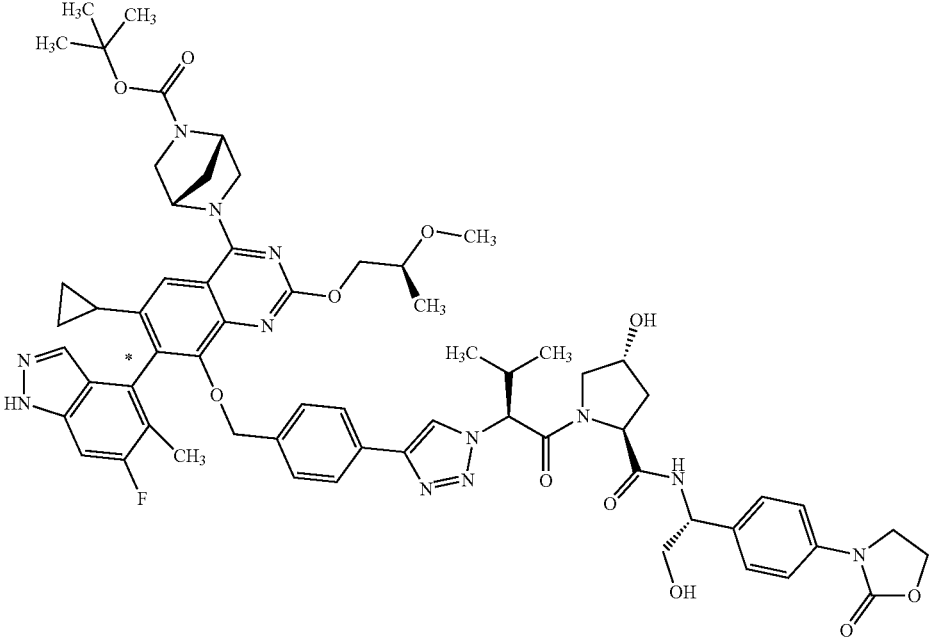 [SMILES: CO[C@@H](C)COc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(N6CCOC6=O)cc5)C(C)C)nn4)cc3)c2n1] | ESI+: 1193.4 |

TABLE 87-continued
| PEx | PSyn | Str | DAT |
|---|---|---|---|
| 234 | 63 | 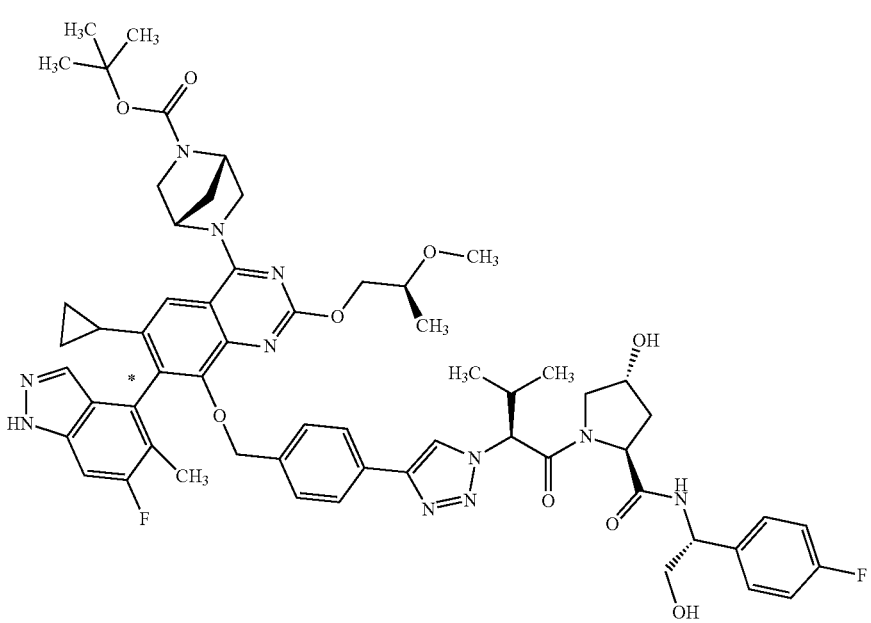 [SMILES: CO[C@@H](C)COc1nc(N2C[C@@H]3C[C@H]2CN3C(=O)OC(C)(C)C)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(F)cc5)C(C)C)nn4)cc3)c2n1] | ESI+: 1126.9 |
TABLE 88
| PEx | PSyn | Str | DAT |
|---|---|---|---|
| 235 | 63 | 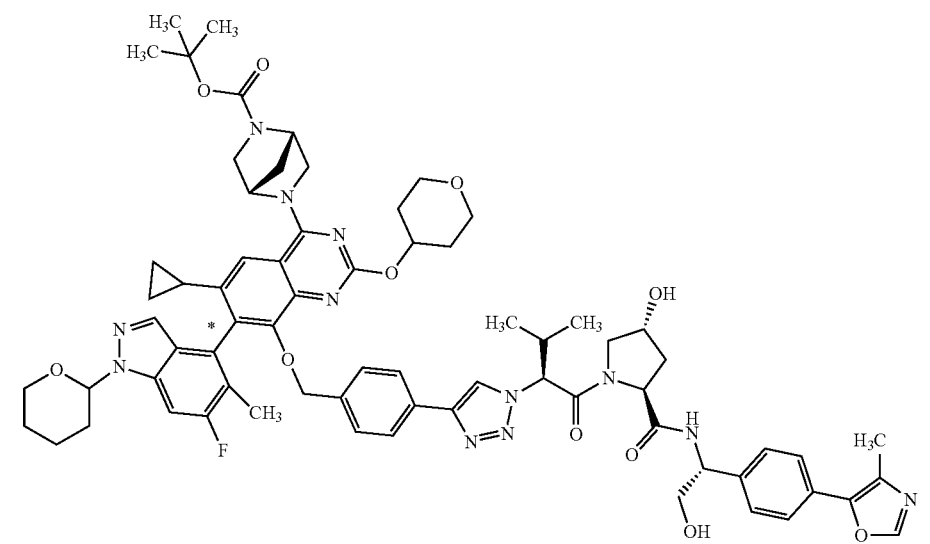 [SMILES: Cc1ncoc1-c1ccc([C@H](CO)NC(=O)[C@@H]2C[C@@H](O)CN2C(=O)[C@H](C(C)C)n2cc(-c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCOCC6)nc45)cc3)nn2)cc1] | ESI+: 1285.8 |

TABLE 88-continued
| PEx | PSyn | Str | DAT |
|---|---|---|---|
| 236 | 63 | | ESI+: 1302.3 |
| 237 | 98 | | ESI+: 336.2 |
| 238 | 238 | | ESI+: 359.2 |
TABLE 89
| PEx | PSyn | Str | DAT |
|---|---|---|---|
| 239 | 239 | 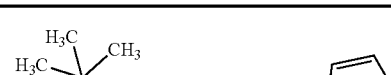 | ESI+: 358.0 |

TABLE 89-continued
| PEx | PSyn | Str | DAT |
|---|---|---|---|
| 240 | 71 | 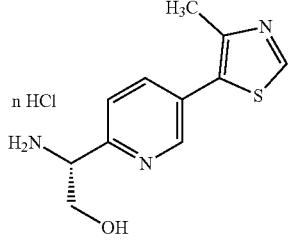 [SMILES: Cc1ncsc1-c1ccc([C@@H](N)CO)nc1] | ESI+: 236.1 |
| 241 | 71 | 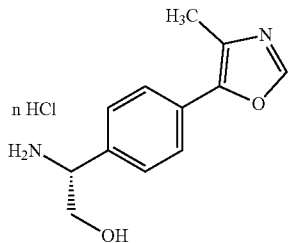 [SMILES: Cc1ncoc1-c1ccc([C@@H](N)CO)cc1] | ESI+: 219.1 |
| 242 | 71 | 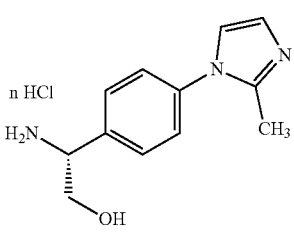 [SMILES: Cc1nccn1-c1ccc([C@@H](N)CO)cc1] | ESI+: 218.2 |
| 243 | 79 | 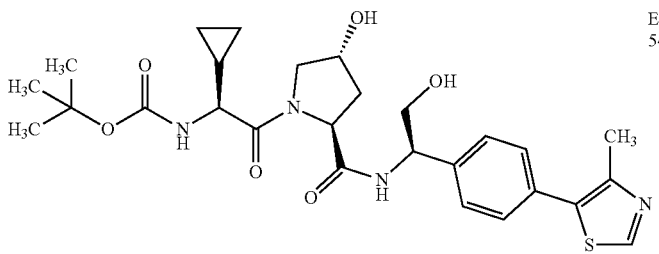 | ESI+: 545.5 |
| 244 | 83 88 | 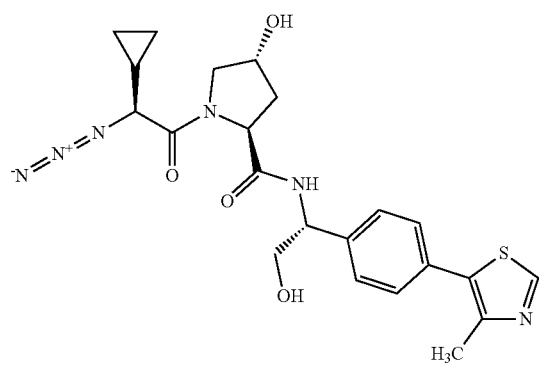 | ESI+: 471.5 |

TABLE 90
| PEx | PSyn | Str | DAT |
|---|---|---|---|
| 245 | 245 | 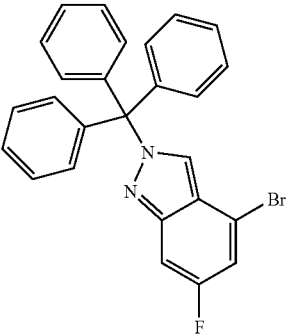 [SMILES: Fc1cc(Br)c2cn(C(c3ccccc3)(c3ccccc3)c3ccccc3)nc2c1] | NMR:<br>7.08-7.15 (6H, m),<br>7.36-7.44 (10H, m),<br>7.49-7.54 (1H, m),<br>7.89 (1H, d) |
| 246 | 246 | 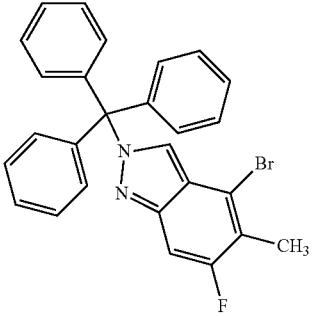 [SMILES: Cc1c(F)cc2nn(C(c3ccccc3)(c3ccccc3)c3ccccc3)cc2c1Br] | NMR:<br>2.34 (3H, d),<br>7.07-7.13 (6H, m),<br>7.36-7.43 (9H, m),<br>7.51 (1H, d),<br>7.79 (1H, d) |
| 247 | 247 | 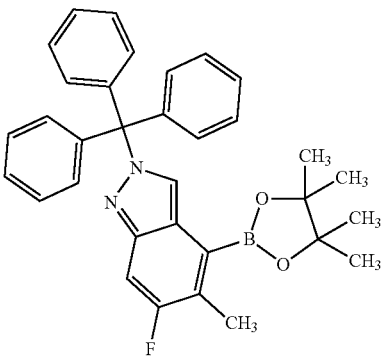 [SMILES: Cc1c(F)cc2nn(C(c3ccccc3)(c3ccccc3)c3ccccc3)cc2c1B1OC(C)(C)C(C)(C)O1] | NMR:<br>1.21 (12H, s),<br>2.44 (3H, d),<br>7.04-7.11 (6H, m),<br>7.34-7.44 (9H, m),<br>7.49 (1H, d),<br>8.09 (1H, d) |

TABLE 91
| PEx | PSyn | Str | DAT |
|---|---|---|---|
| 248 | 248 | 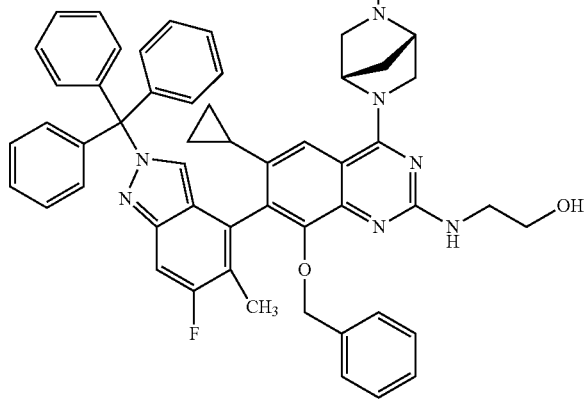 | ESI+: 922.7 |
| 249 | 249 | 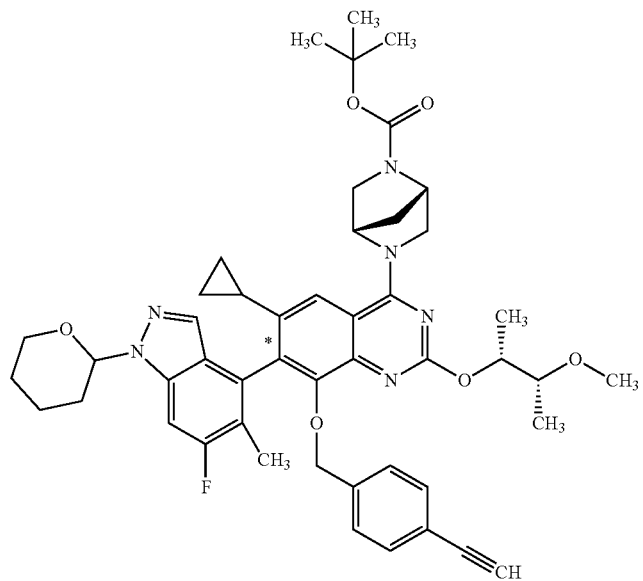 [SMILES: C#Cc1ccc(COc2c(-c3c(C)c(F)cc4c3cnn4C3CCCCO3)c(C3CC3)cc3c(N4C[C@@H]5C[C@H]4CN5C(=O)OC(C)(C)C)nc(O[C@H](C)[C@@H](C)OC)nc23)cc1] | ESI+: 831.7 |

TABLE 91-continued
| PEx | PSyn | Str | DAT |
|---|---|---|---|
| 250 | 249 | 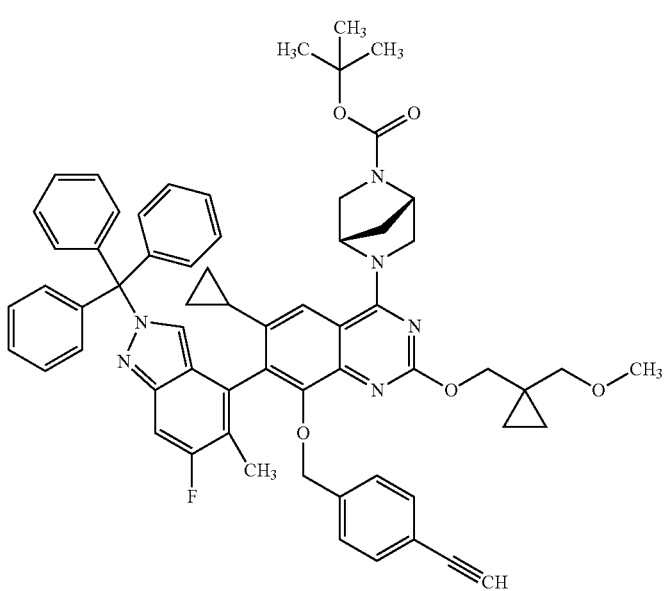 [SMILES: C#Cc1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)nc(OCC4(COC)CC4)nc23)cc1] | ESI+: 1001.4 |
TABLE 92
| PEx | PSyn | Str | DAT |
|---|---|---|---|
| 251 | 249 | 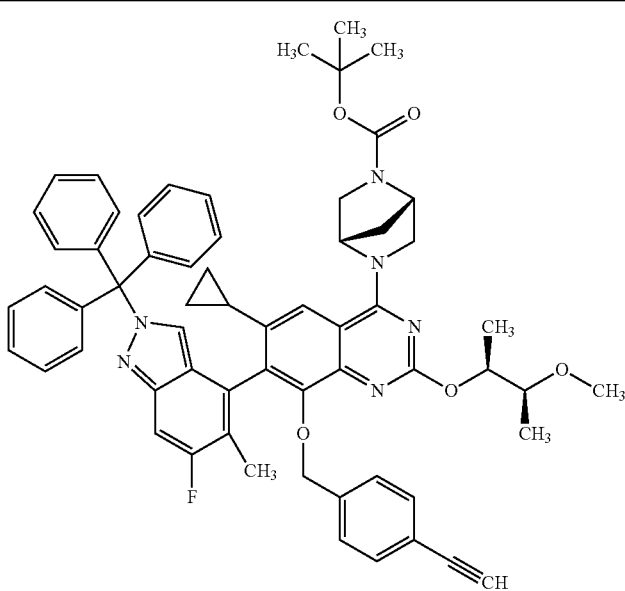 | ESI+: 989.3 |

TABLE 92-continued
| PEx | PSyn | Str | DAT |
|---|---|---|---|
| 252 | 252 | 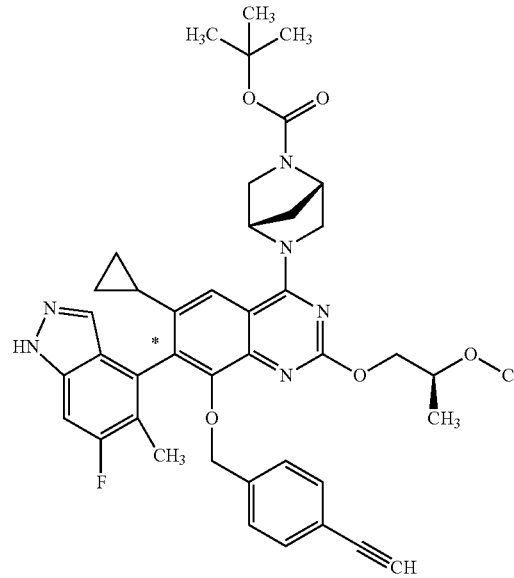 | ESI+: 733.4 |
| 253 | 252 | 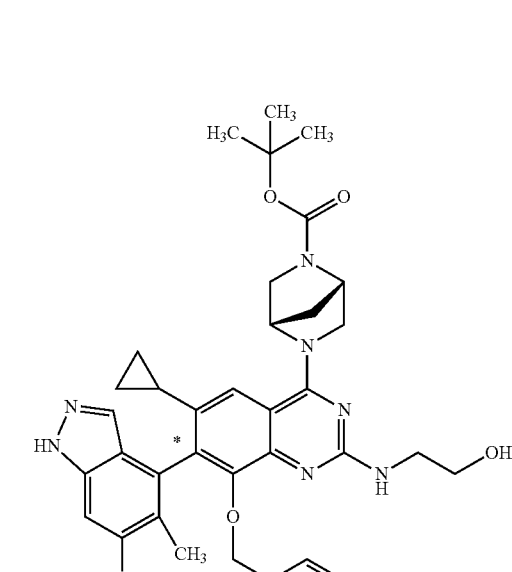 | ESI+: 704.6 |

TABLE 93
| PEx | PSyn | Str | DAT |
|---|---|---|---|
| 254 | 252 | 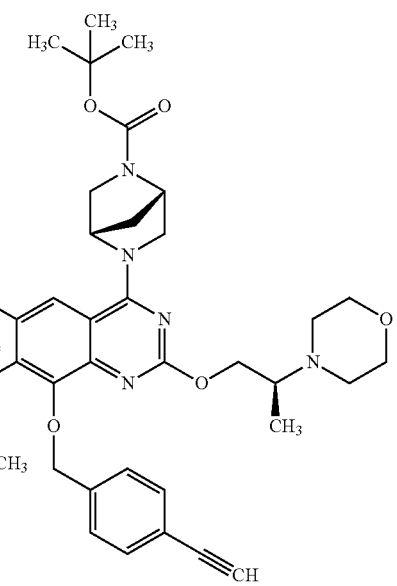 | ESI+: 788.6 |
| 255 | 252 | 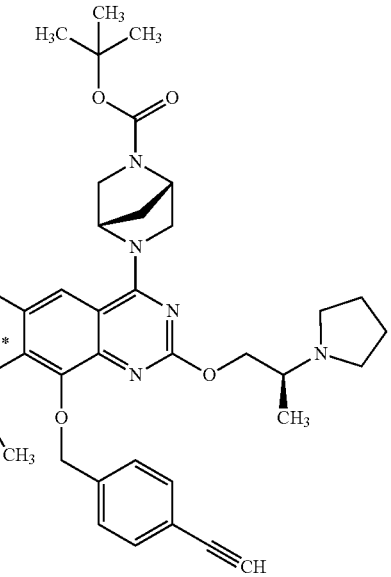 | ESI+: 772.6 |

TABLE 93-continued
| PEx | PSyn | Str | DAT |
|---|---|---|---|
| 256 | 252 | 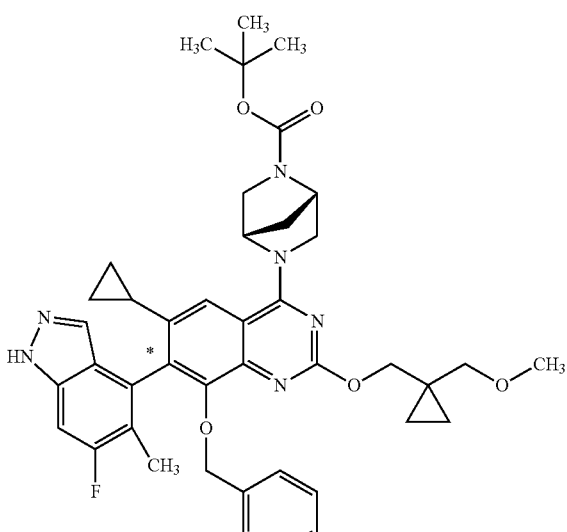 | ESI+: 759.7 |
TABLE 94
| PEx | PSyn | Str | DAT |
|---|---|---|---|
| 257 | 252 | 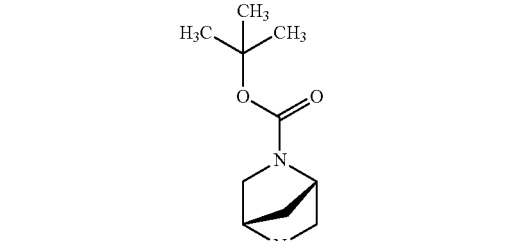 | ESI+: 745.4 |

TABLE 94-continued
| PEx | PSyn | Str | DAT |
|---|---|---|---|
| 258 | 252 | 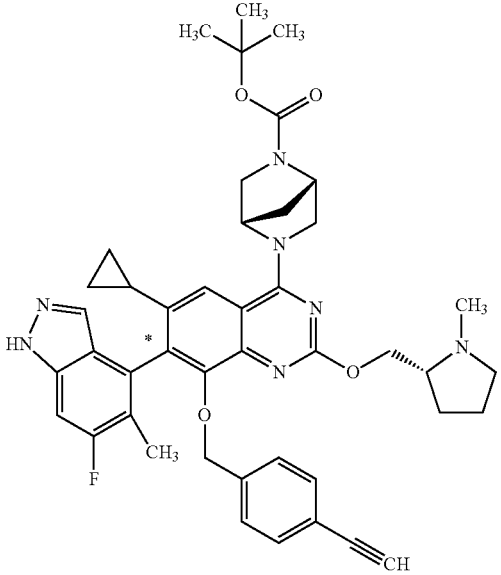 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(OC[C@H]4CCCN4C)nc23)cc1] | ESI+: 758.6 |
| 259 | 252 | 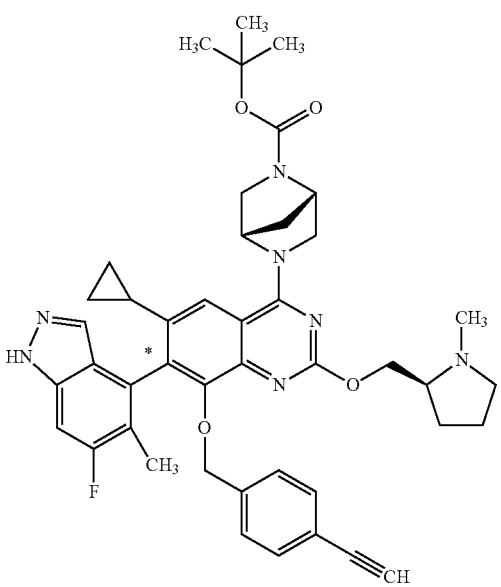 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(OC[C@@H]4CCCN4C)nc23)cc1] | ESI+: 758.6 |

TABLE 95

| PEx | PSyn | Str | DAT |
|---|---|---|---|
| 260 | 252 | | ESI+: 745.4 |
| 261 | 252 | | ESI+: 818.6 |

TABLE 95-continued
| PEx | PSyn | Str | DAT |
|---|---|---|---|
| 262 | 252 | 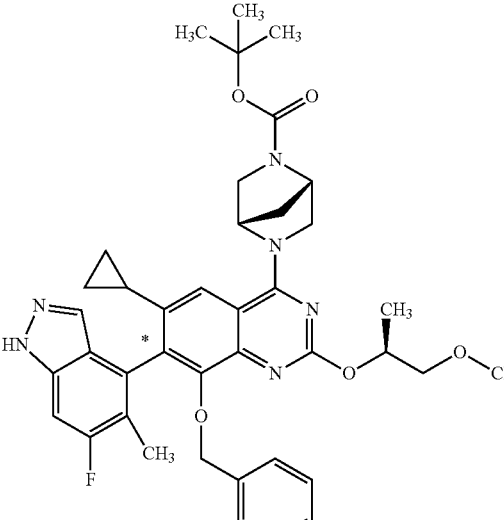 | ESI+: 733.5 |
TABLE 96
| PEx | PSyn | Str | DAT |
|---|---|---|---|
| 263 | 252 | | ESI+: 745.4 |

TABLE 96-continued
| PEx | PSyn | Str | DAT |
|---|---|---|---|
| 264 | 252 | 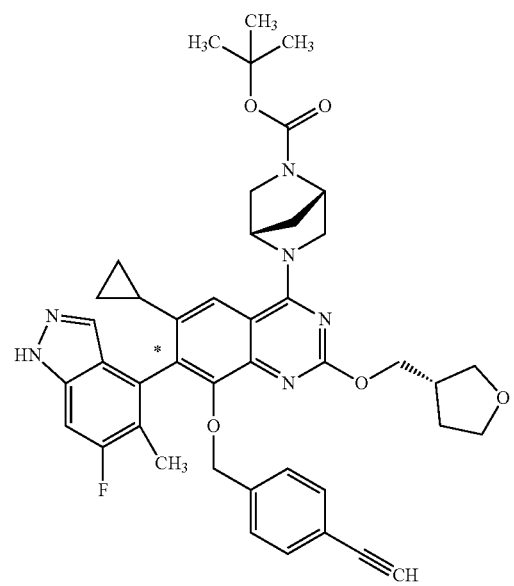 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(OC[C@H]4CCOC4)nc23)cc1] | ESI+: 745.4 |
| 265 | 252 | 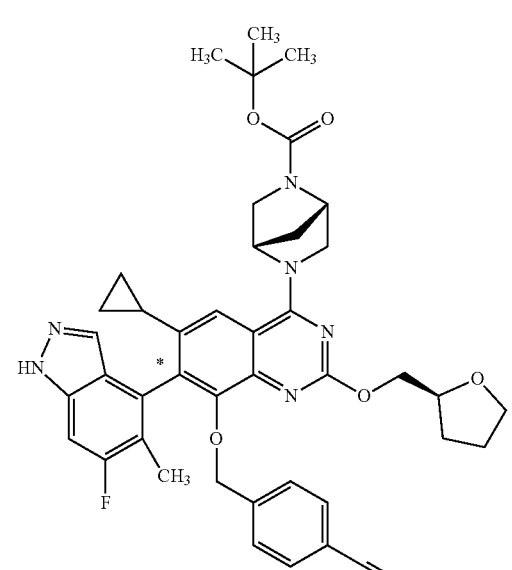 | ESI+: 745.4 |

TABLE 97
| PEx | PSyn | Str | DAT |
|---|---|---|---|
| 266 | 252 | 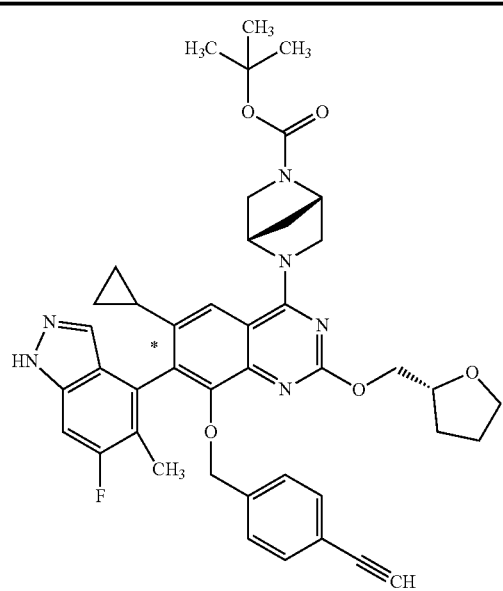 | ESI+: 745.6 |
| 267 | 252 | 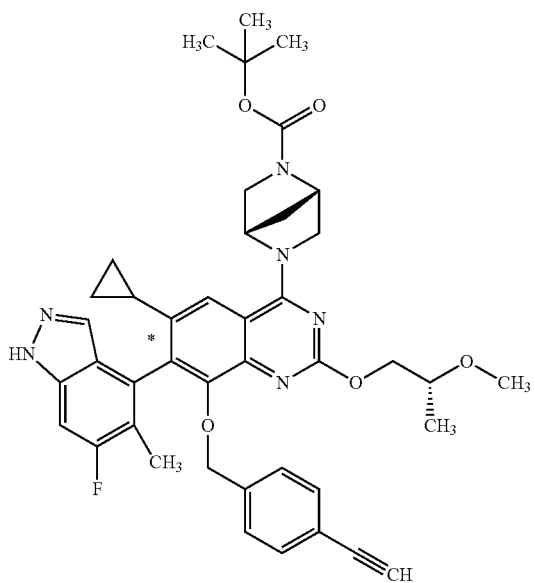 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(OC[C@@H](C)OC)nc23)cc1] | ESI+: 733.4 |

TABLE 97-continued
| PEx | PSyn | Str | DAT |
|---|---|---|---|
| 268 | 252 | 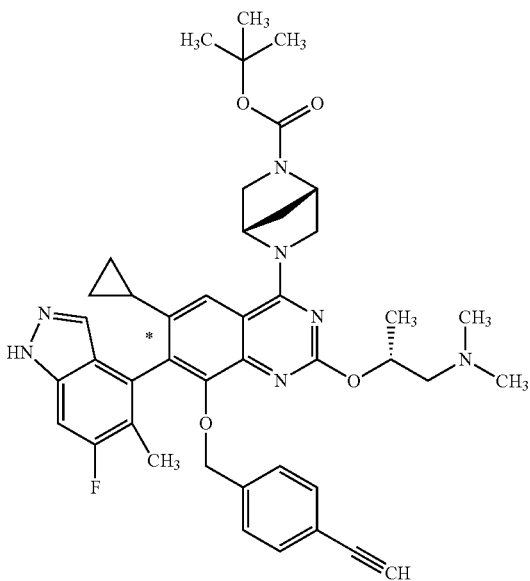 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(O[C@H](C)CN(C)C)nc23)cc1] | ESI+: 746.4 |
TABLE 98
| PEx | PSyn | Str | DAT |
|---|---|---|---|
| 269 | 252 | 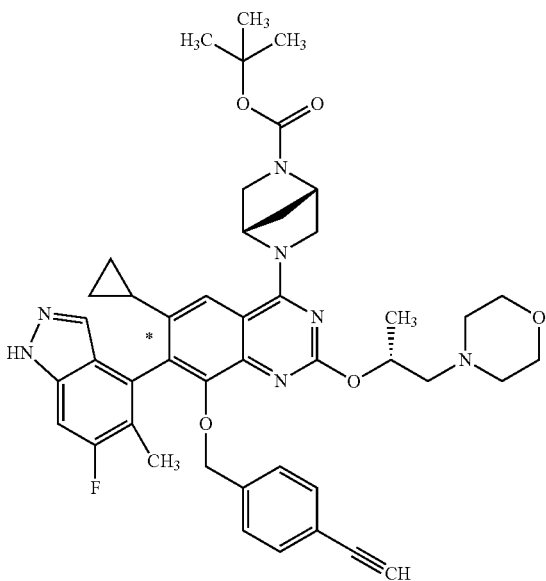 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(O[C@H](C)CN4CCOCC4)nc23)cc1] | ESI+: 788.4 |

TABLE 98-continued

| PEx | PSyn | Str | DAT |
|---|---|---|---|
| 270 | 252 | | ESI+: 784.4 |
| 271 | 252 | | ESI+: 717.5 |

TABLE 99
| PEx | PSyn | Str | DAT |
|---|---|---|---|
| 272 | 252 | 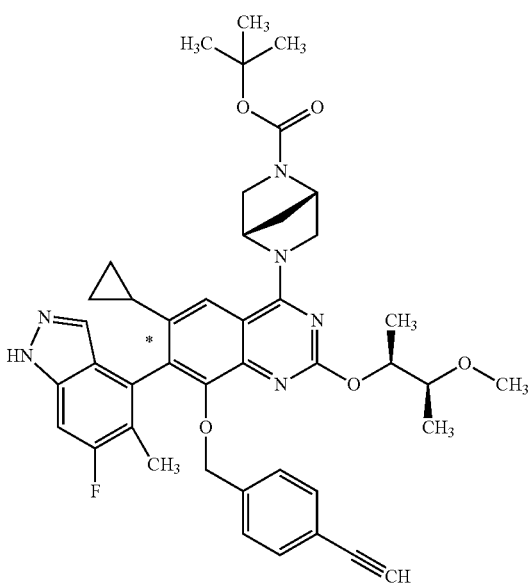 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(O[C@@H](C)[C@H](C)OC)nc23)cc1] | ESI+: 747.5 |
| 273 | 252 | 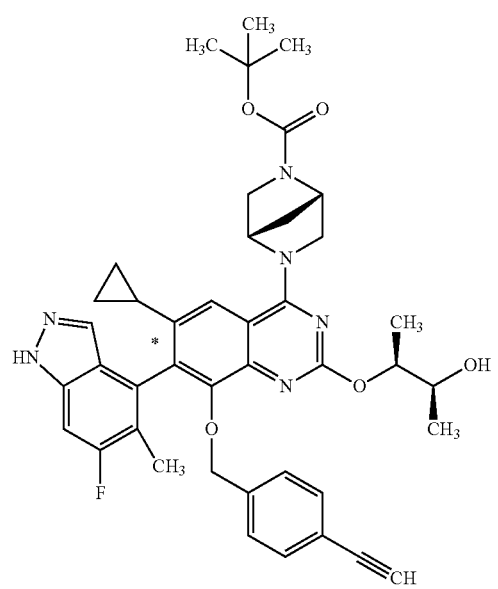 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(O[C@@H](C)[C@H](C)O)nc23)cc1] | ESI+: 733.5 |

TABLE 99-continued
| PEx | PSyn | Str | DAT |
|---|---|---|---|
| 274 | 252 | 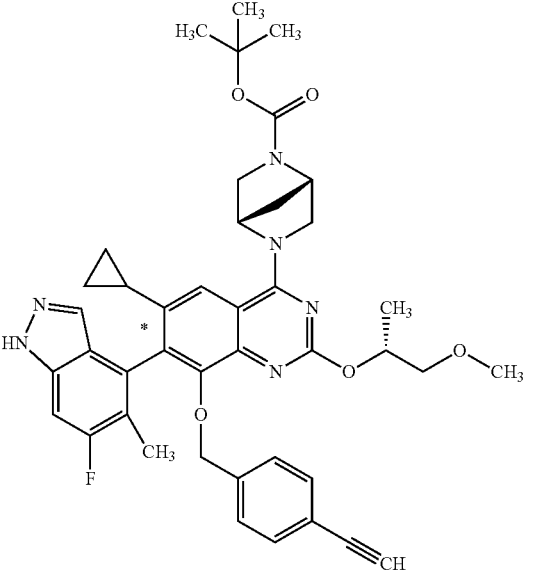 [SMILES: C#Cc1ccc(COc2c(-c3c(C)c(F)cc4[nH]ncc34)c(C3CC3)cc3c(N4C[C@@H]5C[C@H]4CN5C(=O)OC(C)(C)C)nc(O[C@H](C)COC)nc23)cc1] | ESI+: 733.4 |
TABLE 100
| PEx | PSyn | Str | DAT |
|---|---|---|---|
| 275 | 79 | 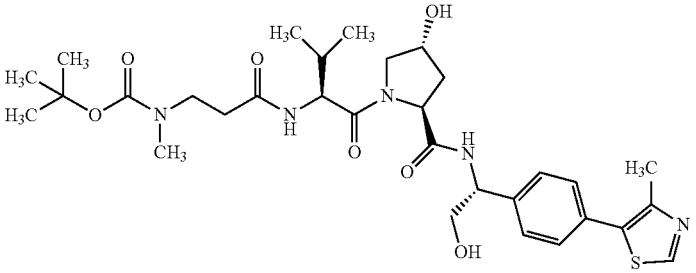 [SMILES: Cc1ncsc1-c1ccc([C@H](CO)NC(=O)[C@@H]2C[C@@H](O)CN2C(=O)[C@@H](NC(=O)CCN(C)C(=O)OC(C)(C)C)C(C)C)cc1] | ESI+: 632.5 |
| 276 | 79 | 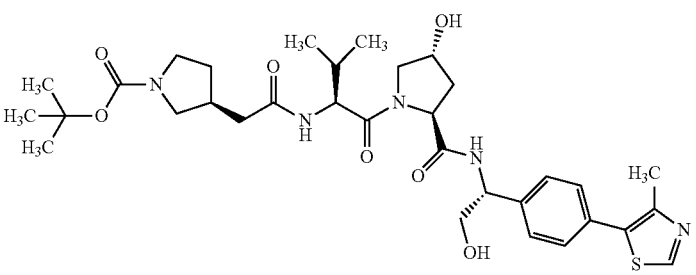 [SMILES: Cc1ncsc1-c1ccc([C@H](CO)NC(=O)[C@@H]2C[C@@H](O)CN2C(=O)[C@@H](NC(=O)C[C@@H]2CCN(C(=O)OC(C)(C)C)C2)C(C)C)cc1] | ESI+: 658.5 |
| 277 | 83 | 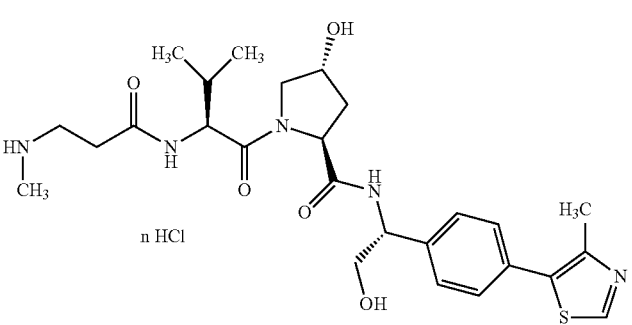 [SMILES: CNCCC(=O)N[C@H](C(=O)N1C[C@H](O)C[C@H]1C(=O)N[C@@H](CO)c1ccc(-c2scnc2C)cc1)C(C)C] | ESI+: 532.3 |

TABLE 100-continued
| PEx | PSyn | Str | DAT |
|---|---|---|---|
| 278 | 83 | 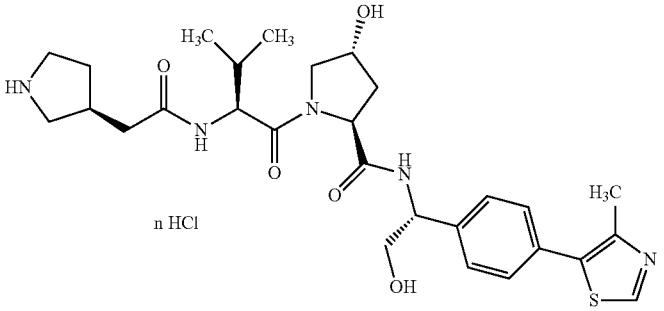 [SMILES: Cc1ncsc1-c1ccc([C@H](CO)NC(=O)[C@@H]2C[C@@H](O)CN2C(=O)[C@@H](NC(=O)C[C@@H]2CCNC2)C(C)C)cc1] | ESI+: 558.5 |
TABLE 101
| PEx | PSyn | Str | DAT |
|---|---|---|---|
| 279 | 63 | 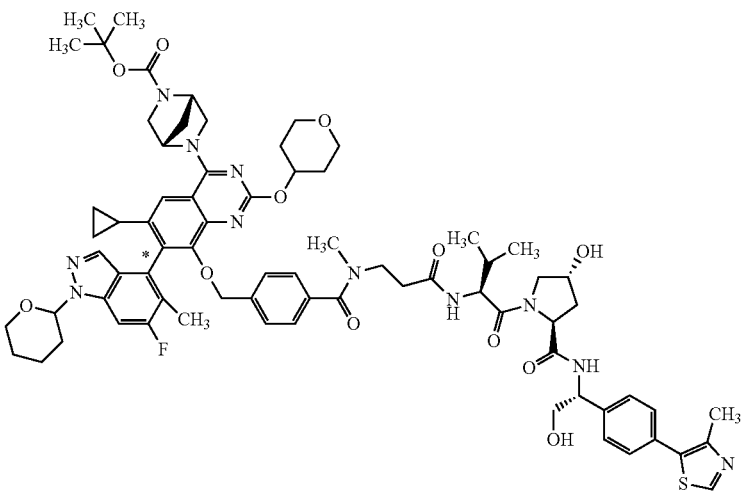 [SMILES: Cc1ncsc1-c1ccc([C@H](CO)NC(=O)[C@@H]2C[C@@H](O)CN2C(=O)[C@@H](NC(=O)CCN(C)C(=O)c2ccc(COc3c(-c4c(C)c(F)cc5c4cnn5C4CCCCO4)c(C4CC4)cc4c(N5C[C@@H]6C[C@H]5CN6C(=O)OC(C)(C)C)nc(OC5CCOCC5)nc34)cc2)C(C)C)cc1] | ESI+: 1385.1 [M + Na]+ |
| 280 | 63 | 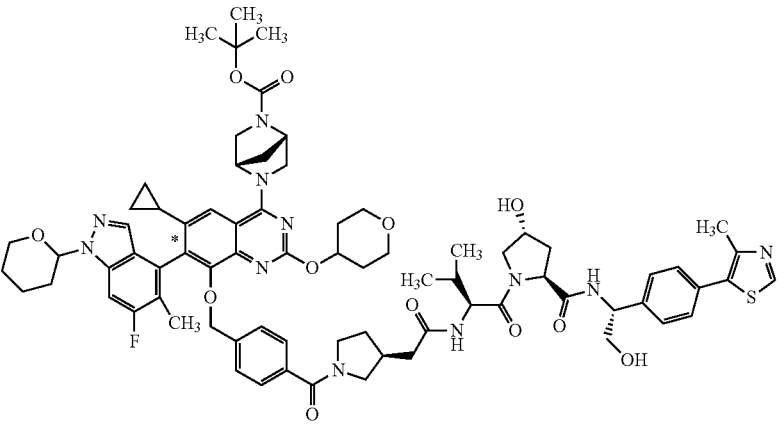 [SMILES: Cc1ncsc1-c1ccc([C@H](CO)NC(=O)[C@@H]2C[C@@H](O)CN2C(=O)[C@@H](NC(=O)C[C@@H]2CCN(C(=O)c3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCOCC6)nc45)cc3)C2)C(C)C)cc1] | ESI+: 1389.3 |

TABLE 101-continued
| PEx | PSyn | Str | DAT |
|---|---|---|---|
| 281 | 281 | 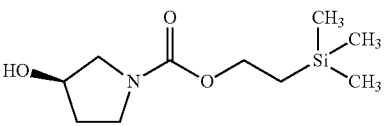 | ESI+:<br>254.1<br>[M + Na]+ |
| 282 | 281 | 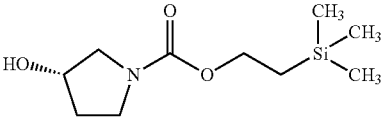 | EI+:<br>231.2 |
TABLE 102
| Ex | Str |
|---|---|
| 1 | 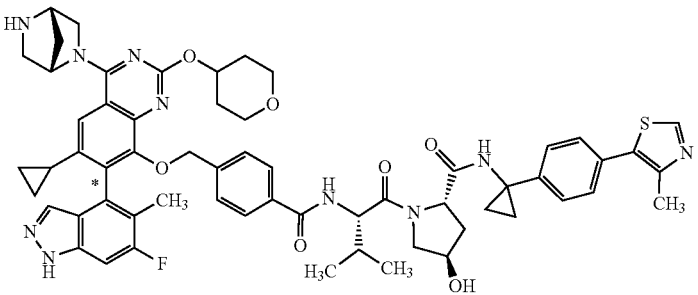 [SMILES: Cc1ncsc1-c1ccc(C2(NC(=O)[C@@H]3C[C@@H](O)CN3C(=O)[C@@H](NC(=O)c3ccc(COc4c(-c5c(C)c(F)cc6[nH]ncc56)c(C5CC5)cc5c(N6C[C@@H]7C[C@H]6CN7)nc(OC6CCOCC6)nc45)cc3)C(C)C)CC2)cc1] |
| 2 | 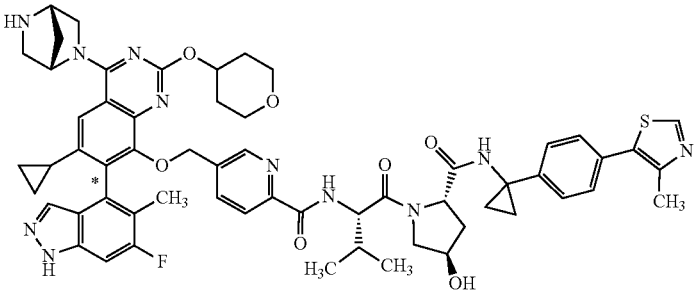<br>n HCl |
| 3 | 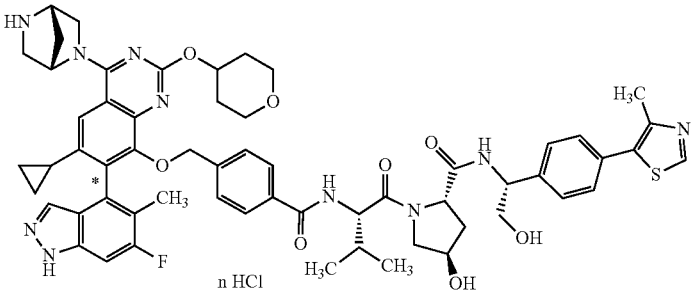 [SMILES: Cc1ncsc1-c1ccc([C@H](CO)NC(=O)[C@@H]2C[C@@H](O)CN2C(=O)[C@@H](NC(=O)c2ccc(COc3c(-c4c(C)c(F)cc5[nH]ncc45)c(C4CC4)cc4c(N5C[C@@H]6C[C@H]5CN6)nc(OC5CCOCC5)nc34)cc2)C(C)C)cc1]<br>n HCl |

TABLE 103
| Ex | Str |
|---|---|
| 4 | 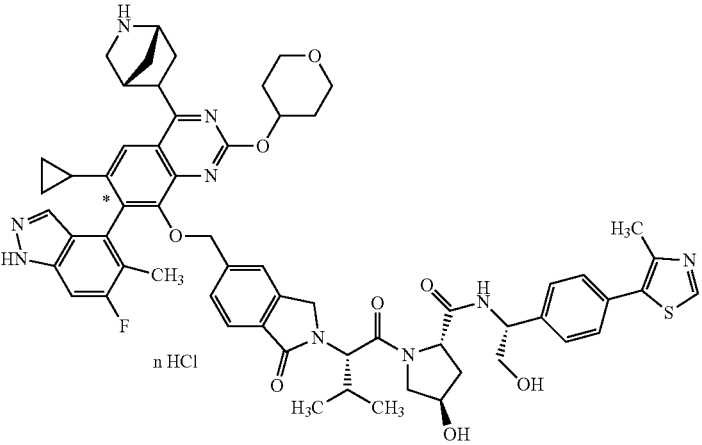 [SMILES: Cc1ncsc1-c1ccc([C@H](CO)NC(=O)[C@@H]2C[C@@H](O)CN2C(=O)[C@H](C(C)C)N2Cc3cc(COc4c(-c5c(C)c(F)cc6[nH]ncc56)c(C5CC5)cc5c(C6C[C@@H]7C[C@H]6CN7)nc(OC6CCOCC6)nc45)ccc3C2=O)cc1] |
| 5 | 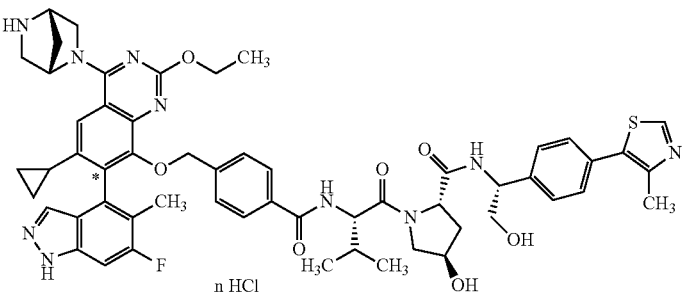 [SMILES: CCOc1nc(N2C[C@@H]3C[C@H]2CN3)c2cc(C3CC3)c(-c3c(C)c(F)cc4[nH]ncc34)c(OCc3ccc(C(=O)N[C@H](C(=O)N4C[C@H](O)C[C@H]4C(=O)N[C@@H](CO)c4ccc(-c5scnc5C)cc4)C(C)C)cc3)c2n1] |
| 6 | 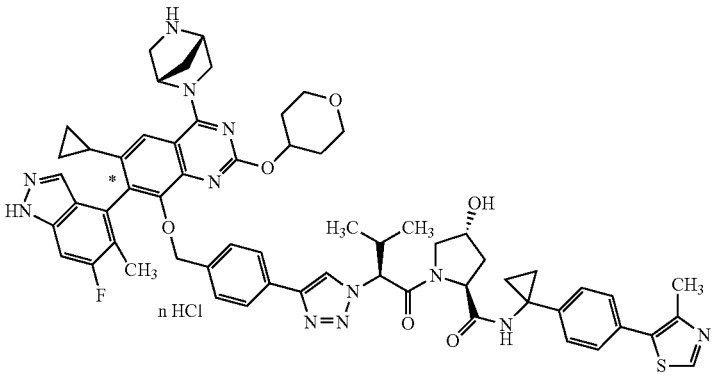 [SMILES: Cc1ncsc1-c1ccc(C2(NC(=O)[C@@H]3C[C@@H](O)CN3C(=O)[C@H](C(C)C)n3cc(-c4ccc(COc5c(-c6c(C)c(F)cc7[nH]ncc67)c(C6CC6)cc6c(N7C[C@@H]8C[C@H]7CN8)nc(OC7CCOCC7)nc56)cc4)nn3)CC2)cc1] |

TABLE 104
| Ex | Str |
|---|---|
| 7 |  n HCl |
| 8 | (structure) |
| 9 | (structure) n HCl |
TABLE 105
| Ex | Str |
|---|---|
| 10 | (structure) n HCl |

TABLE 105-continued
| Ex | Str |
|---|---|
| 11 | 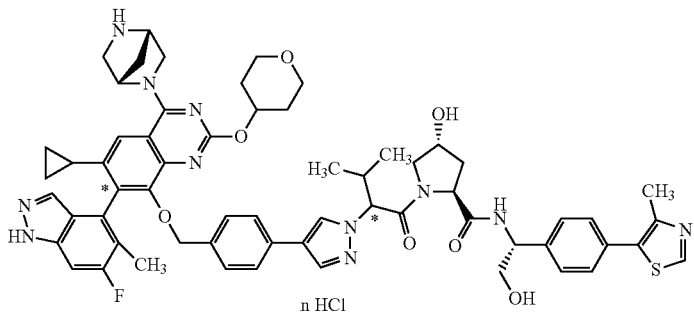 [SMILES: Cc1ncsc1-c1ccc([C@H](CO)NC(=O)[C@@H]2C[C@@H](O)CN2C(=O)C(C(C)C)n2cc(-c3ccc(COc4c(-c5c(C)c(F)cc6[nH]ncc56)c(C5CC5)cc5c(N6C[C@@H]7C[C@H]6CN7)nc(OC6CCOCC6)nc45)cc3)cn2)cc1] n HCl |
| 12 | 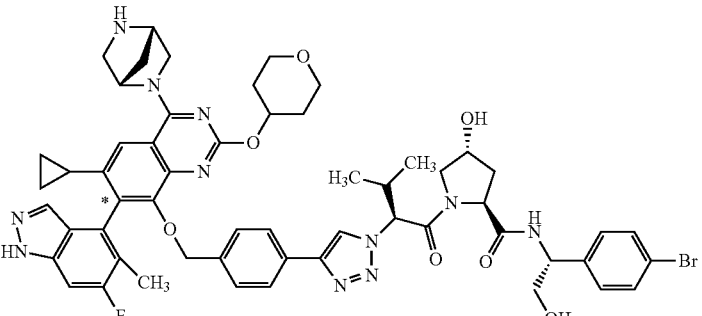 n HCl |
TABLE 106
| Ex | Str |
|---|---|
| 13 | 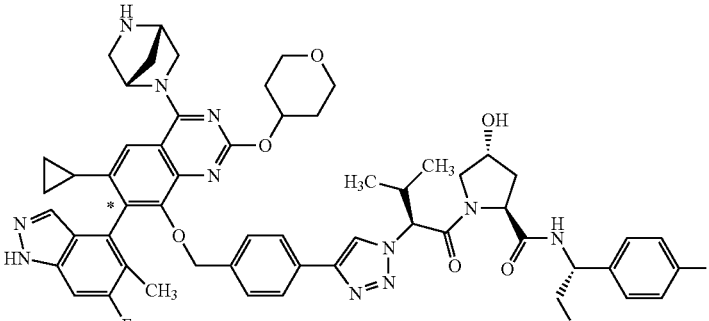 |
| 14 | 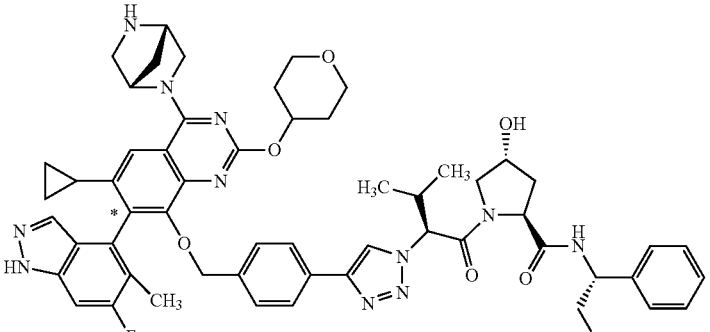 n HCl |

TABLE 106-continued
| Ex | Str |
|---|---|
| 15 | 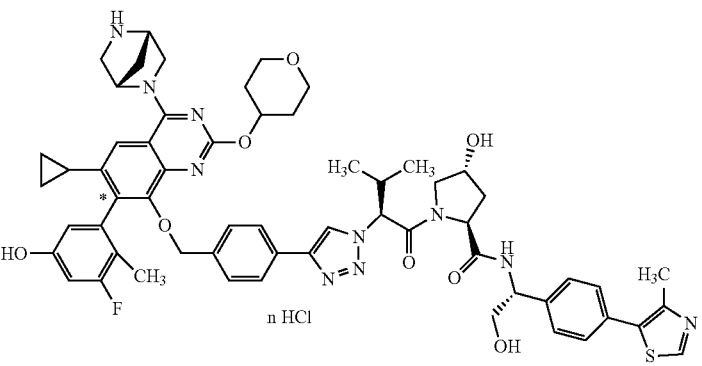 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5cc(O)cc(F)c5C)c(C5CC5)cc5c(N6C[C@@H]7C[C@H]6CN7)nc(OC6CCOCC6)nc45)cc3)nn2)cc1] |
TABLE 107
| Ex | Str |
|---|---|
| 16 | 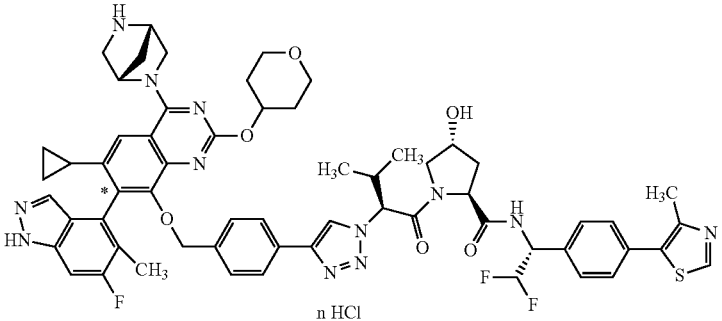 [SMILES: Cc1ncsc1-c1ccc([C@@H](NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OC6CCOCC6)nc45)cc3)nn2)C(F)F)cc1] |
| 17 | 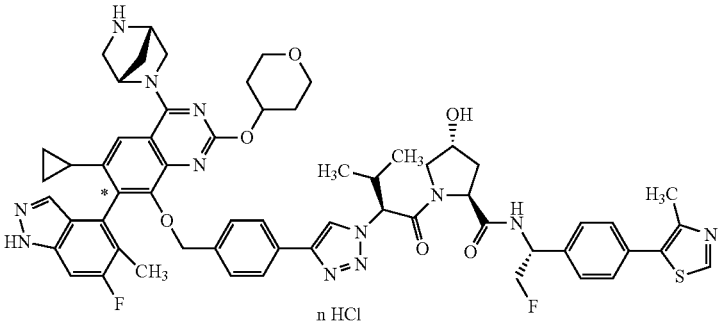 [SMILES: Cc1ncsc1-c1ccc([C@H](CF)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OC6CCOCC6)nc45)cc3)nn2)cc1] |
| 18 | 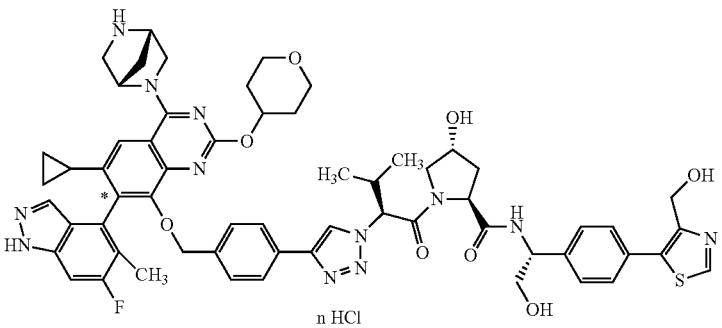 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(-c2cn([C@H](C(=O)N3C[C@H](O)C[C@H]3C(=O)N[C@@H](CO)c3ccc(-c4scnc4CO)cc3)C(C)C)nn2)cc1] |

TABLE 108
| Ex | Str |
|---|---|
| 19 | 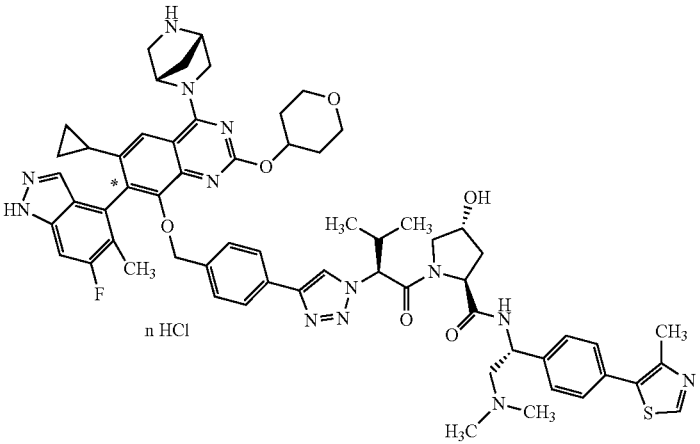 [SMILES: Cc1ncsc1-c1ccc([C@H](CN(C)C)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OC6CCOCC6)nc45)cc3)nn2)cc1] |
| 20 | 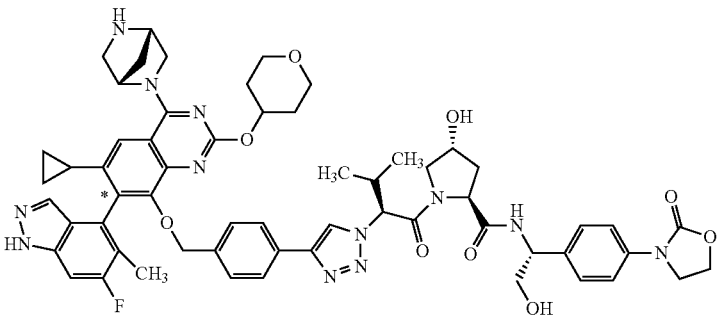 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(-c2cn([C@H](C(=O)N3C[C@H](O)C[C@H]3C(=O)N[C@@H](CO)c3ccc(N4CCOC4=O)cc3)C(C)C)nn2)cc1] |
| 21 | 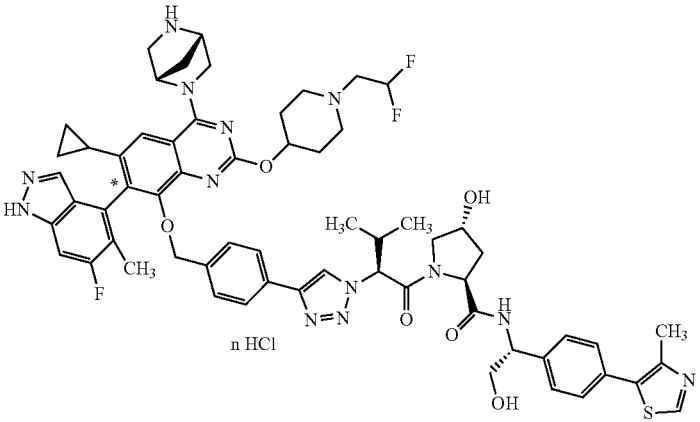 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OC6CCN(CC(F)F)CC6)nc45)cc3)nn2)cc1] |

TABLE 109

| Ex | Str |
|---|---|
| 22 | (structure, n HCl) |
| 23 | (structure) |
| 24 | (structure) |

TABLE 110

| Ex | Str |
|---|---|
| 25 | |
| 26 | |
| 27 | |

TABLE 111
| Ex | Str |
|---|---|
| 28 | 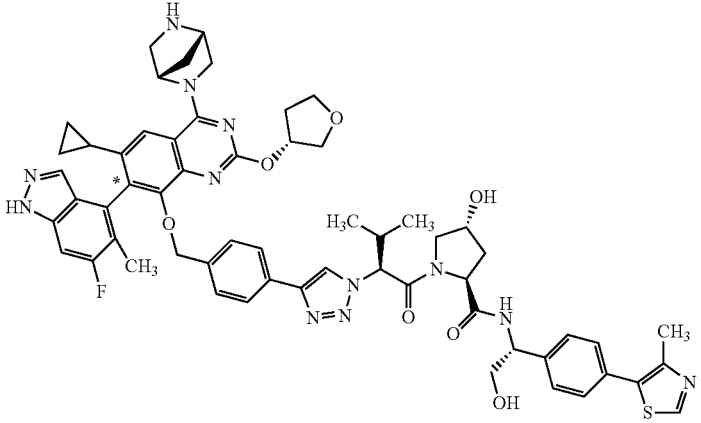 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(O[C@@H]6CCOC6)nc45)cc3)nn2)cc1] |
| 29 | 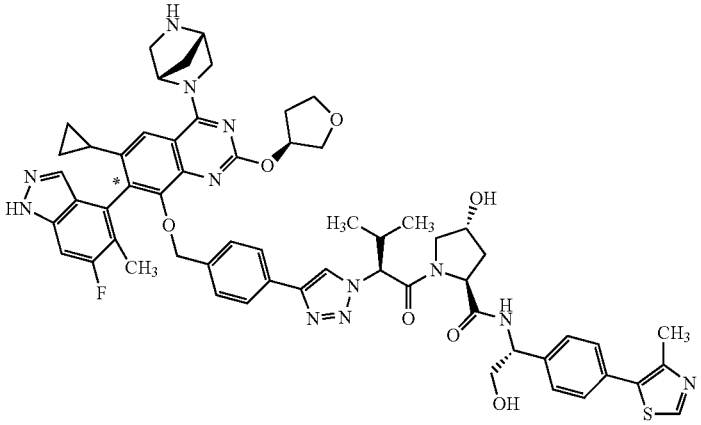 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(O[C@H]6CCOC6)nc45)cc3)nn2)cc1] |
| 30 | 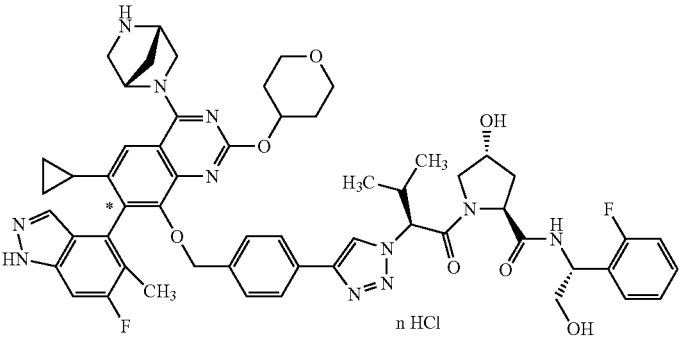 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(-c2cn([C@H](C(=O)N3C[C@H](O)C[C@H]3C(=O)N[C@@H](CO)c3ccccc3F)C(C)C)nn2)cc1] |

TABLE 112
| Ex | Str |
|---|---|
| 31 | 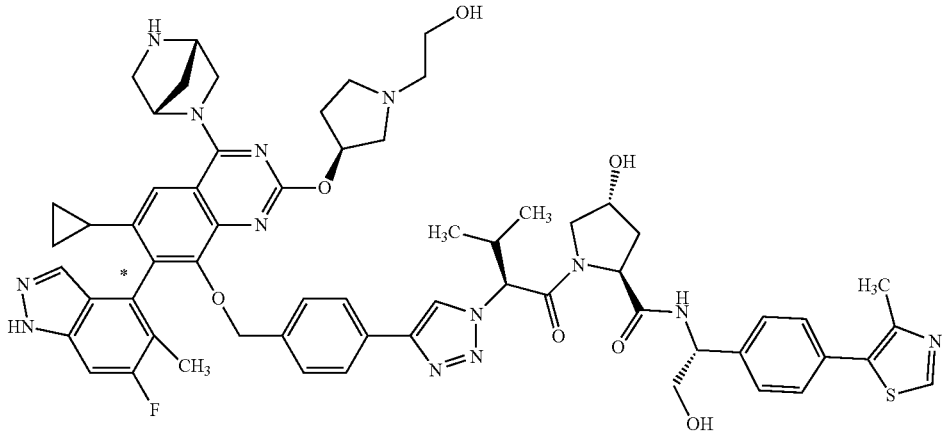 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(O[C@H]6CCN(CCO)C6)nc45)cc3)nn2)cc1] |
| 32 | 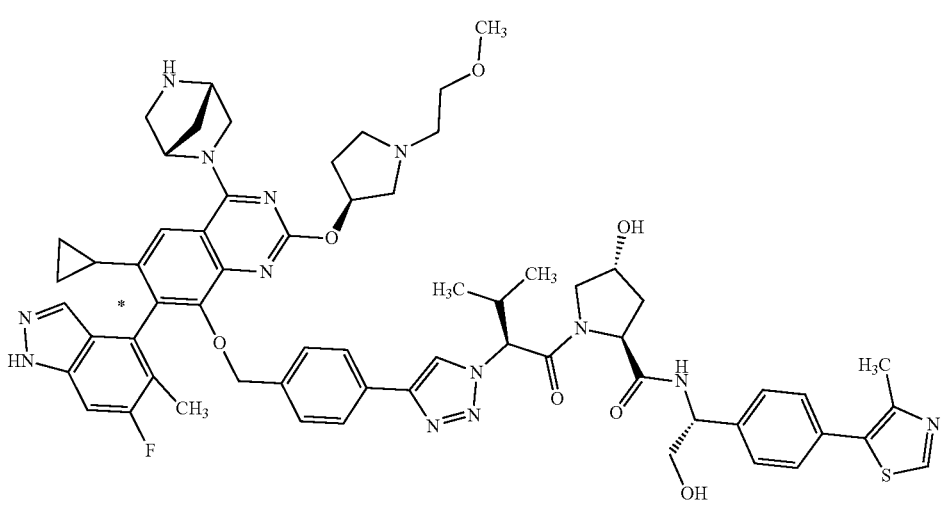 [SMILES: COCCN1CC[C@H](Oc2nc(N3C[C@@H]4C[C@H]3CN4)c3cc(C4CC4)c(-c4c(C)c(F)cc5[nH]ncc45)c(OCc4ccc(-c5cn([C@H](C(=O)N6C[C@H](O)C[C@H]6C(=O)N[C@@H](CO)c6ccc(-c7scnc7C)cc6)C(C)C)nn5)cc4)c3n2)C1] |
| 33 | 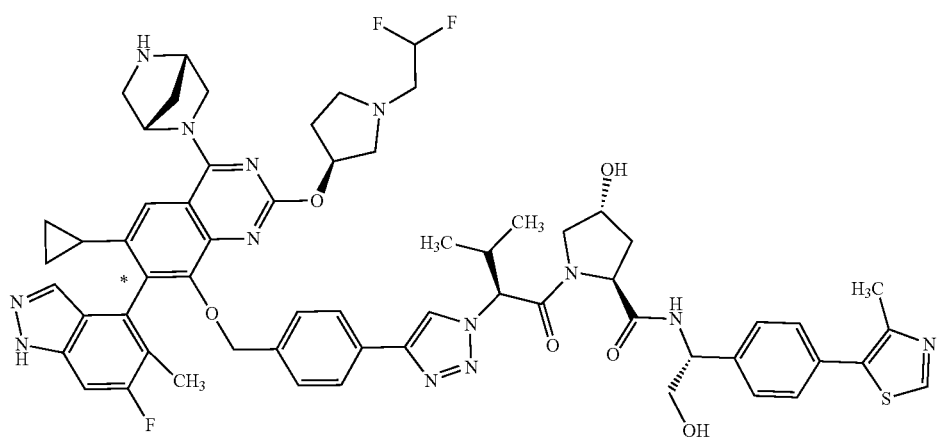 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(O[C@H]6CCN(CC(F)F)C6)nc45)cc3)nn2)cc1] |

TABLE 113

| Ex | Str |
|---|---|
| 34 | |
| 35 | |
| 36 | |

TABLE 114

| Ex | Str |
|---|---|
| 37 | |
| 38 | |
| 39 | |

TABLE 115

| Ex | Str |
|---|---|
| 40 | (chemical structure) |
| 41 | (chemical structure) |
| 42 | (chemical structure) |

TABLE 116
| Ex | Str |
|---|---|
| 43 | 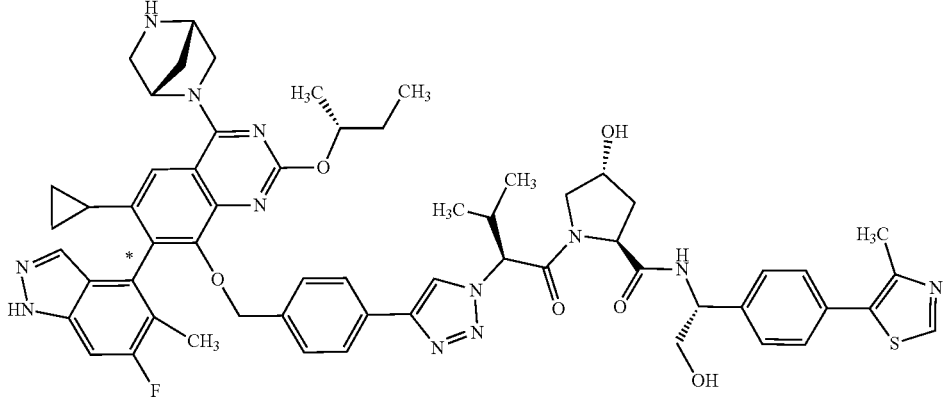 [SMILES: CC[C@@H](C)Oc1nc(N2C[C@@H]3C[C@H]2CN3)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(-c6scnc6C)cc5)C(C)C)nn4)cc3)c2n1] |
| 44 | 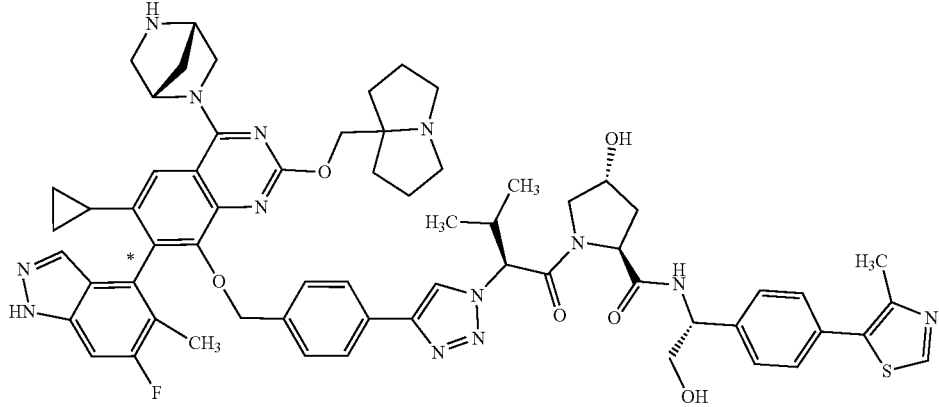 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OCC67CCCN6CCC7)nc45)cc3)nn2)cc1] |
| 45 | 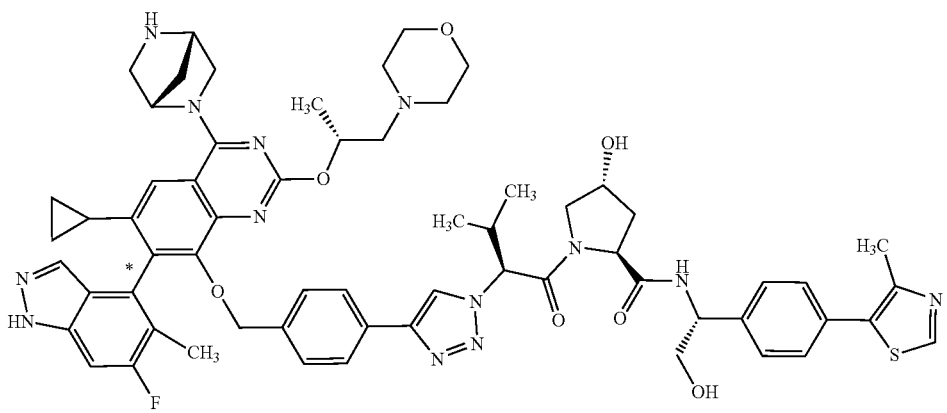 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(O[C@H](C)CN6CCOCC6)nc45)cc3)nn2)cc1] |

TABLE 117

| Ex | Str |
|---|---|
| 46 | (structure) n HCl |
| 47 | (structure) |
| 48 | (structure) |

TABLE 118

| Ex | Str |
|---|---|
| 49 | (chemical structure) |
| 50 | (chemical structure) |
| 51 | (chemical structure) |

TABLE 119

| Ex | Str |
|---|---|
| 52 | (structure) |
| 53 | (structure) |
| 54 | (structure) |

TABLE 120

| Ex | Str |
|---|---|
| 55 | (structure) |
| 57 | (structure) |

TABLE 121

| Ex | Str |
|---|---|
| 58 | (structure) |

TABLE 121-continued
| Ex | Str |
|---|---|
| 59 | 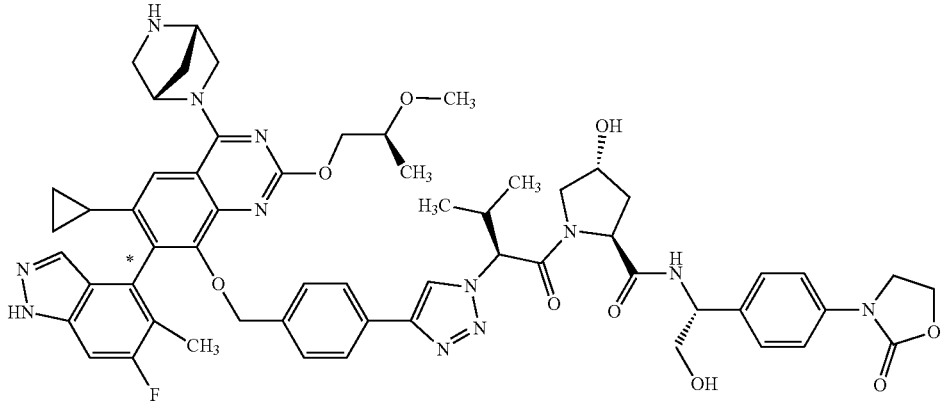 [SMILES: CO[C@@H](C)COc1nc(N2C[C@@H]3C[C@H]2CN3)c2cc(C3CC3)c(-c3c(C)c(F)cc4[nH]ncc34)c(OCc3ccc(-c4cn([C@H](C(=O)N5C[C@H](O)C[C@H]5C(=O)N[C@@H](CO)c5ccc(N6CCOC6=O)cc5)C(C)C)nn4)cc3)c2n1] |
| 60 | 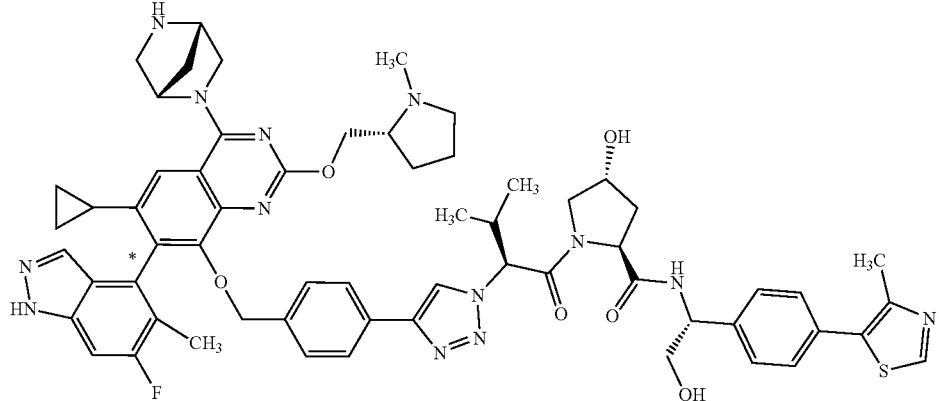 [SMILES: Cc1ncsc1-c1ccc([C@H](CO)NC(=O)[C@@H]2C[C@@H](O)CN2C(=O)[C@H](C(C)C)n2cc(-c3ccc(COc4c(-c5c(C)c(F)cc6[nH]ncc56)c(C5CC5)cc5c(N6C[C@@H]7C[C@H]6CN7)nc(OC[C@H]6CCCN6C)nc45)cc3)nn2)cc1] |
TABLE 122
| Ex | Str |
|---|---|
| 61 | 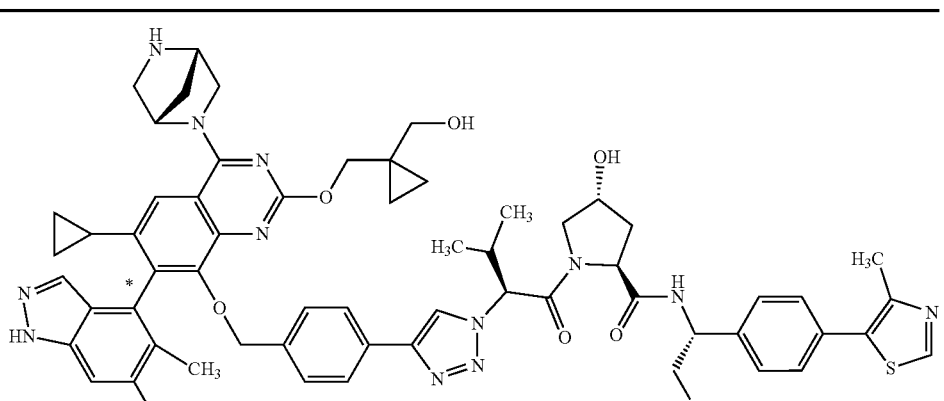 |

TABLE 122-continued

| Ex | Str |
|---|---|
| 62 | |
| 63 | |

TABLE 123

| Ex | Str |
|---|---|
| 64 | |

TABLE 123-continued

| Ex | Str |
|---|---|
| 65 | |
| 66 | |

TABLE 124

| Ex | Str |
|---|---|
| 67 | |

TABLE 124-continued

| Ex | Str |
|---|---|
| 68 | (chemical structure) |
| 69 | (chemical structure) |

TABLE 125

| Ex | Str |
|---|---|
| 70 | (chemical structure) |

TABLE 125-continued

| Ex | Str |
|---|---|
| 71 | (structure) |
| 72 | (structure) |

TABLE 126

| Ex | Str |
|---|---|
| 73 | (structure) |

TABLE 126-continued

| Ex | Str |
|---|---|
| 74 | |
| 75 | |

TABLE 127

| Ex | Syn | DAT |
|---|---|---|
| 1 | 18# | ESI+: 1089.4 |
| 2 | 18 | ESI−: 1088.6 |
| 3 | 18 | ESI+: 1093.5 |
| 4 | 18 | ESI+: 1105.9 |
| 5 | 18 | ESI+: 1037.7 |
| 6 | 20, 7 | ESI+: 1113.3 |
| 7 | 7 | ESI+: 1117.8 |
| 8 | 8 | ESI+: 1117.3 |
|  |  | NMR (100° C.): 0.48-0.68 (4H, m), 0.77 (3H, br d), 1.07 (3H, br d), 1.35-1.43 (1H, m), 1.66-1.77 (3H, m), 1.87 (1H, br d), 1.89-1.97 (1H, m), 1.98-2.10 (3H, m), 2.01 (3H, d), 2.10-2.21 (1H, m), 2.45 (3H, s), 2.50-2.59 (1H, m), 3.06 (1H, dd), 3.13 (1H, d), 3.35-3.45 (2H, m), 3.57-3.64 (1H, m), 3.65-3.75 (3H, m), 3.75-3.79 (1H, m), 3.80-3.90 (3H, m), 4.16 (1H, dd), 4.35 (1H, br s), 4.41-4.48 (1H, m), 4.48-4.56 (1H, m), 4.78-4.84 (2H, m), 4.84-4.95 (1H, m), 5.13 (1H, br s), 5.17-5.24 (1H, m), 5.24-5.31 (2H, m), 6.82 (2H, d), 7.30 (1H, d), 7.38-7.44 (4H, m), 7.44-7.48 (2H, m), 7.61 (2H, br d), 8.00 (1H, br d), 8.43 (1H, br s), 8.88 (1H, s), 12.75 (1H, br s) |
| 9 | 18 | ESI+: 1101.7 |
| 10 | 18 | ESI+: 1087.7 |
| 11 | 18 | ESI−: 1114.5 |
| 12 | 18 | ESI+: 1098.6, 1100.8 |
| 13 | 20 | ESI+: 1038.7 |
| 14 | 18 | ESI+: 1020.5 |
| 15 | 20, 7 | ESI+: 1093.5 |
| 16 | 18 | ESI+: 1137.8 |
| 17 | 18 | ESI+: 1119.7 |
| 18 | 18 | ESI+: 1133.3 |
| 19 | 20, 7 | ESI+: 1144.4 |
| 20 | 20 | ESI+: 1105.7 |

TABLE 128

| Ex | Syn | DAT |
|---|---|---|
| 21 | 8, 7 | ESI+: 1180.3 |
| 22 | 8, 7 | ESI+: 1100.4 |
| 23 | 8 | ESI+: 1100.4 |
|  |  | NMR (100° C.): 0.48-0.68 (4H, m), 0.77 (3H, br d), 1.03-1.10 (3H, m), 1.35-1.44 (1H, m), 1.66-1.77 (3H, m), 1.87 (1H, br d), 1.89-1.97 (1H, m), 1.98-2.10 (3H, m), 2.01 (3H, d), 2.11-2.24 (1H, m), 2.50-2.60 (1H, m), 3.06 (1H, dd), 3.14 (1H, d), 3.36-3.44 (2H, |

TABLE 128-continued

| Ex | Syn | DAT |
|---|---|---|
| | | m), 3.56-3.64 (1H, m), 3.65-3.75 (3H, m), 3.77 (1H, br s), 3.80-3.92 (6H, m), 4.16 (1H, dd), 4.36 (1H, br s), 4.41-4.48 (1H, m), 4.49-4.57 (1H, m), 4.73-4.84 (2H, m), 4.87-4.96 (1H, m), 5.13 (1H, br s), 5.17-5.24 (1H, m), 5.24-5.32 (2H, m), 6.31 (1H, d), 6.82 (2H, d), 7.30 (1H, d), 7.38-7.45 (5H, m), 7.45 (1H, d), 7.47 (1H, br s), 7.61 (2H, br d), 8.01 (1H, br d), 8.43 (1H, s), 12.75 (1H, br s) |
| 24 | 8 | ESI+: 1173.2 |
| 25 | 18# | ESI+: 1160.6 [M + Na]+ |
| 26 | 8 | ESI+:1114.5 NMR (100° C.): 0.48-0.68 (4H, m), 0.77 (3H, br d), 1.03-1.10 (3H, m), 1.30 (3H, t), 1.35-1.43 (1H, m), 1.66-1.77 (3H, m), 1.87 (1H, br d), 1.89-1.97 (1H, m), 1.98-2.10 (3H, m), 2.01 (3H, d), 2.11-2.20 (1H, m), 2.50-2.60 (1H, m), 3.06 (1H, dd), 3.13 (1H, d), 3.35-3.45 (2H, m), 3.57-3.64 (1H, m), 3.65-3.75 (3H, m), 3.75-3.79 (1H, m), 3.80-3.93 (3H, m), 4.11 (2H, q), 4.16 (1H, dd), 4.35 (1H, br s), 4.41-4.48 (1H, m), 4.49-4.57 (1H, m), 4.78-4.84 (2H, m), 4.87-4.96 (1H, m), 5.12 (1H, br s), 5.17-5.24 (1H, m), 5.24-5.32 (2H, m), 6.27 (1H, d), 6.82 (2H, d), 7.30 (1H, d), 7.35-7.40 (2H, m), 7.40-7.48 (5H, m), 7.61 (2H, br d), 8.01 (1H, br d), 8.43 (1H, s), 12.75 (1H, br s) |

TABLE 129

| Ex | Syn | DAT |
|---|---|---|
| 27 | 8 | ESI+: 1089.5 |
| 28 | 8 | ESI+: 1103.3 |
| 29 | 8 | ESI+: 1103.4 |
| 30 | 18 | ESI+: 1038.3 |
| 31 | 8 | ESI+: 1168.7 [M + Na]+ |
| 32 | 8 | ESI+: 1183.0 [M + Na]+ |
| 33 | 8 | ESI+: 1166.2 |
| 34 | 8 | ESI+: 1166.3 |
| 35 | 20 | ESI−: 1116.6 |
| 36 | 8 | ESI+: 1161.3 |
| 37 | 8 | ESI+: 1105.3 |
| 38 | 20 | ESI+: 1101.3 |
| 39 | 8 | ESI+: 1119.3 NMR (100° C.): 0.48-0.68 (4H, m), 0.77 (3H, br d), 1.07 (3H, d), 1.11 (3H, d), 1.20-1.29 (3H, m), 1.34-1.45 (1H, m), 1.78 (1H, br d), 1.87-1.98 (2H, m), 1.98-2.09 (1H, m), 2.01 (3H, d), 2.45 (3H, s), 2.50-2.60 (1H, m), 3.10 (1H, dd), 3.20 (1H, d), 3.28 (3H, s), 3.50-3.64 (3H, m), 3.64-3.74 (2H, m), 3.74-3.89 (3H, m), 4.19 (1H, dd), 4.28-4.40 (1H, m), 4.40-4.50 (1H, m), 4.52 (1H, t), 4.72-4.86 (2H, m), 4.86-4.96 (1H, m), 5.14 (1H, s), 5.25-5.34 (3H, m), 6.81 (2H, d), 7.30 (1H, d), 7.36-7.51 (6H, m), 7.59 (2H, br d), 8.01 (1H, br d), 8.42 (1H, s), 8.88 (1H, s), 12.74 (1H, br s) |
| 40 | 8 | ESI+: 1105.4 |

TABLE 130

| Ex | Syn | DAT |
|---|---|---|
| 41 | 8 | ESI+: 1119.4 |
| 42 | 8 | ESI+: 1105.3 |
| 43 | 8 | ESI+: 1089.3 |
| 44 | 8 | ESI+: 1156.4 |
| 45 | 8 | ESI+: 1160.5 |
| 46 | 20, 7 | ESI+: 1118.4 |
| 47 | 8 | ESI+: 1105.8 |
| 48 | 8 | ESI+: 1105.7 NMR (100° C.): 0.48-0.68 (4H, m), 0.77 (3H, br d), 1.04-1.10 (3H, m), 1.14 (3H, d), 1.35-1.43 (1H, m), 1.74 (1H, br d), 1.87 (1H, br d), 1.89-1.97 (1H, m), 2.00 (3H, d), 2.01-2.10 (2H, m), 2.10-2.32 (1H, m), 2.45 (3H, s), 2.45-2.60 (1H, m), 3.06 (1H, dd), 3.14 (1H, d), 3.30 (3H, s), 3.60 (1H, br d), 3.65-3.78 (5H, m), 3.84 (1H, dd), 4.16 (1H, dd), 4.28 (1H, dd), 4.32-4.38 (2H, m), 4.45 (1H, br t), 4.52 (1H, br t), 4.78-4.85 (2H, m), 4.86-4.94 (1H, m), 5.14 (1H, br s), 5.28 (2H, d), 6.83 (2H, d), 7.30 (1H, d), 7.37-7.43 (4H, m), 7.45 (1H, d), 7.47 (1H, s), 7.59 (2H, br d), 8.00 (1H, br d), 8.42 (1H, s), 8.88 (1H, s), 12.75 (1H, br s) |
| 49 | 49 | ESI+: 1135.3 |
| 50 | 8 | ESI+: 1117.4 |
| 51 | 8 | ESI+: 1117.4 |
| 52 | 49 | ESI+: 1117.4 |
| 53 | 49 | ESI+: 1117.3 |
| 54 | 8 | ESI+: 1105.2 |
| 55 | 8 | ESI+: 1190.4 |
| 57 | 8 | ESI+: 1130.7 |
| 58 | 8 | ESI+: 1026.8 |
| 59 | 8 | ESI+: 1093.8 |
| 60 | 8 | ESI+: 1130.4 |
| 61 | 8 | ESI+: 1117.8 |
| 62 | 8 | ESI+: 1131.8 |
| 63 | 8 | ESI+: 1038.7 |
| 64 | 8 | ESI+: 1144.3 |
| 65 | 8 | ESI+: 1160.4 |

TABLE 131

| Ex | Syn | DAT |
|---|---|---|
| 66 | 8 | ESI+: 1076.6 |
| 67 | 8 | ESI+: 1098.6 |
| 68 | 8 | ESI+: 1117.6 |
| 69 | 8 | ESI+: 1123.8 [M + Na]+ |
| 70 | 8 | ESI+: 1102.8 NMR (100° C.): 0.48-0.68 (4H, m), 0.77 (3H, br d), 1.07 (3H, d), 1.14 (3H, d), 1.30 (3H, t), 1.35-1.43 (1H, m), 1.75 (1H, br d), 1.85-1.98 (2H, m), 2.00 (3H, d), 2.01-2.10 (1H, m), 2.42-2.51 (1H, m), 2.51-2.60 (1H, m), 3.07 (1H, dd), 3.16 (1H, d), 3.30 (3H, s), 3.60 (1H, br d), 3.65-3.78 (4H, m), 3.80 (1H, br s), 3.84 (1H, br dd), 4.07-4.15 (2H, m), 4.17 (1H, dd), 4.28 (1H, dd), 4.32-4.39 (2H, m), 4.42-4.48 (1H, m), 4.52 (1H, br t), 4.73-4.85 (2H, m), 4.87-4.96 (1H, m), 5.14 (1H, br s), 5.28 (2H, br d), 6.27 (1H, d), 6.83 (2H, d), 7.30 (1H, d), 7.35-7.40 (2H, m), 7.40-7.49 (5H, m), 7.59 (2H, br d), 8.01 (1H, br d), 8.42 (1H, s), 12.75 (1H, br s) |
| 71 | 8 | ESI+: 1088.9 |
| 72 | 8 | ESI+: 1089.9 |
| 73 | PSyn40, Syn8 | ESI−: 1113.6 |
| 74 | 8 | ESI+: 1200.8 [M + Na]+ |
| 75 | 8 | ESI+: 1226.9 [M + Na]+ |

As examples of specific compounds of the formula (I) included in the present invention, compounds having any of the following structures are shown. These compounds can be produced also by the typical production methods shown above, the production methods of the Production Examples and the Examples, a combination of the production methods or a method that is obvious to a person skilled in the art.

These compounds are expected to be excellent in the degradation-inducing action on a G12D mutant KRAS protein and useful as a G12D mutant KRAS inhibitor and can be used as an active ingredient of a pharmaceutical composition, for example, a pharmaceutical composition for treating pancreatic cancer.

[Chem. 44]
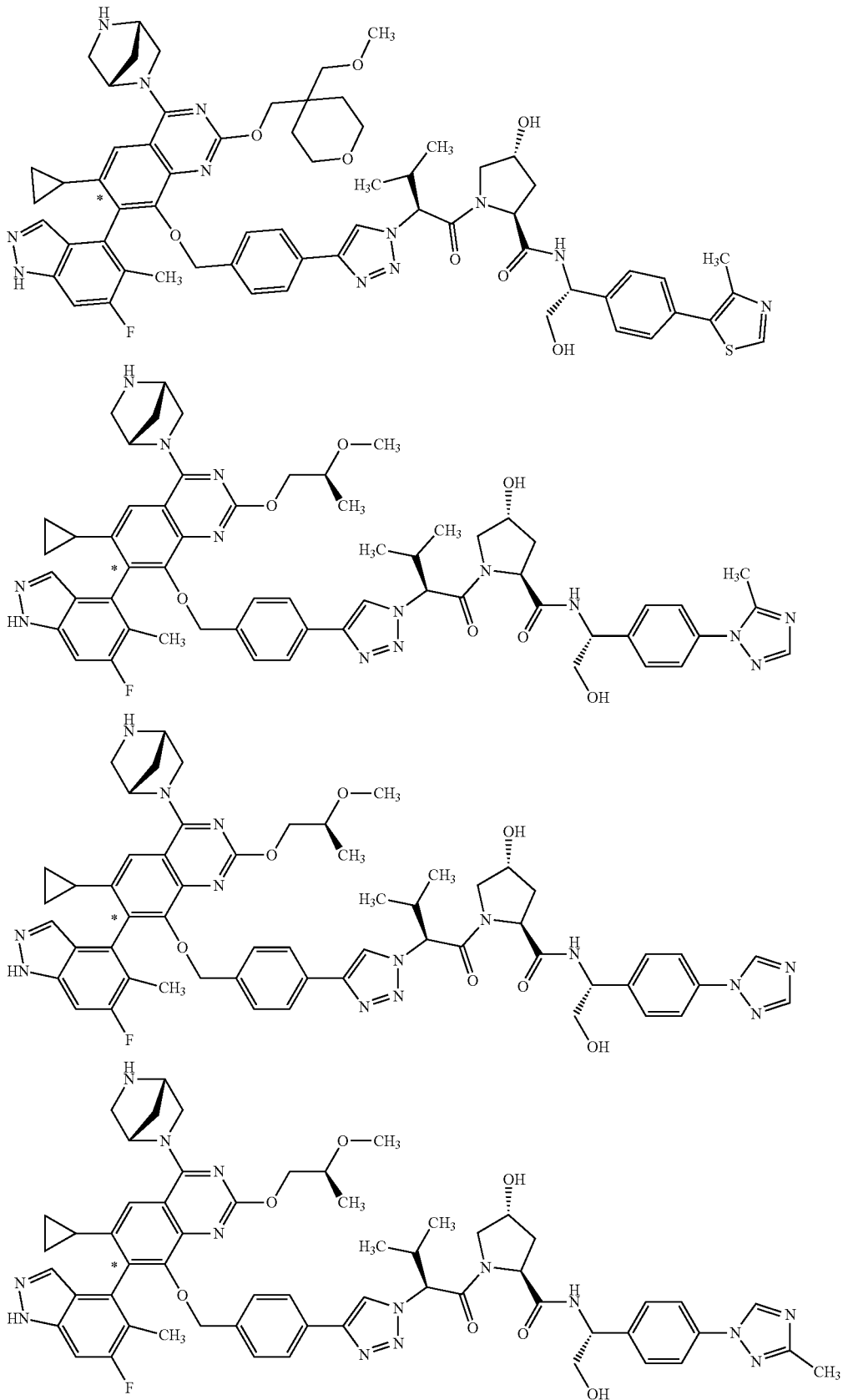

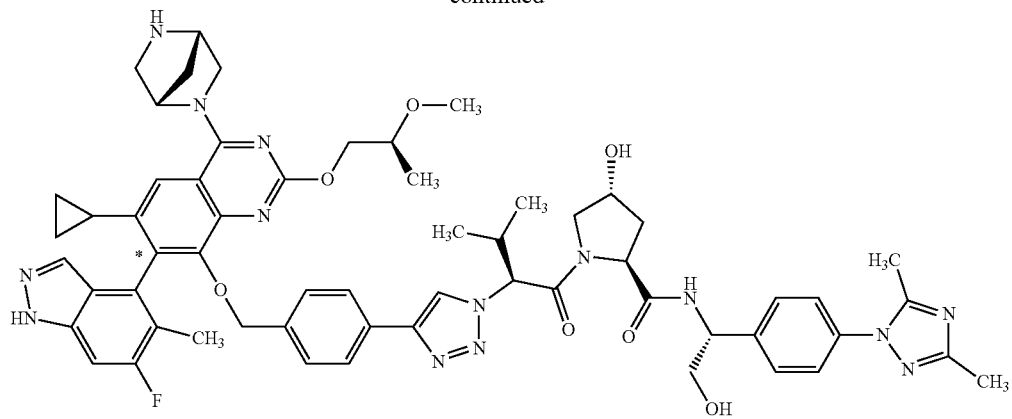
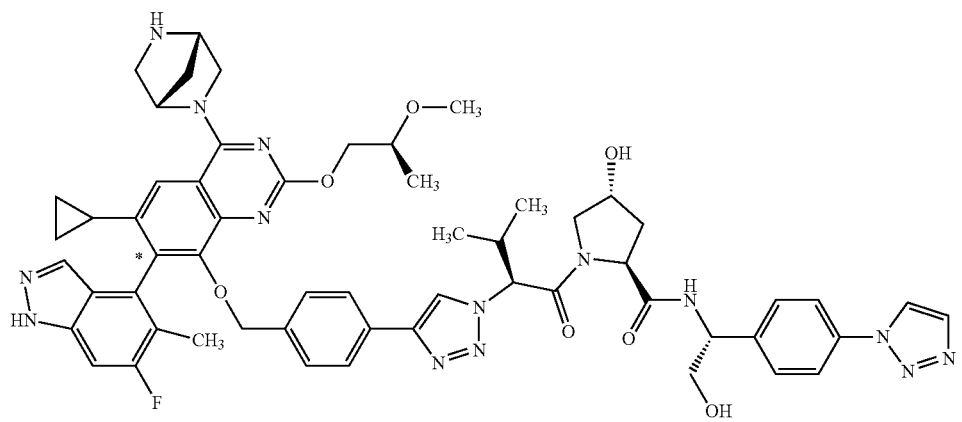
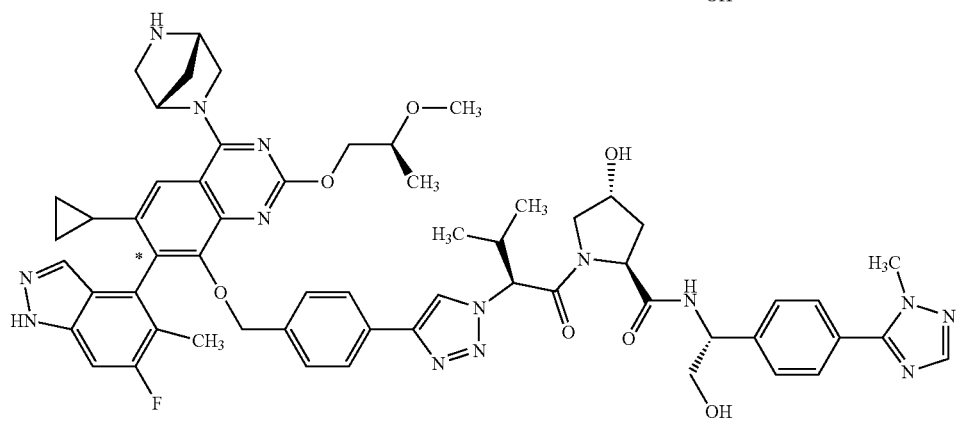
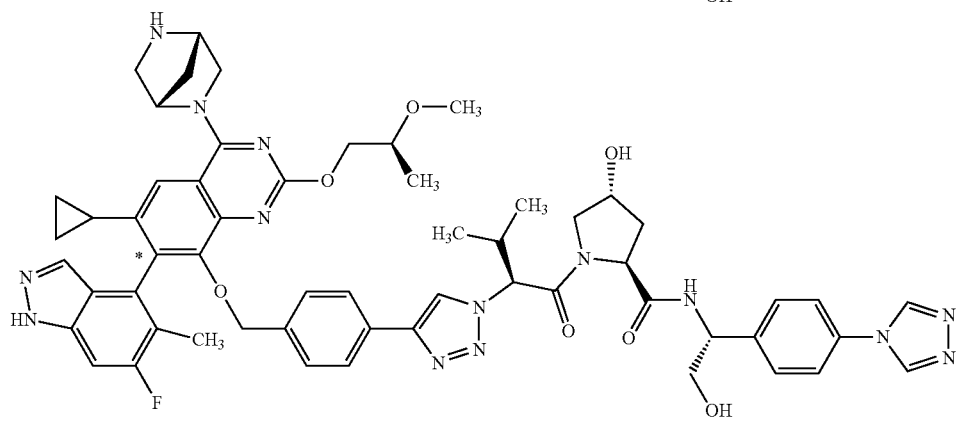

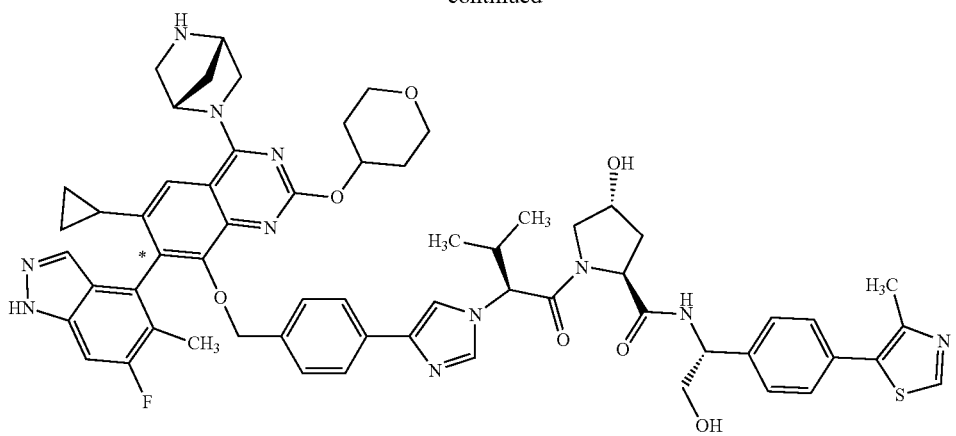
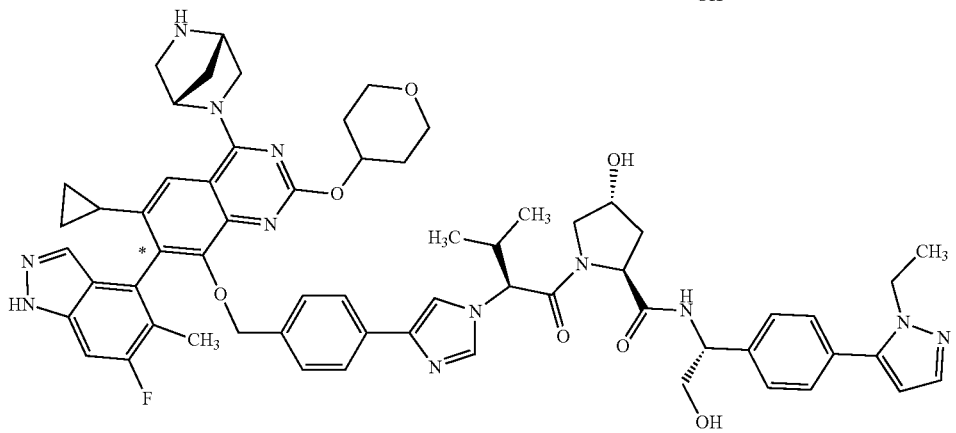
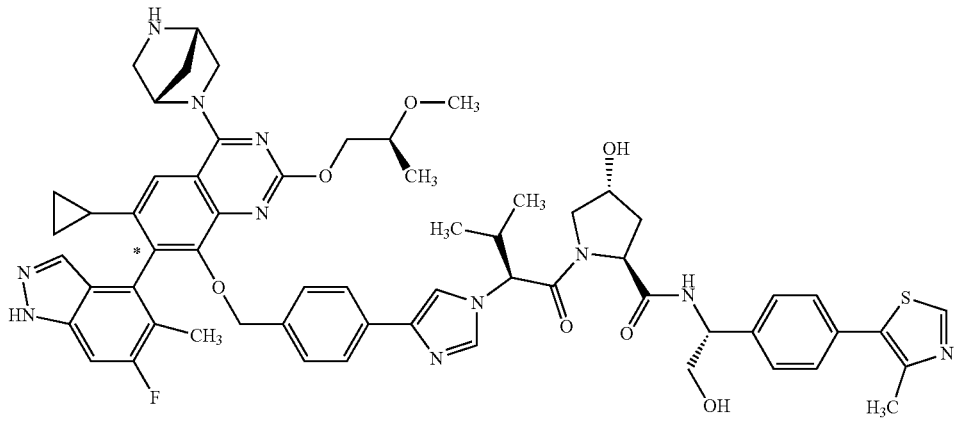
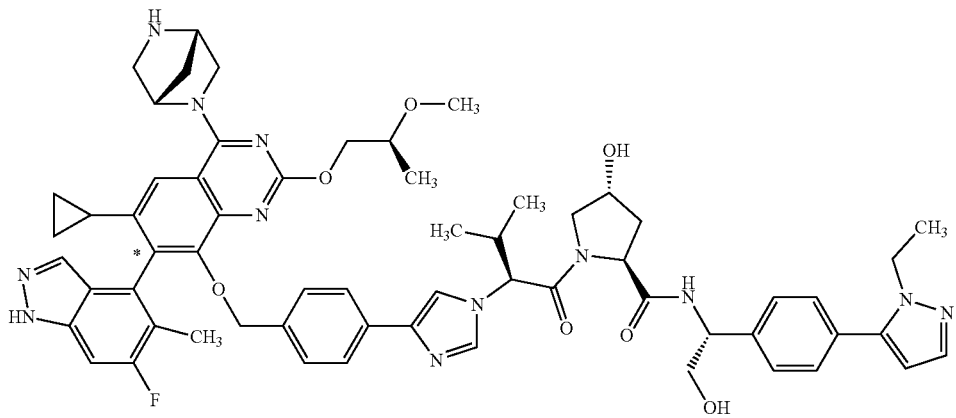

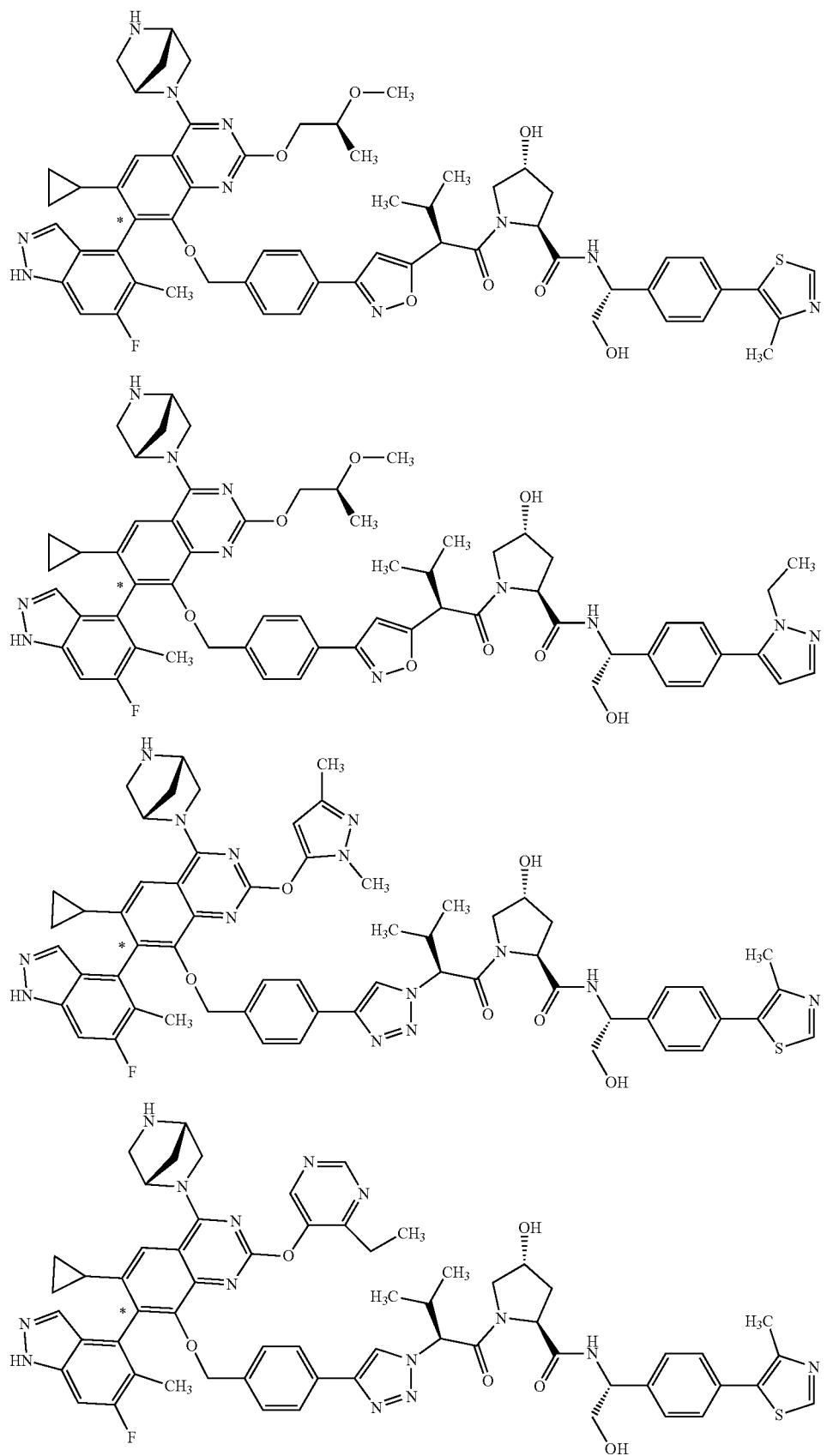

INDUSTRIAL APPLICABILITY

The compound or a salt thereof of the present invention is excellent in the degradation-inducing action on a G12D mutant KRAS protein, is useful as a G12D mutant KRAS inhibitor and can be used as an active ingredient of a pharmaceutical composition, for example, a pharmaceutical composition for treating pancreatic cancer.

The invention claimed is:

1. A compound or a salt thereof, wherein the compound is selected from the group consisting of
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl] phenyl}ethyl]-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide,
   (4R)-1-{(2S)-2-[4-(4-{[(6-cyclopropyl-4-[(1S,4S)-2,5-diazabicyclo [2.2.1]heptan-2-yl]-7-(6-fluoro-5-methyl-1H-indazol-4-yl)-2-{[(2R,3R)-3-methoxybutan-2-yl] oxy}quinazolin-8-yl) oxy] methyl}phenyl)-1H-1,2,3-triazol-1-yl]-3-methylbutanoyl}-4-hydroxy-N-{(1R)-2-hydroxy-1-[4-(4-methyl-1,3-thiazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide, and
   (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

2. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

3. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide.

4. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl) phenyl] ethyl}-L-prolinamide.

5. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

6. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide.

7. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

8. The compound or salt according to claim 1, wherein the compound is (4R)-1-{(2S)-2-[4-(4-{[(6-cyclopropyl-4-[(1S, 4S)-2,5-diazabicyclo [2.2.1]heptan-2-yl]-7-(6-fluoro-5-methyl-1H-indazol-4-yl)-2-{[(2R,3R)-3-methoxybutan-2-yl]oxy}quinazolin-8-yl) oxy] methyl}phenyl)-1H-1,2,3-triazol-1-yl]-3-methylbutanoyl]-4-hydroxy-N-{(1R)-2-hydroxy-1-[4-(4-methyl-1,3-thiazol-5-yl) phenyl] ethyl}-L-prolinamide.

9. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

10. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

11. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

12. The compound or salt according to claim 1, wherein the compound is (4R)-1-[(2S)-2-(4-{4-[({6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

13. A compound or a salt thereof, wherein the compound is selected from the group consisting of
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide,
(4R)-1-[(2S)-2-{4-[4-({[(7M)-6-cyclopropyl-4-[(1S,4S)-2,5-diazabicyclo [2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl) phenyl]-1H-1,2,3-triazol-1-yl}-3-methylbutanoyl]-4-hydroxy-N-{(1R)-2-hydroxy-1-[4-(4-methyl-1,3-thiazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide,
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide, and
(4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

14. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

15. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide.

16. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3- methylbutanoyl]-4-hydroxy-N-{(1R)-2-hydroxy-1-[4-(2-oxo-1,3-oxazolidin-3-yl) phenyl] ethyl}-L-prolinamide.

17. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

18. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide.

19. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

20. The compound or salt according to claim 13, wherein the compound is (4R)-1-[(2S)-2-{4-[4-({[(7M)-6-cyclopropyl-4-[(1S,4S)-2,5-diazabicyclo [2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl) phenyl]-1H-1,2,3-triazol-1-yl}-3-methylbutanoyl]-4-hydroxy-N-{(1R)-2-hydroxy-1-[4-(4-methyl-1,3-thiazol-5-yl) phenyl] ethyl}-L-prolinamide.

21. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

22. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

23. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

24. The compound or salt according to claim 13, wherein the compound is (4R)-1-[(2S)-2-(4-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

25. A compound or a salt thereof, wherein the compound is selected from the group consisting of (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide, (4R)-1-[(2S)-2-{4-[4-({[(7P)-6-cyclopropyl-4-[(1S,4S)-2,5-diazabicyclo [2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl) phenyl]-1H-1,2,3-triazol-1-yl}-3-methylbutanoyl]-4-hydroxy-N-{(1R)-2-hydroxy-1-[4-(4-methyl-1,3-thiazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy) quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide, (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol- 1-yl)-3-methylbutanoyl]-N-{(1R)-1-[4-(1-ethyl-1H-pyrazol-5-yl) phenyl]-2-hydroxyethyl}-4-hydroxy-L-prolinamide, and (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

26. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

27. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-[(1R)-2-hydroxy-1-{4-[4-(hydroxymethyl)-1,3-thiazol-5-yl]phenyl}ethyl]-L-prolinamide.

28. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(2-oxo-1,3-oxazolidin-3-yl) phenyl] ethyl}-L-prolinamide.

29. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-2-{[1-(2,2-difluoroethyl) piperidin-4-yl]oxy}-7-(6-fluoro-5-methyl-1H-indazol-4-yl) quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

30. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-4-hydroxy-N-{(1R)-2-hydroxy-1-[4-(1-methyl-1H-pyrazol-5-yl) phenyl] ethyl}-L-prolinamide.

31. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

32. The compound or salt according to claim 25, wherein the compound is (4R)-1-[(2S)-2-{4-[4-({[(7P)-6-cyclopropyl-4-[(1S,4S)-2,5-diazabicyclo [2.2.1]heptan-2-yl]-7-(6-fluoro-5-methyl-1H-indazol-4-yl)-2-{[(2R,3R)-3-methoxybutan-2-yl]oxy}quinazolin-8-yl]oxy}methyl) phenyl]-1H-1,2,3-triazol-1-yl}-3-methylbutanoyl]-4-hydroxy-N-{(1R)-2-hydroxy-1-[4-(4-methyl-1,3-thiazol-5-yl) phenyl] ethyl}-L-prolinamide.

33. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

34. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl) oxy] quinazolin-8-yl}oxy)methyl]-2-fluorophenyl}-1H-1,2,3-triazol-1-yl)-3-methylbutanoyl]-4-hydroxy-N-{(1R)-2-hydroxy-1-[4-(4-methyl-1,3-thiazol-5-yl) phenyl] ethyl}-L-prolinamide.

35. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-N-{(1R)-1-[4-(1-ethyl-1H-pyrazol-5-yl) phenyl]-2-hydroxyethyl}-4-hydroxy-L-prolinamide.

36. The compound or salt according to claim 25, wherein the compound is (4R)-1-[(2S)-2-(4-{4-[({(7P)-6-cyclopropyl-4-[(1S,4S)-2,5-diazabicyclo [2.2.1]heptan-2-yl]-7-(6-fluoro-5-methyl-1H-indazol-4-yl)-2-[(2S)-2-methoxypropoxy] quinazolin-8-yl}oxy)methyl]phenyl}-1H-1,2,3-triazol-1-yl)-3-methylbutanoyl]-4-hydroxy-N-{(1R)-2-hydroxy-1-[4-(4-methyl-1,3-oxazol-5-yl) phenyl] ethyl}-L-prolinamide.

37. A pharmaceutical composition comprising the compound or salt according to any one of claims 1, 13, and 25, and one or more pharmaceutically acceptable excipients.

* * * * *